US011702670B2

(12) United States Patent
Dietrich et al.

(10) Patent No.: US 11,702,670 B2
(45) Date of Patent: Jul. 18, 2023

(54) COMPOSITIONS AND METHODS FOR IMPROVING CROP YIELDS THROUGH TRAIT STACKING

(71) Applicant: Monsanto Technology LLC, St. Louis, MO (US)

(72) Inventors: Charles R. Dietrich, Chesterfield, MO (US); Natalia Ivleva, Webster Groves, MO (US); Thomas L. Slewinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/967,704

(22) PCT Filed: Feb. 15, 2019

(86) PCT No.: PCT/US2019/018134
§ 371 (c)(1),
(2) Date: Aug. 5, 2020

(87) PCT Pub. No.: WO2019/161150
PCT Pub. Date: Aug. 22, 2019

(65) Prior Publication Data
US 2021/0032653 A1 Feb. 4, 2021

Related U.S. Application Data

(60) Provisional application No. 62/631,335, filed on Feb. 15, 2018.

(51) Int. Cl.
*C12N 15/82* (2006.01)

(52) U.S. Cl.
CPC ..... *C12N 15/8297* (2013.01); *C12N 15/8218* (2013.01)

(58) Field of Classification Search
None
See application file for complete search history.

(56) References Cited

U.S. PATENT DOCUMENTS 6,329,573 B1 * 12/2001 Lightfoot ........... C12N 15/8277 800/300
7,138,567 B2 * 11/2006 Okawa ................. C12N 9/0071 536/23.6
2003/0233675 A1 12/2003 Cao et al.
2014/0380525 A1 12/2014 Good et al.
2016/0010109 A1 1/2016 Albertsen et al.
2017/0002374 A1 1/2017 Mirkov et al.
2017/0114356 A1 4/2017 Li et al.

FOREIGN PATENT DOCUMENTS

CN 103451200 A 12/2013
WO 0009722 A2 2/2000

OTHER PUBLICATIONS

Gen Bank Accession NM 001279524, dated 2009. (Year: 2009).*
Gen Bank Accession AAA23868, dated 1993. (Year: 1993).*
Song et al. (Gene 482.1-2 (2011): 34-42). (Year: 2011).*
Helliwell et al. (Methods in Enzymology 30.4 (2003): 289-295). (Year: 2003).*
Gen Bank Accession BT068785, dated Jun. 15, 2012. (Year: 2012).*
Anonymous. (Jan. 1, 1998). “Dwarf Corn Earns Tall Praise,” Retrieved from the Internet:URL:https ://www.farmprogress.com/dwarf-corn-earns-tall-prai se[retrieved on Sep. 21, 2021], 4 pages.
Coles, J. P et al. (1999). “Modification of Gibberellin Production and Plant Development in Arabidopsis by Sense and Antisense Expression of Gibberellin 20-oxidase Genes,” The Plant Journal, 17(5): 547-556.
Hedden, P et al. (2012). “Gibberellin Biosynthesis and Its Regulation,” Biochem. J. 444: 11-25.
International Search Report and Written Opinion, dated Jul. 5, 2019, for PCT Application No. PCT/US2019/018134, filed Feb. 15, 2019, 14 pages.
McAllister, C. H (2012) “Engineering Nitrogen Use Efficient Crop Plants: the Current Status,” Plant Biotechnology Journal, 10:9:1011-1025.
Qiao, F. et al. (Jun. 19, 2013) “Alteration of Rice Growth and Development via Antisense Expression of OsGA20ox2 Gene,” African Journal of Biotechnology. 12(25): 3898-3904.

* cited by examiner

*Primary Examiner* — Charles Logsdon
(74) *Attorney, Agent, or Firm* — Morrison & Foerster LLP

(57) ABSTRACT

The present disclosure provides modified, transgenic, or genome edited/mutated corn plants that are semi-dwarf and have one or more improved ear traits relative to a control plant, such as increase in ear fresh weight, ear area, ear volume, ear diameter, ear length, ear tip void, number of kernels per ear, single kernel weight, and yield. The modified, transgenic, or genome edited/mutated corn plants comprise a transgene encoding one or more glutamate dehydrogenase (GDH) polypeptides and have a reduced expression of one or more GA20 or GA3 oxidase genes. Also provided are methods for producing the modified, transgenic, or genome edited/mutated corn plants.

19 Claims, 9 Drawing Sheets

Specification includes a Sequence Listing.

EVENTS

COMPOSITIONS AND METHODS FOR IMPROVING CROP YIELDS THROUGH TRAIT STACKING

CROSS-REFERENCE TO RELATED APPLICATION

This application is a U.S. national phase application of International application number PCT/US2019/018134, filed Feb. 15, 2019, which claims benefit under 35 U.S.C. § 119(e) of U.S. Provisional Appln. No. 62/631,335, filed Feb. 15, 2018; all the foregoing applications are hereby incorporated by reference in their entirety.

INCORPORATION OF SEQUENCE LISTING

A sequence listing contained in the file named "SequenceListing_P34591US01" which is 384,652 bytes (measured in MS-Windows®) 10 and was created on Aug. 4, 2020, is filed electronically herewith and incorporated by reference in its entirety.

FIELD

The present disclosure relates to modified, transgenic, and/or genome edited or mutated corn plants that are semi-dwarf and have one or more improved ear traits relative to a control plant, as well as methods for producing transgenic and/or genome edited or mutated corn plants through stacking.

BACKGROUND

Cereal crop yields have been steadily increasing over the past decades due to improved agronomic practices and traits. However, there continues to be a need in the art for improved corn yield through intrinsic yield gains and/or reduced yield losses from improved lodging resistance, stress tolerances and other traits.

SUMMARY

Figure 1:
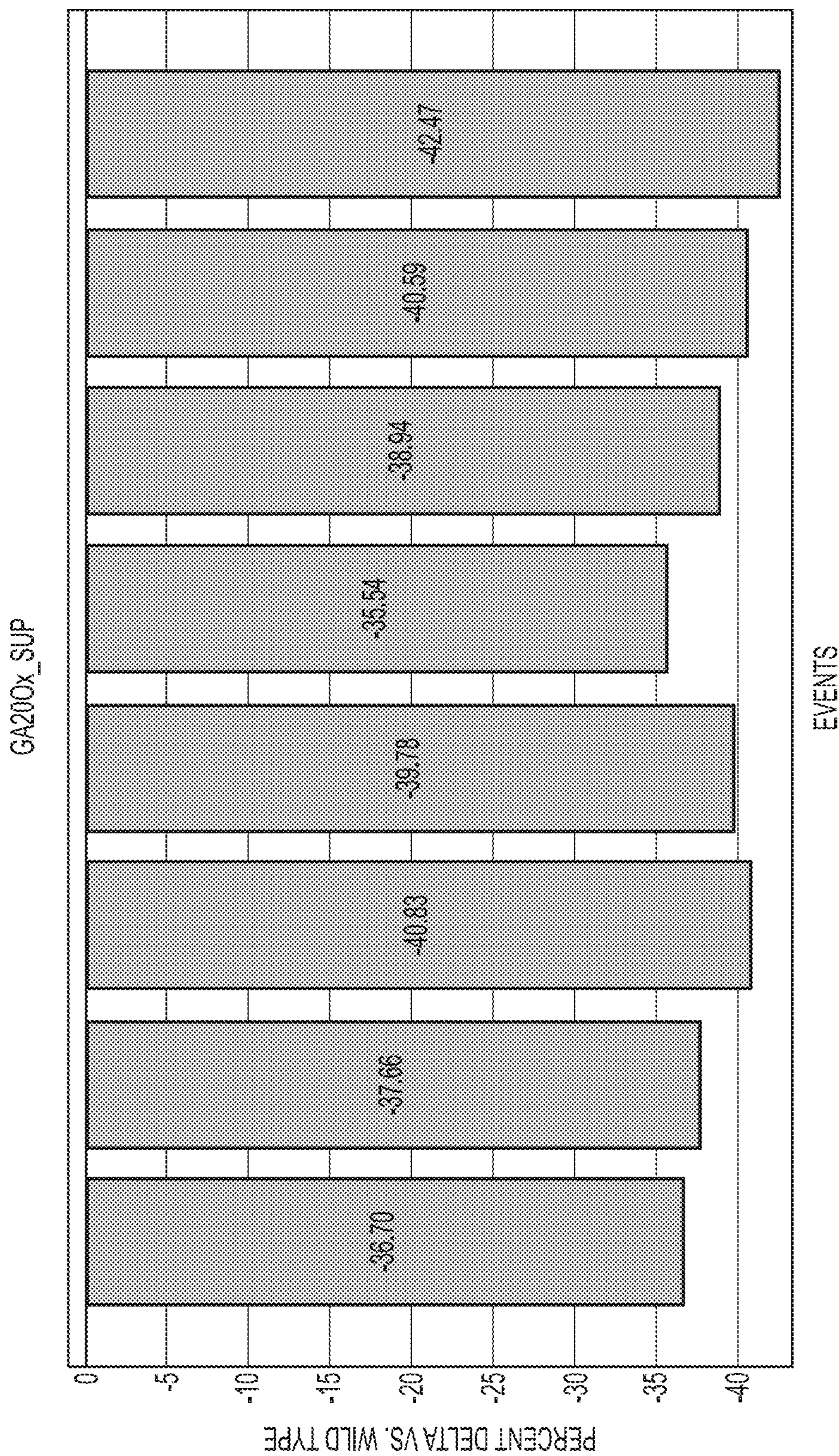
FIG. 1 shows plant heights of corn plants comprising a DNA sequence encoding a miRNA for the suppression of GA20 oxidase ("GA20Ox_SUP single") with each of two transformation events tested in two nurseries and two locations, relative to control corn plants.

The present disclosure provides a modified corn plant or a plant part thereof comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a glutamate dehydrogenase (GDH) polypeptide.

The present disclosure also provides a plurality of modified corn plants in a field, each modified corn plant comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a GDH polypeptide.

Also provided in the present disclosure is a method for producing a modified corn plant, the method comprising: a) introducing into a corn cell a first recombinant expression cassette comprising a DNA sequence encoding a GDH polypeptide, wherein the corn cell comprises a second recombinant expression cassette comprising a transcribable DNA sequence encoding a non-coding RNA for suppression of one or more GA3 oxidase genes and/or one or more GA20 oxidase genes; and b) regenerating or developing a modified corn plant from the corn cell, wherein the modified corn plant comprises the first and second recombinant expression cassettes.

Further provided in the present disclosure is a method for producing a modified corn plant, the method comprising: a) introducing into a corn cell a first recombinant expression cassette comprising a transcribable DNA sequence encoding a non-coding RNA for suppression of one or more GA3 oxidase genes and/or GA20 oxidase genes, wherein the corn cell comprises a second recombinant expression cassette comprising a DNA sequence encoding a GDH polypeptide; and b) regenerating or developing a modified corn plant from the corn cell, wherein the modified corn plant comprises the first and second recombinant expression cassettes.

In an aspect, the present disclosure provides a method for producing a modified corn plant, the method comprising a) introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a GDH polypeptide; and b) regenerating or developing a modified corn plant from the corn cell, wherein the modified corn plant comprises the first and second recombinant expression cassettes.

In another aspect, the present disclosure provides a method for producing a modified corn plant, the method comprising a) introducing into a corn cell a first recombinant expression cassette comprising a transcribable DNA sequence encoding a non-coding RNA for suppression of one or more GA3 oxidase genes and/or GA20 oxidase genes; b) introducing into the corn cell of step (a) a second recombinant expression cassette comprising a DNA sequence encoding a GDH polypeptide to create a modified corn cell; and c) regenerating or developing a modified corn plant from the modified corn cell of step (b), wherein the modified corn plant comprises the first and second recombinant expression cassettes.

In another aspect, the present disclosure provides a method for producing a modified corn plant, the method comprising a) introducing into a corn cell a first recombinant expression cassette comprising a DNA sequence encoding a GDH polypeptide; b) introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and c) regenerating or developing a modified corn plant from the modified corn cell of step (b), wherein the modified corn plant comprises the first and second recombinant expression cassettes.

In still another aspect, the present disclosure provides a method for producing a modified corn plant, the method comprising: a) crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a GDH polypeptide; and b) producing a progeny corn plant comprising the recombinant expression cassette and has the reduced expression of the one or more endogenous GA3 oxidase genes and/or GA20 oxidase genes.

In an aspect, the present disclosure provides a method for producing a modified corn plant, the method comprising: a) introducing into a corn cell a recombinant expression cassette comprising a DNA sequence encoding a GDH polypeptide, wherein the DNA sequence is operably linked to a plant-expressible promoter, and wherein the corn cell comprises one or more mutations and/or edits in one or more endogenous GA3 oxidase and/or GA20 oxidase genes; and b) regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

Also provided in the present disclosure is a method for producing a modified corn plant, the method comprising: a) mutating or editing one or more endogenous GA3 oxidase genes and/or one or more GA20 oxidase genes in a corn cell, wherein the corn cell comprises a recombinant expression cassette encoding a GDH polypeptide, wherein the DNA sequence is operably linked to a plant-expressible promoter; and b) regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

Further provided in the present disclosure is a modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a GDH polypeptide, wherein the DNA sequence is operably linked to a plant-expressible promoter.

In an aspect, the present disclosure provides a plurality of modified corn plants in a field, each modified corn plant comprising 1) one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and 2) a recombinant expression cassette comprising a DNA sequence encoding a GDH polypeptide, wherein the DNA sequence is operably linked to a plant-expressible promoter.

The present disclosure also provides a recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a GDH polypeptide, wherein the DNA sequence is operably linked to a plant-expressible promoter.

Further provided in the present disclosure is a recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a GDH polypeptide, wherein the DNA sequence is operably linked to a plant-expressible promoter.

Description

Definitions

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5th Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007.

Any references cited herein, including, e.g., all patents, published patent applications, and non-patent publications, are incorporated by reference in their entirety. To facilitate understanding of the disclosure, several terms and abbreviations as used herein are defined below as follows:

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

The term "about" as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

As used herein, a "plant" includes an explant, plant part, seedling, plantlet or whole plant at any stage of regeneration or development. The term "cereal plant" as used herein refers a monocotyledonous (monocot) crop plant that is in the Poaceae or Gramineae family of grasses and is typically harvested for its seed, including, for example, wheat, corn, rice, millet, barley, sorghum, oat and rye. As commonly understood, a "corn plant" or "maize plant" refers to any plant of species *Zea mays* and includes all plant varieties that can be bred with corn, including wild maize species.

As used herein, a "plant part" can refer to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts of the present disclosure can be viable, nonviable, regenerable, and/or non-regenerable. A "propagule" can include any plant part that can grow into an entire plant.

As used herein, a "transgenic plant" refers to a plant whose genome has been altered by the integration or insertion of a recombinant DNA molecule, construct, cassette or sequence for expression of a non-coding RNA molecule, mRNA and/or protein in the plant. A transgenic plant includes an $R_0$ plant developed or regenerated from an originally transformed plant cell(s) as well as progeny transgenic plants in later generations or crosses from the $R_0$ transgenic plant that comprise the recombinant DNA molecule, construct, cassette or sequence. A plant having an integrated or inserted recombinant DNA molecule, construct, cassette or sequence is considered a transgenic plant even if the plant also has other mutation(s) or edit(s) that would not themselves be considered transgenic.

A plant cell is a biological cell of a plant, taken from a plant or derived through culture from a cell taken from a plant. As used herein, a "transgenic plant cell" refers to any plant cell that is transformed with a stably-integrated recombinant DNA molecule, construct, cassette, or sequence. A transgenic plant cell can include an originally-transformed plant cell, a transgenic plant cell of a regenerated or developed $R_0$ plant, a transgenic plant cell cultured from another transgenic plant cell, or a transgenic plant cell from any progeny plant or offspring of the transformed $R_0$ plant, including cell(s) of a plant seed or embryo, or a cultured plant cell, callus cell, etc.

As used herein, the term "transcribable DNA sequence" refers to a DNA sequence that can be transcribed into an RNA molecule. The RNA molecule can be coding or non-coding and may or may not be operably linked to a promoter and/or other regulatory sequences.

For purposes of the present disclosure, a "non-coding RNA molecule" is a RNA molecule that does not encode a protein. Non-limiting examples of a non-coding RNA molecule include a microRNA (miRNA), a miRNA precursor, a small interfering RNA (siRNA), a siRNA precursor, a small RNA (18-26 nt in length) and precursors encoding the same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single-guide RNA (sgRNA).

The terms "suppressing"/"suppression" or "reduced"/"reduction" when used in reference to a gene(s), refers to a lowering, reduction, or elimination of the expression level of a mRNA and/or protein encoded by the gene(s), and/or a lowering, reduction, or elimination of the activity of a protein encoded by the gene(s) in a plant, plant cell or plant tissue, at one or more stage(s) of plant development, as compared to the expression level of such target mRNA and/or protein, and/or the activity of such encoded protein in a wild-type or control plant, cell or tissue at the same stage(s) of plant development.

As used herein, the term "consecutive" in reference to a polynucleotide or protein sequence means without deletions or gaps in the sequence.

As commonly understood in the art, a "mutation" refers to any alteration of the nucleotide sequence of the genome, extrachromosomal DNA, or other genetic element of an organism (e.g., a gene or regulatory element operably linked to a gene in a plant), such as a nucleotide insertion, deletion, inversion, substitution, duplication, etc.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. For purposes of calculating "percent identity" between DNA and RNA sequences, a uracil (U) of a RNA sequence is considered identical to a thymine (T) of a DNA sequence. If the window of comparison is defined as a region of alignment between two or more sequences (i.e., excluding nucleotides at the 5' and 3' ends of aligned polynucleotide sequences, or amino acids at the N-terminus and C-terminus of aligned protein sequences, that are not identical between the compared sequences), then the "percent identity" can also be referred to as a "percent alignment identity". If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

It is recognized that residue positions of proteins that are not identical often differ by conservative amino acid substitutions, where amino acid residues are substituted for other amino acid residues with similar size and chemical properties (e.g., charge, hydrophobicity, polarity, etc.), and therefore may not change the functional properties of the molecule. When sequences differ in conservative substitutions, the percent sequence similarity can be adjusted upwards to correct for the conservative nature of the non-identical substitution(s). Sequences that differ by such conservative substitutions are said to have "sequence similarity" or "similarity." Thus, "percent similarity" or "percent similar" as used herein in reference to two or more protein sequences is calculated by (i) comparing two optimally aligned protein sequences over a window of comparison, (ii) determining the number of positions at which the same or similar amino acid residue occurs in both sequences to yield the number of matched positions, (iii) dividing the number of matched positions by the total number of positions in the window of comparison (or the total length of the reference or query protein if a window of comparison is not specified), and then (iv) multiplying this quotient by 100% to yield the percent similarity. Conservative amino acid substitutions for proteins are known in the art.

For optimal alignment of sequences to calculate their percent identity or similarity, various pair-wise or multiple sequence alignment algorithms and programs are known in the art, such as ClustalW, or Basic Local Alignment Search Tool® (BLAST®), etc., that can be used to compare the sequence identity or similarity between two or more nucleotide or protein sequences. Although other alignment and comparison methods are known in the art, the alignment between two sequences (including the percent identity ranges described above) can be as determined by the ClustalW or BLAST® algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); and Larkin M A et al., "Clustal W and Clustal X version 2.0," *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

The terms "percent complementarity" or "percent complementary", as used herein in reference to two nucleotide sequences, is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen bonding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the "percent complementarity" for the query sequence is equal to the number of base-paired positions between the two sequences divided by the total number of positions in the query sequence over its length (or by the number of positions in the query sequence over a comparison window), which is then multiplied by 100%.

The term "operably linked" refers to a functional linkage between a promoter or other regulatory element and an associated transcribable DNA sequence or coding sequence of a gene (or transgene), such that the promoter, etc., operates or functions to initiate, assist, affect, cause, and/or promote the transcription and expression of the associated transcribable DNA sequence or coding sequence, at least in certain cell(s), tissue(s), developmental stage(s), and/or condition(s).

As commonly understood in the art, the term "promoter" can generally refer to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied or derived from a known or naturally occurring promoter sequence or other promoter sequence. A promoter can also include a chimeric promoter comprising a combination of two or more heterologous sequences. A promoter of the present disclosure can thus include variants of promoter sequences that are similar in composition, but not identical to, other promoter sequence(s) known or provided herein. A promoter can be classified according to a variety of criteria relating to the pattern of expression of an associated coding or transcribable sequence or gene (including a transgene) operably linked to the promoter, such as constitutive, developmental, tissue-specific, inducible, etc. Promoters that drive expression in all or most tissues of the plant are referred to as "constitutive" promoters. Promoters that drive expression during certain periods or stages of development are referred to as "developmental" promoters. Promoters that drive enhanced expression in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. An "inducible" promoter is a promoter that initiates transcription in response to an environmental stimulus such as cold, drought or light, or other stimuli, such as wounding or chemical application. A promoter can also be classified in terms of its origin, such as being heterologous, homologous, chimeric, synthetic, etc.

As used herein, a "plant-expressible promoter" refers to a promoter that can initiate, assist, affect, cause, and/or promote the transcription and expression of its associated transcribable DNA sequence, coding sequence or gene in a corn plant cell or tissue.

As used herein, a "heterologous plant-expressible promoter" refers to a plant-expressible promoter which does not naturally occur adjacent to or associated with the referenced gene or nucleic acid sequence in its natural environment, but which is positioned by laboratory manipulation.

As used herein, a "vascular promoter" refers to a plant-expressible promoter that drives, causes or initiates expression of a transcribable DNA sequence or transgene operably linked to such promoter in one or more vascular tissue(s) of the plant, even if the promoter is also expressed in other non-vascular plant cell(s) or tissue(s). Such vascular tissue(s) can comprise one or more of the phloem, vascular parenchymal, and/or bundle sheath cell(s) or tissue(s) of the plant. A "vascular promoter" is distinguished from a constitutive promoter in that it has a regulated and relatively more limited pattern of expression that includes one or more vascular tissue(s) of the plant. A vascular promoter includes both vascular-specific promoters and vascular-preferred promoters.

As used herein, a "leaf promoter" refers to a plant-expressible promoter that drives, causes or initiates expression of a transcribable DNA sequence or transgene operably linked to such promoter in one or more leaf tissue(s) of the plant, even if the promoter is also expressed in other non-leaf plant cell(s) or tissue(s). A leaf promoter includes both leaf-specific promoters and leaf-preferred promoters. A "leaf promoter" is distinguished from a vascular promoter in that it is expressed more predominantly or exclusively in leaf tissue(s) of the plant relative to other plant tissues, whereas a vascular promoter is expressed in vascular tissue(s) more generally including vascular tissue(s) outside of the leaf, such as the vascular tissue(s) of the stem, or stem and leaves, of the plant.

The term "heterologous" in reference to a promoter or other regulatory sequence in relation to an associated polynucleotide sequence (e.g., a transcribable DNA sequence or coding sequence or gene) is a promoter or regulatory sequence that is not operably linked to such associated polynucleotide sequence in nature—e.g., the promoter or regulatory sequence has a different origin relative to the associated polynucleotide sequence and/or the promoter or regulatory sequence is not naturally occurring in a plant species to be transformed with the promoter or regulatory sequence.

As used herein, a "functional portion" of a promoter sequence refers to a part of the promoter sequence that provides essentially the same or similar expression pattern of an operably linked coding sequence or gene as the full promoter sequence. For this definition, "essentially the same or similar" means that the pattern and level of expression of a coding sequence operably linked to the functional portion of the promoter sequence closely resembles the pattern and level of expression of the same coding sequence operably linked to the full promoter sequence.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of two or more polynucleotide or protein sequences that would not naturally occur together in the same manner without human intervention, such as a polynucleotide molecule, protein, construct, etc., comprising at least two polynucleotide or protein sequences that are operably linked but heterologous with respect to each other. For example, the term "recombinant" can refer to any combination of two or more DNA or protein sequences in the same molecule (e.g., a plasmid, construct, vector, chromosome, protein, etc.) where such a combination is man-made and not normally found in nature. As used in this definition, the phrase "not normally found in nature" means not found in nature without human introduction. A recombinant polynucleotide or protein molecule, construct, etc., can comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., can also refer to a polynucleotide or protein molecule or sequence that has been genetically engineered and/or constructed outside of a cell. For example, a recombinant DNA molecule can comprise any engineered or man-made plasmid, vector, etc., and can include a linear or circular DNA molecule. Such plasmids, vectors, etc., can contain various maintenance elements including a prokaryotic origin of replication and selectable marker, as well as one or more transgenes or expression cassettes perhaps in addition to a plant selectable marker gene, etc.

As used herein, the term "isolated" refers to at least partially separating a molecule from other molecules typically associated with it in its natural state. In an aspect, the term "isolated" refers to a DNA molecule that is separated from the nucleic acids that normally flank the DNA molecule in its natural state. For example, a DNA molecule encoding a protein that is naturally present in a bacterium would be an isolated DNA molecule if it was not within the DNA of the bacterium from which the DNA molecule encoding the protein is naturally found. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

As used herein, an "encoding region" or "coding region" refers to a portion of a polynucleotide that encodes a functional unit or molecule (e.g., without being limiting, a mRNA, protein, or non-coding RNA sequence or molecule).

As used herein, "modified" in the context of a plant, plant seed, plant part, plant cell, and/or plant genome, refers to a plant, plant seed, plant part, plant cell, and/or plant genome comprising an engineered change in the expression level and/or coding sequence of one or more gene(s) relative to a wild-type or control plant, plant seed, plant part, plant cell, and/or plant genome, such as via a transgenic event or a genome editing event or mutation affecting the expression level or activity of one or more genes. Modified plants, plant parts, seeds, etc., can be subjected to or created by mutagenesis, genome editing or site-directed integration (e.g., without being limiting, via methods using site-specific nucleases), genetic transformation (e.g., without being limiting, via methods of Agrobacterium transformation or microprojectile bombardment), or a combination thereof. Such "modified" plants, plant seeds, plant parts, and plant cells include plants, plant seeds, plant parts, and plant cells that are offspring or derived from "modified" plants, plant seeds, plant parts, and plant cells that retain the molecular change (e.g., change in expression level and/or activity) to the one or more genes. A modified seed provided herein can give rise to a modified plant provided herein. A modified plant, plant seed, plant part, plant cell, or plant genome provided herein can comprise a recombinant DNA construct or vector or genome edit as provided herein. A "modified plant product" can be any product made from a modified plant, plant part, plant cell, or plant chromosome provided herein, or any portion or component thereof.

As used herein, the term "control plant" (or likewise a "control" plant seed, plant part, plant cell and/or plant genome) refers to a plant (or plant seed, plant part, plant cell and/or plant genome) that is used for comparison to a modified plant (or modified plant seed, plant part, plant cell and/or plant genome) and has the same or similar genetic background (e.g., same parental lines, hybrid cross, inbred line, testers, etc.) as the modified plant (or plant seed, plant part, plant cell and/or plant genome), except for a transgene, expression cassette, mutation, and/or genome edit affecting one or more genes. For purposes of comparison to a modified plant, plant seed, plant part, plant cell and/or plant genome, a "wild-type plant" (or likewise a "wild-type" plant seed, plant part, plant cell and/or plant genome) refers to a non-transgenic, non-mutated, and non-genome edited control plant, plant seed, plant part, plant cell and/or plant genome. Alternatively as can be specified herein, such a "control plant" (or likewise a "control" plant seed, plant part, plant cell and/or plant genome) can refer to a plant (or plant seed, plant part, plant cell and/or plant genome) that (i) is used for comparison to a modified plant (or modified plant seed, plant part, plant cell and/or plant genome) having a stack of two or more transgene(s), expression cassette(s), mutation(s) and/or genome edit(s), (ii) has the same or similar genetic background (e.g., same parental lines, hybrid cross, inbred line, testers, etc.) as the modified plant (or plant seed, plant part, plant cell and/or plant genome), but (iii) lacks at least one of the two or more transgene(s), expression cassette(s), mutation(s) and/or genome edit(s) of the modified plant (e.g., a stack in comparison to a single of one of the members of the stack). As used herein, such a "control" plant, plant seed, plant part, plant cell and/or plant genome can also be a plant, plant seed, plant part, plant cell and/or plant genome having a similar (but not the same or identical) genetic background to a modified plant, plant seed, plant part, plant cell and/or plant genome, if deemed sufficiently similar for comparison of the characteristics or traits to be analyzed.

As used herein, "crossed" or "cross" means to produce progeny via fertilization (e.g., cells, seeds or plants) and includes crosses between plants (sexual) and self-fertilization (selfing).

As used herein, "ear trait" of a corn plant refers to a characteristics of an ear of a corn plant. In an aspect, an ear trait can include, but is not limited to, ear area, ear diameter, ear fresh weight, ear volume, ear length, ear tip void, number of kernels per ear, single kernel weight, and/or yield. In another aspect, an ear trait can include, but is not limited to, ear void, kernel number, kernel number per row, kernels per field area, kernel rank, kernel row number, kernel weight, number of florets, and/or grain yield estimate. In yet another aspect, an ear trait can include, but is not limited to, ear attitude, ear cob color, ear cob diameter, ear cob strength, ear dry husk color, ear fresh husk color, ear husk bract, ear husk cover, ear husk opening, ear number per stalk, ear shank length, ear shelling percent, ear silk color, ear taper, ear weight, ear rot rating, kernel aleurone color, kernel cap color, kernel endosperm color, kernel endosperm type, kernel grade, kernel length, kernel pericarp color, kernel row direction, kernel side color, kernel thickness, kernel type, kernel width, cob weight, and/or prolificacy. A modified or genome edited/mutated corn plant of the present disclosure exhibits one or more improved ear trait compared to a control corn plant. In an aspect, a modified or genome edited/mutated corn plant exhibits an increased ear diameter relative to a control corn plant. In an aspect, a modified or genome edited/mutated corn plant exhibits increased single kernel weight relative to a control corn plant. In an aspect, a modified or genome edited/mutated corn plant exhibits an increased ear fresh weight relative to a control corn plant. In an aspect, a modified or genome edited/mutated corn plant exhibits an increased yield relative to a control corn plant. In an aspect, a modified or genome edited/mutated corn plant exhibits an increased ear area relative to a control corn plant. In an aspect, a modified or genome edited/mutated corn plant exhibits an increased ear volume relative to a control corn plant. In an aspect, a modified or genome edited/mutated corn plant exhibits an increased ear length relative to a control corn plant. In an aspect, a modified or genome edited/mutated corn plant exhibits a decreased ear tip void relative to a control corn plant. In an aspect, a modified or genome edited/mutated corn plant exhibits an increased number of kernels per ear relative to a control corn plant.

As used herein, "yield" refers to the total amount of an agricultural product (e.g., seeds, fruit, etc.) produced or harvested from a plurality of crop plants per unit area of land cultivation (e.g., a field of crop plants) as understood in the art. Yield can be measured or estimated in a greenhouse, in a field, or under specific environment, treatment and/or stress conditions. For example, as known and understood in the art, yield can be measured in units of kilograms per hectare, bushels per acre, or the like. Indeed, yield can be measured in terms of "broad acreage yield" or "BAY" as known and understood in the art.

As used herein, "foliar nitrogen percentage" refers to the percentage of nitrogen ("N") content divided by the total dry weight of a leaf punch sample [% Nitrogen=100*(weight of nitrogen)/(total weight of dry sample)]. Foliar nitrogen percentage of a sample can be measured using various methods known to a skilled person in the art. Such methods may include but are not limited to: tissue analysis (Kjeldahl digestion or Dumas combustion), leaf-level optical meters (transmittance or fluorescence), canopy-level optical meters (ground-based or satellite-mounted), and sap and electrical meters (nitrate test strips, nitrate ion-selective electrode, or electrical impedance spectroscopy). For example, nitrogen content can be measured using an elemental analyzer and calculated using various methods such as the K-factor method.

As used herein, "comparable conditions" for plants refers to the same or similar environmental conditions and agronomic practices for growing and making meaningful comparisons between two or more plant genotypes so that neither environmental conditions nor agronomic practices would significantly contribute to, or explain, any differences observed between the two or more plant genotypes. Environmental conditions include, for example, light, temperature, water, humidity, soil, and nutrition (e.g., nitrogen and phosphorus).

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase.

As used herein, "editing" or "genome editing" refers to generating a targeted mutation, deletion, inversion or substitution of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides of an endogenous plant genome nucleic acid sequence using a targeted genome editing technique. As used herein, "editing" or "genome editing" also encompasses the targeted insertion or site-directed integration of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 750, at least 1000, at least 1500, at least 2000, at least 2500, at least 3000, at least 4000, at least 5000, at least 10,000, or at least 25,000 nucleotides into the endogenous genome of a plant using a targeted genome editing technique.

As used herein, a "target site" for genome editing refers to the location of a polynucleotide sequence within a plant genome that is targeted and cleaved by a site-specific nuclease introducing a double stranded break (or single-stranded nick) into the nucleic acid backbone of the polynucleotide sequence and/or its complementary DNA strand. A site-specific nuclease can bind to a target site, such as via a non-coding guide RNA (e.g., without being limiting, a CRISPR RNA (crRNA) or a single-guide RNA (sgRNA) as described further below). A non-coding guide RNA provided herein can be complementary to a target site (e.g., complementary to either strand of a double-stranded nucleic acid molecule or chromosome at the target site). A "target site" also refers to the location of a polynucleotide sequence within a plant genome that is bound and cleaved by another site-specific nuclease that may not be guided by a non-coding RNA molecule, such as a meganuclease, zinc finger nuclease (ZFN), or a transcription activator-like effector nuclease (TALEN), to introduce a double stranded break (or single-stranded nick) into the polynucleotide sequence and/or its complementary DNA strand. As used herein, a "target region" or a "targeted region" refers to a polynucleotide sequence or region that is flanked by two or more target sites. Without being limiting, in some aspects a target region can be subjected to a mutation, deletion, insertion or inversion. As used herein, "flanked" when used to describe a target region of a polynucleotide sequence or molecule, refers to two or more target sites of the polynucleotide sequence or molecule surrounding the target region, with one target site on each side of the target region.

Apart from genome editing, the term "target site" can also be used in the context of gene suppression to refer to a portion of a mRNA molecule (e.g., a "recognition site") that is complementary to at least a portion of a non-coding RNA molecule (e.g., a miRNA, siRNA, etc.) encoded by a suppression construct. As used herein, a "target site" for a RNA-guided nuclease can comprise the sequence of either complementary strand of a double-stranded nucleic acid (DNA) molecule or chromosome at the target site. It will be appreciated that perfect identity or complementarity may not be required for a non-coding guide RNA to bind or hybridize to a target site. For example, at least 1, at least 2, at least 3, at least 4, at least 5, at least 6, at least 7, or at least 8 mismatches (or more) between a target site and a non-coding RNA can be tolerated.

As used herein, a "donor molecule", "donor template", or "donor template molecule" (collectively a "donor template"), which can be a recombinant DNA donor template, is defined as a nucleic acid molecule having a nucleic acid template or insertion sequence for site-directed, targeted insertion or recombination into the genome of a plant cell via repair of a nick or double-stranded DNA break in the genome of a plant cell. For example, a "donor template" can be used for site-directed integration of a transgene or suppression construct, or as a template to introduce a mutation, such as an insertion, deletion, etc., into a target site within the genome of a plant. A targeted genome editing technique provided herein can comprise the use of one or more, two or more, three or more, four or more, or five or more donor molecules or templates. A donor template can be a single-stranded or double-stranded DNA or RNA molecule or plasmid. A donor template can also have at least one homology sequence or homology arm, such as two homology arms, to direct the integration of a mutation or insertion sequence into a target site within the genome of a plant via homologous recombination, wherein the homology sequence or homology arm(s) are identical or complementary, or have a percent identity or percent complementarity, to a sequence at or near the target site within the genome of the plant. When a donor template comprises homology arm(s) and an insertion sequence, the homology arm(s) will flank or surround the insertion sequence of the donor template. Further, the donor template can be linear or circular, and can be single-stranded or double-stranded. A donor template can be delivered to the cell as a naked nucleic acid (e.g., via particle bombardment), as a complex with one or more delivery agents (e.g., liposomes, proteins, poloxamers, T-strand encapsulated with proteins, etc.), or contained in a bacterial or viral delivery vehicle, such as, for example, *Agrobacterium tumefaciens* or a geminivirus, respectively.

An insertion sequence of a donor template can comprise one or more genes or sequences that each encode a transcribed non-coding RNA or mRNA sequence and/or a translated protein sequence. A transcribed sequence or gene of a donor template can encode a protein or a non-coding RNA molecule. An insertion sequence of a donor template can comprise a polynucleotide sequence that does not comprise a functional gene or an entire gene sequence (e.g., the donor template can simply comprise regulatory sequences, such as a promoter sequence, or only a portion of a gene or coding sequence), or may not contain any identifiable gene expression elements or any actively transcribed gene sequence. An insertion sequence of a donor template provided herein can comprise a transcribable DNA sequence that can be transcribed into an RNA molecule, which can be non-coding and may or may not be operably linked to a promoter and/or other regulatory sequence.

As used herein, the term "guide RNA" or "gRNA" is a short RNA sequence comprising (1) a structural or scaffold RNA sequence necessary for binding or interacting with an RNA-guided nuclease and/or with other RNA molecules (e.g., tracrRNA), and (2) an RNA sequence (referred to herein as a "guide sequence") that is identical or complementary to a target sequence or a target site. A "single-chain guide RNA" (or "sgRNA") is a RNA molecule comprising a crRNA covalently linked a tracrRNA by a linker sequence, which can be expressed as a single RNA transcript or molecule. The guide RNA comprises a guide or targeting sequence (a "guide sequence") that is identical or complementary to a target site within the plant genome, such as at or near a GA oxidase gene. A protospacer-adjacent motif (PAM) can be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. The genomic PAM sequence on the sense (+) strand adjacent to the target site (relative to the targeting sequence of the guide RNA) can comprise 5'-NGG-3'. However, the corresponding sequence of the guide RNA (i.e., immediately downstream (3') to the targeting sequence of the guide RNA) can generally not be complementary to the genomic PAM sequence. The guide RNA can typically be a non-coding RNA molecule that does not encode a protein.

As used herein, an "RNA-guided nuclease" refers to an RNA-guided DNA endonuclease associated with the CRISPR system. Non-limiting examples of RNA-guided nucleases include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. In an aspect, the RNA-guided nuclease is Cas9. In an aspect, the RNA-guided nuclease comprises the N and C terminal nuclear localization sequences (NLS).

Description

The present disclosure provides certain stacked combinations of transgenes and/or mutations or edits in corn plants, plant parts, etc., comprising a transgene that encodes one or more glutamate dehydrogenase (GDH) polypeptides, such as *E. coli* gdhA, in addition to a reduction in the expression level of one or more GA20 and/or GA3 oxidase genes through suppression, mutation and/or editing of the GA oxidase genes, wherein the corn plants have a semi-dwarf phenotype and one or more improved traits related to yield, lodging resistance, and/or stress tolerance. As described in co-pending PCT Application No. PCT/US2017/047405, the entire contents and disclosure of which are incorporated herein by reference, reducing the level of active GAs in corn or other cereal plants, such as through suppression, mutation or editing of one or more GA20 and/or GA3 oxidase genes, can result in a semi-dwarf phenotype with improved agronomic traits, such as lodging resistance and/or increased yield. However, it is proposed herein that lower active GA levels can be combined with an expression cassette or transgene encoding a GDH protein, such as gdhA, to produce a semi-dwarf corn plant having positive ear traits leading to further increased yield, thus providing greater agronomic benefits than either GDH gene expression or lower active GA levels alone.

Gibberellins (gibberellic acids or GAs) are plant hormones that regulate a number of major plant growth and developmental processes. Manipulation of GA levels in semi-dwarf wheat, rice and sorghum plant varieties led to increased yield and reduced lodging in these cereal crops during the 20$^{th}$ century, which was largely responsible for the Green Revolution. However, successful yield gains in other cereal crops, such as corn, have not been realized through manipulation of the GA pathway. Corn or maize is unique among the grain-producing grasses in that it forms separate male (tassel) and female (ear) inflorescences, and mutations in the GA pathway in corn have been shown to negatively impact reproductive development. Indeed, some mutations in the GA pathway genes in corn have been associated with various off-types that are incompatible with yield, which has led researchers away from finding semi-dwarf, high-yielding corn varieties via manipulation of the GA pathway.

Despite these prior difficulties in achieving higher grain yields in corn through manipulation of the GA pathway, co-pending PCT Application No. PCT/US2017/047405 describes a way to manipulate active GA levels in corn plants in a manner that reduces overall plant height and stem internode length and increases resistance to lodging, but does not cause the reproductive off-types previously associated with mutations of the GA pathway in corn. Further evidence indicates that these short stature or semi-dwarf corn plants with reduced GA levels can also have one or more additional yield and/or stress tolerance traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

Active or bioactive gibberellic acids (i.e., "active gibberellins" or "active GAs") are known in the art for a given plant species, as distinguished from inactive GAs. For example, active GAs in corn and higher plants include the following: GA1, GA3, GA4, and GA7. Thus, an "active GA-producing tissue" is a plant tissue that produces one or more active GAs.

Certain biosynthetic enzymes (e.g., GA20 oxidase and GA3 oxidase) and catabolic enzymes (e.g., GA2 oxidase) in the GA pathway participate in GA synthesis and degradation, respectively, to affect active GA levels in plant tissues. Thus, in addition to suppression of certain GA20 oxidase genes, it is further proposed that suppression of a GA3 oxidase gene in a constitutive or tissue-specific or tissue-preferred manner can also produce corn plants having a short stature phenotype and increased lodging resistance, with possible increased yield, but without off-types in the ear.

Without being bound by theory, it is proposed that incomplete suppression of GA20 or GA3 oxidase gene(s) and/or targeting of a subset of one or more GA oxidase gene(s) can be effective in achieving a short stature, semi-dwarf phenotype with increased resistance to lodging, but without reproductive off-types in the ear. It is further proposed, without being limited by theory, that restricting the suppression of GA20 and/or GA3 oxidase gene(s) to certain active GA-producing tissues, such as the vascular and/or leaf tissues of the plant, can be sufficient to produce a short-stature plant with increased lodging resistance, but without significant off-types in reproductive tissues. Expression of a GA20 or GA3 oxidase suppression element in a tissue-specific or tissue-preferred manner can be sufficient and effective at producing plants with the short stature phenotype, while avoiding potential off-types in reproductive tissues that were previously observed with GA mutants in corn (e.g., by avoiding or limiting the suppression of the GA20 oxidase gene(s) in those reproductive tissues). For example, GA20 and/or GA3 oxidase gene(s) can be targeted for suppression using a vascular promoter, such as a rice tungro bacilliform virus (RTBV) promoter, that drives expression in vascular tissues of plants. The expression pattern of the RTBV promoter is enriched in vascular tissues of corn plants relative to non-vascular tissues, which is sufficient to produce a semi-dwarf phenotype in corn plants when operably linked to a suppression element targeting GA20 and GA3 oxidase gene(s). Lowering of active GA levels in tissue(s) of a corn plant that produce active GAs can reduce plant height and increase lodging resistance, and off-types can be avoided in those plants if active GA levels are not also significantly impacted or lowered in reproductive tissues, such as the developing female organ or ear of the plant. If active GA levels could be reduced in the stalk, stem, or internode(s) of corn or cereal plants without significantly affecting GA levels in reproductive tissues (e.g., the female or male reproductive organs or inflorescences), then corn or cereal plants having reduced plant height and increased lodging resistance could be created without off-types in the reproductive tissues of the plant.

Without being limited by theory, it is further proposed that short stature, semi-dwarf phenotypes in corn plants can result from a sufficient level of expression of a suppression construct targeting certain GA oxidase gene(s) in active GA-producing tissue(s) of the plant. For targeted suppression of certain GA20 oxidase genes in corn, restricting the pattern of expression to avoid reproductive ear tissues may not be necessary to avoid reproductive off-types in the developing ear. However, expression of a GA20 oxidase suppression construct at low levels, and/or in a limited number of plant tissues, can be insufficient to cause a significant short stature, semi-dwarf phenotype. Given that the observed semi-dwarf phenotype with targeted GA20 oxidase suppression is the result of shortening the stem internodes of the plant, it was surprisingly found that suppression of GA20 oxidase genes in at least some stem tissues was not sufficient to cause shortening of the internodes and reduced plant height. Without being bound by theory, it is proposed that suppression of certain GA oxidase gene(s) in tissue(s) and/or cell(s) of the plant where active GAs are produced, and not necessarily in stem or internode tissue(s), can be sufficient to produce semi-dwarf plants, even though the short stature trait is due to shortening of the stem internodes. Given that GAs can migrate through the vasculature of the plant, manipulating GA oxidase genes in plant tissue(s) where active GAs are produced can result in a short stature, semi-dwarf plant, even though this can be largely achieved by suppressing the level of active GAs produced in non-stem tissues (i.e., away from the site of action in the stem where reduced internode elongation leads to the semi-dwarf phenotype). Indeed, suppression of certain GA20 oxidase genes in leaf tissues causes a moderate semi-dwarf phenotype in corn plants. Given that expression of a GA20 oxidase suppression construct with several different "stem" promoters did not produce the semi-dwarf phenotype in corn, it is noteworthy that expression of the same GA20 oxidase suppression construct with a vascular promoter was effective at consistently producing the semi-dwarf phenotype with a high degree of penetrance across events and germplasms. A semi-dwarf phenotype was also observed with expression of the same GA20 oxidase suppression construct using other vascular promoters and with various constitutive promoters without any observable off-types.

By targeting a subset of one or more endogenous GA3 or GA20 oxidase genes for suppression within a plant, a more pervasive pattern of expression (e.g., with a constitutive promoter) can be used to produce semi-dwarf plants without significant reproductive off-types and/or other undesirable traits in the plant, even with expression of the suppression construct in reproductive tissue(s). Indeed, suppression elements and constructs are provided herein that selectively target the GA20 oxidase_3 and/or GA20 oxidase_5 genes for suppression, which can be operably linked to a vascular, leaf and/or constitutive promoter.

Thus, recombinant DNA constructs and modified corn plants are provided herein comprising a GA20 or GA3 oxidase suppression element or sequence operably linked to a plant expressible promoter, which can be a constitutive or tissue-specific or tissue-preferred promoter. Such a tissue-specific or tissue-preferred promoter can drive expression of its associated GA oxidase suppression element or sequence in one or more active GA-producing tissue(s) of the plant to suppress or reduce the level of active GAs produced in those tissue(s). Such a tissue-specific or tissue-preferred promoter can drive expression of its associated GA oxidase suppression construct or transgene during one or more vegetative stage(s) of development. Such a tissue-specific or tissue-preferred promoter can also have little or no expression in one or more cell(s) or tissue(s) of the developing female organ or ear of the plant to avoid the possibility of off-types in those reproductive tissues. According to an aspect, the tissue-specific or tissue-preferred promoter is a vascular promoter, such as the RTBV promoter. The sequence of the RTBV promoter is provided herein as SEQ ID NO: 65, and a truncated version of the RTBV promoter is further provided herein as SEQ ID NO: 66. However, other types of tissue-specific or tissue preferred promoters can potentially be used for GA3 oxidase suppression in active GA-producing tissues of a corn or cereal plant to produce a semi-dwarf phenotype without significant off-types. As introduced above, instead of suppressing one or more GA oxidase gene(s), active GA levels can also be reduced in a corn plant by mutation or editing of one or more GA20 and/or GA3 oxidase gene(s).

Corn has a family of at least nine GA20 oxidase genes that includes GA20 oxidase_1, GA20 oxidase_2, GA20 oxidase_3, GA20 oxidase_4, GA20 oxidase_5, GA20 oxidase_6, GA20 oxidase_7, GA20 oxidase_8, and GA20 oxidase_9. However, there are only two GA3 oxidases in corn, GA3 oxidase_1 and GA3 oxidase_2. The DNA and protein sequences by SEQ ID NOs for each of these GA20 oxidase genes are provided in Table 1, and the DNA and protein sequences by SEQ ID NOs for each of these GA3 oxidase genes are provided in Table 2.

TABLE 1

DNA and protein sequences by sequence identifier for GA20 oxidase genes in corn.

| GA20 oxidase Gene | cDNA | Coding Sequence (CDS) | Protein |
|---|---|---|---|
| GA20 oxidase_1 | SEQ ID NO: 1 | SEQ ID NO: 2 | SEQ ID NO: 3 |
| GA20 oxidase_2 | SEQ ID NO: 4 | SEQ ID NO: 5 | SEQ ID NO: 6 |
| GA20 oxidase_3 | SEQ ID NO: 7 | SEQ ID NO: 8 | SEQ ID NO: 9 |
| GA20 oxidase_4 | SEQ ID NO: 10 | SEQ ID NO: 11 | SEQ ID NO: 12 |
| GA20 oxidase_5 | SEQ ID NO: 13 | SEQ ID NO: 14 | SEQ ID NO: 15 |
| GA20 oxidase_6 | SEQ ID NO: 16 | SEQ ID NO: 17 | SEQ ID NO: 18 |
| GA20 oxidase_7 | SEQ ID NO: 19 | SEQ ID NO: 20 | SEQ ID NO: 21 |
| GA20 oxidase_8 | SEQ ID NO: 22 | SEQ ID NO: 23 | SEQ ID NO: 24 |
| GA20 oxidase_9 | SEQ ID NO: 25 | SEQ ID NO: 26 | SEQ ID NO: 27 |

TABLE 2

DNA and protein sequences by sequence identifier for GA3 oxidase genes in corn.

| GA3 oxidase Gene | cDNA | Coding Sequence (CDS) | Protein |
|---|---|---|---|
| GA3 oxidase_1 | SEQ ID NO: 28 | SEQ ID NO: 29 | SEQ ID NO: 30 |
| GA3 oxidase_2 | SEQ ID NO: 31 | SEQ ID NO: 32 | SEQ ID NO: 33 |

In addition to lowering active GA levels in corn plants through suppression, mutation or editing of GA oxidase gene(s), such corn plants as provided herein may further comprise an ectopically expressed transgene expressing one or more glutamate dehydrogenase (GDH) polypeptides.

Without being bound by any theory, GDH is a hexameric enzyme that can catalyze the reversible conversion of glutamate to α-ketoglutarate and ammonia while reducing $NAD(P)^+$ to NAD(P)H. In mammalian cells, in addition to contributing to Krebs cycle anaplerosis and energy production, GDH can be linked to redox homeostasis and cell signaling processes. Lower life forms, such as bacteria or yeasts, often express distinct GDH isoenzymes that show strict specificity for $NAD^+$ or $NADP^+$. The $NAD^+$-dependent GDH enzymes can serve mainly a metabolic role, whereas the $NADP^+$-specific enzymes can be involved in biosynthetic functions. Without being bound by any theory, organisms that live in an environment rich in nutrient amino acids, use the $NAD^+$-dependent GDHs for their catabolic needs, including disposal of excess nitrogen, whereas organisms such as *E.coli* capable of utilizing inorganic nitrogen (e.g., nitrates or ammonia) use the $NADP^+$-specific GDHs for their synthetic needs. In an aspect, a glutamate dehydrogenase (GDH) polypeptide is a $NAD^+$ or $NADP^+$ glutamate dehydrogenase gene. In an aspect, a glutamate dehydrogenase (GDH) polypeptide is a $NADP^+$ glutamate dehydrogenase gene.

Without being bound by any theory, expression of the *E.coli* glutamate dehydrogenase (gdhA) gene in cyanobacteria can cause an ammonium tolerant phenotype, consistent with the action of the GDH activity as an ammonium detoxification mechanism. See Lightfoot et al., *Plant Mol. Biol.,* 11:335-44 (1988), the entire contents and disclosure of which are incorporated herein by reference. Transgenic expression of gdhA in corn plants is shown to improve germination and grain biomass during seasons with significant water deficits, suggesting that crops modified with gdhA may have value in semi-arid locations. See Lightfoot et al., *Euphytica,* 156:103-116 (2007), the entire contents and disclosure of which are incorporated herein by reference. Crop plants transformed with gdhA gene are also shown to be resistant to herbicides. See U.S. Pat. Nos. 8,383,887, 6,329,573, and 5,998,700, the entire contents and disclosure of which are incorporated herein by reference. Transgenic expression of gdhA gene in corn plants can also improve ear traits or metrics, such as ear volume, ear length, ear tip void, kernels per ear, and kernels per row longitudinally.

As used herein, a GDH polynucleotide refers to a polynucleotide, gene or coding sequence encoding a polypeptide having glutamate dehydrogenase activity and encompasses any variants (e.g., polymorphism), isoforms, homologs, orthologs, and/or paralogs thereof.

In an aspect, a GDH polypeptide of the present disclosure is an *E.coli* gdhA polypeptide or homologs, orthologs, and/or paralogs thereof. In an aspect, a GDH polynucleotide provided herein comprises an amino acid sequence comprising SEQ ID NOs: 168, and homologs, orthologs, and paralogs thereof. In another aspect, a GDH polynucleotide provided herein comprises an amino acid sequence selected from the group consisting of SEQ ID NOs: 176-192, and homologs, orthologs, and paralogs thereof.

According to another aspect, a modified corn plant or a plant part thereof is provided comprising 1) a first recombinant expression cassette (or a construct) comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette (or a construct) comprising a DNA sequence encoding a GDH polypeptide.

According to another aspect, a plurality of modified corn plants in a field, each modified corn plant comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a GDH polypeptide. In an aspect, the modified corn plants have increased yield relative to control corn plants. In another aspect, the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

Such modified corn plants can have semi-dwarf plant height in addition to one or more improved yield-related traits as described further herein, relative to control corn plant(s) that do not have the first and second expression cassettes or the combination of GDH transgene and edited/mutated GA oxidase gene(s). Modified corn plants comprising a combination of the first and second expression cassettes, or a combination of an expression cassette comprising a GDH transgene and one or more mutated or edited GA oxidase genes, can each be referred to as a "stack" or "stacked" combination. Such stacked combinations for the reduction of active GA levels and expression of a GDH transgene can be brought together in the same corn plant, or population of corn plants, by (1) crossing a first plant comprising a GA oxidase suppression element(s), edit(s) and/or mutation(s) to a second plant comprising a GDH transgene, (2) co-transformation of a plant or plant part with a GA oxidase suppression element(s) and a GDH transgene, (3) transformation of a plant or plant part already having a GA oxidase suppression element(s), edit(s) and/or mutation (s) with a GDH transgene, (4) transformation of a plant or plant part already having a GDH transgene with a GA oxidase suppression element(s), or (5) editing or mutating a GA oxidase gene(s) in a plant or plant part already having a GDH transgene, each of which can be followed by further crosses to obtain a desired genotype, plant parts can be regenerated, grown or developed into plants, and plant parts can be taken from any of the foregoing plants.

As provided above, a corn plant or plant part can comprise a first expression cassette comprising a first sequence encoding a non-coding RNA molecule that targets one or more GA20 or GA3 oxidase gene(s) for suppression. In an aspect, the non-coding RNA molecule can target one or more GA20 oxidase gene(s) for suppression, such as a GA20 oxidase_3 gene, a GA20 oxidase_4 gene, a GA20 oxidase_5 gene, or any combination thereof. According to an aspect, the first expression cassette comprises a first transcribable DNA sequence encoding a non-coding RNA targeting a GA20 oxidase_3 gene for suppression. According to another aspect, the first expression cassette comprises a first transcribable DNA sequence encoding a non-coding RNA targeting a GA20 oxidase_5 gene for suppression. According to another aspect, the first expression cassette comprises a first transcribable DNA sequence encoding a non-coding RNA that targets both the GA20 oxidase_3 gene and the GA20 oxidase_5 gene for suppression. In addition to targeting a mature mRNA sequence (including either or both of the untranslated or exonic sequences), a non-coding RNA molecule can also target the intronic sequences of a GA20 oxidase gene or transcript.

A genomic DNA sequence of GA20 oxidase_3 is provided in SEQ ID NO: 34, and the genomic DNA sequence of GA20 oxidase_5 is provided in SEQ ID NO: 35. For the GA20 oxidase_3 gene, SEQ ID NO: 34 provides 3000 nucleotides upstream of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 34 also provides 3000 nucleotides downstream of the end of the 3'-UTR (nucleotides 5801-8800). For the GA20 oxidase 5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

A genomic DNA sequence of GA20 oxidase_4 is provided in SEQ ID NO: 38. For the GA oxidase_4 gene, SEQ ID NO: 38 provides nucleotides 1-1416 upstream of the 5'-UTR; nucleotides 1417-1543 of SEQ ID NO: 38 correspond to the 5'-UTR; nucleotides 1544-1995 of SEQ ID NO: 38 correspond to the first exon; nucleotides 1996-2083 of SEQ ID NO: 38 correspond to the first intron; nucleotides 2084-2411 of SEQ ID NO: 38 correspond to the second exon; nucleotides 2412-2516 of SEQ ID NO: 38 correspond to the second intron; nucleotides 2517-2852 of SEQ ID NO: 38 correspond to the third exon; nucleotides 2853-3066 of SEQ ID NO: 38 correspond to the 3'-UTR; and nucleotides 3067-4465 of SEQ ID NO: 38 corresponds to genomic sequence downstream of to the 3'-UTR.

For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

For suppression of a GA20 oxidase_3 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 7 and 8.

For suppression of a GA20 oxidase_4 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 10 and 11.

For suppression of a GA20 oxidase_5 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 13 and 14.

For suppression of a GA20 oxidase_3 gene and a GA20 oxidase_5 gene, a transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 7 and 8; and the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 13 and 14.

In an aspect, a non-coding RNA molecule encoded by a transcribable DNA sequence comprises (i) a sequence that is at least 95%, at least 96%, at least 97%, at least 98%, at least 99%, at least 99.5%, or 100% complementary to SEQ ID NO: 39, 41, 43 or 45, and/or (ii) a sequence or suppression element encoding a non-coding RNA molecule comprising a sequence that is at least 95%, at least 96%, at least 97%, at least 98%, at least 99%, at least 99.5%, or 100% identical to SEQ ID NO: 40, 42, 44 or 46. According to an aspect, the non-coding RNA molecule encoded by a transcribable DNA sequence can comprise a sequence with one or more mismatches, such as 1, 2, 3, 4, 5 or more complementary mismatches, relative to the sequence of a target or recognition site of a targeted GA20 oxidase gene mRNA, such as a sequence that is nearly complementary to SEQ ID NO: 40 but with one or more complementary mismatches relative to SEQ ID NO: 40. According to a particular aspect, the non-coding RNA molecule encoded by the transcribable DNA sequence comprises a sequence that is 100% identical to SEQ ID NO: 40, which is 100% complementary to a target sequence within the cDNA and coding sequences of the GA20 oxidase_3 (i.e., SEQ ID NOs: 7 and 8, respectively), and/or to a corresponding sequence of a mRNA encoded by an endogenous GA20 oxidase_3 gene. However, the sequence of a non-coding RNA molecule encoded by a transcribable DNA sequence that is 100% identical to SEQ ID NO: 40, 42, 44 or 46 may not be perfectly complementary to a target sequence within the cDNA and coding sequences of the GA20 oxidase_5 gene (i.e., SEQ ID NOs: 13 and 14, respectively), and/or to a corresponding sequence of a mRNA encoded by an endogenous GA20 oxidase_5 gene. For example, the closest complementary match between the non-coding RNA molecule or miRNA sequence in SEQ ID NO: 40 and the cDNA and coding sequences of the GA20 oxidase_5 gene can include one mismatch at the first position of SEQ ID NO: 39 (i.e., the "C" at the first position of SEQ ID NO: 39 is replaced with a "G"; i.e., <u>G</u>TCCATCATGCGGTGCAACTA). However, the non-coding RNA molecule or miRNA sequence in SEQ ID NO: 40 can still bind and hybridize to the mRNA encoded by the endogenous GA20 oxidase_5 gene despite this slight mismatch.

For suppression of a GA20 oxidase_1 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 1 and 2.

For suppression of a GA20 oxidase_2 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 4 and 5.

For suppression of a GA2 oxidase 6, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 16 and 17.

For suppression of a GA20 oxidase 7 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 19 and 20.

For suppression of a GA20 oxidase_8 gene, a first transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 22 and 23.

For suppression of a GA20 oxidase_9 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 25 and 26.

A non-coding RNA can target an intron sequence of a GA20 oxidase gene instead of, or in addition to, an exonic, 5' UTR or 3' UTR of the GA20 oxidase gene. Thus, a non-coding RNA targeting the GA20 oxidase_3 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 34, and/or of nucleotides 3666-3775 or 4098-5314 of SEQ ID NO: 34.

In another aspect, a non-coding RNA molecule targeting the GA20 oxidase 5 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 35, and/or of nucleotides 3792-3906 or 4476-5197 of SEQ ID NO: 35.

In another aspect, a non-coding RNA molecule targeting the GA20 oxidase_4 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 38, and/or of nucleotides 1996-2083 or 2412-2516 of SEQ ID NO: 38.

In another aspect, a first expression cassette comprises a first transcribable DNA sequence encoding a non-coding RNA targeting a GA3 oxidase gene(s) for suppression in corn, such as a GA3 oxidase_1 gene or a GA3 oxidase_2 gene. In another aspect, a first transcribable DNA sequence encoding a non-coding RNA targets both the GA3 oxidase_1 gene and the GA3 oxidase_2 gene for suppression. In addition to targeting a mature mRNA sequence (including either or both of the untranslated or exonic sequences), a non-coding RNA molecule can also target the intronic sequences of a GA3 oxidase gene or transcript.

The genomic DNA sequence of GA3 oxidase_1 is provided in SEQ ID NO: 36, and the genomic DNA sequence of GA3 oxidase_2 is provided in SEQ ID NO: 37. For the GA3 oxidase_1 gene, nucleotides 1-29 of SEQ ID NO: 36 correspond to the 5'-UTR; nucleotides 30-514 of SEQ ID NO: 36 correspond to the first exon; nucleotides 515-879 of SEQ ID NO: 36 correspond to the first intron; nucleotides 880-1038 of SEQ ID NO: 36 correspond to the second exon; nucleotides 1039-1158 of SEQ ID NO: 36 correspond to the second intron; nucleotides 1159-1663 of SEQ ID NO: 36 correspond to the third exon; and nucleotides 1664-1788 of SEQ ID NO: 36 correspond to the 3'-UTR. For the GA3 oxidase_2 gene, nucleotides 1-38 of SEQ ID NO: 37 correspond to the 5-UTR; nucleotides 39-532 of SEQ ID NO: 37 correspond to the first exon; nucleotides 533-692 of SEQ ID NO: 37 correspond to the first intron; nucleotides 693-851 of SEQ ID NO: 37 correspond to the second exon; nucleotides 852-982 of SEQ ID NO: 37 correspond to the second intron; nucleotides 983-1445 of SEQ ID NO: 37 correspond to the third exon; and nucleotides 1446-1698 of SEQ ID NO: 37 correspond to the 3'-UTR.

For suppression of a GA3 oxidase_1 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 28 and 29.

As mentioned above, a non-coding RNA molecule can target an intron sequence of a GA3 oxidase gene instead of, or in addition to, an exonic, 5' UTR or 3' UTR of the GA oxidase gene. Thus, a non-coding RNA molecule targeting the GA3 oxidase_1 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 36, and/or of nucleotides 515-879 or 1039-1158 of SEQ ID NO: 36.

For suppression of a GA3 oxidase_2 gene, a first transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 31 and 32.

As mentioned above, a non-coding RNA molecule can target an intron sequence of a GA3 oxidase gene instead of, or in addition to, an exonic, 5' UTR or 3' UTR of the GA3 oxidase gene. Thus, a non-coding RNA molecule targeting the GA3 oxidase_2 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 37, and/or of nucleotides 533-692 or 852-982 of SEQ ID NO: 37.

For suppression of a GA3 oxidase_1 gene and a GA3 oxidase_2 gene, a transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 9'7%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 28 and 29; and the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 31 and 32.

In an aspect, a transcribable DNA sequence for the suppression of a GA20 oxidase gene and/or a GA3 oxidase comprises a sequence selected from the group consisting of SEQ ID NOs: 47, 49, 51, 53, 55, 57, 59, 61, and 63. In another aspect, a transcribable DNA sequence for the suppression of a GA20 oxidase gene and/or a GA3 oxidase encodes a non-coding RNA sequence, wherein the non-coding RNA sequence comprises a sequence selected from the group consisting of SEQ ID NOs: 48, 50, 52, 54, 56, 58, 60, 62, and 64.

In an aspect, an expression cassette is provided comprising a second DNA sequence encoding a GDH polypeptide. In an aspect, the second DNA sequence encodes a protein that comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to an amino acid sequence selected from the group consisting of SEQ ID NOs: 176-192, or a functional fragment thereof. The second DNA sequence encoding a GDH polypeptide is operatively linked to a plant-expressible promoter, such as a constitutive or tissue-specific or tissue preferred promoter. In an aspect, such a plant-expressible promoter is a constitutive promoter. In another aspect, such a plant-expressible promoter is a leaf promoter, such as a leaf-preferred or leaf-specific promoter. In another aspect, such a plant-expressible promoter is selected from the group consisting of a stress-inducible promoter, a nitrogen-inducible promoter, a drought-inducible promoter, a root promoter, and a combination thereof.

In an aspect, an expression cassette is provided comprising a second DNA sequence encoding *E.coli* gdhA. In an aspect, the second DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NO: 169. In another aspect, the second DNA sequence comprises a sequence encoding a polypeptide that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168, or a functional fragment thereof. The second DNA sequence encoding a GDH polypeptide is operatively linked to a plant-expressible promoter, such as a constitutive or tissue-specific or tissue preferred promoter. In an aspect, such a plant-expressible promoter is a constitutive promoter. In another aspect, such a plant-expressible promoter is a leaf promoter, such as a leaf-preferred or leaf-specific promoter. In another aspect, such a plant-expressible promoter is selected from the group consisting of a stress-inducible promoter, a nitrogen-inducible promoter, a drought-inducible promoter, a root promoter, and a combination thereof.

In addition to targeting a mature mRNA sequence, a non-coding RNA molecule can instead target an intronic sequence of a GA oxidase gene or mRNA transcript, or a GA oxidase mRNA sequence overlapping coding and non-coding sequences. According to other aspects, a recombinant DNA molecule, vector or construct is provided comprising a transcribable DNA sequence encoding a non-coding RNA (precursor) molecule that is cleaved or processed into a mature non-coding RNA molecule that binds or hybridizes to a target mRNA in a plant cell, wherein the target mRNA molecule encodes a GA20 or GA3 oxidase protein, and wherein the transcribable DNA sequence is operably linked to a constitutive or tissue-specific or tissue-preferred promoter.

Any method known in the art for suppression of a target gene can be used to suppress GA oxidase gene(s) according to aspects of the present disclosure including expression of antisense RNAs, double stranded RNAs (dsRNAs) or inverted repeat RNA sequences, or via co-suppression or RNA intereference (RNAi) through expression of small interfering RNAs (siRNAs), short hairpin RNAs (shRNAs), trans-acting siRNAs (ta-siRNAs), or micro RNAs (miRNAs). Furthermore, sense and/or antisense RNA molecules can be used that target the non-coding genomic sequences or regions within or near a gene to cause silencing of the gene. Accordingly, any of these methods can be used for the targeted suppression of an endogenous GA oxidase gene(s) in a tissue-specific or tissue-preferred manner. See, e.g., U.S. Patent Application Publication Nos. 2009/0070898, 2011/0296555, and 2011/0035839, the contents and disclosures of which are incorporated herein by reference.

In an aspect, an expression level(s) of one or more endogenous GA20 oxidase and/or GA3 oxidase gene(s) is/are reduced or eliminated in the modified corn plant, thereby suppressing the endogenous GA20 oxidase and/or GA3 oxidase gene(s).

According to an aspect, a modified or transgenic plant is provided having the expression level(s) of one or more GA20 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant.

According to an aspect, a modified or transgenic plant is provided having the expression level(s) of one or more GA3 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant.

According to an aspect, a modified or transgenic plant is provided having the expression level(s) of one or more GA20 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant.

According to an aspect, a modified or transgenic plant is provided having the expression level(s) of one or more GA3 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant.

According to an aspect, the at least one tissue of a modified or transgenic plant having a reduced expression level of a GA20 oxidase and/or GA3 oxidase gene(s) includes one or more active GA producing tissue(s) of the plant, such as the vascular and/or leaf tissue(s) of the plant, during one or more vegetative stage(s) of development.

In an aspect, the non-coding RNA is a precursor miRNA or siRNA capable of being processed or cleaved to form a mature miRNA or siRNA.

In an aspect, suppression of an endogenous GA20 oxidase gene or a GA3 oxidase gene is tissue-specific (e.g., only in leaf and/or vascular tissue). Suppression of a GA20 oxidase gene can be constitutive and/or vascular or leaf tissue specific or preferred. In other aspects, suppression of a GA20 oxidase gene or a GA3 oxidase gene is constitutive and not tissue-specific. According to an aspect, expression of an endogenous GA20 oxidase gene and/or a GA3 oxidase gene is reduced in one or more tissue types (e.g., in leaf and/or vascular tissue(s)) of a modified or transgenic plant as compared to the same tissue(s) of a control plant.

Engineered miRNAs can be useful for targeted gene suppression with increased specificity. See, e.g., Parizotto et al., *Genes Dev.* 18:2237-2242 (2004), and U.S. Patent Application Publication Nos. 2004/0053411, 2004/0268441, 2005/0144669, and 2005/0037988, the contents and disclosures of which are incorporated herein by reference. miRNAs are non-protein coding RNAs. When a miRNA precursor molecule is cleaved, a mature miRNA is formed that is typically from about 19 to about 25 nucleotides in length (commonly from about 20 to about 24 nucleotides in length in plants), such as 19, 20, 21, 22, 23, 24, or 25 nucleotides in length, and has a sequence corresponding to the gene targeted for suppression and/or its complement. Mature miRNA hybridizes to target mRNA transcripts and guides the binding of a complex of proteins to the target transcripts, which can function to inhibit translation and/or result in degradation of the transcript, thus negatively regulating or suppressing expression of the targeted gene. miRNA precursors are also useful in plants for directing in-phase production of siRNAs, trans-acting siRNAs (ta-siRNAs), in a process that requires a RNA-dependent RNA polymerase to cause suppression of a target gene. See, e.g., Allen et al., *Cell,* 121:207-221 (2005), Vaucheret, *Science STKE,* 2005: pe43 (2005), and Yoshikawa et al. *Genes Dev.,* 19:2164-2175 (2005), the contents and disclosures of which are incorporated herein by reference.

Without being limited by any scientific theory, plant miRNAs regulate their target genes by recognizing and binding to a complementary or near-perfectly complementary sequence (miRNA recognition site) in the target mRNA transcript, followed by cleavage of the transcript by RNase III enzymes, such as ARGONAUTE1. In plants, certain mismatches between a given miRNA recognition site and the corresponding mature miRNA are typically not tolerated, particularly mismatched nucleotides at positions 10 and 11 of the mature miRNA. Positions within the mature miRNA are given in the 5' to 3' direction. Perfect complementarity between a given miRNA recognition site and the corresponding mature miRNA is usually required at positions 10 and 11 of the mature miRNA. See, for example, Franco-Zorrilla et al. (2007) *Nature Genetics,* 39:1033-1037; and Axtell et al. (2006) *Cell,* 127:565-577.

Many microRNA genes (MIR genes) have been identified and made publicly available in a database ("miRBase", available on line at microrna.sanger.ac.uk/sequences; also see Griffiths-Jones et al. (2003) *Nucleic Acids Res.,* 31:439-441). MIR genes have been reported to occur in intergenic regions, both isolated and in clusters in the genome, but can also be located entirely or partially within introns of other genes (both protein-coding and non-protein-coding). For a review of miRNA biogenesis, see Kim (2005) *Nature Rev. Mol. Cell. Biol.,* 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA. See, for example, FIG. 1 in Kim (2005) *Nature Rev. Mol. Cell. Biol.,* 6:376-385.

Transgenic expression of miRNAs (whether a naturally occurring sequence or an artificial sequence) can be employed to regulate expression of the miRNA's target gene or genes. Recognition sites of miRNAs have been validated in all regions of a mRNA, including the 5' untranslated region, coding region, intron region, and 3' untranslated region, indicating that the position of the miRNA target or recognition site relative to the coding sequence may not necessarily affect suppression (see, e.g., Jones-Rhoades and Bartel (2004). *Mol. Cell,* 14:787-799, Rhoades et al. (2002) *Cell,* 110:513-520, Allen et al. (2004) *Nat. Genet.,* 36:1282-1290, Sunkar and Zhu (2004) Plant Cell, 16:2001-2019). miRNAs are important regulatory elements in eukaryotes, and transgenic suppression with miRNAs is a useful tool for manipulating biological pathways and responses. A description of native miRNAs, their precursors, recognition sites, and promoters is provided in U.S. Patent Application Publication No. 2006/0200878, the contents and disclosures of which are incorporated herein by reference.

Designing an artificial miRNA sequence can be achieved by substituting nucleotides in the stem region of a miRNA precursor with a sequence that is complementary to the intended target, as demonstrated, for example, by Zeng et al. (2002) *Mol. Cell,* 9:1327-1333. According to many aspects, the target can be a sequence of a GA20 oxidase gene or a GA3 oxidase gene. One non-limiting example of a general method for determining nucleotide changes in a native miRNA sequence to produce an engineered miRNA precursor for a target of interest includes the following steps: (a) selecting a unique target sequence of at least 18 nucleotides specific to the target gene, e.g., by using sequence alignment tools such as BLAST (see, for example, Altschul et al. (1990) *J. Mol. Biol.,* 215:403-410; Altschul et al. (1997) *Nucleic Acids Res.,* 25:3389-3402); cDNA and/or genomic DNA sequences can be used to identify target transcript orthologues and any potential matches to unrelated genes, thereby avoiding unintentional silencing or suppression of non-target sequences; (b) analyzing the target gene for undesirable sequences (e.g., matches to sequences from non-target species), and score each potential target sequence for GC content, Reynolds score (see Reynolds et al. (2004) *Nature Biotechnol.,* 22:326-330), and functional asymmetry characterized by a negative difference in free energy ("ΔΔG") (see Khvorova et al. (2003) *Cell,* 115:209-216). Preferably, target sequences (e.g., 19-mers) can be selected that have all or most of the following characteristics: (1) a Reynolds score>4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. In an aspect, a non-coding RNA molecule used here to suppress a target gene (e.g., a GA20 or GA3 oxidase gene) is designed to have a target sequence exhibiting one or more, two or more, three or more, four or more, or five or more of the foregoing characteristics. Positions at every third nucleotide of a suppression element can be important in influencing RNAi efficacy; for example, an algorithm, "siExplorer" is publicly available at rna.chem.t.u-tokyo.ac.jp/siexplorer.htm (see Katoh and Suzuki (2007) *Nucleic Acids Res.,* 10.1093/nar/gkl1120); (c) determining a reverse complement of the selected target sequence (e.g., 19-mer) to use in making a modified mature miRNA. Relative to a 19-mer sequence, an additional nucleotide at position 20 can be matched to the selected target or recognition sequence, and the nucleotide at position 21 can be chosen to either be unpaired to prevent spreading of silencing on the target transcript or paired to the target sequence to promote spreading of silencing on the target transcript; and (d) transforming the artificial miRNA into a plant.

Multiple sense and/or anti-sense suppression elements for more than one GA oxidase target can be arranged serially in tandem or arranged in tandem segments or repeats, such as tandem inverted repeats, which can also be interrupted by one or more spacer sequence(s), and the sequence of each suppression element can target one or more GA oxidase gene(s). Furthermore, a sense or anti-sense sequence of the suppression element may not be perfectly matched or complementary to the targeted GA oxidase gene sequence, depending on the sequence and length of the suppression element. Even shorter RNAi suppression elements from about 19 nucleotides to about 27 nucleotides in length can have one or more mismatches or non-complementary bases, yet still be effective at suppressing the target GA oxidase gene. Accordingly, a sense or anti-sense suppression element sequence can be at least 80%, at least 85%, at least 90%, at least 95%, at least 96%, at least 97%, at least 98%, at least 99%, at least 99.5% or 100% identical to a corresponding sequence of at least a segment or portion of the targeted GA oxidase gene, or its complementary sequence, respectively.

For suppression of GA oxidase gene(s) using an inverted repeat or a transcribed dsRNA, a transcribable DNA sequence or suppression element can comprise a sense sequence that comprises a segment or portion of a targeted GA oxidase gene and an anti-sense sequence that is complementary to a segment or portion of the targeted GA oxidase gene, where the sense and anti-sense DNA sequences are arranged in tandem. The sense and/or anti-sense sequences, respectively, can each be less than 100% identical or complementary to a segment or portion of the targeted GA oxidase gene as described above. A sense and anti-sense sequences can be separated by a spacer sequence, such that the RNA molecule transcribed from the suppression element forms a stem, loop or stem-loop structure between the sense and anti-sense sequences. A suppression element can instead comprise multiple sense and anti-sense sequences that are arranged in tandem, which can also be separated by one or more spacer sequences. Suppression elements comprising multiple sense and anti-sense sequences can be arranged as a series of sense sequences followed by a series of anti-sense sequences, or as a series of tandemly arranged sense and anti-sense sequences. Alternatively, one or more sense DNA sequences can be expressed separately from the one or more anti-sense sequences (i.e., one or more sense DNA sequences can be expressed from a first transcribable DNA sequence, and one or more anti-sense DNA sequences can be expressed from a second transcribable DNA sequence, wherein the first and second transcribable DNA sequences are expressed as separate transcripts).

For suppression of GA oxidase gene(s) using a microRNA (miRNA), the transcribable DNA sequence or suppression element can comprise a DNA sequence derived from a miRNA sequence native to a virus or eukaryote, such as an animal or plant, or modified or derived from such a native miRNA sequence. Such native or native-derived miRNA sequences can form a fold back structure and serve as a scaffold for the precursor miRNA (pre-miRNA), and can correspond to the stem region of a native miRNA precursor sequence, such as from a native (or native-derived) primarymiRNA (pri-miRNA) or pre-miRNA sequence. However, in addition to these native or native-derived miRNA scaffold or preprocessed sequences, engineered or synthetic miRNAs of the present aspects further comprise a sequence corresponding to a segment or portion of the targeted GA oxidase gene(s). Thus, in addition to the pre-processed or scaffold miRNA sequences, the suppression element can further comprise a sense and/or anti-sense sequence that corresponds to a segment or portion of a targeted GA oxidase gene, and/or a sequence that is complementary thereto, although one or more sequence mismatches can be tolerated.

GA oxidase gene(s) can also be suppressed using one or more small interfering RNAs (siRNAs). The siRNA pathway involves the non-phased cleavage of a longer double-stranded RNA intermediate ("RNA duplex") into small interfering RNAs (siRNAs). The size or length of siRNAs ranges from about 19 to about 25 nucleotides or base pairs, but common classes of siRNAs include those containing 21 or 24 base pairs. Thus, a transcribable DNA sequence or suppression element can encode a RNA molecule that is at least about 19 to about 25 nucleotides (or more) in length, such as at least 19, 20, 21, 22, 23, 24, or 25 nucleotides in length. For siRNA suppression, a recombinant DNA molecule, construct or vector can be provided comprising a transcribable DNA sequence and suppression element encoding a siRNA molecule for targeted suppression of a GA oxidase gene(s). A transcribable DNA sequence and suppression element can be at least 19 nucleotides in length and have a sequence corresponding to one or more GA oxidase gene(s), and/or a sequence complementary to one or more GA oxidase gene(s).

GA oxidase gene(s) can also be suppressed using one or more trans-acting small interfering RNAs (ta-siRNAs). In the ta-siRNA pathway, miRNAs serve to guide in-phase processing of siRNA primary transcripts in a process that requires an RNA-dependent RNA polymerase for production of a double-stranded RNA precursor. ta-siRNAs are defined by lack of secondary structure, a miRNA target site that initiates production of double-stranded RNA, requirements of DCL4 and an RNA-dependent RNA polymerase (RDR6), and production of multiple perfectly phased ~21-nt small RNAs with perfectly matched duplexes with 2-nucleotide 3' overhangs (see Allen et al. (2005) *Cell,* 121:207-221). The size or length of ta-siRNAs ranges from about 20 to about 22 nucleotides or base pairs, but are mostly commonly 21 base pairs. A transcribable DNA sequence or suppression element of the present invention can encode a RNA molecule that is at least about 20 to about 22 nucleotides in length, such as 20, 21, or 22 nucleotides in length. For ta-siRNA suppression, a recombinant DNA molecule, construct or vector is thus provided comprising a transcribable DNA sequence or suppression element encoding a ta-siRNA molecule for targeted suppression of a GA oxidase gene(s). Such a transcribable DNA sequence and suppression element can be at least 20 nucleotides in length and have a sequence corresponding to one or more GA oxidase gene(s) and/or a sequence complementary to one or more GA oxidase gene(s). For methods of constructing suitable ta-siRNA scaffolds, see, e.g., U.S. Pat. No. 9,309,512, which is incorporated herein by reference in its entirety.

According to an aspect of the present disclosure, a seed of the modified corn plant is produced, in which the seed comprises a first expression cassette and DNA sequence encoding a non-coding RNA for suppression of one more GA20 oxidase genes and/or one or more GA3 oxidase genes, or one or more mutated or edited GA20 and/or GA3 oxidase genes, and a second expression cassette and DNA sequence encoding one or more GDH polypeptides. In an aspect, a progeny plant grown from the seed is semi-dwarf and has one or more improved ear traits, relative to a control corn plant that does not have the suppression element, mutation or edit and the GDH transgene. In another aspect, a commodity or commodity product is produced from the seed of the modified corn plant comprising the first transcribable DNA sequence encoding a non-coding RNA for suppression of one more GA20 oxidase genes and/or one or more GA3 oxidase genes, or one or more mutated or edited GA20 and/or GA3 oxidase genes, and the second DNA sequence encoding one or more GDH polypeptides.

A transgenic plant can be produced by any suitable transformation method as provided herein to produce a transgenic $R_0$ plant, which can then be selfed or crossed to other plants to generate $R_1$ seed and subsequent progeny generations and seed through additional crosses, etc. Aspects of the present disclosure further include a plant cell, tissue, explant, plant part, etc., comprising one or more transgenic cells having a transformation event or genomic insertion of a recombinant DNA or polynucleotide sequence comprising a transcribable DNA sequence encoding a non-coding RNA molecule that targets an endogenous GA3 or GA20 oxidase gene for suppression and a transgene encoding a GDH polypeptide Transgenic plants, plant cells, seeds, and plant parts of the present disclosure can be homozygous or hemizygous for a transgenic event or insertion in at least one plant cell thereof, or a targeted genome editing event or mutation, and plants, plant cells, seeds, and plant parts of the present disclosure can contain any number of copies of such transgenic event(s), insertion(s) mutation(s), and/or edit(s). The dosage or amount of expression of a transgene or transcribable DNA sequence can be altered by its zygosity and/or number of copies, which can affect the degree or extent of phenotypic changes in the transgenic plant, etc.

Transgenic plants provided herein can include a variety of monocot cereal plants, including crop plants, such as corn, wheat, rice and sorghum. Indeed, recombinant DNA molecules or constructs of the present disclosure can be used to create beneficial traits in cereal plants such as corn without off-types using only a single copy of the transgenic event, insertion or construct.

Aspects of the present disclosure further include methods for making or producing transgenic plants, such as by transformation, crossing, etc., wherein the method comprises introducing a recombinant DNA molecule, construct or sequence into a plant cell, and then regenerating or developing the transgenic plant from the transformed or edited plant cell, which can be performed under selection pressure favoring a transgenic event.

Provided in the present disclosure is a method for producing a modified corn plant, the method comprising: introducing into a corn cell a first recombinant expression cassette comprising a DNA sequence encoding a GDH polypeptide, wherein the corn cell comprises a second recombinant expression cassette comprising a transcribable DNA sequence encoding a non-coding RNA for suppression of one or more GA3 oxidase genes and/or one or more GA20 oxidase genes; and regenerating or developing a modified corn plant from the corn cell, wherein the modified corn plant comprises the first and second recombinant expression cassettes.

Also provided in the present disclosure is a method for producing a transgenic corn plant, the method comprising: (a) introducing into a first corn cell a transgene that encodes one or more GDH polypeptides to create a transgenic corn cell, wherein the first corn cell comprises a transcribable DNA sequence encoding a non-coding RNA for suppression of one or more GA3 oxidase genes or GA20 oxidase genes; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising: introducing into a corn cell a first recombinant expression cassette comprising a transcribable DNA sequence encoding a non-coding RNA for suppression of one or more GA3 oxidase genes and/or GA20 oxidase genes, wherein the corn cell comprises a second recombinant expression cassette comprising a DNA sequence encoding a GDH polypeptide; and regenerating or developing a modified corn plant from the corn cell, wherein the modified corn plant comprises the first and second recombinant expression cassettes.

Also provided in the present disclosure is a method for producing a transgenic corn plant, the method comprising: (a) introducing into a first corn cell a transcribable DNA sequence encoding a non-coding RNA for suppression of one or more GA3 oxidase genes or GA20 oxidase genes to create a transgenic corn cell, wherein the first corn cell comprises a transgene that encodes one or more GDH polypeptides; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a GDH polypeptide; and regenerating or developing a modified corn plant from the corn cell, wherein the modified corn plant comprises the first and second recombinant expression cassettes.

Also provided in the present disclosure is a method for producing a transgenic corn plant, the method comprising (a) introducing into a first corn cell 1) a transcribable DNA sequence encoding a non-coding RNA for suppression of one or more GA3 oxidase genes or GA20 oxidase genes and 2) a transgene that encodes one or more GDH polypeptides, to create a transgenic corn cell; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising introducing into a corn cell a first recombinant expression cassette comprising a transcribable DNA sequence encoding a non-coding RNA for suppression of one or more GA3 oxidase genes and/or GA20 oxidase genes; introducing into the corn cell of step (a) a second recombinant expression cassette comprising a DNA sequence encoding a GDH polypeptide to create a modified corn cell; and regenerating or developing a modified corn plant from the modified corn cell of step (b), wherein the modified corn plant comprises the first and second recombinant expression cassettes.

Also provided in the present disclosure is a method for producing a modified corn plant, the method comprising introducing into a corn cell a first recombinant expression cassette comprising a DNA sequence encoding a GDH polypeptide; introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and regenerating or developing a modified corn plant from the modified corn cell of step (b), wherein the modified corn plant comprises the first and second recombinant expression cassettes.

Also provided in the present disclosure is a method for producing a transgenic corn plant, the method comprising (a) introducing into a first corn cell a transcribable DNA sequence encoding a non-coding RNA for suppression of one or more GA3 oxidase genes and/or one or more GA20 oxidase genes to create a transgenic corn cell, wherein the first corn cell is genome edited or mutated and comprises a transgene that encodes one or more GDH polypeptides; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the DNA sequence and the transgene.

Also provided in the present disclosure is a method for producing a transgenic corn plant, the method comprising (a) introducing into a first corn cell a DNA sequence that encodes one or more GDH polypeptides to create a transgenic corn cell, wherein the first corn cell is genome edited or mutated and has a reduced expression of one or more endogenous GA3 oxidase genes and/or one or more GA20 oxidase genes; and (b) generating a transgenic corn plant from the transgenic corn cell. In an aspect, the first corn cell comprises one or more mutation(s) or edit(s) at or near one or more endogenous GA20 oxidase and/or GA3 oxidase gene(s) (e.g., a mutation or edit in two or more endogenous GA20 oxidase and/or GA3 oxidase gene(s), wherein the expression of the endogenous GA20 oxidase and/or GA3 oxidase gene(s) is reduced relative to a wildtype control. In an aspect, the method further comprises identifying a transgenic corn plant with a desired trait. In another aspect, the identified transgenic corn plant is semi-dwarf and has one or more improved ear traits, relative to a control corn plant not having both the DNA sequence and the reduced expression of the one or more endogenous GA3 oxidase and/or GA20 oxidase genes.

Also provided in the present disclosure is a method for producing a modified corn plant, the method comprising: crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a GDH polypeptide; and producing a progeny corn plant comprising the recombinant expression cassette and has the reduced expression of the one or more endogenous GA3 oxidase genes and/or GA20 oxidase genes.

Also provided in the present disclosure is a method for producing a transgenic corn plant, the method comprising (a) crossing a first corn plant with a second corn plant to create a modified corn plant, wherein the expression of one or more endogenous GA3 oxidase gene(s) and/or one or more GA20 oxidase gene(s) is reduced in the first corn plant relative to a wildtype control, and wherein the second corn plant comprises a transgene encoding one or more GDH polypeptides; and (b) producing an offspring of the transgenic corn plant of step (a). In an aspect, the method further comprises identifying a modified corn plant with a desired trait. In another aspect, the identified modified corn plant is semi-dwarf and has one or more improved ear traits, relative to a control corn plant not having both the transgene and a reduced expression of the one or more endogenous GA3 oxidase and/or GA20 oxidase gene(s).

According to an aspect of the present disclosure, methods are provided for transforming a cell, tissue or explant with a recombinant DNA molecule or construct comprising DNA sequences or transgenes operably linked to one or more promoters to produce a transgenic or genome edited cell. According to other aspects of the present disclosure, methods are provided for transforming a plant cell, tissue or explant with a recombinant DNA molecule or construct comprising transcribable DNA sequences or transgenes operably linked to one or more plant-expressible promoters to produce a transgenic or genome edited plant or plant cell.

Numerous methods for transforming chromosomes or plastids in a plant cell with a recombinant DNA molecule or construct are known in the art, which can be used according to methods of the present disclosure to produce a transgenic plant cell and plant. Any suitable method or technique for transformation of a plant cell known in the art can be used according to present methods.

Effective methods for transformation of plants include bacterially mediated transformation, such as *Agrobacterium*-mediated or *Rhizobium*-mediated transformation and microprojectile particle bombardment-mediated transformation. A variety of methods are known in the art for transforming explants with a transformation vector via bacterially mediated transformation or microprojectile particle bombardment and then subsequently culturing, etc., those explants to regenerate or develop transgenic plants.

In an aspect, the methods for producing a transgenic or modified corn plant disclosed in the present disclosure comprise obtaining the first corn cell and the transgenic corn cell via *Agrobacterium*-mediated transformation.

In another aspect, the methods for producing a transgenic or modified corn plant disclosed in the present disclosure comprise obtaining the first corn cell and the transgenic corn cell via microprojectile particle bombardment-mediated transformation.

In yet another aspect, the methods for producing a transgenic corn plant disclosed in the present disclosure comprises (1) introducing into a first corn cell a transgene via site-directed integration to create a modified or mutated corn cell, wherein the transgene encodes one or more GDH polypeptides, and (2) introducing into the modified or mutated corn cell a transcribable DNA sequence via transformation to create a transgenic corn cell, wherein the transcribable DNA sequence encodes a non-coding RNA for suppression of one or more GA3 oxidase genes and/or one or more GA20 oxidase genes. In an aspect, the transformation can be *Agrobacterium*-mediated transformation or microprojectile particle bombardment-mediated transformation.

In still another aspect, the methods for producing a transgenic corn plant disclosed in the present disclosure comprise (1) obtaining a modified corn cell via genome editing, wherein the modified corn cell has a reduced expression of one or more GA3 oxidase genes and/or one or more GA20 oxidase genes; and (2) introducing into the modified corn cell a transgene via transformation to create a transgenic corn cell, wherein the transgene encodes one or more GDH polypeptides. In an aspect, the transformation can be *Agrobacterium*-mediated transformation or microprojectile particle bombardment-mediated transformation.

Other methods for plant transformation, such as microinjection, electroporation, vacuum infiltration, pressure, sonication, silicon carbide fiber agitation, PEG-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile particle bombardment with particles coated with recombinant DNA are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell with any of the nucleic acid molecules provided herein.

In an aspect, described herein are methods of integrating an insertion sequence encoding one or more GDH polypeptides into the genome of a plant cell via site-directed integration. Such methods comprise creating a double-stranded break (DSB) in the genome of the plant cell such that the insertion sequence is integrated at the site of the DSB. In an aspect, the insertion/donor sequence encoding one or more GDH polypeptides can be integrated in a targeted manner into the genome of a cell at the location of a DSB. DSBs can be created by any mechanism, including but are not limited to, zinc finger nucleases (ZFN), transcription activator-like effector nuclease (TALEN), meganucleases, recombinases, transposases, and RNA-guided nucleases (e.g., Cas9 and Cpf1) in a CRISPR based genome editing system.

When Cas9 cleaves targeted DNA, endogenous double stranded break (DSB) repair mechanisms are activated. DSBs can be repaired via non-homologous end joining (NHEJ), which can incorporate insertions or deletions (indels) into the targeted locus. If two DSBs flanking one target region are created, the breaks can be repaired by reversing the orientation of the targeted DNA. Alternatively, if an insertion sequence of a donor template with homology to the target DNA sequence is provided, the DSB can be repaired via homology-directed repair or homologous recombination (HR). This repair mechanism allows for the precise integration of an insertion sequence into the targeted DNA sequence.

As used herein, an "insertion sequence" of a donor template is a sequence designed for targeted insertion into the genome of a plant cell, which can be of any suitable length. For example, an insertion sequence can be between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000, between 20 and 10,000, between 50 and 250, between 50 and 500, between 50 and 1000, between 50 and 5000, between 50 and 10,000, between 100 and 250, between 100 and 500, between 100 and 1000, between 100 and 5000, between 100 and 10,000, between 250 and 500, between 250 and 1000, between 250 and 5000, or between 250 and 10,000 nucleotides or base pairs in length.

According to some aspects, a donor template may not comprise a sequence for insertion into a genome, and instead comprise one or more homology sequences that include(s) one or more mutations, such as an insertion, deletion, substitution, etc., relative to the genomic sequence at a target site within the genome of a plant. Alternatively, a donor template can comprise a sequence that does not comprise a coding or transcribable DNA sequence, wherein the insertion sequence is used to introduce one or more mutations into a target site within the genome of a plant.

A donor template provided herein can comprise at least one, at least two, at least three, at least four, at least five, at least six, at least seven, at least eight, at least nine, or at least ten genes or transcribable DNA sequences. Alternatively, a donor template can comprise no genes. Without being limiting, a gene or transcribable DNA sequence of a donor template can include, for example, an insecticidal resistance gene, an herbicide tolerance gene, a nitrogen use efficiency gene, a water use efficiency gene, a nutritional quality gene, a DNA binding gene, a selectable marker gene, an RNAi or suppression construct, a site-specific genome modification enzyme gene, a single guide RNA of a CRISPR/Cas9 system, a geminivirus-based expression cassette, or a plant viral expression vector system. A donor template can comprise a promoter, such as a tissue-specific or tissue-preferred promoter, a constitutive promoter, or an inducible promoter. A donor template can comprise a leader, enhancer, promoter, transcriptional start site, 5'-UTR, one or more exon(s), one or more intron(s), transcriptional termination site, region or sequence, 3'-UTR, and/or polyadenylation signal. The leader, enhancer, and/or promoter can be operably linked to a gene or transcribable DNA sequence encoding a non-coding RNA, a guide RNA, an mRNA and/or protein.

In an aspect, an insertion sequence of a donor template of the present disclosure comprises a DNA sequence encoding a GDH polypeptide, wherein the GDH polypeptide is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 176-192.

In an aspect, an insertion sequence of a donor template of the present disclosure comprises a DNA sequence encoding an *E.coli* gdhA polypeptide, wherein the DNA sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

In an aspect, a "modified plant(s)," "modified corn plant(s)," "transgenic plant(s)," or "transgenic corn plant(s)" produced according to a method disclosed in the present disclosure comprises (1) a first transcribable DNA sequence encoding a non-coding RNA for suppression of one or more GA20 oxidase genes and/or one or more GA3 oxidase genes, and (2) a second DNA sequence encoding one or more GDH polypeptides.

In another aspect, a "modified plant(s)," "modified corn plant(s)," "transgenic plant(s)," or "transgenic corn plant(s)" produced according to a method disclosed in the present disclosure comprises (1) a DNA sequence encoding one or more GDH polypeptides, and (2) a reduced expression of one or more endogenous GA3 oxidase genes or GA20 oxidase genes relative to a wildtype control. In an aspect, the reduced expression of the one or more endogenous GA20 oxidase genes or GA3 oxidase genes is caused by a mutation or edit at or near the one or more endogenous GA20 oxidase genes or GA3 oxidase genes.

Transgenic or modified plants produced by transformation methods can be chimeric or non-chimeric for the transformation event depending on the methods and explants used. Methods are further provided for expressing a non-coding RNA molecule that targets an endogenous GA oxidase gene for suppression in one or more plant cells or tissues under the control of a plant-expressible promoter, such as a constitutive, tissue-specific, tissue-preferred, vascular and/or leaf promoter as provided herein. Such methods can be used to create transgenic cereal or corn plants having a shorter, semi-dwarf stature, reduced internode length, increased stalk/stem diameter, and/or improved lodging resistance. Such transgenic cereal or corn plants can further have other traits that can be beneficial for yield, such as reduced green snap, deeper roots, increased leaf area, earlier canopy closure, improved drought tolerance, increased nitrogen use efficiency, increased water use efficiency, higher stomatal conductance, lower ear height, increased foliar water content, reduced anthocyanin content and/or area in leaves under normal or nitrogen or water limiting stress conditions, increased ear weight, increased seed or kernel number, increased seed or kernel weight, increased yield, and/or increased harvest index, relative to a wild type or control plant. As used herein, "harvest index" refers to the mass of the harvested grain divided by the total mass of the above-ground biomass of the plant over a harvested area.

Alternatively, nucleotide sequences of the disclosure can be introduced into an organism and allowed to undergo recombination with homologous regions of the organism's genome. Such homologous recombination approaches are well known to those of ordinary skill in the art and can be used to stably incorporate sequences of the disclosure into an organism. In an aspect, nucleotide sequences of the disclosure can be used to introduce "knockout mutations" into a specific gene of an organism that shares substantial homology to the sequences of the disclosure. A knockout mutation is any mutation in the sequence of a gene that eliminates or substantially reduces the function or the level of the product encoded by the gene. Methods involving transformation of an organism followed by homologous recombination to stably integrate the sequences of the disclosure into the genome organism are encompassed by the disclosure. The disclosure is particularly directed to methods where sequences of the disclosure are utilized to alter the growth of an organism. Such methods encompass use of the sequences of the disclosure to interfere with the function of one or more GA20 oxidase genes or GA3 oxidase genes. In an aspect, a knockout mutation of one or more GA20 oxidase or GA3 oxidase genes can be introduced into a corn cell via recombination to reduce the expression of the one or more of GA20 oxidase or GA3 oxidase genes in the corn cell.

Cells that have been transformed can be grown into plants in accordance with conventional ways. See, for example, McCormick et al. (1986) *Plant Cell Reports* 5:81-84. These plants can then be grown, and either pollinated with the same transformed strain or different strains, and the resulting hybrid having constitutive expression of the desired phenotypic characteristic identified. Two or more generations can be grown to ensure that constitutive expression of the desired phenotypic characteristic is stably maintained and inherited and then seeds harvested to ensure constitutive expression of the desired phenotypic characteristic has been achieved.

In an aspect, the methods for producing a transgenic or modified corn plant further comprises culturing the transgenic corn plant of step (b) or a plant part thereof in the presence of a selection agent. In another aspect, the selection agent is kanamycin.

Recipient cell or explant targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a stomata cell, a trichome cell, a root hair cell, a storage root cell, or a tuber cell. In another aspect, this disclosure provides a protoplast. In another aspect, this disclosure provides a plant callus cell.

Transformation of a target plant material or explant can be practiced in tissue culture on nutrient media, for example a mixture of nutrients that allow cells to grow in vitro or cell culture. Transformed explants, cells or tissues can be subjected to additional culturing steps, such as callus induction, selection, regeneration, etc., as known in the art. Transformation can also be carried out without creation or use of a callus tissue. Transformed cells, tissues or explants containing a recombinant DNA sequence insertion or event can be grown, developed or regenerated into transgenic plants in culture, plugs, or soil according to methods known in the art. Transgenic plants can be further crossed to themselves or other plants to produce transgenic seeds and progeny. A transgenic plant can also be prepared by crossing a first plant comprising the recombinant DNA sequence or transformation event with a second plant lacking the insertion. For example, a recombinant DNA construct or sequence can be introduced into a first plant line that is amenable to transformation, which can then be crossed with a second plant line to introgress the recombinant DNA construct or sequence into the second plant line. Progeny of these crosses can be further back crossed into the more desirable line multiple times, such as through 6 to 8 generations or back crosses, to produce a progeny plant with substantially the same genotype as the original parental line, but for the introduction of the recombinant DNA construct or sequence.

Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U. S. Pat. Nos. 6,194,636 and 6,232,526 and U. S. Patent Application Publication 2004/0216189, all of which are incorporated herein by reference.

Transformed explants, cells or tissues can be subjected to additional culturing steps, such as callus induction, selection, regeneration, etc., as known in the art. Transformed cells, tissues or explants containing a recombinant DNA insertion can be grown, developed or regenerated into transgenic plants in culture, plugs or soil according to methods known in the art. In an aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction.

Transgenic plants can be further crossed to themselves or other plants to produce transgenic seeds and progeny. A transgenic plant can also be prepared by crossing a first plant comprising the recombinant DNA sequence or transformation event with a second plant lacking the insertion. For example, a recombinant DNA construct or sequence can be introduced into a first plant line that is amenable to transformation, which can then be crossed with a second plant line to introgress the recombinant DNA construct or sequence into the second plant line. Progeny of these crosses can be further back crossed into the more desirable line multiple times, such as through 6 to 8 generations or back crosses, to produce a progeny plant with substantially the same genotype as the original parental line but for the introduction of the recombinant DNA construct or sequence.

A plant, cell, or explant provided herein can be of an elite variety or an elite line. An elite variety or an elite line refers to any variety that has resulted from breeding and selection for superior agronomic performance. A plant, cell, or explant provided herein can be a hybrid plant, cell, or explant. As used herein, a "hybrid" is created by crossing two plants from different varieties, lines, or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

For *Agrobacterium*-mediated transformation, the transformation vector can comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. In other words, the transgene, a transcribable DNA sequence, transgene or expression cassette encoding the site-specific nuclease(s), and/or sgRNA(s) or crRNA(s) would be located between the left and right borders of the T-DNA, perhaps along with an additional transgene(s) or expression cassette(s), such as a plant selectable marker transgene and/or other gene(s) of agronomic interest that can confer a trait or phenotype of agronomic interest to a plant.

A plant selectable marker transgene in a transformation vector or construct of the present disclosure can be used to assist in the selection of transformed cells or tissue due to the presence of a selection agent, such as an antibiotic or herbicide, wherein the plant selectable marker transgene provides tolerance or resistance to the selection agent. Thus, the selection agent can bias or favor the survival, development, growth, proliferation, etc., of transformed cells expressing the plant selectable marker gene, such as to increase the proportion of transformed cells or tissues in the $R_0$ plant.

A plant selectable marker transgene in a transformation vector or construct of the present disclosure can be used to assist in the selection of transformed cells or tissue due to the presence of a selection agent, such as an antibiotic or herbicide, wherein the plant selectable marker transgene provides tolerance or resistance to the selection agent. Thus, the selection agent can bias or favor the survival, development, growth, proliferation, etc., of transformed cells expressing the plant selectable marker gene, such as to increase the proportion of transformed cells or tissues in the $R_0$ plant. Commonly used plant selectable marker genes include, for example, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or EPSPS). Plant screenable marker genes can also be used, which provide an ability to visually screen for transformants, such as luciferase or green fluorescent protein (GFP), or a gene expressing a beta glucuronidase or uidA gene (GUS) for which various chromogenic substrates are known. In some aspects, a vector or polynucleotide provided herein comprises at least one selectable marker gene selected from the group consisting of nptII, aph IV, aadA, aac3, aacC4, bar, pat, DMO, EPSPS, aroA, GFP, and GUS. Plant transformation can also be carried out in the absence of selection during one or more steps or stages of culturing, developing or regenerating transformed explants, tissues, plants and/or plant parts.

An aspect of the present disclosure relate to screening cells, tissues or plants for mutations, targeted edits or transgenes and selecting cells or plants comprising targeted edits or transgenes. Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In an aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified or transgenic plants or plant cells can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, marker genotyping, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

Modified corn plants of the present disclosure having a reduced plant height and improved ear traits relative to a wild-type or control plant can comprise a mutation (e.g., an insertion, deletion, substitution, etc.) introduced through other plant mutagenesis technique or genome editing, wherein expression of one or more GA20 or GA3 oxidase gene is reduced or eliminated in one or more tissues of the modified plant. Modified corn plants of the present disclosure having a reduced plant height and improved ear traits relative to a wild-type or control plant can comprise a transgene encoding one or more GDH polypeptides. The transgene can be introduced through other plant mutagenesis technique or genome editing.

Plant mutagenesis techniques (excluding genome editing) can include chemical mutagenesis (i.e., treatment with a chemical mutagen, such as an azide, hydroxylamine, nitrous acid, acridine, nucleotide base analog, or alkylating agent—e.g., EMS (ethylmethane sulfonate), MNU (N-methyl-N-nitrosourea), etc.), physical mutagenesis (e.g., gamma rays, X-rays, UV, ion beam, other forms of radiation, etc.), and insertional mutagenesis (e.g., transposon or T-DNA insertion). Plants or various plant parts, plant tissues or plant cells can be subjected to mutagenesis. Treated plants can be reproduced to collect seeds or produce a progeny plant, and treated plant parts, plant tissues or plant cells can be developed or regenerated into plants or other plant tissues. Mutations generated with chemical or physical mutagenesis techniques can include a frameshift, missense or nonsense mutation leading to loss of function or expression of a targeted gene, such as a GA3 or GA20 oxidase gene.

One method for mutagenesis of a gene is called "TILLING" (for targeting induced local lesions in genomes), in which mutations are created in a plant cell or tissue, preferably in the seed, reproductive tissue or germline of a plant, for example, using a mutagen, such as an EMS treatment. The resulting plants are grown and self-fertilized, and the progeny are used to prepare DNA samples. PCR amplification and sequencing of a nucleic acid sequence of a GA20 or GA3 oxidase gene can be used to identify whether a mutated plant has a mutation in the GA oxidase gene. Plants having mutations in the GA20 or GA3 oxidase gene can then be tested for an altered trait, such as reduced plant height. Alternatively, mutagenized plants can be tested for an altered trait, such as reduced plant height, and then PCR amplification and sequencing of a nucleic acid sequence of a GA20 or GA3 oxidase gene can be used to determine whether a plant having the altered trait also has a mutation in the GA oxidase gene. See, e.g., Colbert et al., 2001, *Plant Physiol* 126:480-484; and McCallum et al., 2000, *Nat. Biotechnol.,* 18:455-457. TILLING can be used to identify mutations that alter the expression a gene or the activity of proteins encoded by a gene, which can be used to introduce and select for a targeted mutation in a GA20 or GA3 oxidase gene of a corn or cereal plant.

Provided in the present disclosure is a recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a GDH polypeptide, wherein the DNA sequence is operably linked to a plant-expressible promoter. In an aspect, the first and second expression cassettes are in a single T-DNA segment of a transformation vector. In another aspect, the first and second expression cassettes are in two different T-DNA segments of a transformation vector.

In an aspect, the transcribable DNA sequence encodes a non-coding RNA for suppression of a GA3 oxidase_1 gene, a GA3 oxidase_2 gene, or both. In another aspect, the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37. In another aspect, the transcribable DNA sequence encodes a non-coding RNA comprising a sequence that is 80% complementary to at least 15 consecutive nucleotides of one or more of SEQ ID NOs: 28, 29, 31, 32, 36, and 37.

In another aspect, the transcribable DNA sequence encodes a non-coding RNA for suppression of a GA20 oxidase_3 gene, a GA20 oxidase_4 gene, a GA20 oxidase_5 gene, or a combination thereof. In another aspect, the transcribable DNA sequence comprises a sequence that is at least 80% complementary to at least 15 consecutive nucleotides of SEQ ID NO: 39, 53, or 55. In another aspect, the transcribable DNA sequence encodes a sequence that is at least 80% complementary to at least 15 consecutive nucleotides of SEQ ID NO: 40, 54, or 56.

In an aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9, 12, 15, 30, or 33.

In another aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 9'7%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

In an aspect, the DNA sequence comprised in the second expression cassette comprises a sequence that encodes a protein having an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-192.

In an aspect, the DNA sequence comprised in the second expression cassette encodes an *E.coli* gdhA polypeptide. In another aspect, the GDH polypeptide comprises an amino acid sequence that is at least 60% identical to SEQ ID NO: 168. In another aspect, the DNA sequence comprises a sequence that is at least 60% identical to SEQ ID NO: 169.

Also provided herein is a recombinant DNA construct comprising 1) a first transcribable DNA sequence encoding a non-coding RNA for suppression of one or more GA20 oxidase or one or more GA3 oxidase genes, and 2) a second DNA sequence encoding one or more GDH polypeptides.

In an aspect, a recombinant DNA construct of the present disclosure comprises a transcribable DNA sequence encoding a non-coding RNA for suppression of one or more GA20 oxidase or one or more GA3 oxidase genes, wherein the DNA sequence is operably linked to a plant-expressible promoter. Such a recombinant DNA construct can be used to transform a corn plant cell expressing a transgene encoding one or more GDH polypeptides to create a transgenic corn plant with desired traits. In another aspect, desired traits comprise semi-dwarf and improved ear traits as compared to a control corn plant not having the transgene and the DNA sequence.

In an aspect, a recombinant DNA construct of the present disclosure comprises a DNA sequence encoding one or more GDH polypeptides, wherein the DNA sequence is operably linked to a plant-expressible promoter. Such a recombinant DNA construct can be used to transform a corn plant cell having a reduced expression of one or more GA20 oxidase genes and/or one or more GA3 oxidase genes to create a transgenic corn plant with desired traits. In another aspect, desired traits comprise semi-dwarf and improved ear traits as compared to a control corn plant not having the DNA sequence and the reduced expression of the one or more GA20 oxidase genes and/or GA3 oxidase genes.

Also provided in the present disclosure is a transgenic corn plants comprising the recombinant DNA construct. In an aspect, the first and second DNA sequences are in a single T-DNA molecule. In another aspect, the first and second DNA sequences are in two different T-DNA molecules. In an aspect, the first transcribable DNA sequence is operably linked to a plant-expressible promoter.

In an aspect, a recombinant DNA construct of the present disclosure comprises a transcribable DNA sequence encoding a non-coding RNA molecule, wherein the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9, 12, 15, 30 or 33, and wherein the transcribable DNA sequence is operably linked to a plant-expressible promoter. In another aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31 or 32.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 15. In yet another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or SEQ ID NO: 14.

In another aspect, the non-coding RNA molecule comprises a sequence that is (i) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9; and/or (ii) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 15.

In another aspect, the non-coding RNA molecule comprises a sequence that is (i) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7 or 8; and/or (ii) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or 14.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 12.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 10 or 11.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein, the endogenous GA3 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 30 or 33.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 28, 29, 31 or 32.

In an aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 98%, identical to one or more of SEQ ID NOs: 3, 6, 9, 12, 15, 18, 21, 24, 27, 30 and 33.

In another aspect, the non-coding RNA molecule comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 1, 2, 4, 5, 7, 8, 10, 11, 13, 14, 16, 17, 19, 20, 22, 23, 25, 26, 28, 29, 31, and 32.

In an aspect, a recombinant DNA molecule, vector or construct is provided for suppression of an endogenous GA oxidase (or GA oxidase-like) gene in a corn or cereal plant, the recombinant DNA molecule, vector or construct comprising a transcribable DNA sequence encoding a non-coding RNA molecule, wherein the non-coding RNA molecule comprises a sequence that is (i) at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of any one or more of SEQ ID NO: 84, 85, 87, 88, 89, 91, 92, 93, 95, 96, 98, 99, 100, 102, 103, 105, 106, 107, 109, 110, 111, 113, 114, 115, 117, 119, 120, 122, 123, 124, 126, 127, 128, 130, 131, 132, 134, 135, and/or 137, and/or (ii) at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding a protein in the cereal plant that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to any one or more of SEQ ID NO: 86, 90, 94, 97, 101, 104, 108, 112, 116, 118, 121, 125, 129, 133, and/or 136. Likewise, a non-coding RNA molecule can target an endogenous GA oxidase (or GA oxidase-like) gene in a cereal plant having a percent identity to the GA oxidase gene(s) shown to affect plant height in corn. Thus, a non-coding RNA molecule is further provided comprising a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous protein in a cereal plant that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to any one or more of SEQ ID NO: 9, 12, 15, 30, and/or 33. As mentioned above, the non-coding RNA molecule can target an exon, intron and/or UTR sequence of a GA oxidase (or GA oxidase-like) gene.

A recombinant DNA construct of the present disclosure can comprise or be included within a DNA transformation vector for use in transformation of a target plant cell, tissue or explant. Such a transformation vector of the present disclosure can generally comprise sequences or elements necessary or beneficial for effective transformation in addition to at least one selectable marker gene, at least one expression cassette and/or transcribable DNA sequence encoding one or more site-specific nucleases, and, optionally, one or more sgRNAs or crRNAs.

According to an aspect of the present disclosure, suitable tissue-specific or tissue preferred promoters can include those promoters that drive or cause expression of its associated suppression element or sequence at least in the vascular and/or leaf tissue(s) of a corn or cereal plant, or possibly other tissues.

Expression of the GA oxidase suppression element or construct with a tissue-specific or tissue-preferred promoter can also occur in other tissues of the cereal or corn plant outside of the vascular and leaf tissues, but active GA levels in the developing reproductive tissues of the plant (particularly in the female reproductive organ or ear) are preferably not significantly reduced or impacted (relative to wild type or control plants), such that development of the female organ or ear can proceed normally in the transgenic plant without off-types in the ear and a loss in yield potential.

According to some aspects, constructs and transgenes are provided comprising the first transcribable DNA sequence and the second DNA sequence that are operably linked to a constitutive or tissue-specific or tissue-preferred promoter, such as a vascular or leaf promoter.

In an aspect, the plant-expressible promoter is a vascular promoter. Any vascular promoters known in the art can potentially be used as the tissue-specific or tissue-preferred promoter. Examples of vascular promoters include the RTBV promoter, a known sucrose synthase gene promoter, such as a corn sucrose synthase-1 (Sus1 or Sh1) promoter, a corn Sh1 gene paralog promoter, a barley sucrose synthase promoter (Ss1) promoter, a rice sucrose synthase-1 (RSs1) promoter, or a rice sucrose synthase-2 (RSs2) promoter, a known sucrose transporter gene promoter, such as a rice sucrose transporter promoter (SUT1), or various known viral promoters, such as a Commelina yellow mottle virus (CoYMV) promoter, a wheat dwarf geminivirus (WDV) large intergenic region (LIR) promoter, a maize streak geminivirus (MSV) coat protein (CP) promoter, or a rice yellow stripe 1 (YS1)-like or OsYSL2 promoter, and any functional sequence portion or truncation of any of the foregoing promoters with a similar pattern of expression, such as a truncated RTBV promoter.

In another aspect, the vascular promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 67, SEQ ID NO: 68, SEQ ID NO: 69, SEQ ID NO: 70, or SEQ ID NO: 71, or a functional portion thereof.

In another aspect, the plant-expressible promoter is a rice tungro bacilliform virus (RTBV) promoter. In an aspect, the RTBV promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 65 or SEQ ID NO: 66, or a functional portion thereof.

In another aspect, the plant-expressible promoter is a leaf promoter. Any leaf promoters known in the art can potentially be used as the tissue-specific or tissue-preferred promoter. Examples of leaf promoters include a corn pyruvate phosphate dikinase or PPDK promoter, a corn fructose 1,6 bisphosphate aldolase or FDA promoter, and a rice Nadh-Gogat promoter, and any functional sequence portion or truncation of any of the foregoing promoters with a similar pattern of expression. Other examples of leaf promoters from monocot plant genes include a ribulose biphosphate carboxylase (RuBisCO) or RuBisCO small subunit (RBCS) promoter, a chlorophyll a/b binding protein gene promoter, a phosphoenolpyruvate carboxylase (PEPC) promoter, and a Myb gene promoter, and any functional sequence portion or truncation of any of these promoters with a similar pattern of expression.

In another aspect, the leaf promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 72, SEQ ID NO: 73 or SEQ ID NO: 74, or a functional portion thereof.

In another aspect, the plant-expressible promoter is a constitutive promoter. Examples of constitutive promoters that can be used in monocot plants, such as cereal or corn plants, include, for example, various actin gene promoters, such as a rice Actin 1 promoter (see, e.g., U.S. Pat. No. 5,641,876) and a rice Actin 2 promoter (see, e.g., U.S. Pat. No. 6,429,357), a CaMV 35S or 19S promoter (see, e.g., U.S. Pat. No. 5,352,605), a maize ubiquitin promoter (see, e.g., U.S. Pat. No. 5,510,474), a Coix lacryma-jobi polyubiquitin promoter, a rice or maize Gos2 promoter (see, e.g., Pater et al., *Plant J.,* 2(6): 837-44 1992), a FMV 35S promoter (see, e.g., U.S. Pat. No. 6,372,211), a dual enhanced CMV promoter (see, e.g., U.S. Pat. No. 5,322,938), a MMV promoter (see, e.g., U.S. Pat. No. 6,420,547), a PCLSV promoter (see, e.g., U.S. Pat. No. 5,850,019), an Emu promoter (see, e.g., Last et al., *Theor. Appl. Genet.,* 81:581 (1991); and Mcelroy et al., *Mol. Gen. Genet.,* 231:150 (1991)), a tubulin promoter from maize, rice or other species, a nopaline synthase (nos) promoter, an octopine synthase (ocs) promoter, a mannopine synthase (mas) promoter, or a plant alcohol dehydrogenase (e.g., maize Adh1) promoter, any other promoters including viral promoters known or later-identified in the art to provide constitutive expression in a cereal or corn plant, any other constitutive promoters known in the art that can be used in monocot or cereal plants, and any functional sequence portion or truncation of any of the foregoing promoters.

In another aspect, the constitutive promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

Tissue-specific and tissue-preferred promoters that drive, etc., a moderate or strong level of expression of their associated transcribable DNA sequence in active GA-producing tissue(s) of a plant can be preferred. Furthermore, such tissue-specific and tissue-preferred should drive, etc., expression of their associated transcribable DNA sequence during one or more vegetative stage(s) of plant development when the plant is growing and/or elongating including one or more of the following vegetative stage(s): $V_E$, V1, V2, V3, V4, V5, V6, V7, V8, V9, V10, V11, V12, V13, V14, Vn, $V_T$, such as expression at least during V3-V12, V4-V12, V5-V12, V6-V12, V7-V12, V8-V12, V3-V14, V5-V14, V6-V14, V7-V14, V8-V14, V9-V14, V10-V14, etc., or during any other range of vegetative stages when growth and/or elongation of the plant is occurring.

According to an aspect, the plant-expressible promoter can preferably drive expression constitutively or in at least a portion of the vascular and/or leaf tissues of the plant. Different promoters driving expression of a suppression element targeting the endogenous GA20 oxidase_3 and/or GA20 oxidase_5 gene(s), the GA20 oxidase_4 gene, the GA3 oxidase_1 and/or GA3 oxidase_2 gene(s) in corn, or similar genes and homologs in other cereal plants, can be effective at reducing plant height and increasing lodging resistance to varying degrees depending on their particular pattern and strength of expression in the plant. However, some tissue-specific and tissue-preferred promoters driving expression of a GA20 or GA3 oxidase suppression element in a plant may not produce a short stature or anti-lodging phenotypes due to the spatial-temporal pattern of expression of the promoter during plant development, and/or the amount or strength of expression of the promoter being too low or weak. Furthermore, some suppression constructs can only reduce and not eliminate expression of the targeted GA20 or GA3 oxidase gene(s) when expressed in a plant, and thus depending on the pattern and strength of expression with a given promoter, the pattern and level of expression of the GA20 or GA3 oxidase suppression construct with such a promoter may not be sufficient to produce an observable plant height and lodging resistance phenotype in plants.

Any other vascular and/or leaf promoters known in the art can also be used, including promoter sequences from related genes (e.g., sucrose synthase, sucrose transporter, and viral gene promoter sequences) from the same or different plant species or virus that have a similar pattern of expression. Further provided are promoter sequences with a high degree of homology to any of the foregoing. Examples of vascular and/or leaf promoters can further include other known, engineered and/or later-identified promoter sequences shown to have a pattern of expression in vascular and/or leaf tissue(s) of a cereal or corn plant. Furthermore, any known or later-identified constitutive promoter can also be used for expression of a GA20 oxidase or GA3 oxidase suppression element.

According to some aspects, recombinant expression cassettes, constructs, transgenes, and recombinant DNA donor template molecules are provided comprising a DNA sequence encoding a glutamate dehydrogenase (GDH) polypeptide operably linked to a stress-inducible promoter, a nitrogen-inducible promoter, a drought-inducible promoter, or a root promoter.

In an aspect, a DNA sequence encoding a GDH polypeptide is operably linked to a stress-inducible promoter for driving gene expression under conditions of stress. Under non-stress conditions (e.g., well-watered conditions), these promoters drive gene expression at low or non-detectable levels. Stress-inducible promoters can be used in directing the expression of a gene or a nucleotide sequence, such as a DNA sequence encoding a GDH polypeptide, to express under conditions of stress, such as water deficit, nutrient, or other environmental stress. A stress-inducible promoter refers to a promoter that causes or drives expression, or increases expression, of a gene (or transgene) operably linked to the promoter in one or more tissues of a corn or maize plant in response to a stress condition(s), such as water deficient stress, nutrient or nitrogen deficient stress, or other environmental stress. A stress-inducible promoter includes any low nitrogen or nitrogen stress promoter and any low water or drought-inducible promoter. A stress-inducible promoter includes any promoter which causes, drives or increases, or can cause, drive or increase, expression of a gene or transgene operably linked to the promoter in a corn or maize seed in response to a stress condition, such as water deficient stress, nutrient or nitrogen deficient stress, or other environmental stress, including any such promoter from a monocot or Poaceae plant, such as maize, barley, wheat, oat, millet, sorghum, rice, etc. In an aspect, the stress-inducible promoter is a low-nitrogen or nitrogen stress inducible or responsive promoter. A low-nitrogen or nitrogen stress inducible or responsive promoter can confer transcription under nitrogen deficiency and/or starvation. In another aspect, the stress-inducible promoter is a drought inducible or responsive promoter. Such a promoter can confer transcription in response to a period of water deficit or drought.

According to present embodiments, a stress inducible promoter can include any promoter known in the art to cause, drive or increase expression of a gene (or transgene) in one or more tissues of a corn or maize plant in response to a stress condition, such as water deficient stress or nutrient or nitrogen deficient stress, such as for example, a promoter from a rice or maize RAB17, CA4H, HVA22, HSP17.5, HSP22, or HSP16.9 gene (see, e.g., U.S. Pat. Nos. 8,395,024 and 7,674,952), or a Dhn gene (see, e.g., Xiao and Xue, Plant Cell Rep. 20:667-673 (2001); and US Patent Pub No. 2017/0318840), DREB1 or DREB2 or ABF3 gene (see, e.g., Liu et al., Plant Cell 10:1391-1406 (1998); Plant Physiol. 138(1): 341-351 (2005); and U.S. Pat. No. 7,314,757), or a HVA1 or HVA2 gene (see, e.g., Plant Molecular Biology, 26(2): 617-630 (1994); and Shen et al Plant Cell, 7: 295-307 (1995)), or a functional portion of any of the foregoing known stress-inducible promoters, or a promoter sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to any of the foregoing known seed promoters, or any functional portion thereof. All of the above-cited references are incorporated herein by reference in their entirety. In an aspect, a stress-inducible promoter may comprise a sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to SEQ ID NO: 197-200, or a functional portion thereof.

In an aspect, a DNA sequence encoding a GDH polypeptide is operably linked to a root promoter, such as a root-specific promoter or root-preferred promoter. Such a promoter can confer transcription in root tissue, e.g., root endodermis, root epidermis, and/or root vascular tissues. A root-preferred promoter refers to a promoter that preferentially or predominantly causes or drives expression of a gene (or transgene) operably linked to the promoter in one or more root tissues of a corn or maize plant, such as the root endodermis, root epidermis, root vascular tissue, etc., although the root-preferred promoter may also cause or drive expression of the gene (or transgene) operably linked to the promoter in other tissues. A root-specific promoter refers to a promoter that causes or drives expression of a gene (or transgene) operably linked to the promoter specifically in one or more root tissues of a corn plant, such as the root endodermis, root epidermis, root vascular tissue, etc. As used herein, a "root promoter" refers to any root-preferred promoter or root-specific promoter. A root promoter includes any promoter which causes or drives, or can cause or drive, root-specific or root-preferred expression of a gene or transgene operably linked to the promoter in a corn or maize seed, including any such promoter from a monocot or Poaceae plant, such as maize, barley, wheat, oat, millet, sorghum, rice, etc.

According to present embodiments, a root promoter can include any root promoter known in the art to cause or drive expression of a gene (or transgene) in one or more root tissues of a corn or maize plant, such as for example, a root-specific subdomain of the CaMV 35S promoter (see, e.g., Lam et al., PNAS USA, 86:7890-7894 (1989)) or other root cell specific promoters (see, e.g., Plant Physiol., 93:1203-1211 (1990)), one of the YP0128, YP0275, PT0625, PT0660, PT0683, PT0758, PT0613, PT0672, PT0678, PT0688, and PT0837 promoters (see, e.g., US Patent Pub. No. 2008/0131581), a GL5 promoter (see, e.g., US Patent Pub. No. 2007/174938), or a promoter from an acid chitanse gene, a RCc2 or RCc3 gene (see, e.g., U.S. Pat. No. 7,547,774 (rice); PCT Pub. No. WO 2009/126470 (millet); and Plant Mol Biol. 27(2): 237-48 (1995)), or a Zm.PIIG gene (see, e.g., U.S. Pat. No. 7,491,813), or a functional portion of any of the foregoing known root promoters, or a promoter sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to any of the foregoing known root promoters, or any functional portion thereof. In another aspect, a root promoter comprises a sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to SEQ ID NO: 193-196, or a functional portion thereof. In another aspect, a root promoter is from a *Oryza sativa* RCc3 gene promoter and/or comprises a sequence that is at least 60% identical, at least 65% identical, at least 70% identical, at least 75% identical, at least 80% identical, at least 85% identical, at least 90% identical, at least 95% identical, at least 96% identical, at least 97% identical, at least 98% identical, at least 99% identical, or 100% identical to SEQ ID NO: 170, or a functional portion thereof.

The following are exemplary promoters of the present specification.

TABLE 3

| Exemplary promoters | | | |
|---|---|---|---|
| SEQ ID NO. | Expression Pattern | Sequence Name | Source organism |
| 193 | Root Preferred | P-Os.Rcc3-1:1:24 | *Oryza sativa* |
| 194 | Root Preferred | P-SETit.Ifr-1:1:2 | *Setaria italica* |
| 195 | Root Preferred | P-At.Mt-1a-1:1:1 | *Arabidopsis thaliana* |
| 196 | Root Preferred | P-Zm.RCC3 | *Zea mays* |
| 197 | Stress Inducible | P-Os.RAB17:22 | *Oryza sativa* |
| 198 | Stress Inducible | P-Zm.HSP | *Zea mays* |
| 199 | Stress Inducible | P-Zm.DREB1a | *Zea mays* |
| 200 | Stress Inducible | P-Zm.Rab17-1:1:3 | *Zea mays* |

In addition to its associated promoter, a transcribable DNA sequence or a transgene can also be operatively linked to one or more additional regulatory element(s), such as an enhancer(s), leader, transcription start site (TSS), linker, 5' and 3' untranslated region(s) (UTRs), intron(s), polyadenylation signal, termination region or sequence, etc., that are suitable, necessary or preferred for strengthening, regulating or allowing expression of the transcribable DNA sequence in a plant cell. Such additional regulatory element(s) can be optional and/or used to enhance or optimize expression of the transgene or transcribable DNA sequence. As provided herein, an "enhancer" can be distinguished from a "promoter" in that an enhancer typically lacks a transcription start site, TATA box, or equivalent sequence and is thus insufficient alone to drive transcription. As used herein, a "leader" can be defined generally as the DNA sequence of the 5'-UTR of a gene (or transgene) between the transcription start site (TSS) and 5' end of the transcribable DNA sequence or protein coding sequence start site of the transgene.

In an aspect, the second DNA sequence encoding one or more GDH polypeptides comprised in a recombinant DNA construct of the present application is operably linked to a plant-expressible promoter, such as a constitutive or tissue-specific promoter. According to an aspect, the plant-expressible promoter is a medium or high-constitutive promoter with a high-constitutive promoter having a relatively more robust or strong constitutive expression. In an aspect, the plant-expressible promoter is a constitutive promoter, which can be selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

In an aspect, a transformation vector comprising the recombinant DNA construct is produced. In another aspect, a transgenic corn plant or a plant part thereof comprising the recombinant DNA construct is produced. In still another aspect, the transgenic corn plant is semi-dwarf and has one or more improved ear traits, relative to a control corn plant not having both the first transcribable DNA sequence and the second DNA sequence.

A recombinant DNA molecule or construct of the present disclosure can comprise or be included within a DNA transformation vector for use in transformation of a target plant cell, tissue or explant. Such a transformation vector can generally comprise sequences or elements necessary or beneficial for effective transformation in addition to at least one transgene, expression cassette and/or transcribable DNA sequence.

For *Agrobacterium*-mediated, *Rhizobia*-mediated or other bacteria-mediated transformation, the transformation vector can comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. Thus, a transcribable DNA sequence, transgene or expression cassette can be located between the left and right borders of the T-DNA, perhaps along with an additional transgene(s) or expression cassette(s), such as a plant selectable marker transgene and/or other gene(s) of agronomic interest that can confer a trait or phenotype of agronomic interest to a plant. According to alternative aspects, the transcribable DNA sequence, transgene or expression cassette encoding a non-coding RNA molecule targeting an endogenous GA oxidase gene for suppression and the plant selectable marker transgene (or other gene of agronomic interest) can be present in separate T-DNA segments on the same or different recombinant DNA molecule(s), such as for co-transformation. A transformation vector or construct can further comprise prokaryotic maintenance elements, which can be located in the vector outside of the T-DNA region(s).

The present disclosure provides a modified corn plant with a semi-dwarf phenotype and one or more improved ear traits relative to a control plant. The modified corn plant has its expression of one or more GA20 oxidase genes and/or one or more GA3 oxidase genes reduced and comprises a transgene expressing one or more GDH polypeptides. In an aspect, the reduced expression of the one or more GA20 oxidase genes and/or one or more GA3 oxidase genes is caused by a mutation or edit at or near the one or more GA20 oxidase genes and/or GA3 oxidase genes introduced via genome editing. In another aspect, the reduced expression of one or more GA20 oxidase genes and/or one or more GA3 oxidase genes is caused by a site-directed integration of a transcribable DNA sequence encoding a non-coding RNA for suppression of the one or more GA20 oxidase genes and/or one or more GA3 oxidase genes. In an aspect, the site-directed integration is mediated by genome editing. In an aspect, the introduction of the transgene expressing one or more GDH polypeptides is caused by a site-directed integration of a sequence comprising the transgene. In another aspect, the site-directed integration is mediated by genome editing.

In an aspect, a genome editing system provided herein comprises a CRISPR system. The CRISPR systems are based on RNA-guided engineered nucleases that use complementary base pairing to recognize DNA sequences at target sites. In an aspect, a vector provided herein can comprise any combination of a nucleic acid sequence encoding a RNA-guided nuclease.

In an aspect, a method and/or composition provided herein comprises one or more, two or more, three or more, four or more, or five or more Cas9 nucleases. In an aspect, a method and/or composition provided herein comprises one or more polynucleotides encoding one or more, two or more, three or more, four or more, or five or more Cas9 nucleases. In another aspect, a Cas9 nuclease provided herein is capable of generating a targeted DSB. In an aspect, a method and/or composition provided herein comprises one or more, two or more, three or more, four or more, or five or more Cpf1 nucleases. In an aspect, a method and/or composition provided herein comprises one or more polynucleotides encoding one or more, two or more, three or more, four or more, or five or more Cpf1 nucleases. In another aspect, a Cpf1 nuclease provided herein is capable of generating a targeted DSB.

In an aspect, a vector or construct provided herein comprises polynucleotides encoding at least 1, at least 2, at least 3, at least 4, at least 5, at least 6, at least 7, at least 8, at least 9, or at least 10 site-specific nuclease. In another aspect, a cell provided herein already comprises a site-specific nuclease. In an aspect, a polynucleotide encoding a site-specific nuclease provided herein is stably transformed into a cell. In another aspect, a polynucleotide encoding a site-specific nuclease provided herein is transiently transformed into a cell. In another aspect, a polynucleotide encoding a site-specific nuclease is under the control of a regulatable promoter, a constitutive promoter, a tissue specific promoter, or any promoter useful for expression of the site-specific nuclease.

In an aspect, vectors comprising polynucleotides encoding a site-specific nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

In an aspect, a vector comprises in cis a cassette encoding a site-specific nuclease and an insertion sequence such that when contacted with the genome of a cell, the site-specific nuclease enables site-specific integration of the insertion sequence. In an aspect, a first vector comprises a cassette encoding a site-specific nuclease and a second vector comprises an insertion sequence such that when contacted with the genome of a cell, the site-specific nuclease provided in trans enables site-specific integration of the insertion sequence.

Site-specific nucleases provided herein can be used as part of a targeted editing technique. Non-limiting examples of site-specific nucleases used in methods and/or compositions provided herein include meganucleases, zinc finger nucleases (ZFNs), transcription activator-like effector nucleases (TALENs), RNA-guided nucleases (e.g., Cas9 and Cpf1), a recombinase (without being limiting, for example, a serine recombinase attached to a DNA recognition motif, a tyrosine recombinase attached to a DNA recognition motif), a transposase (without being limiting, for example, a DNA transposase attached to a DNA binding domain), or any combination thereof. In an aspect, a method provided herein comprises the use of one or more, two or more, three or more, four or more, or five or more site-specific nucleases to induce one, two, three, four, five, or more than five DSBs at one, two, three, four, five, or more than five target sites.

In an aspect, a genome editing system provided herein (e.g., a meganuclease, a ZFN, a TALEN, a CRISPR/Cas9 system, a CRISPR/Cpf1 system, a recombinase, a transposase), or a combination of genome editing systems provided herein, is used in a method to introduce one or more insertions, deletions, substitutions, or inversions to a locus in a cell to introduce a mutation, or generate a dominant negative allele or a dominant positive allele.

Site-specific nucleases, such as meganucleases, ZFNs, TALENs, Argonaute proteins (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, or modified versions thereof), Cas9 nucleases (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof), induce a double-strand DNA break at the target site of a genomic sequence that is then repaired by the natural processes of HR or NHEJ. Sequence modifications then occur at the cleaved sites, which can include inversions, deletions, or insertions that result in gene disruption in the case of NHEJ, or integration of nucleic acid sequences by HR.

In an aspect, a site-specific nuclease provided herein is selected from the group consisting of a zinc-finger nuclease, a meganuclease, an RNA-guided nuclease, a TALE-nuclease, a recombinase, a transposase, or any combination thereof. In another aspect, a site-specific nuclease provided herein is selected from the group consisting of a Cas9 or a Cpf1.

In another aspect a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a homolog thereof, or a modified version thereof. In another aspect, an RNA-guided nuclease provided herein is selected from the group consisting of a Cas9 or a Cpf1.

In another aspect an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a homolog thereof, or a modified version thereof.

In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

In an aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof, an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, modified versions thereof), a DNA guide for an Argonaute protein, and any combination thereof. In another aspect, an RNA-guided nuclease provided herein is selected from the group consisting of Cas9 and Cpf1.

In another aspect, an RNA-guided nuclease provided herein comprises Cas9. In an aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. In an aspect a site-specific nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, TtAgo, PfAgo, and NgAgo. In another aspect, an RNA-guided nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, TtAgo, PfAgo, and NgAgo.

A target site can be positioned in a polynucleotide sequence encoding a leader, an enhancer, a transcriptional start site, a promoter, a 5'-UTR, an exon, an intron, a 3'-UTR, a polyadenylation site, or a termination sequence. It will be appreciated that a target site can also be positioned upstream or downstream of a sequence encoding a leader, an enhancer, a transcriptional start site, a promoter, a 5'-UTR, an exon, an intron, a 3'-UTR, a polyadenylation site, or a termination sequence. In an aspect, a target site is positioned within 10, within 20, within 30, within 40, within 50, within 75, within 100, within 125, within 150, within 200, within 250, within 300, within 400, within 500, within 600, within 700, within 800, within 900, within 1000, within 1250, within 1500, within 2000, within 2500, within 5000, within 10,000, or within 25,000 nucleotides of a polynucleotide encoding a leader, an enhancer, a transcriptional start site, a promoter, a 5'-UTR, an exon, an intron, a 3'-UTR, a polyadenylation site, a gene, or a termination sequence.

In an aspect, a target site bound by an RNA-guided nuclease is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In an aspect, a targeted genome editing technique described herein can comprise the use of a recombinase. In an aspect, a tyrosine recombinase attached to a DNA recognition motif is selected from the group consisting of a Cre recombinase, a Gin recombinase a Flp recombinase, and a Tnpl recombinase. In an aspect, a Cre recombinase or a Gin recombinase provided herein is tethered to a zinc-finger DNA binding domain. The Flp-FRT site-directed recombination system comes from the 2μ plasmid from the baker's yeast Saccharomyces cerevisiae. In this system, Flp recombinase (flippase) recombines sequences between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, 1ox66, M2, M3, M7, or M11 site.

In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Several site-specific nucleases, such as recombinases, zinc finger nucleases (ZFNs), meganucleases, and TALENs, are not RNA-guided and instead rely on their protein structure to determine their target site for causing the DSB or nick, or they are fused, tethered or attached to a DNA-binding protein domain or motif.

ZFNs are synthetic proteins consisting of an engineered zinc finger DNA-binding domain fused to the cleavage domain of the FokI restriction nuclease. ZFNs can be designed to cleave almost any long stretch of double-stranded DNA for modification of the zinc finger DNA-binding domain. ZFNs form dimers from monomers composed of a non-specific DNA cleavage domain of FokI nuclease fused to a zinc finger array engineered to bind a target DNA sequence.

DNA-binding domain of a ZFN is typically composed of 3-4 zinc-finger arrays. The amino acids at positions −1, +2, +3, and +6 relative to the start of the zinc finger α-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

FokI nuclease domain requires dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can be re-engineered using one of various methods, customized ZFNs can theoretically be constructed to target nearly any target sequence (e.g., at or near a GA oxidase gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection, or *Agrobacterium*-mediated transformation). The ZFNs can be introduced as ZFN proteins, as polynucleotides encoding ZFN proteins, and/or as combinations of proteins and protein-encoding polynucleotides.

In an aspect, a method and/or composition provided herein comprises one or more, two or more, three or more, four or more, or five or more ZFNs. In another aspect, a ZFN provided herein is capable of generating a targeted DSB. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection or *Agrobacterium*-mediated transformation).

Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some aspects, a meganuclease can comprise a scaffold or base enzyme selected from the group consisting of I-CreI, I-CeuI, I-MsoI, I-SceI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease can be selected or engineered to bind to a genomic target sequence in a plant, such as at or near the genomic locus of a GA oxidase gene. In an aspect, a method and/or composition provided herein comprises one or more, two or more, three or more, four or more, or five or more meganucleases. In another aspect, a meganuclease provided herein is capable of generating a targeted DSB. In an aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI and FokI, AlwI, MlyI, SbfI, SdaI, StsI, CleDORF, Clo051, Pept071. When each member of a TALEN pair binds to the DNA sites flanking a target site, the FokI monomers dimerize and cause a double-stranded DNA break at the target site.

The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One*. 8: e82539). MutH is capable of introducing strand-specific nicks in DNA (see Gabsalilow et al. 2013. *Nucleic Acids Research*. 41: e83). TevI introduces double-stranded breaks in DNA at targeted sites (see Beurdeley et al., 2013. *Nature Communications*. 4: 1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122.; Cermak et al., *Nucleic Acids Research* (2011). 39:e82; and tale-nt.cac.cornell.edu/about.

In an aspect, a method and/or composition provided herein comprises one or more, two or more, three or more, four or more, or five or more TALENs. In another aspect, a TALEN provided herein is capable of generating a targeted DSB. In an aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation).

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase.

Provided in the present disclosure is a modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a GDH polypeptide, wherein the DNA sequence is operably linked to a plant-expressible promoter. In an aspect, the modified corn plant is semi-dwarf and has one or more improved ear traits, relative to a control corn plant that does not comprise both the one or more mutations or edits and the recombinant expression cassette. In another aspect, the one or more mutations or edits are selected from the group consisting of an insertion, a substitution, an inversion, a deletion, a duplication, and a combination thereof. In yet another aspect, the one or more mutations or edits are introduced using a meganuclease, a zinc-finger nuclease (ZFN), a RNA-guided endonuclease, a TALE-endonuclease (TALEN), a recombinase, or a transposase.

Also provided is a plurality of modified corn plants in a field, each modified corn plant comprising one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and a recombinant expression cassette comprising a DNA sequence encoding a GDH polypeptide, wherein the DNA sequence is operably linked to a plant-expressible promoter. In an aspect, the modified corn plants have increased yield relative to control corn plants. In another aspect, the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

Also provided is a genome edited or mutated corn plant comprising (1) a mutation or edit at or near an endogenous GA20 oxidase or GA3 oxidase gene, wherein the expression of the endogenous GA20 oxidase or GA3 oxidase gene is reduced relative to a wildtype control, and (2) a heterologous DNA sequence encoding a GDH polypeptide. In an aspect, the genome edited or mutated corn plant is semi-dwarf and has one or more improved ear traits, relative to a control corn plant that does not comprise both the mutation and the heterologous DNA sequence. In an aspect, a genome edited or mutated corn cell is obtained via a CRISPR based genome editing system.

Aspects of the present disclosure further include methods for making or producing modified plants, such as by genome editing, crossing, etc., wherein the method comprises editing the genomic locus of an endogenous GA3 or GA20 oxidase gene and introducing a transgene encoding one or more GDH polypeptide, and then regenerating or developing the modified plant from the edited plant cell.

In an aspect, a method comprises introducing a mutation or edit via CRISPR based genome editing at or near one or more endogenous GA3 or GA20 oxidase genes to reduce the expression of the one or more endogenous GA3 or GA20 oxidase genes. The method comprises creating a double-stranded break (DSB) in the genome of the plant cell, wherein a mutation or edit is introduced therein, thereby reducing the expression of the one or more endogenous GA3 or GA20 oxidase genes. In an aspect, the mutation or edit can be created (or integrated with a donor template) in a targeted manner into the genome of a cell at the location of a DSB via RNA-guided nucleases (e.g., Cas9 and Cpf1). In another aspect, a guide RNA recognizes a target site and acts in association with an RNA-guided nuclease that creates a DSB at the target site, wherein a mutation or edit is created (or integrated with a donor template) into the target site. In another aspect, the target site is near or at one or more endogenous GA3 or GA20 oxidase genes.

In an aspect, a method comprises introducing an insertion sequence encoding one or more GDH polypeptides into the genome of a plant cell via site-directed integration. Such a method comprises creating a DSB in the genome of the plant cell such that the insertion sequence is integrated at the site of the DSB. In an aspect, the insertion sequence encoding one or more GDH polypeptides can be inserted or integrated in a targeted manner into the genome of a cell at the location of a DSB via RNA-guided nucleases (e.g., Cas9 and Cpf1) in a CRISPR based genome editing system. In another aspect, a guide RNA recognizes a target site and acts in association with an RNA-guided nuclease that creates a double-stranded break at the target site, wherein the insertion sequence encoding one or more GDH polypeptides inserts or integrates into the target site.

In an aspect, an insertion sequence of a donor template of the present disclosure comprises a DNA sequence encoding a GDH polypeptide, wherein the GDH polypeptide sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 176-192.

In an aspect, an insertion sequence of a donor template of the present disclosure comprises a DNA sequence encoding a gdhA polypeptide, wherein the DNA sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169. In another aspect, an insertion sequence of the present disclosure comprises a DNA sequence encoding a polypeptide comprising an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a polypeptide or amino acid sequence selected from the group consisting of SEQ ID NO: 168 and a functional fragment thereof.

Provided in the present disclosure is a method for producing a modified corn plant, the method comprising: introducing into a corn cell a recombinant expression cassette comprising a DNA sequence encoding a GDH polypeptide, wherein the DNA sequence is operably linked to a plant-expressible promoter, and wherein the corn cell comprises one or more mutations and/or edits in one or more endogenous GA3 oxidase and/or GA20 oxidase genes; and regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits. In an aspect, the method further comprises introducing a recombinant DNA construct encoding a guide RNA that targets the one or more endogenous GA3 oxidase and/or GA20 oxidase genes.

In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes. In another aspect, In yet another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto. In an aspect, the guide RNA is a CRISPR RNA (crRNA) or a single-chain guide RNA (sgRNA), or the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

Also provided is a method for producing a genome edited or mutated corn plant, the method comprising: (a) introducing into a first corn cell a transgene that encodes one or more GDH polypeptides to create a genome edited or mutated corn cell, wherein the first corn cell has its expression of one or more endogenous GA3 oxidase genes or GA20 oxidase genes reduced relative to a wildtype control; and (b) generating a genome edited or mutated corn plant from the genome edited or mutated corn cell. In an aspect, the method further comprises identifying a genome edited or mutated corn plant with a desired trait. In another aspect, the identified genome edited or mutated corn plant is semi-dwarf and has one or more improved ear traits, relative to a control corn plant not having both the transgene and a reduced expression of one or more endogenous GA3 oxidase genes or GA20 oxidase genes.

In another aspect, the first corn cell of step (a) is obtained by being provided with a first guide RNA and a first RNA-guided nuclease, and wherein the genome edited or mutated corn cell of step (b) is obtained by being provided with a second guide RNA, an insertion sequence, and a second RNA-guided nuclease.

In another aspect, the first guide RNA recognizes a target site in a GA20 oxidase, wherein the first guide RNA acts in association with the first RNA-guided nuclease that creates a double-stranded break at the target site, and whereby the expression of the endogenous GA20 oxidase is reduced.

In another aspect, the method further comprises integrating into the double-stranded break at least one insertion, at least one substitution, at least one inversion, at least one deletion, at least one duplication, or a combination thereof.

In yet another aspect, the second guide RNA recognizes a target site and acts in association with the second RNA-guided nuclease that creates a double-stranded break at the target site, wherein the insertion sequence integrates into the target site, and wherein the donor/insertion sequence encodes a GDH polypeptide, such as gdhA polypeptide.

Provided in the present disclosure is A method for producing a modified corn plant, the method comprising: mutating or editing one or more endogenous GA3 oxidase genes and/or one or more GA20 oxidase genes in a corn cell, wherein the corn cell comprises a recombinant expression cassette encoding a GDH polypeptide, wherein the DNA sequence is operably linked to a plant-expressible promoter; and regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

In an aspect, the mutating or editing is obtained by using a site-specific nuclease selected from the group consisting of a RNA-guided endonuclease, a meganuclease, a zinc-finger nuclease (ZFN), a TALE-endonuclease (TALEN), a recombinase, and a transposase. In another aspect, a method further comprises introducing a recombinant DNA construct encoding a guide RNA that targets the one or more endogenous GA3 oxidase and/or GA20 oxidase genes. In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto. In another aspect, the guide RNA is a CRISPR RNA (crRNA) or a single-chain guide RNA (sgRNA). In yet another aspect, the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

Also provided is a method for producing a genome edited or mutated corn plant, the method comprising: (a) reducing the expression of one or more endogenous GA3 oxidase genes or GA20 oxidase genes in a first corn cell to create a genome edited or mutated corn cell, wherein the first corn cell comprises a transgene that encodes one or more GDH polypeptides; and (b) generating a genome edited or mutated corn plant from the genome edited or mutated corn cell. In an aspect, the method further comprises identifying a genome edited or mutated corn plant with a desired trait. In another aspect, the identified genome edited or mutated corn plant is semi-dwarf and has one or more improved ear traits, relative to a control corn plant not having both the transgene and a reduced expression of one or more endogenous GA3 oxidase genes or GA20 oxidase genes.

In an aspect, the first corn cell of step (a) is obtained by being provided with a first guide RNA, an insertion sequence, and a first RNA-guided nuclease, and wherein the genome edited or mutated corn cell of step (b) is obtained by being provided with a second guide RNA and a second RNA-guided nuclease.

In another aspect, the first guide RNA recognizes a target site and acts in association with the first RNA-guided nuclease that creates a double-stranded break at the target site, wherein the insertion sequence integrates into the target site, and wherein the insertion sequence encodes a gdhA polypeptide.

In another aspect, the second guide RNA recognizes a target site in a GA20 oxidase, wherein the second guide RNA acts in association with the second RNA-guided nuclease that creates a double-stranded break at the target site, and whereby the expression level of the endogenous GA20 oxidase is reduced.

The gRNA can be transformed or introduced into a plant cell or tissue (perhaps along with a nuclease, or nuclease-encoding DNA molecule, construct or vector) as a gRNA molecule, or as a recombinant DNA molecule, construct or vector comprising a transcribable DNA sequence encoding the guide RNA operably linked to a plant-expressible promoter. The guide sequence of the guide RNA can be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The guide sequence can be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

For genome editing at or near the GA20 oxidase_3 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 34 or a sequence complementary thereto (e.g., 12, 13, 14, 15, 16, 17, 18, 19, 20, 21, 22, 23, 24, 25 or more consecutive nucleotides of SEQ ID NO: 34 or a sequence complementary thereto).

For genome editing at or near the GA20 oxidase_4 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 38 or a sequence complementary thereto (e.g., 12, 13, 14, 15, 16, 17, 18, 19, 20, 21, 22, 23, 24, 25 or more consecutive nucleotides of SEQ ID NO: 38 or a sequence complementary thereto).

For genome editing at or near the GA20 oxidase_5 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 35 or a sequence complementary thereto (e.g., 10, 11, 12, 13, 14, 15, 16, 17, 18, 19, 20, 21, 22, 23, 24, 25 or more consecutive nucleotides of SEQ ID NO: 35 or a sequence complementary thereto).

In an aspect, a guide RNA for targeting an endogenous GA20 oxidase_3 and/or GA20 oxidase_5 gene is provided comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of any one or more of SEQ ID NOs: 138-167.

For genome editing at or near the GA3 oxidase_1 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 36 or a sequence complementary thereto (e.g., 10, 11, 12, 13, 14, 15, 16, 17, 18, 19, 20, 21, 22, 23, 24, 25 or more consecutive nucleotides of SEQ ID NO: 36 or a sequence complementary thereto).

For genome editing at or near the GA3 oxidase_2 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 37 or a sequence complementary thereto (e.g., 10, 11, 12, 13, 14, 15, 16, 17, 18, 19, 20, 21, 22, 23, 24, 25 or more consecutive nucleotides of SEQ ID NO: 37 or a sequence complementary thereto).

In an aspect, a guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 87, 91, 95, 98, 105, 109, 113, 117, 122, 126, 130 or 137, or a sequence complementary thereto.

In an aspect, a guide RNA comprises a sequence complementary to a protospacer adjacent motif (PAM) sequence present in the genome of a corn plant immediately adjacent to a target DNA sequence at or near the genomic locus of one or more endogenous GA20 or GA3 oxidase gene.

In addition to the guide sequence, a guide RNA can further comprise one or more other structural or scaffold sequence(s), which can bind or interact with an RNA-guided endonuclease. Such scaffold or structural sequences can further interact with other RNA molecules (e.g., tracrRNA). Methods and techniques for designing targeting constructs and guide RNAs for genome editing and site-directed integration at a target site within the genome of a plant using an RNA-guided endonuclease are known in the art.

Mutations such as deletions, insertions, inversions and/or substitutions can be introduced at a target site via imperfect repair of the DSB or nick to produce a knock-out or knock-down of a GA oxidase gene. Such mutations can be generated by imperfect repair of the targeted locus even without the use of a donor template molecule. A "knock-out" of a GA oxidase gene can be achieved by inducing a DSB or nick at or near the endogenous locus of the GA oxidase gene that results in non-expression of the GA oxidase protein or expression of a non-functional protein, whereas a "knock-down" of a GA oxidase gene can be achieved in a similar manner by inducing a DSB or nick at or near the endogenous locus of the GA oxidase gene that is repaired imperfectly at a site that does not affect the coding sequence of the GA oxidase gene in a manner that would eliminate the function of the encoded GA oxidase protein.

For example, the site of the DSB or nick within the endogenous locus can be in the upstream or 5' region of the GA oxidase gene (e.g., a promoter and/or enhancer sequence) to affect or reduce its level of expression. Similarly, such targeted knock-out or knock-down mutations of a GA oxidase gene can be generated with a donor template molecule to direct a particular or desired mutation at or near the target site via repair of the DSB or nick.

The donor template molecule can comprise a homologous sequence with or without an insertion sequence and comprising one or more mutations, such as one or more deletions, insertions, inversions and/or substitutions, relative to the targeted genomic sequence at or near the site of the DSB or nick. For example, targeted knock-out mutations of a GA oxidase gene can be achieved by deleting or inverting at least a portion of the gene or by introducing a frame shift or premature stop codon into the coding sequence of the gene. A deletion of a portion of a GA oxidase gene can also be introduced by generating DSBs or nicks at two target sites and causing a deletion of the intervening target region flanked by the target sites.

Provided herein is a recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a GDH polypeptide, wherein the DNA sequence is operably linked to a plant-expressible promoter.

In an aspect, the DNA donor template molecule comprises two of the homology sequences, wherein the two homology sequences flank the insertion sequence. In another aspect, the insertion sequence comprises a recombinant DNA construct or expression cassette comprising a DNA sequence encoding a GDH polypeptide, wherein the GDH polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-192.

In another aspect, the GDH polypeptide comprises an *E.coli* gdhA polypeptide. In another aspect, the DNA sequence comprised in the expression cassette comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169. In another aspect, the GDH polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168, or a functional fragment thereof. In another aspect, a recombinant DNA construct or expression cassette comprising a DNA sequence encoding a GDH polypeptide operably linked to a plant-expressible promoter. The plant-expressible promoter can comprise a DNA sequence that is at least 80%, at least 85%, at least 90%, at least 95%, at least 96%, at least 97%, at least 98%, at least 99%, at least 99.5% or 100% identical to SEQ ID NO: 170 or a functional portion thereof. In another aspect, the plant-expressible promoter is a constitutive promoter. In another aspect, the plant-expressible promoter is a leaf promoter. In another aspect, the plant-expressible promoter is selected from the group consisting of a stress-inducible promoter, a nitrogen-inducible promoter, a drought-inducible promoter, a root promoter, and a combination thereof.

In another aspect, a DNA donor template molecule further comprises a transcribable DNA sequence encoding a non-coding RNA for suppression of one or more GA20 oxidase genes and/or one or more GA3 oxidase genes, wherein the transcribable DNA sequence is operably linked to a promoter.

In an aspect, a donor template comprising at least one homology sequence or homology arm, wherein the at least one homology sequence or homology arm is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence, wherein the target DNA sequence is a genomic sequence at or near the genomic locus of an endogenous GA oxidase gene of a corn or cereal plant.

In another aspect, the at least one homology sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In an aspect, a donor template comprising two homology arms including a first homology arm and a second homology arm, wherein the first homology arm comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a first flanking DNA sequence, wherein the second homology arm comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a second flanking DNA sequence, and wherein the first flanking DNA sequence and the second flanking DNA sequence are genomic sequences at or near the genomic locus of an endogenous GA oxidase gene of a corn or cereal plant.

In another aspect, each of the two homology arms is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In another aspect, the method further comprises integrating into the double-stranded break at least one insertion, at least one substitution, at least one inversion, at least one deletion, at least one duplication, or a combination thereof.

In yet another aspect, an insertion sequence of a donor template comprises a sequence encoding a protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 168 and 176-192.

Further provided is a method for producing a modified corn plant, the method comprising: (a) crossing a first corn plant with a second corn plant to create a modified corn plant, wherein the expression of one or more endogenous GA3 oxidase genes or GA20 oxidase genes is reduced in the first corn plant relative to a wildtype control, and wherein the second corn plant comprising a transgene encoding one or more GDH polypeptides; and (b) producing an offspring of the modified corn plant of step (a). In an aspect, the method further comprises identifying a modified corn plant with a desired trait. In another aspect, the identified modified corn plant is semi-dwarf and has one or more improved ear traits, relative to a control corn plant not having both the transgene and a reduced expression of one or more endogenous GA3 oxidase genes or GA20 oxidase genes.

In an aspect, a target site can comprise at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides.

In an aspect, the target site is a GA3 oxidase 1 gene. In another aspect, the target site is a GA3 oxidase_2 gene. In yet another aspect, the target site is a combination of the GA3 oxidase_1 and GA3 oxidase_2 genes. In still another aspect, the target site is within the open reading frame of the GA3 oxidase_1 or GA3 oxidase_2 gene. In still another aspect, the target site is within the promoter/enhancer of the GA3 oxidase 1 or GA3 oxidase 2 gene. In still another aspect, the target site is within the intron of the GA3 oxidase 1 or GA3 oxidase_2 gene. In still another aspect, the target site is within the 5'UTR of the GA3 oxidase_1 or GA3 oxidase_2 gene. In still another aspect, the target site is within the 3'UTR of the GA3 oxidase_1 or GA3 oxidase_2 gene.

In an aspect, the target site is a GA20 oxidase_3 gene. In another aspect, the target site is a GA20 oxidase_4 gene. In another aspect, the target site is a GA20 oxidase_5 gene. In yet another aspect, the target site is a combination of the GA20 oxidase_3 gene, GA20 oxidase_4 gene, and GA20 oxidase_5 gene. In still another aspect, the target site is within the open reading frame of the GA20 oxidase_3, GA20 oxidase_4, or GA20 oxidase_5 gene. In still another aspect, the target site is within the promoter/enhancer of the GA20 oxidase_3, GA20 oxidase_4, or GA20 oxidase_5 gene. In still another aspect, the target site is within the intron of the GA20 oxidase_3, GA20 oxidase_4, or GA20 oxidase_5 gene. In still another aspect, the target site is within the 5'UTR of the GA20 oxidase 3, GA20 oxidase 4, or GA20 oxidase_5 gene. In still another aspect, the target site is within the 3'UTR of the GA20 oxidase_3, GA20 oxidase_4, or GA20 oxidase_5 gene.

In an aspect, the target site comprises a nucleotide sequence selected from the group consisting of SEQ ID NOs: 34, 35, and 38.

A targeted genome editing technique provided herein can comprise the use of one or more, two or more, three or more, four or more, or five or more donor molecules or templates. A "donor template" can be a single-stranded or double-stranded DNA or RNA molecule or plasmid.

According to other aspects, an insertion sequence of a donor template can comprise a transcribable DNA sequence that encodes a non-coding RNA molecule, which targets one or more GA oxidase gene(s), such as a GA3 oxidase or GA20 oxidase gene(s), for suppression. In an aspect, the transcribable DNA sequence that encodes a non-coding RNA for the suppression of the GA3 oxidase and/or GA20 oxidase gene(s) is selected from the group consisting of SEQ ID NOs: 35-38. In another aspect, an insertion sequence of a donor template can comprise a DNA sequence encoding one or more GDH polypeptides, wherein the DNA sequence encodes protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 168 and 176-192. In yet another aspect, an insertion sequence of a donor template can comprise a first transcribable DNA sequence encoding a non-coding RNA molecule for the suppression of the one or more GA3 oxidase or GA20 oxidase gene(s), wherein the first transcribable DNA sequence is selected from the group consisting of SEQ ID NOs: 35-38; and an insertion sequence of a donor template can comprise a second DNA sequence encoding one or more GDH polypeptides, wherein the second DNA sequence encodes a protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 168 and 176-192, or a functional fragment thereof.

An insertion sequence provided herein can be of any length. For example, a donor or insertion sequence provided herein is between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000 or between 20 and 10,000 nucleotides in length.

In an aspect, a sequence can be inserted into a double-stranded break created by a CRISPR based genome editing system without the presence of a donor template. In an aspect, at least one insertion, at least one substitution, at least one deletion, at least one duplication, and/or at least one inversion can be inserted/introduced into a double-stranded break created by a CRISPR based genome editing system via non-homologous end joining (NHEJ) without a donor template. In an aspect, at least one insertion, at least one substitution, at least one deletion, at least one duplication, and/or at least one inversion can be inserted/introduced into a double-stranded break created by a CRISPR based genome editing system via homologous recombination (HR) with a donor template.

According to other aspects, at least one insertion is integrated into the double-stranded break at the GA3 oxidase or GA20 oxidase locus and introduces a premature stop codon therein which leads to truncation of the GA3 oxidase or GA20 oxidase proteins and subsequent suppression of the GA3 oxidase or GA20 oxidase genes. In an aspect, the at least one insertion is a single nucleobase insertion. In another aspect, the single nucleobase insertion is selected from the group consisting of guanine, cytosine, adenine, thymine, and uracil. In an aspect, the at least one insertion is inserted within the open reading frame of the GA3 oxidase or GA20 oxidase gene. In another aspect, the at least one insertion is inserted within the promoter/enhancer, intron, 5'UTR, 3'UTR, or a combination thereof.

In another aspect, the at least one insertion at the GA3 oxidase or GA20 oxidase locus comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

According to an aspect, at least one substitution is integrated into the double-stranded break at the GA3 oxidase or GA20 oxidase locus that leads to the suppression of the GA3 oxidase or GA20 oxidase gene. In an aspect, the at least one substitution is integrated within the open reading frame of the GA3 oxidase or GA20 oxidase gene. In another aspect, the at least one substitution is integrated within the promoter/enhancer, intron, 5'UTR, 3'UTR, or a combination thereof.

According to an aspect, at least one deletion is introduced into the double-stranded break at the GA3 oxidase or GA20 oxidase locus that leads to the suppression of the GA3 oxidase or GA20 oxidase gene. In an aspect, the at least one deletion is introduced within the open reading frame of the GA3 oxidase or GA20 oxidase gene. In another aspect, the at least one deletion is introduced within the promoter/enhancer, intron, 5'UTR, 3'UTR, or a combination thereof.

According to an aspect, at least one duplication is introduced into the double-stranded break at the GA3 oxidase or GA20 oxidase locus that leads to the suppression of the GA3 oxidase or GA20 oxidase gene. In an aspect, the at least one duplication is introduced within the open reading frame of the GA3 oxidase or GA20 oxidase gene. In another aspect, the at least one duplication is introduced within the promoter/enhancer, intron, 5'UTR, 3'UTR, or a combination thereof.

According to an aspect, at least one inversion is integrated into the double-stranded break at the GA3 oxidase or GA20 oxidase locus that leads to the suppression of the GA3 oxidase or GA20 oxidase gene. In an aspect, the at least one inversion is integrated within the open reading frame of the GA3 oxidase or GA20 oxidase gene. In another aspect, the at least one inversion is integrated within the promoter/enhancer, intron, 5'UTR, 3'UTR, or a combination thereof.

According to an aspect, a recombinant DNA construct or vector can comprise a first polynucleotide sequence encoding a site-specific nuclease and a second polynucleotide sequence encoding a guide RNA that can be introduced into a plant cell together via plant transformation techniques. Alternatively, two recombinant DNA constructs or vectors can be provided including a first recombinant DNA construct or vector and a second DNA construct or vector that can be introduced into a plant cell together or sequentially via plant transformation techniques, where the first recombinant DNA construct or vector comprises a polynucleotide sequence encoding a site-specific nuclease and the second recombinant DNA construct or vector comprises a polynucleotide sequence encoding a guide RNA.

According to an aspect, a recombinant DNA construct or vector comprising a polynucleotide sequence encoding a site-specific nuclease can be introduced via plant transformation techniques into a plant cell that already comprises (or is transformed with) a recombinant DNA construct or vector comprising a polynucleotide sequence encoding a guide RNA. Alternatively, a recombinant DNA construct or vector comprising a polynucleotide sequence encoding a guide RNA can be introduced via plant transformation techniques into a plant cell that already comprises (or is transformed with) a recombinant DNA construct or vector comprising a polynucleotide sequence encoding a site-specific nuclease. According to yet further aspects, a first plant comprising (or transformed with) a recombinant DNA construct or vector comprising a polynucleotide sequence encoding a site-specific nuclease can be crossed with a second plant comprising (or transformed with) a recombinant DNA construct or vector comprising a polynucleotide sequence encoding a guide RNA. Such recombinant DNA constructs or vectors can be transiently transformed into a plant cell or stably transformed or integrated into the genome of a plant cell.

In an aspect, vectors comprising polynucleotides encoding a site-specific nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

Dwarf or semi-dwarf corn disclosed herein can have characteristics that make it suitable for grain and forage production, especially, production in short-season environments. In particular, limited heat units in short-season environments reduce grain yield and lessen the probability of the crop reaching physiological maturity in a given year. The disclosed dwarf or semi-dwarf corn plants require fewer heat units (e.g., required 10%) than conventional hybrids to reach anthesis and generally reach physiological maturity earlier than conventional cultivars. Semi-dwarf corn plants disclosed herein are less prone to stalk and root lodging due to the shorter stalks and lower ear placement. Corn plants disclosed herein also have the potential to produce high-quality forage due to its high ear-to-stover ratio.

Short stature or semi-dwarf corn plants can also have one or more additional traits, including, but not limited to, increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, increased seed number, increased seed weight, and increased prolificacy, and/or increased harvest index.

According to aspects of the present disclosure, modified, transgenic, or genome edited/mutated cereal or corn plants are provided that have at least one beneficial agronomic trait and at least one female reproductive organ or ear that is substantially or completely free of off-types. The beneficial agronomic trait can include, but is not limited to, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. As used herein, “harvest index” refers to the mass of the harvested grain divided by the total mass of the above-ground biomass of the plant over a harvested area.

In an aspect, a modified, transgenic, or genome edited/mutated corn plant exhibits improved lodging resistance, reduced green snap, or both, relative to a control corn plant.

In an aspect, the height at maturity of a modified, transgenic, or genome edited/mutated corn plant exhibiting semi-dwarf phenotype is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, relative to a control corn plant grown under comparable conditions.

According to another aspect of the present disclosure, a modified, transgenic, or genome edited/mutated corn plant provided herein comprises a height that is between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 15%, between 1% and 10%, between 1% and 5%, or between 1% and 2%, of that of a control plant grown under comparable conditions.

According to another aspect of the present disclosure, a modified, transgenic, or genome edited/mutated corn plant provided herein comprises a height that is between 2% and 75%, between 5% and 75%,between 10% and 75%, between 15% and 75%, between 20% and 75%, between 25% and 75%, between 30% and 75%, between 35% and 75%, between 40% and 75%, between 45% and 75%, between 50% and 75%, between 55% and 75%, between 60% and 75%, between 65% and 75%, or between 70% and 75%, of that of a control plant grown under comparable conditions.

According to another aspect of the present disclosure, a modified, transgenic, or genome edited/mutated corn plant provided herein comprises a foliar nitrogen percentage that is between 0.02% and 10%, between 0.04% and 9.5%, between 0.06% and 9.0%, between 0.08% and 8.5%, between 0.1% and 8.0%, between 0.2% and 7.5%, between 0.3% and 7.0%, between 0.4% and 6.5%, between 0.5% and 6.0%, between 0.6% and 5.5%, between 0.7% and 5.0%, between 0.8% and 4.5%, between 0.9% and 4.0%, between 1.0% and 3.5%, between 1.5% and 3.0%, or between 2.0% and 2.5%, greater than that of a control plant grown under comparable conditions.

According to another aspect of the present disclosure, a modified, transgenic, or genome edited/mutated corn plant provided herein comprises a foliar nitrogen percentage that is between 0.02% and 0.04%, between 0.04% and 0.06%, between 0.06% and 0.08%, between 0.08% and 0.1%, between 0.1% and 0.2%, between 0.2% and 0.3%, between 0.3% and 0.4%, between 0.4% and 0.5%, between 0.5% and 0.6%, between 0.6% and 0.7%, between 0.7% and 0.8%, between 0.8% and 0.9%, between 0.9% and 1.0%, between 1.0% and 1.5%, between 1.5% and 2.0%, between 2.0% and 2.5%, between 2.5% and 3.0%, between 3.0% and 3.5%, between 3.5% and 4.0%, between 4.0% and 4.5%, between 4.5% and 5.0%, between 5.0% and 5.5%, between 5.5% and 6.0%, between 6.0% and 6.5%, between 6.5% and 7.0%, between 7.0% and 7.5%, between 7.5% and 8.0%, between 8.0% and 8.5%, between 8.5% and 9.0%, between 9.0% and 9.5%, or between 9.5% and 10.0%, greater than that of a control plant grown under comparable conditions.

In an aspect, the foliar nitrogen percentage of a transgenic corn plant or genome edited/mutated corn plant is increased by at least 0.02%, at least 0.04%, at least 0.06%, at least 0.08%, at least 0.1%, at least 0.2%, at least 0.3%, at least 0.4%, at least 0.5%, at least 0.6%, at least 0.7%, at least 0.8%, at least 0.9%, at least 1.0%, at least 1.5%, at least 2.0%, at least 2.5%, at least 3.0%, at least 3.5%, at least 4.0%, at least 4.5%, at least 5.0%, at least 5.5%, at least 6.0%, at least 6.5%, at least 7.0%, at least 7.5%, at least 8.0%, at least 8.5%, at least 9.0%, at least 9.5%, at least 10%, relative to a control corn plan grown under comparable conditions.

According to another aspect of the present disclosure, a modified, transgenic, or genome edited/mutated corn plant provided herein comprises a foliar nitrogen percentage that is between 0.02% and 10%, between 0.04% and 10%, between 0.06% and 10%, between 0.08% and 10%, between 1.0% and 10%, between 1.5% and 10%, between 2% and 10%, between 2.5% and 10%, between 3% and 10%, between 3.5% and 10%, between 4% and 10%, between 4.5% and 10%, between 5% and 10%, between 5.5% and 10%, between 6% and 10%, between 6.5% and 10%, between 7% and 10%, between 7.5% and 10%, between 8% and 10%, between 8.5% and 10%, between 9% and 10%, between 9.5% and 10%, greater than that of a control corn plan grown under comparable conditions.

According to another aspect of the present disclosure, a modified, transgenic, or genome edited/mutated corn plant provided herein comprises a foliar nitrogen percentage that is between 0.02% and 9.5%, between 0.02% and 9.0%, between 0.02% and 8.5%, between 0.02% and 8.0%, between 0.02% and 7.5%, between 0.02% and 7.0%, between 0.02% and 6.5%, between 0.02% and 6.0%, between 0.02% and 5.5%, between 0.02% and 5.0%, between 0.02% and 4.5%, between 0.02% and 4.0%, between 0.02% and 3.5%, between 0.02% and 3.0%, between 0.02% and 2.5%, between 0.02% and 2.0%, between 0.02% and 1.5%, between 0.02% and 1.0%, between 0.02% and 0.9%, between 0.02% and 0.8%, between 0.02% and 0.7%, between 0.02% and 0.6%, between 0.02% and 0.5%, between 0.02% and 0.4%, between 0.02% and 0.3%, between 0.02% and 0.2%, between 0.02% and 0.1%, between 0.02% and 0.08%, between 0.02% and 0.06%, between 0.02% and 0.04%, greater than that that of a control corn plan grown under comparable conditions.

In another aspect, the yield of a modified, transgenic, or genome edited/mutated exhibiting semi-dwarf phenotype is equal to or more then the yield of a control plant grown under comparable conditions.

In another aspect, a modified, transgenic, or genome edited/mutated corn plant exhibiting semi-dwarf phenotype requires about 5%, 10%, 15%, 20%, or 25% fewer heat units than a control plant to reach anthesis.

In yet another aspect, a modified, transgenic, or genome edited/mutated corn plant exhibiting semi-dwarf phenotype has a relative maturity of about 10%, 15%, 20%, 25%, 30%, 35%, 40%, or 45% fewer days than the relative maturity of a control plant grown under comparable conditions.

According to an aspect of the present disclosure, a modified, transgenic, or genome edited/mutated corn plant provided herein comprises a height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm and an average stem diameter of at least 17.5 mm, at least 18 mm, at least 18.5 mm, at least 19 mm, at least 19.5 mm, at least 20 mm, at least 20.5 mm, at least 21 mm, at least 21.5 mm, or at least 22 mm. According to another aspect the modified corn plant further comprises at least one ear that is substantially free of mature male reproductive tissue.

According to aspects of the present disclosure, modified, transgenic, or genome edited/mutated corn plants are provided that comprise a plant height during late vegetative and/or reproductive stages of development (e.g., at R3 stage) of between 1000 mm and 1800 mm, between 1000 mm and 1700 mm, between 1050 mm and 1700 mm, between 1100 mm and 1700 mm, between 1150 mm and 1700 mm, between 1200 mm and 1700 mm, between 1250 mm and 1700 mm, between 1300 mm and 1700 mm, between 1350 mm and 1700 mm, between 1400 mm and 1700 mm, between 1450 mm and 1700 mm, between 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, between 1350 mm and 1600 mm, between 1400 mm and 1600 mm, between 1450 mm and 1600 mm, of between 1000 mm and 2000 mm, between 1200 mm and 2000 mm, between 1200 mm and 1800 mm, between 1300 mm and 1700 mm, between 1400 mm and 1700 mm, between 1400 mm and 1600 mm, between 1400 mm and 1700 mm, between 1400 mm and 1800 mm, between 1400 mm and 1900 mm, between 1400 mm and 2000 mm, or between 1200 mm and 2500 mm, and/or an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. A modified corn plant can be substantially free of off-types, such as male reproductive tissues or structures in one or more ears of the modified corn plant.

According to an aspect of the present disclosure a modified, transgenic, or genome edited/mutated corn plant provided herein comprises a height of between 1000 mm and 1600 mm, 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, or between 1000 mm and 1300 mm, and an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. According to another aspect the modified corn plant further comprises at least one ear that is substantially free of mature male reproductive tissue.

According to an aspect of the present disclosure, a modified, transgenic, or genome edited/mutated corn plant provided herein comprises a height that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the height of a control plant and a stalk or stem diameter that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the stem diameter of a control plant.

According to an aspect of the present disclosure, a modified, transgenic, or genome edited/mutated corn plant provided herein comprises a fresh ear weight that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the fresh ear weight of a control plant.

According to an aspect of the present disclosure, a population of modified, transgenic, or genome edited/mutated corn plants provided herein comprises a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% lower as compared to a population of unmodified control plants. According to another aspect of the present disclosure, a population of modified corn plants provided herein comprises a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% lower as compared to a population of control plants.

According to an aspect of the present disclosure, modified, transgenic, or genome edited/mutated corn plants are provided that comprise an average internode length (or a minus-2 internode length and/or minus-4 internode length relative to the position of the ear) that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the same or average internode length of a control plant.

The "minus-2 internode" of a corn plant refers to the second internode below the ear of the plant, and the "minus-4 internode" of a corn plant refers to the fourth internode below the ear of the plant. According to many aspects, modified, transgenic, or genome edited/mutated corn plants are provided that have an average internode length (or a minus-2 internode length and/or minus-4 internode length relative to the position of the ear) that is between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the same or average internode length of a control plant.

A modified, transgenic, or genome edited/mutated corn plant can have a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater than the harvest index of a wild-type or control plant. A modified corn plant can have a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater than the harvest index of a control plant.

According to an aspect of the present disclosure, modified, transgenic, or genome edited/mutated corn plants are provided that have an increase in harvestable yield of at least 1 bushel per acre, at least 2 bushels per acre, at least 3 bushels per acre, at least 4 bushels per acre, at least 5 bushels per acre, at least 6 bushels per acre, at least 7 bushels per acre, at least 8 bushels per acre, at least 9 bushels per acre, or at least 10 bushels per acre, relative to a wild-type or control plant. A modified corn plant can have an increase in harvestable yield between 1 and 10, between 1 and 8, between 2 and 8, between 2 and 6, between 2 and 5, between 2.5 and 4.5, or between 3 and 4 bushels per acre. A modified corn plant can have an increase in harvestable yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, or at least 25% greater than the harvestable yield of a wild-type or control plant. A modified corn plant can have a harvestable yield that is between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 25%, between 2% and 10%, between 2% and 9%, between 2% and 8%, between 2% and 7%, between 2% and 6%, between 2% and 5%, or between 2% and 4% greater than the harvestable yield of a control plant.

According to an aspect, the present disclosure provides a population of a modified, transgenic, or genome edited/mutated corn plants, where the population of a modified, transgenic, or genome edited/mutated corn plants shares ancestry with a single a modified, transgenic, or genome edited/mutated corn plant, where the population of a modified, transgenic, or genome edited/mutated corn plants comprises an average height of 1500 mm or less, wherein the population of a modified, transgenic, or genome edited/mutated corn plants comprises an average stalk or stem diameter of 18 mm or more, wherein less than 5%, less than 10%, less than 15%, less than 20%, or less than 25% of the population of modified, transgenic, or genome edited/mutated corn plants comprises a height of greater than 1500 mm, and where less than 5%, less than 10%, less than 15%, less than 20%, or less than 25% of the population of a modified, transgenic, or genome edited/mutated corn plants comprises at least one ear comprising mature male reproductive tissue. In another aspect the population of a modified, transgenic, or genome edited/mutated corn plants comprises an average height of 1200 mm or less.

According to an aspect, the present disclosure provides a population of a modified, transgenic, or genome edited/mutated corn plants, where the population of a modified, transgenic, or genome edited/mutated corn plants share ancestry with a single modified corn plant, where the population of a modified, transgenic, or genome edited/mutated corn plants comprises an average height of 1500 mm or less, where less than 5%, less than 10%, less than 15%, less than 20%, or less than 25% of the population of modified corn plants comprises a height of greater than 1500 mm, and where the population of a modified, transgenic, or genome edited/mutated corn plants comprises a lodging frequency that is at least 5%, at least 10%, at least 20%, at least 30%, at least 40%, at least 50%, at least 60%, at least 70% at least 80%, at least 90%, or 100% lower as compared to a population of control corn plants.

According to an aspect, the present disclosure provides a modified, transgenic, or genome edited/mutated corn plant comprising a height of 1500 mm or less, where the a modified, transgenic, or genome edited/mutated corn plant further comprises a stalk or stem diameter of 18 mm or more, and where at least one ear of the a modified, transgenic, or genome edited/mutated corn plant is substantially free of mature male reproductive tissue.

According to an aspect, the present disclosure provides a modified, transgenic, or genome edited/mutated corn plant comprising a height of 1500 mm or less, wherein the a modified, transgenic, or genome edited/mutated corn plant further comprises a harvest index of at least 0.58, and where the a modified, transgenic, or genome edited/mutated corn plant further comprises at least one ear that is substantially free of mature male reproductive tissue.

According to an aspect of the present disclosure, modified, transgenic, or genome edited/mutated corn plants are provided having a significantly reduced or eliminated expression level of one or more GA3 oxidase and/or GA20 oxidase gene transcript(s) and/or protein(s) in one or more tissue(s), such as one or more stem, internode, leaf and/or vascular tissue(s), of the modified, transgenic, or genome edited/mutated plants, as compared to the same tissue(s) of wild-type or control plants. In an aspect, the level of one or more GA3 oxidase and/or GA20 oxidase gene transcript(s) and/or protein(s), or one or more GA oxidase (or GA oxidase-like) gene transcript(s) and/or protein(s), in one or more stem, internode, leaf and/or vascular tissue(s) of a modified corn plant can be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a control corn or cereal plant.

According to an aspect of the present disclosure, modified, transgenic, or genome edited/mutated cereal or corn plants are provided that have at least one beneficial agronomic trait and at least one female reproductive organ or ear that is substantially or completely free of off-types. The beneficial agronomic trait can include, for example, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. A modified, transgenic, or genome edited/mutated cereal or corn plant can have a female reproductive organ or ear that appears normal relative to a control or wild-type plant. Indeed, modified, transgenic, or genome edited/mutated cereal or corn plants are provided that comprise at least one reproductive organ or ear that does not have or exhibit, or is substantially or completely free of, off-types including male sterility, reduced kernel or seed number, and/or masculinized structure(s) in one or more female organs or ears.

A modified, transgenic, or genome edited/mutated cereal or corn plant is provided herein that lacks significant off-types in the reproductive tissues of the plant. Off-types can include male (tassel or anther) sterility, reduced kernel or seed number, and/or the presence of one or more masculinized or male (or male-like) reproductive structures in the female organ or ear (e.g., anther ear) of the plant.

As used herein, a female organ or ear of a plant, such as corn, is "substantially free" of male reproductive structures if male reproductive structures are absent or nearly absent in the female organ or ear of the plant based on visual inspection of the female organ or ear at later reproductive stages. A female organ or ear of a plant, such as corn, is "completely free" of mature male reproductive structures if male reproductive structures are absent or not observed or observable in the female organ or ear of the plant, such as a corn plant, by visual inspection of the female organ or ear at later reproductive stages.

In an aspect, a modified, transgenic, or genome edited/mutated corn plant exhibits increased ear area relative to a control corn plant.

According to an aspect of the present disclosure, a modified, transgenic, or genome edited/mutated corn plant exhibits an increase in ear area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear area that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear area that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear area that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear area that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased ear volume relative to a control corn plant grown under comparable conditions.

According to an aspect of the present disclosure, a modified, transgenic, or genome edited/mutated corn plant exhibits an increase in ear volume by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear volume that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear volume that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear volume that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear volume that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased ear diameter relative to a control corn plant grown under comparable conditions.

According to an aspect of the present disclosure, a modified, transgenic, or genome edited/mutated corn plant exhibits an ear diameter that is at least 0.2%, at least 0.4%, at least 0.6%, at least 0.8%, at least 1.0%, at least 1.2%, at least 1.4%, at least 1.6%, at least 1.8%, at least 2.0%, at least 2.2%, at least 2.4%, at least 2.6%, at least 2.8%, at least 3.0%, at least 3.2%, at least 3.4%, at least 3.6%, at least 3.8%, at least 4.0%, at least 4.5%, at least 5.0%, at least 5.5%, at least 6.0%, at least 6.5%, at least 7.0%, at least 7.5%, at least 8.0%, at least 8.5%, at least 9.0%, at least 9.5%, at least 10.0%, relative to a control corn plant.

According to an aspect of the present disclosure, a modified, transgenic, or genome edited/mutated corn plant exhibits an ear diameter that is between 0.2% and 10.0%, between 0.4% and 10.0%, between 0.6% and 10.0%, between 0.8% and 10.0%, between 1.0% and 10.0%, between 1.2% and 10.0%, between 1.4% and 10.0%, between 1.6% and 10.0%, between 1.8% and 10.0%, between 2.0% and 10.0%, between 2.2% and 10.0%, between 2.4% and 10.0%, between 2.6% and 10.0%, between 2.8% and 10.0%, between 3.0% and 10.0%, between 3.2% and 10.0%, between 3.4% and 10.0%, between 3.6% and 10.0%, between 3.8% and 10.0%, between 4.0% and 10.0%, between 4.5% and 10.0%, between 5.0% and 10.0%, between 5.5% and 10.0%, between 6.0% and 10.0%, between 6.5% and 10.0%, between 7.0% and 10.0%, between 7.5% and 10.0%, between 8.0% and 10.0%, between 8.5% and 10.0%, between 9.0% and 10.0%, or between 9.5% and 10.0%, greater than that of a control corn plant grown under comparable conditions.

According to an aspect of the present disclosure, a modified, transgenic, or genome edited/mutated corn plant exhibits an ear diameter that is between 0.2% and 9.5%, between 0.2% and 9.0%, between 0.2% and 8.5%, between 0.2% and 8.0%, between 0.2% and 7.5%, between 0.2% and 7.0%, between 0.2% and 6.5%, between 0.2% and 6.0%, between 0.2% and 5.5%, between 0.2% and 5.0%, between 0.2% and 4.5%, between 0.2% and 4.0%, between 0.2% and 3.8%, between 0.2% and 3.6%, between 0.2% and 3.4%, between 0.2% and 3.2%, between 0.2% and 3.0%, between 0.2% and 2.8%, between 0.2% and 2.6%, between 0.2% and 2.4%, between 0.2% and 2.2%, between 0.2% and 2.0%, between 0.2% and 1.8%, between 0.2% and 1.6%, between 0.2% and 1.4%, between 0.2% and 1.2%, between 0.2% and 1.0%, between 0.2% and 0.8%, between 0.2% and 0.6%, or between 0.2% and 0.4%, greater than that of a control corn plant grown under comparable conditions.

According to an aspect of the present disclosure, a modified, transgenic, or genome edited/mutated corn plant exhibits an ear diameter that is between 0.4% and 9.5%, between 0.6% and 9.0%, between 0.8% and 8.5%, between 1.0% and 8.0%, between 1.2% and 7.5%, between 1.4% and 7.0%, between 1.6% and 6.5%, between 1.8% and 6.0%, between 2.0% and 5.5%, between 2.2% and 5.0%, between 2.4% and 4.5%, between 2.6% and 4.0%, between 2.8% and 3.8%, between 3.0% and 3.6%, or between 3.2% and 3.4%, greater than that of a control corn plant grown under comparable conditions.

According to an aspect of the present disclosure, a modified, transgenic, or genome edited/mutated corn plant exhibits an ear diameter that is between 0.2% and 0.6%, between 0.6% and 1.0%, between 1.0% and 1.4%, between 1.4% and 1.8%, between 1.8% and 2.2%, between 2.2% and 2.6%, between 2.6% and 3.0%, between 3.0% and 3.5%, between 3.5% and 4.0%, between 4.0% and 4.5%, between 4.5% and 5.0%, between 5.0% and 5.5%, between 5.5% and 6.0%, between 6.0% and 6.5%, between 6.5% and 7.0%, between 7.0% and 7.5%, between 7.5% and 8.0%, between 8.0% and 8.5%, between 8.5% and 9.0%, between 9.0% and 9.5%, or between 9.5% and 10.0%, greater than that of a control corn plant grown under comparable conditions.

In an aspect, a modified, transgenic, or genome edited/mutated corn plant exhibits increased ear length relative to a control corn plant grown under comparable conditions.

According to an aspect of the present disclosure, a modified, transgenic, or genome edited/mutated corn plant exhibits an increase in ear length by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear length that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a corn plant grown under comparable conditions.

According to an aspect of the present disclosure, a modified, transgenic, or genome edited/mutated corn plant exhibits an ear length that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear length that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear length that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits decreased ear tip void relative to a control corn plant grown under comparable conditions.

According to an aspect of the present disclosure, a modified, transgenic, or genome edited/mutated corn plant exhibits a decrease in ear tip void by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear tip void that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% less than that of a control corn plant grown under comparable conditions.

According to an aspect of the present disclosure, a modified, transgenic, or genome edited/mutated corn plant exhibits an ear tip void that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% less than that of a control corn plant grown under comparable conditions.

According to an aspect of the present disclosure, a modified, transgenic, or genome edited/mutated corn plant exhibits an ear tip void that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% less than that of a control corn plant grown under comparable conditions.

According to an aspect of the present disclosure, a modified, transgenic, or genome edited/mutated corn plant exhibits an ear tip void that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% less than that of a control corn plant grown under comparable conditions.

In an aspect, a modified, transgenic, or genome edited/mutated corn plant exhibits an increased number of kernels per ear relative to a control corn plant grown under comparable conditions.

According to an aspect of the present disclosure, a modified, transgenic, or genome edited/mutated corn plant exhibits an increase in number of kernels per ear by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits kernels per ear that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits kernels per ear that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits kernels per ear that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits kernels per ear that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased single kernel weight relative to a control corn plant grown under comparable conditions.

According to an aspect of the present disclosure, a modified, transgenic, or genome edited/mutated corn plant exhibits an increase in single kernel weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits a single kernel weight that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits a single kernel weight that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits a single kernel weight that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits a single kernel weight that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits a single kernel weight that is between 1% and 2%, between 2% and 3%, between 3% and 4%, between 4% and 5%, between 5% and 6%, between 6% and 7%, between 7% and 8%, between 8% and 9%, or between 9% and 10% greater than that of a control corn plant grown under comparable conditions.

In an aspect, a modified, transgenic, or genome edited/mutated corn plant exhibits increased ear fresh weight relative to a control corn plant.

According to an aspect of the present disclosure, a modified, transgenic, or genome edited/mutated corn plant exhibits an increased ear fresh weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control corn plant grown under comparable conditions.

According to an aspect of the present disclosure, a modified, transgenic, or genome edited/mutated corn plant exhibits an ear fresh weight that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%,between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear fresh weight that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear fresh weight that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear fresh weight that is between 1% and 5%, between 5% and 10%, between 10% and 15%, between 15% and 20%, between 20% and 25%, between 25% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits an ear fresh weight that is between 1% and 2%, between 2% and 3%, between 3% and 4%, between 4% and 5%, between 5% and 6%, between 6% and 7%, between 7% and 8%, between 8% and 9%, between 9% and 10%, between 10% and 11%, between 11% and 12%, between 12% and 13%, between 13% and 14%, between 14% and 15%, between 15% and 16%, between 16% and 17%, between 17% and 18%, between 18% and 19%, between 19% and 20%, between 20% and 21%, between 21% and 22%, between 22% and 23%, between 23% and 24%, between 24% and 25%, between 25% and 26%, between 26% and 27%, between 27% and 28%, between 28% and 29%, between 29% and 30%, greater than that of a control corn plant grown under comparable conditions.

In an aspect, a modified, transgenic, or genome edited/mutated corn plant exhibits an increased yield relative to a control corn plant.

According to an aspect of the present disclosure, a modified, transgenic, or genome edited/mutated corn plant exhibits an increased yield by at least 1%, at least 3%, at least 5%, at least 7%, at least 9%, at least 11%, at least 13%, at least 15%, at least 17%, at least 19%, at least 21%, at least 23%, at least 25%, at least 27%, at least 29%, at least 31%, at least 33%, at least 35%, at least 37%, at least 39%, at least 41%, at least 43%, at least 45%, at least 47%, at least 49%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits a yield that is between 1% and 100%, between 3% and 100%, between 5% and 100%, between 7% and 100%, between 9% and 100%, between 11% and 100%, between 13% and 100%, between 15% and 100%, between 17% and 100%, between 19% and 100%, between 21% and 100%, between 23% and 100%, between 25% and 100%, between 27% and 100%, between 29% and 100%, between 31% and 100%, between 33% and 100%, between 35% and 100%, between 37% and 100%, between 39% and 100%, between 41% and 100%, between 43% and 100%, between 45% and 100%, between 47% and 100%, between 49% and 100%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, greater than that of a control corn plant grown under comparable conditions.

According to an aspect of the present disclosure, a modified, transgenic, or genome edited/mutated corn plant exhibits a yield that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 49%, between 1% and 47%, between 1% and 45%, between 1% and 43%, between 1% and 41%, between 1% and 39%, between 1% and 37%, between 1% and 35%, between 1% and 33%, between 1% and 31%, between 1% and 29%, between 1% and 27%, between 1% and 25%, between 1% and 23%, between 1% and 21%, between 1% and 19%, between 1% and 17%, between 1% and 15%, between 1% and 13%, between 1% and 11%, between 1% and 9%, between 1% and 7%, between 1% and 5%, or between 1% and 3%, greater than that of a control corn plant grown under comparable conditions.

According to an aspect of the present disclosure, a modified, transgenic, or genome edited/mutated corn plant exhibits a yield that is between 3% and 95%, between 5% and 90%, between 7% and 85%, between 9% and 80%, between 11% and 75%, between 13% and 70%, between 15% and 65%, between 17% and 60%, between 19% and 55%, between 21% and 50%, between 23% and 49%, between 25% and 47%, between 27% and 45%, between 29% and 43%, between 31% and 41%, between 33% and 39%, or between 35% and 37%, greater than that of a control corn plant grown under comparable conditions.

According to an aspect of the present disclosure, a modified, transgenic, or genome edited/mutated corn plant exhibits a yield that is between 1% and 7%, between 7% and 13%, between 13% and 19%, between 19% and 25%, between 25% and 31%, between 31% and 37%, between 37% and 43%, between 43% and 49%, between 49% and 55%, between 55% and 60%, between 60% and 65%, between 65% and 70%, between 70% and 75%, between 75% and 80%, between 80% and 85%, between 85% and 90%, between 90% and 95%, or between 95% and 100%, greater than that of a control corn plant grown under comparable conditions.

In an aspect, modified, transgenic, or genome edited/mutated corn plants exhibit increased kernels per field area relative to control corn plants.

According to an aspect of the present disclosure, modified, transgenic, or genome edited/mutated corn plants exhibit increased kernels per field area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to control corn plants.

According to an aspect of the present disclosure, modified, transgenic, or genome edited/mutated corn plants exhibit kernels per field area that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of control corn plants grown under comparable conditions.

According to an aspect of the present disclosure, modified, transgenic, or genome edited/mutated corn plants exhibit kernels per field area that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of control corn plants grown under comparable conditions.

According to an aspect of the present disclosure, modified, transgenic, or genome edited/mutated corn plants exhibit kernels per field area that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of control corn plants grown under comparable conditions.

According to an aspect of the present disclosure, modified, transgenic, or genome edited/mutated corn plants exhibit kernels per field area that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of control corn plants grown under comparable conditions.

According to an aspect of the present disclosure, modified, transgenic, or genome edited/mutated corn plants exhibit kernels per field area that is between 1% and 3%, between 3% and 5%, between 5% and 7%, between 7% and 9%, between 9% and 11%, between 11% and 13%, between 13% and 15%, between 15% and 17%, between 17% and 19%, between 19% and 21%, between 21% and 23%, between 23% and 25%, between 25% and 27%, between 27% and 29%, or between 29% and 30% greater than that of control corn plants grown under comparable conditions.

A modified, transgenic, or genome edited/mutated corn plant disclosed in the present disclosure can display a positive trait interaction in which a trait, such as a positive or negative trait, attributable to a transgene (or mutation or edit) can be enhanced, out-performed, neutralized, offset or mitigated due to the presence of a second transgene (or mutation or edit). Such a transgenic and/or genome edited/mutated corn plant can exhibit improved ear traits as compared to a control corn plant comprising only one transgene (or mutation or edit). For example, GA20Ox_SUP/gdhA stack plants can have enhanced traits and/or positive trait interactions relative to gdhA single and/or GA20Ox_SUP single plants, in terms of increased ear fresh weight, ear area, ear volume, ear diameter, ear length, kernels per ear, single kernel weight, yield, and/or decreased ear tip void.

In another aspect, a modified, transgenic, or genome edited/mutated corn plant of the present disclosure exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to a control corn plant.

In yet another aspect, a modified, transgenic, or genome edited/mutated corn plant of the present disclosure does not have any significant off-types in at least one female organ or ear.

According to an aspect of the present disclosure, a modified, transgenic, or genome edited/mutated corn plant has no or reduced adverse effect over a trait or phenotype selected from the group consisting of senescence, delayed flowering, fungal infection, and a combination thereof, relative to a control corn plant.

Short stature or semi-dwarf corn plants can also have one or more additional traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

According to an aspect of the present disclosure, a modified, transgenic, or genome edited/mutated corn plant provided herein comprises a harvest index of at least 0.57, at least 0.58, at least 0.59, at least 0.60, at least 0.61, at least 0.62, at least 0.63, at least 0.64, or at least 0.65. According to another aspect of the present disclosure a modified, transgenic, or genome edited/mutated corn plant provided herein comprises a harvest index of between 0.57 and 0.65, between 0.57 and 0.64, between 0.57 and 0.63, between 0.57 and 0.62, between 0.57 and 0.61, between 0.57 and 0.60, between 0.57 and 0.59, between 0.57 and 0.58, between 0.58 and 0.65, between 0.59 and 0.65, or between 0.60 and 0.65. According to yet another aspect of the present disclosure, a modified, transgenic, or genome edited/mutated corn plant provided herein comprises a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater as compared to an unmodified control plant. According to still another aspect of the present disclosure, a modified, transgenic, or genome edited/mutated corn plant provided herein comprises a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater as compared to a control plant.

According to another aspect of the present disclosure, methods are provided for planting a modified or transgenic plant(s) provided herein at a normal/standard or high density in field. According to some aspects, the yield of a crop plant per acre (or per land area) can be increased by planting a modified or transgenic plant(s) of the present disclosure at a higher density in the field. As described herein, modified or transgenic plants expressing a transcribable DNA sequence that encodes a non-coding RNA molecule targeting one or more endogenous GA20 and/or GA3 oxidase gene for suppression and a transgene encoding one or more GDH polypeptide, can have reduced plant height, shorter internode(s), increased stalk/stem diameter, and/or increased lodging resistance. Modified or transgenic plants described herein can tolerate high density planting conditions since an increase in stem diameter can resist lodging and the shorter plant height can allow for increased light penetrance to the lower leaves under high density planting conditions. Thus, modified or transgenic plants provided herein can be planted at a higher density to increase the yield per acre (or land area) in the field. For row crops, higher density can be achieved by planting a greater number of seeds/plants per row length and/or by decreasing the spacing between rows. In an aspect, the row spacing for high density planting of the modified, transgenic, or genome edited/mutated corn plants is less than or equal to 40 inches. In an aspect, the row spacing for high density planting of the modified, transgenic, or genome edited/mutated corn plants is less than or equal to 30 inches. In another aspect, the row spacing for high density planting of the modified, transgenic, or genome edited/mutated corn plants is less than or equal to 20 inches.

According to an aspect, seeds of a modified or transgenic crop plants can be planted at a density in the field (plants per land/field area) that is at least 5%, 10%, 15%, 20%, 25%, 50%, 75%, 100%, 125%, 150%, 175%, 200%, 225%, or 250% higher than the normal planting density for that crop plant according to standard agronomic practices. A modified or transgenic crop plant can be planted at a density in the field of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, or at least 56,000 plants per acre.

As an example, seeds of corn plants can be planted at a higher density, such as in a range from about 38,000 plants per acre to about 60,000 plants per acre, or about 40,000 plants per acre to about 58,000 plants per acre, or about 42,000 plants per acre to about 58,000 plants per acre, or about 40,000 plants per acre to about 45,000 plants per acre, or about 45,000 plants per acre to about 50,000 plants per acre, or about 50,000 plants per acre to about 58,000 plants per acre, or about 52,000 plants per acre to about 56,000 plants per acre, or about 38,000 plants per acre, about 42,000 plant per acre, about 46,000 plant per acre, or about 48,000 plants per acre, about 50,000 plants per acre, or about 52,000 plants per acre, or about 54,000 plant per acre, as opposed to a standard density range, such as about 18,000 plants per acre to about 38,000 plants per acre.

Exemplary Embodiments

The following are exemplary embodiments of the present specification.

1. A modified corn plant or a plant part thereof comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a glutamate dehydrogenase (GDH) polypeptide.

2. The modified corn plant of embodiment 1, wherein the first and second recombinant expression cassettes are stably integrated into the genome of the corn plant or plant part thereof.

3. The modified corn plant or plant part thereof of embodiment 1, wherein the modified corn plant is semi-dwarf and has one or more improved ear traits, relative to a control corn plant that does not have the first or second recombinant expression cassette.

4. The modified corn plant or plant part thereof of embodiments 1 to 3, wherein the transcribable DNA sequence encodes a non-coding RNA for suppression of a GA3 oxidase gene.

5. The modified corn plant or plant part thereof of embodiment 4, wherein the transcribable DNA sequence encodes a non-coding RNA for suppression of a GA3 oxidase_1 gene, a GA3 oxidase_2 gene, or both.

6. The modified corn plant or plant part thereof of embodiment 5, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

7. The modified corn plant or plant part thereof of embodiment 5, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

8. The modified corn plant or plant part thereof of embodiments 1 to 3, wherein the transcribable DNA sequence encodes a non-coding RNA for suppression of a GA20 oxidase gene.

9. The modified corn plant or plant part thereof of embodiment 8, wherein the transcribable DNA sequence encodes a non-coding RNA for suppression of a GA20 oxidase_3 gene, a GA20 oxidase_4 gene, a GA20 oxidase_5 gene, or a combination thereof.

10. The modified corn plant or plant part thereof of embodiment 8, wherein the transcribable DNA sequence encodes a non-coding RNA for suppression of a GA20 oxidase_3 gene, a GA20 oxidase_5 gene, or both.

11. The modified corn plant or plant part thereof of embodiment 10, wherein the transcribable DNA sequence comprises a sequence that is at least 60% identical or complementary to at least 15 consecutive nucleotides of SEQ ID NO: 39, 53, or 55.

12. The modified corn plant or plant part thereof of embodiment 10, wherein the transcribable DNA sequence encodes a sequence that is at least 60% identical or complementary to at least 15 consecutive nucleotides of SEQ ID NO: 40, 54, or 56.

13. The modified corn plant or plant part thereof of any one of embodiments 4 to 10, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

14. The modified corn plant or plant part thereof of any one of embodiments 4 to 10, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

15. The modified corn plant or plant part thereof of embodiment 1, 2, or 3, wherein the second recombinant expression cassette comprises a DNA sequence encoding a GDH polypeptide.

16. The modified corn plant or plant part thereof of embodiment 15, wherein the GDH polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-192.

17. The modified corn plant or plant part thereof of any one of embodiments 1 to 3, wherein the GDH polypeptide comprises an *Escherichia coli* (*E.coli*) gdhA polypeptide.

18. The modified corn plant or plant part thereof of any one of embodiments 1 to 16, wherein the DNA sequence comprised in the second recombinant expression cassette comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

19. The modified corn plant or plant part thereof of any one of embodiments 1 to 16, wherein the GDH polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

20. The modified corn plant or plant part thereof of embodiment 1 or 3, wherein the expression level of an endogenous GA20 oxidase or GA3 oxidase gene is reduced or eliminated in the modified corn plant or plant part thereof.

21. The modified corn plant or plant part thereof of embodiment 1 or 3, wherein the transcribable DNA sequence is operably linked to a heterologous plant-expressible promoter.

22. The modified corn plant or plant part thereof of embodiment 21, wherein the heterologous plant-expressible promoter is a vascular promoter.

23. The modified corn plant or plant part thereof of embodiment 22, wherein the vascular promoter is selected from the group consisting of a sucrose synthase promoter, a sucrose transporter promoter, a Sh1 promoter, Commelina yellow mottle virus (CoYMV) promoter, a wheat dwarf geminivirus (WDV) large intergenic region (LIR) promoter, a maize streak geminivirus (MSV) coat polypeptide (CP) promoter, a rice yellow stripe 1 (YS1)-like promoter, a rice yellow stripe 2 (OsYSL2) promoter, and a combination thereof.

24. The modified corn plant or plant part thereof of embodiment 23, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70 or SEQ ID NO: 71, or a functional portion thereof.

25. The modified corn plant or plant part thereof of embodiment 21, wherein the heterologous plant-expressible promoter is a rice tungro bacilliform virus (RTBV) promoter.

26. The modified corn plant or plant part thereof of embodiment 25, wherein RTBV promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

27. The modified corn plant or plant part thereof of embodiment 21, wherein the heterologous plant-expressible promoter is a leaf promoter.

28. The modified corn plant or plant part thereof of embodiment 27, wherein the leaf promoter is selected from the group consisting of a RuBisCO promoter, a pyruvate phosphate dikinase (PPDK) promoter, a fructose 1-6 bisphosphate aldolase (FDA) promoter, a Nadh-Gogat promoter, a chlorophyll a/b binding polypeptide gene promoter, a phosphoenolpyruvate carboxylase (PEPC) promoter, a Myb gene promoter, and a combination thereof.

29. The modified corn plant or plant part thereof of embodiment 28, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

30. The modified corn plant or plant part thereof of embodiment 21, wherein the heterologous plant-expressible promoter is a constitutive promoter.

31. The modified corn plant or plant part thereof of embodiment 30, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

32. The modified corn plant or plant part thereof of embodiment 31, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

33. The modified corn plant or plant part thereof of embodiment 1 or 3, wherein the non-coding RNA is a precursor miRNA or siRNA capable of being processed or cleaved to form a mature miRNA or siRNA.

34. The modified corn plant or plant part thereof of embodiment 1 or 3, wherein the DNA sequence comprised in the second recombinant expression cassette is operably linked to a heterologous plant-expressible promoter.

35. The modified corn plant or plant part thereof of embodiment 34, wherein the heterologous plant-expressible promoter is a constitutive promoter.

36. The modified corn plant or plant part thereof of embodiment 35, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

37. The modified corn plant or plant part thereof of embodiment 34, wherein the heterologous plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 170 or a functional portion thereof.

38. The modified corn plant or plant part thereof of embodiment 34, wherein the heterologous plant-expressible promoter is a leaf promoter.

39. The modified corn plant or plant part thereof of embodiment 38, wherein the leaf promoter is selected from the group consisting of a RuBisCO promoter, a PPDK promoter, a FDA promoter, a Nadh-Gogat promoter, a chlorophyll a/b binding polypeptide gene promoter, a PEPC promoter, a Myb gene promoter, and a combination thereof.

40. The modified corn plant or plant part thereof of embodiment 34, wherein the heterologous plant-expressible promoter is selected from the group consisting of a stress-inducible promoter, a nitrogen-inducible promoter, a drought-inducible promoter, a root promoter, and a combination thereof.

41. The modified corn plant or plant part thereof of any one of embodiments 1 to 36, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

42. The modified corn plant or plant part thereof of any one of embodiments 1 to 41, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

43. The modified corn plant or plant part thereof of any one of embodiments 1 to 42, wherein the modified corn plant exhibits improved lodging resistance, reduced green snap, or both, relative to a control corn plant.

44. The modified corn plant or plant part thereof of embodiments 1 to 43, wherein the modified corn plant exhibits increased ear diameter relative to the control corn plant.

45. The modified corn plant or plant part thereof of embodiment 44, wherein the modified corn plant exhibits an increase in ear diameter by at least 0.2%, at least 0.4%, at least 0.6%, at least 0.8%, at least 1.0%, at least 1.2%, at least 1.4%, at least 1.6%, at least 1.8%, at least 2.0%, at least 2.2%, at least 2.4%, at least 2.6%, at least 2.8%, at least 3.0%, at least 3.2%, at least 3.4%, at least 3.6%, at least 3.8%, or at least 4.0%, relative to the control corn plant.

46. The modified corn plant or plant part thereof of embodiments 1 to 45, wherein the modified corn plant exhibits increased single kernel weight relative to the control corn plant.

47. The modified corn plant or plant part thereof of embodiment 46, wherein the modified corn plant exhibits an increase in singe kernel weight by at least at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to the control corn plant.

48. The modified corn plant or plant part thereof of any one of embodiments 1 to 47, wherein the modified corn plant exhibits increased ear fresh weight relative to the control corn plant.

49. The modified corn plant or plant part thereof of embodiment 48, wherein the modified corn plant exhibits increased ear fresh weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30%, relative to the control corn plant.

50. The modified corn plant or plant part thereof of any one of embodiments 1 to 49, wherein the modified corn plant exhibits increased yield relative to the control corn plant.

51. The modified corn plant or plant part thereof of embodiment 50, wherein the modified corn plant exhibits an increase in yield by at least 1%, at least 3%, at least 5%, at least 7%, at least 9%, at least 11%, at least 13%, at least 15%, at least 17%, at least 19%, at least 21%, at least 23%, at least 25%, at least 27%, at least 29%, at least 31%, at least 33%, at least 35%, at least 37%, at least 39%, at least 41%, at least 43%, or at least 45%, relative to the control corn plant.

52. The modified corn plant or plant part thereof of any one of embodiments 1 to 51, wherein the modified corn plant exhibits increased ear area relative to the control corn plant.

53. The modified corn plant or plant part thereof of embodiment 52, wherein the modified corn plant exhibits an increase in ear area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to the control corn plant.

54. The modified corn plant or plant part thereof of any one of embodiments 1 to 53, wherein the modified corn plant exhibits increased ear volume relative to the control corn plant.

55. The modified corn plant or plant part thereof of embodiment 54, wherein the modified corn plant exhibits an increase in ear volume by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to the control corn plant.

56. The modified corn plant or plant part thereof of any one of embodiments 1 to 55, wherein the modified corn plant exhibits increased ear length relative to the control corn plant.

57. The modified corn plant or plant part thereof of embodiment 56, wherein the modified corn plant exhibits an increase in ear length by at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%, at least 16%, at least 17%, at least 18%, at least 19%, or at least 20%, relative to the control corn plant.

58. The modified corn plant or plant part thereof of any one of embodiments 1 to 57, wherein the modified corn plant exhibits decreased ear tip void relative to the control corn plant.

59. The modified corn plant or plant part thereof of embodiment 58, wherein the modified corn plant exhibits a decrease in ear tip void by at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%, at least 16%, at least 17%, at least 18%, at least 19%, or at least 20%, relative to the control corn plant.

60. The modified corn plant or plant part thereof of any one of embodiments 1 to 59, wherein the modified corn plant exhibits increased kernels per ear relative to the control corn plant.

61. The modified corn plant or plant part thereof of embodiment 60, wherein the modified corn plant exhibits an increase in kernels per ear by at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%, at least 16%, at least 17%, at least 18%, at least 19%, or at least 20%, relative to the control corn plant.

62. The modified corn plant or plant part thereof of any one of embodiments 1 to 61, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to the control corn plant.

63. The modified corn plant or plant part thereof of any one of embodiments 1 to 62, wherein the modified corn plant does not have any significant off-types in at least one female organ or ear.

64. A seed of the modified corn plant of any one of embodiments 1 to 63, wherein the seed comprises the first and second recombinant expression cassettes.

65. The seed of embodiment 64, wherein a progeny plant grown from the seed is semi-dwarf and has one or more improved ear traits, relative to a control corn plant that does not comprise the first or second recombinant expression cassette.

66. A commodity or commodity product produced from the seed of embodiment 64, comprising the first and second DNA sequence recombinant expression cassettes.

67. A method comprising planting the seed of embodiment 64 in a growth medium or soil.

68. The method of embodiment 67, further comprising planting a plurality of the seeds with a row spacing of less than or equal to 40 inches.

69. The method of embodiment 67, further comprising planting a plurality of the seeds with a row spacing of less than or equal to 30 inches.

70. The method of embodiment 69, wherein the row spacing is less than or equal to 20 inches.

71. The method of embodiment 67, further comprising growing a corn plant from the seed.

72. The method of embodiment 71, further comprising harvesting a seed from the corn plant.

73. The method of any one of embodiments 69 to 72, wherein the seed is planted at a density selected from the group consisting of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, and at least 56,000 plants per acre.

74. A plurality of modified corn plants in a field, each modified corn plant comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a GDH polypeptide.

75. The plurality of modified corn plants of embodiment 74, wherein the modified corn plants have increased yield relative to control corn plants.

76. The plurality of modified corn plants of embodiment 74 or 75, wherein the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

77. A method for producing a modified corn plant, the method comprising:

a. introducing into a corn cell a first recombinant expression cassette comprising a DNA sequence encoding a GDH polypeptide, wherein the corn cell comprises a second recombinant expression cassette comprising a transcribable DNA sequence encoding a non-coding RNA for suppression of one or more GA3 oxidase genes and/or one or more GA20 oxidase genes; and b. regenerating or developing a modified corn plant from the corn cell, wherein the modified corn plant comprises the first and second recombinant expression cassettes.

78. The method of embodiment 77, wherein the introducing is via site-directed integration using a site-specific nuclease.

79. The method of embodiment 78, wherein the site-specific nuclease is selected from the group consisting of a RNA-guided endonuclease, a meganuclease, a zinc-finger nuclease (ZFN), a TALE-endonuclease (TALEN), a recombinase, and a transposase.

80. The method of embodiment 77, wherein the introducing is via *Agrobacterium*-mediated transformation.

81. The method of embodiment 77, wherein the introducing is via particle bombardment.

82. The method of any one of embodiments 77 to 81, wherein the transcribable DNA sequence encodes a non-coding RNA for suppression of a GA3 oxidase_1 gene, a GA3 oxidase_2 gene, or both.

83. The method of embodiment 82, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

84. The method of embodiment 82, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

85. The method of any one of embodiments 77 to 81, wherein the transcribable DNA sequence encodes a non-coding RNA for suppression of a GA20 oxidase gene.

86. The method of embodiment 85, wherein the transcribable DNA sequence encodes a non-coding RNA for suppression of a GA20 oxidase_3 gene, a GA20 oxidase_4 gene, a GA20 oxidase_5 gene, or a combination thereof.

87. The method of embodiment 86, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

88. The method of embodiment 86, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

89. The method of any one of embodiments 77 to 88, wherein the GDH polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-192.

90. The method of any one of embodiments 77 to 88, wherein the GDH polypeptide comprises an *E.coli* gdhA polypeptide.

91. The method of any one of embodiments 77 to 88, wherein the DNA sequence comprised in the first recombinant expression cassette comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

92. The method of any one of embodiments 77 to 88, wherein the GDH polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

93. The modified corn plant of embodiment 77, wherein the first and second recombinant expression cassettes are stably integrated into the genome of the corn cell.

94. The method of embodiment 77, further comprising selecting a modified corn plant having a desired trait.

95. The method of embodiment 94, wherein the selected modified corn plant is semi-dwarf and has one or more improved ear traits, relative to a control corn plant not having the first or the second recombinant expression cassettes.

96. The method of embodiment 94 or 95, wherein the selecting a modified corn plant having a desired trait comprises the use of one or more molecular techniques.

97. The method of embodiment 96, wherein the one or more molecular techniques are selected from the group consisting of Southern analysis, polymerase chain reaction (PCR) amplification, Northern blots, RNase protection, primer extension, reverse transcription PCR (RT-PCR), Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.

98. The method of any one of embodiments 77 to 97, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

99. The method of any one of embodiments 77 to 98, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

100. The method of any one of embodiments 77 to 98, wherein the modified corn plant exhibit an ear trait selected from the group consisting of increased ear fresh weight, increased ear area, increased ear volume, increased ear diameter, increased ear length, increased kernels per ear, increased single kernel weight, increased yield, decreased ear tip void, and a combination thereof, relative to a control corn plant.

101. The method of any one of embodiments 77 to 98, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to a control corn plant.

102. A method for producing a modified corn plant, the method comprising:

a. introducing into a corn cell a first recombinant expression cassette comprising a transcribable DNA sequence encoding a non-coding RNA for suppression of one or more GA3 oxidase genes and/or GA20 oxidase genes, wherein the corn cell comprises a second recombinant expression cassette comprising a DNA sequence encoding a GDH polypeptide; and b. regenerating or developing a modified corn plant from the corn cell, wherein the modified corn plant comprises the first and second recombinant expression cassettes.

103. The method of embodiment 102, wherein the introducing is via site-directed integration using a site-specific nuclease.

104. The method of embodiment 103, wherein the site-specific nuclease is selected from the group consisting of a RNA-guided endonuclease, a meganuclease, a zinc-finger nuclease (ZFN), a TALE-endonuclease (TALEN), a recombinase, and a transposase.

105. The method of embodiment 102, wherein the introducing is via *Agrobacterium*-mediated transformation.

106. The method of embodiment 102, wherein the introducing is via particle bombardment.

107. The method of any one of embodiments 102 to 106, wherein the transcribable DNA sequence encodes a non-coding RNA for suppression of a GA3 oxidase_1 gene, a GA3 oxidase_2 gene, or both.

108. The method of embodiment 107, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

109. The method of embodiment 107, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

110. The method of any one of embodiments 102 to 106, wherein the transcribable DNA sequence encodes a non-coding RNA for suppression of a GA20 oxidase gene.

111. The method of embodiment 110, wherein the transcribable DNA sequence encodes a non-coding RNA for suppression of a GA20 oxidase_3 gene, a GA20 oxidase_4 gene, a GA20 oxidase_5 gene, or a combination thereof.

112. The method of embodiment 111, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

113. The method of embodiment 111, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

114. The method of any one of embodiments 102 to 113, wherein the GDH polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-192.

115. The method of any one of embodiments 102 to 113, wherein the GDH polypeptide comprises an *E.coli* gdhA polypeptide.

116. The method of any one of embodiments 102 to 113, wherein the DNA sequence comprised in the second recombinant expression cassette comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

117. The method of any one of embodiments 102 to 113, wherein the GDH polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

118. The modified corn plant of embodiment 102, wherein the first and second recombinant expression cassettes are stably integrated into the genome of the corn cell.

119. The method of embodiment 102, further comprising selecting a modified corn plant having a desired trait.

120. The method of embodiment 119, wherein the selected modified corn plant is semi-dwarf and has one or more improved ear traits, relative to a control corn plant not having the first or the second recombinant expression cassette.

121. The method of embodiment 119 or 120, wherein the selecting a modified corn plant having a desired trait comprises the use of one or more molecular techniques.

122. The method of embodiment 121, wherein the one or more molecular techniques are selected from the group consisting of Southern analysis, PCR amplification, Northern blots, RNase protection, primer extension, RT-PCR, Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.

123. The method of any one of embodiments 102 to 122, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

124. The method of any one of embodiments 102 to 123, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

125. The method of any one of embodiments 102 to 124, wherein the modified corn plant exhibit an ear trait selected from the group consisting of increased ear fresh weight, increased ear area, increased ear volume, increased ear diameter, increased ear length, increased kernels per ear, increased single kernel weight, increased yield, decreased ear tip void, and a combination thereof, relative to a control corn plant.

126. The method of any one of embodiments 102 to 125, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to a control corn plant.

127. A method for producing a modified corn plant, the method comprising a. introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a GDH polypeptide; and b. regenerating or developing a modified corn plant from the corn cell, wherein the modified corn plant comprises the first and second recombinant expression cassettes.

128. A method for producing a modified corn plant, the method comprising a. introducing into a corn cell a first recombinant expression cassette comprising a transcribable DNA sequence encoding a non-coding RNA for suppression of one or more GA3 oxidase genes and/or GA20 oxidase genes;

b. introducing into the corn cell of step (a) a second recombinant expression cassette comprising a DNA sequence encoding a GDH polypeptide to create a modified corn cell; and c. regenerating or developing a modified corn plant from the modified corn cell of step (b), wherein the modified corn plant comprises the first and second recombinant expression cassettes.

129. A method for producing a modified corn plant, the method comprising a. introducing into a corn cell a first recombinant expression cassette comprising a DNA sequence encoding a GDH polypeptide;

b. introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and c. regenerating or developing a modified corn plant from the modified corn cell of step (b), wherein the modified corn plant comprises the first and second recombinant expression cassettes.

130. A method for producing a modified corn plant, the method comprising:

a. crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a GDH polypeptide; and b. producing a progeny corn plant comprising the recombinant expression cassette and has the reduced expression of the one or more endogenous GA3 oxidase genes and/or GA20 oxidase genes.

131. The method of embodiment 130, wherein the first and second modified corn plants are obtained via site-directed integration using a site-specific nuclease.

132. The method of embodiment 131, wherein the site-specific nuclease is selected from the group consisting of a RNA-guided endonuclease, a meganuclease, a zinc-finger nuclease (ZFN), a TALE-endonuclease (TALEN), a recombinase, and a transposase.

133. The method of embodiment 130, wherein the first and second modified corn plants are obtained via *Agrobacterium*-mediated transformation.

134. The method of embodiment 130, wherein the first and second modified corn plants are obtained via particle bombardment.

135. The method of embodiment 130 to 134, wherein the first modified corn plant and the progeny corn plant comprise a transcribable DNA sequence encoding a non-coding RNA for suppression of a GA3 oxidase_1 gene, a GA3 oxidase_2 gene, or both.

136. The method of embodiment 135, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

137. The method of embodiment 135, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

138. The method of any one of embodiments 130 to 134, wherein the transcribable DNA sequence encodes a non-coding RNA for suppression of a GA20 oxidase gene.

139. The method of embodiment 138, wherein the transcribable DNA sequence encodes a non-coding RNA for suppression of a GA20 oxidase_3 gene, a GA20 oxidase_4 gene, a GA20 oxidase_5 gene, or a combination thereof.

140. The method of embodiment 139, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

141. The method of embodiment 139, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

142. The method of any one of embodiments 130 to 141, wherein the second modified corn plant and the progeny corn plant comprise a recombinant expression cassette comprising a DNA sequence encoding a GDH polypeptide.

143. The method of embodiment 142, wherein the GDH polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-192.

144. The method of any one of embodiments 130 to 141, wherein the GDH polypeptide comprises an *E. coli* gdhA polypeptide.

145. The method of any one of embodiments 130 to 141, wherein the DNA sequence comprised in the second modified corn plant comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

146. The method of any one of embodiments 130 to 141, wherein the GDH polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

147. The method of embodiment 130, further comprising selecting a progeny corn plant having a desired trait.

148. The method of embodiment 147, wherein the selected progeny corn plant is semi-dwarf and has one or more improved ear traits, relative to a control corn plant.

149. The method of embodiment 147 or 148, wherein the selecting a progeny corn plant having a desired trait comprises the use of one or more molecular techniques.

150. The method of embodiment 149, wherein the one or more molecular techniques are selected from the group consisting of Southern analysis, PCR amplification, Northern blots, RNase protection, primer extension, RT-PCR, Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.

151. The method of any one of embodiments 130 to 150, wherein the height at maturity of the progeny corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

152. The method of any one of embodiments 130 to 151, wherein the stalk or stem diameter of the progeny corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

153. The method of any one of embodiments 130 to 152, wherein the progeny corn plant exhibit an ear trait selected from the group consisting of increased ear fresh weight, increased ear area, increased ear volume, increased ear diameter, increased ear length, increased kernels per ear, increased single kernel weight, increased yield, decreased ear tip void, and a combination thereof, relative to a control corn plant.

154. The method of any one of embodiments 130 to 153, wherein the progeny corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to a control corn plant.

155. A method for producing a modified corn plant, the method comprising:

a. introducing into a corn cell a recombinant expression cassette comprising a DNA sequence encoding a GDH polypeptide, wherein the DNA sequence is operably linked to a plant-expressible promoter, and wherein the corn cell comprises one or more mutations and/or edits in one or more endogenous GA3 oxidase and/or GA20 oxidase genes; and
b. regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

156. The method of embodiment 155, further comprising introducing a recombinant DNA construct encoding a guide RNA that targets the one or more endogenous GA3 oxidase and/or GA20 oxidase genes.

157. The method of embodiment 156, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

158. The method of embodiment 157, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto.

159. The method of any one of embodiments 156 to 158, wherein the guide RNA is a CRISPR RNA (crRNA) or a single-chain guide RNA (sgRNA).

160. The method of any one of embodiments 156 to 159, wherein the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

161. The method of any one of embodiments 156 to 160, wherein the one or more endogenous GA3 oxidase and/or GA20 oxidase genes encode a protein that is at least 80%, at least 85%, at least 90%, at least 95%, at least 96%, at least 97%, at least 98%, at least 99%, at least 99.5%, or 100% identical to SEQ ID NO: 9, 12, 15, 30, or 33.

162. The method of embodiment 155, wherein the introducing is via *Agrobacterium*-mediated transformation or particle bombardment.

163. The method of embodiment 162, wherein the GDH polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-192.

164. The method of embodiment 162, wherein the GDH polypeptide comprises an *E.coli* gdhA polypeptide.

165. The method of any one of embodiments 155 to 164, wherein the DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

166. The method of any one of embodiments 155 to 164, wherein the GDH polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

167. A method for producing a modified corn plant, the method comprising:

a. mutating or editing one or more endogenous GA3 oxidase genes and/or one or more GA20 oxidase genes in a corn cell, wherein the corn cell comprises a recombinant expression cassette encoding a GDH polypeptide, wherein the DNA sequence is operably linked to a plant-expressible promoter; and b. regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

168. The method of embodiment 167, wherein the mutating or editing is obtained by using a site-specific nuclease selected from the group consisting of a RNA-guided endonuclease, a meganuclease, a zinc-finger nuclease (ZFN), a TALE-endonuclease (TALEN), a recombinase, and a transposase.

169. The method of embodiment 167 or 168, further comprising introducing a recombinant DNA construct encoding a guide RNA that targets the one or more endogenous GA3 oxidase and/or GA20 oxidase genes.

170. The method of embodiment 169, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

171. The method of embodiment 170, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto.

172. The method of any one of embodiments 169 to 171, wherein the guide RNA is a CRISPR RNA (crRNA) or a single-chain guide RNA (sgRNA).

173. The method of any one of embodiments 169 to 172, wherein the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

174. The method of any one of embodiments 169 to 173, wherein the one or more endogenous GA3 oxidase and/or GA20 oxidase genes encode a protein that is at least 80%, at least 85%, at least 90%, at least 95%, at least 96%, at least 97%, at least 98%, at least 99%, at least 99.5%, or 100% identical to SEQ ID NO: 9, 12, 15, 30, or 33.

175. The method of embodiment 167, wherein the GDH polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-192.

176. The method of embodiment 167, wherein the recombinant expression cassette encodes an *E. coli* gdhA polypeptide.

177. The method of embodiment 167, wherein the recombinant expression cassette comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

178. The method of embodiment 167, wherein the GDH polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

179. The method of any one of embodiments 167 to 178, further comprising selecting a modified corn plant having a desired trait.

180. The method of embodiment 179, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

181. The method of embodiment 180, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

182. The method of any one of embodiments 179 to 181, wherein the modified corn plant exhibit an ear trait selected from the group consisting of increased ear fresh weight, increased ear area, increased ear volume, increased ear diameter, increased ear length, increased kernels per ear, increased single kernel weight, increased yield, decreased ear tip void, and a combination thereof, relative to a control corn plant.

183. The method of any one of embodiments 179 to 182, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to a control corn plant.

184. A modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a GDH polypeptide, wherein the DNA sequence is operably linked to a plant-expressible promoter.

185. The modified corn plant of embodiment 184, wherein the modified corn plant is semi-dwarf and has one or more improved ear traits, relative to a control corn plant that does not comprise both the one or more mutations or edits and the recombinant expression cassette.

186. The modified corn plant of embodiment 184 or 185, wherein the one or more mutations or edits are selected from the group consisting of an insertion, a substitution, an inversion, a deletion, a duplication, and a combination thereof.

187. The modified corn plant of any one of embodiments 184 to 186, wherein the one or more mutations or edits are introduced using a meganuclease, a zinc-finger nuclease (ZFN), a RNA-guided endonuclease, a TALE-endonuclease (TALEN), a recombinase, or a transposase.

188. The modified corn plant of any one of embodiments 184 to 187, wherein the GDH polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-192.

189. The modified corn plant of any one of embodiments 184 to 187, wherein GDH polypeptide comprises an *E. coli* gdhA polypeptide.

190. The modified corn plant of any one of embodiments 184 to 187, wherein the DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

191. The modified corn plant of any one of embodiments 184 to 187, the GDH polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

192. The modified corn plant of any one of embodiments 184 to 191, wherein the recombinant expression cassette is stably integrated into the genome of the modified corn plant.

193. The modified corn plant of any one of embodiments 184 to 192, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

194. The modified corn plant of any one of embodiments 184 to 193, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

195. The modified corn plant of any one of embodiments 184 to 194, wherein the modified corn plant exhibits improved lodging resistance, reduced green snap, or both, relative to the control corn plant.

196. The modified corn plant of any one of embodiments 184 to 195, wherein the modified corn plant exhibits increased ear diameter relative to a control corn plant.

197. The modified corn plant of any one of embodiments 184 to 196, wherein the modified corn plant exhibits increased single kernel weight relative to a control corn plant.

198. The modified corn plant of any one of embodiments 184 to 197, wherein the modified corn plant exhibits increased ear fresh weight relative to a control corn plant.

199. The modified corn plant of any one of embodiments 184 to 198, wherein the modified corn plant exhibits increased yield relative to a control corn plant.

200. The modified corn plant of any one of embodiments 184 to 199, wherein the modified corn plant exhibits increased ear area relative to a control corn plant.

201. The modified corn plant of any one of embodiments 184 to 200, wherein the modified corn plant exhibits increased ear volume relative to a control corn plant.

202. The modified corn plant of any one of embodiments 184 to 201, wherein the modified corn plant exhibits increased ear length relative to a control corn plant.

203. The modified corn plant of any one of embodiments 184 to 202, wherein the modified corn plant exhibits decreased ear tip void relative to a control corn plant.

204. The modified corn plant of any one of embodiments 184 to 203, wherein the modified corn plant exhibits increased kernels per ear relative to a control corn plant.

205. The modified corn plant of any one of embodiments 184 to 204, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to a control corn plant.

206. The modified corn plant of any one of embodiments 184 to 205, wherein the modified corn plant does not have any significant off-types in at least one female organ or ear.

207. A plurality of modified corn plants in a field, each modified corn plant comprising 1) one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and 2) a recombinant expression cassette comprising a DNA sequence encoding a GDH polypeptide, wherein the DNA sequence is operably linked to a plant-expressible promoter.

208. The plurality of modified corn plants of embodiment 207, wherein the modified corn plants have increased yield relative to control corn plants.

209. The plurality of modified corn plants of embodiment 207 or 208, wherein the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

210. A recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a GDH polypeptide, wherein the DNA sequence is operably linked to a plant-expressible promoter.

211. The recombinant DNA construct of embodiment 210, wherein the first and second expression cassettes are in a single T-DNA segment of a transformation vector.

212. The recombinant DNA construct of embodiment 210, wherein the first and second expression cassettes are in two different T-DNA segments of a transformation vector.

213. The recombinant DNA construct of any one of embodiments 210 to 212, wherein the transcribable DNA sequence encodes a non-coding RNA for suppression of a GA3 oxidase gene.

214. The recombinant DNA construct of embodiment 213, wherein the transcribable DNA sequence encodes a non-coding RNA for suppression of a GA3 oxidase_1 gene, a GA3 oxidase_2 gene, or both.

215. The recombinant DNA construct of embodiment 214, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

216. The recombinant DNA construct of embodiment 214, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

217. The recombinant DNA construct of embodiment 213, wherein the transcribable DNA sequence encodes a non-coding RNA for suppression of a GA20 oxidase gene.

218. The recombinant DNA construct of embodiment 217, wherein the transcribable DNA sequence encodes a non-coding RNA for suppression of a GA20 oxidase_3 gene, a GA20 oxidase_4 gene, a GA20 oxidase_5 gene, or a combination thereof.

219. The recombinant DNA construct of embodiment 217, wherein the transcribable DNA sequence encodes a non-coding RNA for suppression of a GA20 oxidase_3 gene, a GA20 oxidase_5 gene, or both.

220. The recombinant DNA construct of embodiment 219, wherein the transcribable DNA sequence comprises a sequence that is at least 80% identical or complementary to at least 15 consecutive nucleotides of SEQ ID NO: 39, 53, or 55.

221. The recombinant DNA construct of embodiment 220, wherein the transcribable DNA sequence encodes a sequence that is at least 80% complementary to at least 15 consecutive nucleotides of SEQ ID NO: 40, 54, or 56.

222. The recombinant DNA construct of any one of embodiments 210 to 221, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

223. The recombinant DNA construct of any one of embodiments to 210 to 222, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

224. The recombinant DNA construct of any one of embodiments 210 to 223, wherein the DNA sequence comprised in the second expression cassette comprises a sequence that encodes a protein having an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-192.

225. The recombinant DNA construct of any one of embodiments 210 to 223, wherein the DNA sequence comprised in the second expression cassette encodes an *E.coli* gdhA polypeptide.

226. The recombinant DNA construct of any one of embodiments 210 to 223, wherein the GDH polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

227. The recombinant DNA construct of any one of embodiments 210 to 223, wherein the DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

228. The recombinant DNA construct of any one of embodiments 210 to 227, the plant-expressible promoter is a vascular promoter.

229. The recombinant DNA construct of embodiment 228, wherein the vascular promoter is selected from the group consisting of a sucrose synthase promoter, a sucrose transporter promoter, a Sh1 promoter, CoYMV promoter, a WDV large intergenic region (LIR) promoter, a MSV coat polypeptide (CP) promoter, a rice yellow stripe 1 (YS1)-like promoter, a rice yellow stripe 2 (OsYSL2) promoter, and a combination thereof.

230. The recombinant DNA construct of any one of embodiments 210 to 227, wherein the plant-expressible promoter is an RTBV promoter.

231. The recombinant DNA construct of any one of embodiments 210 to 227, wherein the plant-expressible promoter is a leaf promoter.

232. The recombinant DNA construct of embodiment 231, wherein the leaf promoter is selected from the group consisting of a RuBisCO promoter, a PPDK promoter, a FDA promoter, a Nadh-Gogat promoter, a chlorophyll a/b binding polypeptide gene promoter, a PEPC promoter, a Myb gene promoter, and a combination thereof.

233. The recombinant DNA construct of any one of embodiments 210 to 227, wherein the plant-expressible promoter is a constitutive promoter.

234. The recombinant DNA construct of embodiment 233, wherein the constitutive promoter is selected from the group consisting of an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

235. The recombinant DNA construct of any one of embodiments 210 to 227, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 170 or a functional portion thereof.

236. The recombinant DNA construct of any one of embodiments 210 to 227, wherein the plant-expressible promoter is selected from the group consisting of a stress-inducible promoter, a nitrogen-inducible promoter, a drought-inducible promoter, a root promoter, and a combination thereof.

237. The recombinant DNA construct of embodiment 210, wherein the non-coding RNA is a precursor miRNA or siRNA capable of being processed or cleaved to form a mature miRNA or siRNA.

238. A transformation vector comprising the recombinant DNA construct of any one of embodiments 210 to 237.

239. A modified corn plant or a plant part thereof comprising the recombinant DNA construct of embodiment 238.

240. The modified corn plant of embodiment 239, wherein the modified corn plant is semi-dwarf and has one or more improved ear traits, relative to a control corn plant not having both the first and second expression cassettes.

241. The modified corn plant of embodiment 240, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to the control corn plant.

242. The modified corn plant of embodiment 240, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to the control corn plant.

243. The modified corn plant of embodiment 240, wherein the modified corn plant exhibits improved lodging resistance, reduced green snap, or both, relative to the control corn plant.

244. The modified corn plant of embodiment 240, wherein the modified corn plant exhibits increased ear diameter relative to the control corn plant.

245. The modified corn plant of embodiment 240, wherein the modified corn plant exhibits increased single kernel weight relative to the control corn plant.

246. The modified corn plant of embodiment 240, wherein the modified corn plant exhibits increased ear fresh weight relative to the control corn plant.

247. The modified corn plant of embodiment 240, wherein the modified corn plant exhibits increased yield relative to the control corn plant.

248. The modified corn plant of embodiment 240, wherein the modified corn plant exhibits increased ear area relative to the control corn plant.

249. The modified corn plant of embodiment 240, wherein the modified corn plant exhibits increased ear volume relative to the control corn plant.

250. The modified corn plant of embodiment 240, wherein the modified corn plant exhibits increased ear length relative to the control corn plant.

251. The modified corn plant of embodiment 240, wherein the modified corn plant exhibits decreased ear tip void relative to the control corn plant.

252. The modified corn plant of embodiment 240, wherein the modified corn plant exhibits increased kernels per ear relative to the control corn plant.

253. The modified corn plant of embodiment 240, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to the control corn plant.

254. The modified corn plant of embodiment 240, wherein the modified corn plant does not have any significant off-types in at least one female organ or ear.

255. A recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a GDH polypeptide, wherein the DNA sequence is operably linked to a plant-expressible promoter.

256. The recombinant DNA donor template molecule of embodiment 255, comprising two of the homology sequences, wherein the two homology sequences flank the insertion sequence.

257. The recombinant DNA donor template molecule of embodiment 255 or 256, wherein the GDH polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-192.

258. The recombinant DNA donor template molecule of embodiment 255 or 256, wherein the GDH polypeptide comprises an *E.coli* gdhA polypeptide.

259. The recombinant DNA donor template molecule of embodiment 255 or 256, wherein the DNA sequence comprised in the expression cassette comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

260. The recombinant DNA donor template molecule of embodiment 255 or 256, wherein the GDH polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

261. The recombinant DNA donor template molecule of any one of embodiments 255 to 260, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 170 or a functional portion thereof.

262. The recombinant DNA donor template molecule of any one of embodiments 255 to 260, wherein the plant-expressible promoter is a constitutive promoter.

263. The recombinant DNA donor template molecule of embodiment 262, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

264. The recombinant DNA donor template molecule of any one of embodiments 255 to 260, wherein the plant-expressible promoter is a leaf promoter.

265. The recombinant DNA donor template molecule of embodiment 264, wherein the leaf promoter is selected from the group consisting of a RuBisCO promoter, a PPDK promoter, a FDA promoter, a Nadh-Gogat promoter, a chlorophyll a/b binding polypeptide gene promoter, a PEPC promoter, a Myb gene promoter, and a combination thereof.

266. The recombinant DNA donor template molecule of any one of embodiments 255 to 260, wherein the plant-expressible promoter is selected from the group consisting of a stress-inducible promoter, a nitrogen-inducible promoter, a drought-inducible promoter, a root promoter, and a combination thereof.

267. The recombinant DNA donor template molecule of any one of embodiments 255 to 261, further comprising a transcribable DNA sequence encoding a non-coding RNA for suppression of one or more GA20 oxidase genes and/or one or more GA3 oxidase genes, wherein the transcribable DNA sequence is operably linked to a promoter.

268. The recombinant DNA donor template molecule of embodiment 264, wherein the promoter is a vascular promoter.

269. The recombinant DNA donor template molecule of embodiment 265, wherein the vascular promoter is selected from the group consisting of a sucrose synthase promoter, a sucrose transporter promoter, a Sh1 promoter, Commelina yellow mottle virus (CoYMV) promoter, a wheat dwarf geminivirus (WDV) large intergenic region (LIR) promoter, a maize streak geminivirus (MSV) coat polypeptide (CP) promoter, a rice yellow stripe 1 (YS1)-like promoter, a rice yellow stripe 2 (OsYSL2) promoter, and a combination thereof.

270. The recombinant DNA donor template molecule of embodiment 266, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70, or SEQ ID NO: 71, or a functional portion thereof.

271. The recombinant DNA donor template molecule of any one of embodiments 255 to 260, wherein the promoter is a rice tungro bacilliform virus (RTBV) promoter.

272. The recombinant DNA donor template molecule of embodiment 268, wherein the RTBV promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

273. The recombinant DNA donor template molecule of any one of embodiments 255 to 260, wherein the promoter is a leaf promoter.

274. The recombinant DNA donor template molecule of embodiment 270, wherein the leaf promoter is selected from the group consisting of a RuBisCO promoter, a pyruvate phosphate dikinase (PPDK) promoter, a fructose 1-6 bisphosphate aldolase (FDA) promoter, a Nadh-Gogat promoter, a chlorophyll a/b binding polypeptide gene promoter, a phosphoenolpyruvate carboxylase (PEPC) promoter, a Myb gene promoter, and a combination thereof.

275. The recombinant DNA donor template molecule of embodiment 271, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

276. The recombinant DNA donor template molecule of any one of embodiments 255 to 260, wherein the promoter is a constitutive promoter.

277. The recombinant DNA donor template molecule of embodiment 273, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

278. The recombinant DNA donor template molecule of embodiment 274, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

279. The modified corn plant of embodiment 1, wherein the first recombinant expression cassette comprises SEQ ID NO: 39, and the second recombinant expression cassette comprises SEQ ID NO: 169.

280. The modified corn plant of embodiment 279, wherein the modified corn plant is semi-dwarf and exhibits one or more improved ear traits, relative to a control plant that does not comprise the first or second recombinant expression cassette.

281. The modified corn plant of embodiment 280, wherein the one or more improved ear traits are selected from the group consisting of broad acreage yield, ear fresh weight, foliar nitrogen percentage, and a combination thereof.

282. A modified corn plant or a plant part thereof comprising 1) a first transcribable DNA sequence comprising SEQ ID NO: 39, and 2) a second transcribable DNA sequence comprising SEQ ID NO: 169.

283. The modified corn plant of embodiment 282, wherein the modified corn plant is semi-dwarf and has one or more improved ear traits, relative to a control corn plant that does not have the first or second transcribable DNA sequence.

284. The modified corn plant of embodiment 283, wherein the one or more improved ear traits are selected from the group consisting of broad acreage yield, ear fresh weight, foliar nitrogen percentage, and a combination thereof.

285. A method for producing a modified corn plant, the method comprising a. introducing into a corn cell a recombinant expression cassette comprising a first transcribable DNA sequence comprising SEQ ID NO: 39, and a second transcribable DNA sequence comprising SEQ ID NO: 169;

b. regenerating or developing a modified corn plant from the corn cell, wherein the modified corn plant comprises the first and second transcribable DNA sequences.

286. The method of embodiment 285, wherein the modified corn plant is semi-dwarf and has one or more improved ear traits, relative to a control corn plant that does not have the first or second transcribable DNA sequence.

287. The method of embodiment 286, wherein the one or more improved ear traits are selected from the group consisting of broad acreage yield, ear fresh weight, foliar nitrogen percentage, and a combination thereof.

288. A recombinant expression cassette comprising 1) a first transcribable DNA sequence comprising SEQ ID NO: 39, and 2) a second transcribable DNA sequence comprising SEQ ID NO: 169.

EXAMPLES

Example 1

Generation of the GA20Ox_SUP/gdhA Stack Plants

An inbred corn plant line was transformed via *Agrobacterium*-mediated transformation with a transformation vector having an expression construct comprising a miRNA-encoding DNA sequence (SEQ ID NO: 39) encoding a targeting sequence (SEQ ID NO: 40) under the control of a rice tungro bacilliform virus (RTBV) promoter (SEQ ID NO: 65) known to cause expression in vascular tissues of plants. The miRNA encoded by the construct comprises an RNA sequence that targets the GA20 oxidase_3 and GA20 oxidase_5 genes in corn plants. Several transformation events were generated therefrom. The resulting transformed/transgenic inbred line is herein referred to as GA20Ox_SUP or GA20Ox_SUP single.

Plant height was measured up to the uppermost ligulated leaf at the R3 stage. As shown in FIG. 1, statistically significant reductions in plant height between 35% and 45% are consistently observed in GA20Ox_SUP single plants relative to control plants (p-value≤0.2).

Similarly, an inbred corn plant line was transformed via *Agrobacterium*-mediated transformation with a transformation vector having an expression construct comprising an *Oryza sativa* promoter (SEQ ID NO: 170), an enhancer sequence and an intron sequence thereof (SEQ ID NOs: 171 and 174, respectively), a CaMV 35S enhancer (SEQ ID NO: 172), a leader sequence (SEQ ID NO: 173), and a terminator region (SEQ ID NO: 175), operably linked to a polynucleotide sequence (SEQ ID NO: 169) encoding *E.coli* gdhA polypeptide (SEQ ID NO: 168). Several transformation events were generated therefrom. The resulting transformed/transgenic inbred line is herein referred to as gdhA, gdhA transgenic plant, or gdhA single.

Parental GA20Ox_SUP and gdhA singles were crossed to create a stacked transgenic progeny plant comprising both the gdhA transgene and the miRNA-encoding DNA sequence for the suppression of GA20 oxidase_3 and GA20 oxidase_5 genes. The resulting stacked transgenic line is herein referred to as GA20Ox_SUP/gdhA stack. The GA20Ox_SUP/gdhA stack can be an inbred stack if the parental lines are of the same inbred line origin, or a hybrid when the parental lines are of different inbreds.

For each type of transgenic single and stack plants, the corresponding control plants were also produced for comparison having the same inbred line or same parental line combination, but without the transgenic GA20Ox_SUP and gdhA constructs.

Example 2

Reduced Height of the GA20Ox_SUP/gdhA Stack Plants

GA20Ox_SUP/gdhA stack plants were grown to R3 stage in a field under standard agronomic practice and their heights were measured. Plant height was measured as the plot average from the soil line to the base of highest collared leaf at the R3 stage. A sufficient number of plants were measured to meet statistical significance with p-value≤0.2. Control plants of the same parental inbred lines but without the GA20Ox_SUP and gdhA transgenic constructs were also grown under similar conditions.

Figure 2:
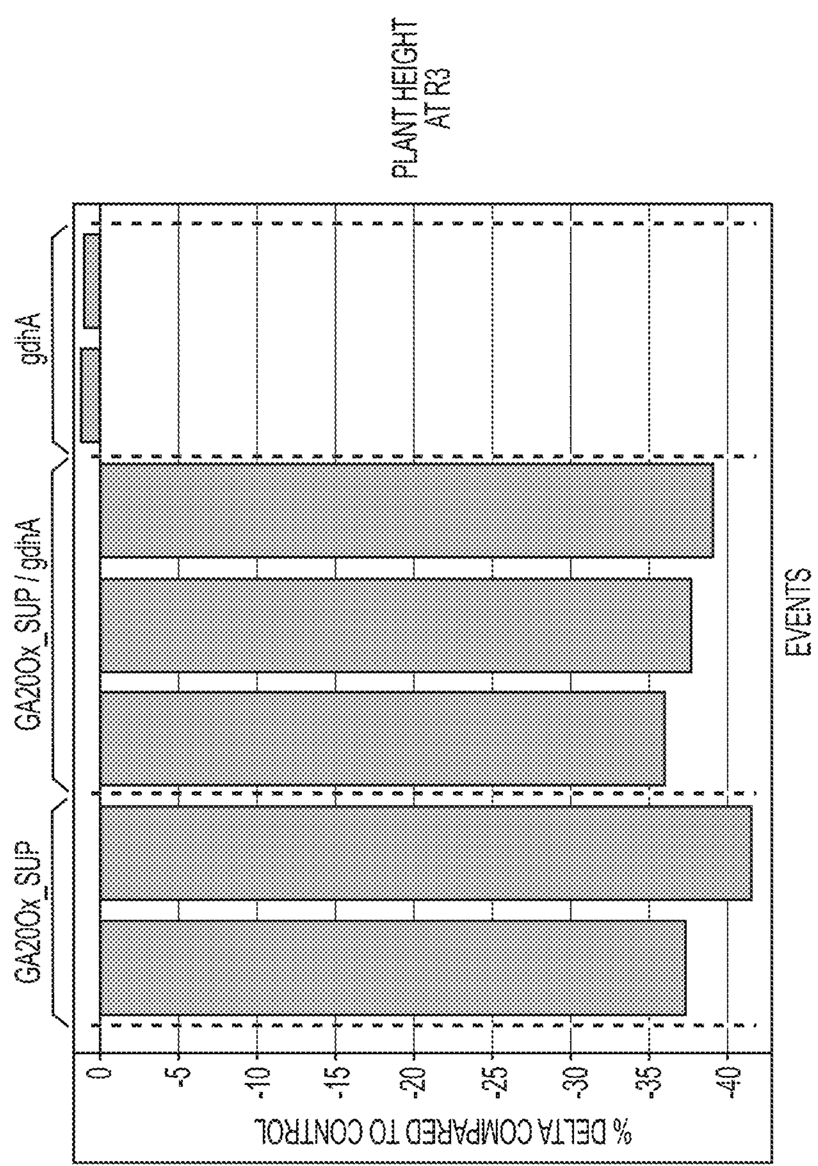
FIG. 2 shows plant heights of stacked transgenic corn plants comprising a DNA sequence encoding a miRNA for suppression of GA20 oxidase genes and a transgene encoding *Escherichia coli* (*E.coli*) gdhA polypeptide ("GA20Ox_SUP/gdhA") across three event-by-event combinations, in comparison to two transformation events of GA20Ox_SUP single corn plants, and two transformation events of gdhA single corn plants, each relative to control corn plants.

Average plant height reduction for the GA20Ox_SUP/gdhA stack (three event-by-event crosses), as well as the GA20Ox_SUP single and gdhA single (two events each), are shown in FIG. 2, each relative to control plants. As shown in FIG. 2, a statistically significant reduction in plant height averaging between 35 to 40% was consistently observed in GA20Ox_SUP/gdhA stack plants relative to control plants. In contrast, the plant height of gdhA single plants was slightly increased in comparison to control plants.

Example 3

Enhanced Ear Traits with Expression of the gdhA Gene

The transgenic single and stack plants and control plants described in Example 1 were grown under standard agronomic practice. Several corn ear traits were measured for the gdhA single plants at the R6 stage. Ear volume is measured as the plot average of the volume of an ear calculated by measuring the diameter and estimating the resulting volume along the length of the ear (one row at a time), accounting for the shape/contour of the ear, but assuming that the ear is a perfect circle for each row. Ear length is a measure of the plot average of the length of an ear measured from the tip of the ear in a straight line to the base of the ear node. The measurement is conducted by measuring distance of the longest identified longitudinal axis of the ear. Ear tip void is a measure of the plot average of the area percentage of ear void within the ear tip defined as the distal 33% of the ear. Kernels per ear is measured as the plot average of the number of kernels of an ear. Similarly, kernels per row longitudinally is measured as the plot average of the number of kernels per row longitudinally of an ear. Similarly, kernels per row longitudinally is measured as the plot average of the number of kernels per row longitudinally of an ear.

Figure 3:
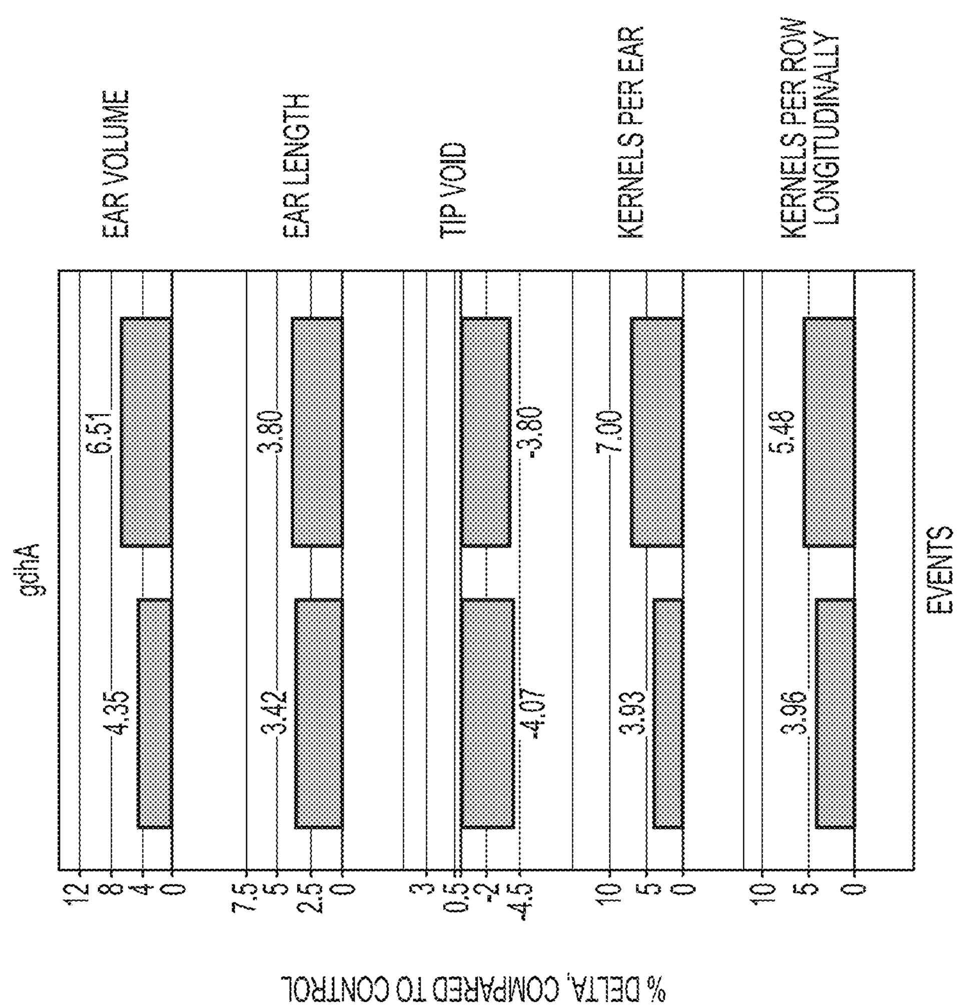
FIG. 3 shows ear traits of transgenic corn plants comprising a transgene encoding *E.coli* gdhA polypeptide ("gdhA single") across two transformation events, relative to control corn plants.

FIG. 3 shows ear trait results for gdhA single plants from two transformation events in one growing season. Results are shown as percent difference (delta) between gdhA single plants and control plants of the same hybrid without the gdhA transgenic construct. As shown in FIG. 3, in comparison to controls, gdhA single plants exhibit statistically significant improvement in a number of ear traits, including increased ear volume, increased ear length, increased number of kernels per ear, increased number of kernels per row longitudinally, and decreased ear tip void.

Example 4

Enhanced Ear Traits of the GA20Ox_SUP/gdhA Stack Plants

Figure 4:
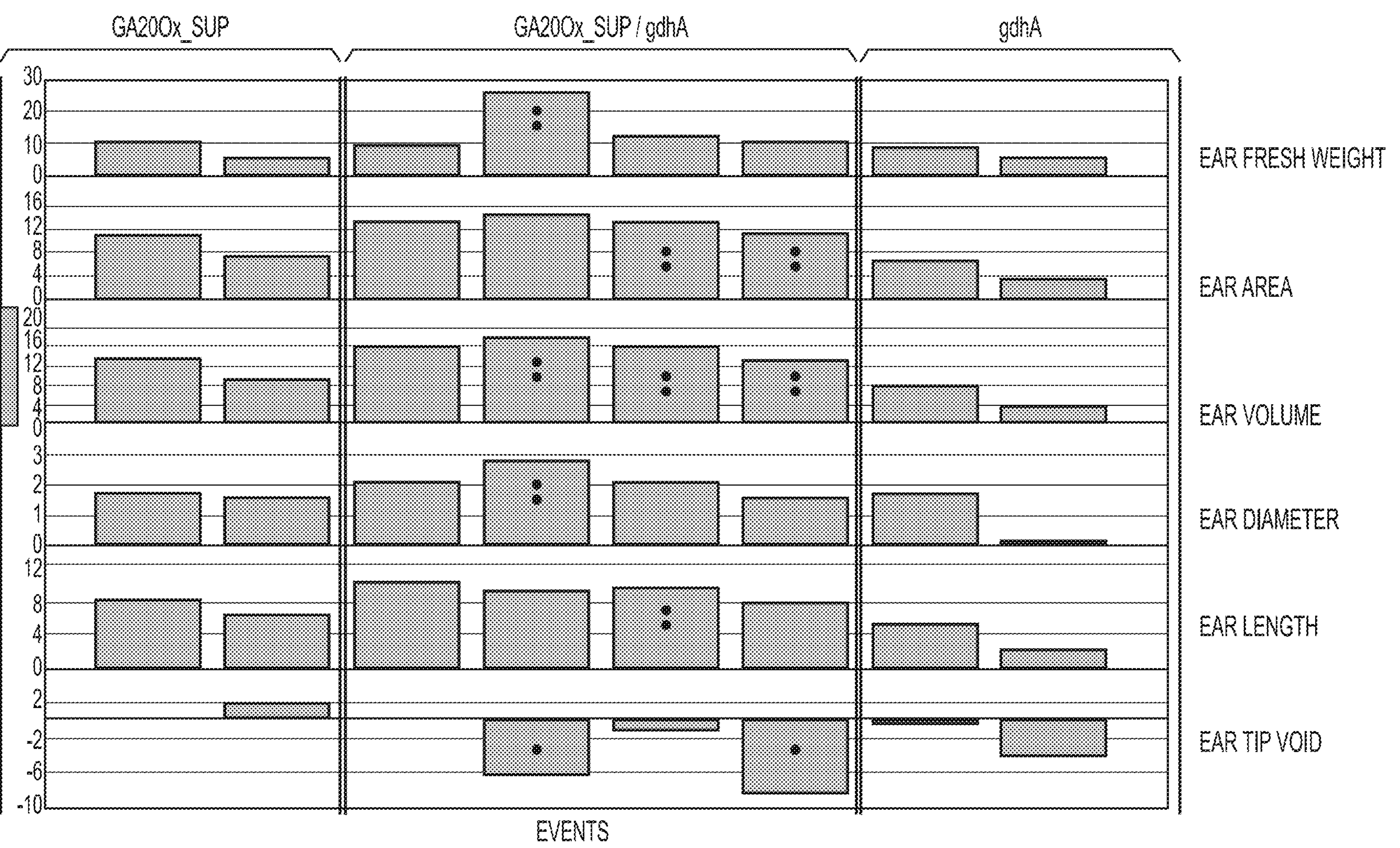
FIGS. 4 and 5 each show ear traits of GA20Ox_SUP/gdhA stack corn plants across four event-by-event combinations, GA20Ox_SUP single corn plants across two transformation events, and gdhA single corn plants across two transformation events, including ear fresh weight, ear area, ear volume, ear diameter, ear length, ear tip void, the number of kernels per ear, and single kernel weight, under standard agronomic conditions in the field, relative to control corn plants.

Positive effects on ear traits were observed when both the GA20Ox_SUP and gdhA constructs were present in the same plants. As shown in FIG. 4, ear traits such as ear fresh weight, ear area, ear volume, ear diameter, ear length, and ear tip void were measured in plants containing one of two events of GA200X_SUP single, one of two events of gdhA single, or one of four event combinations of the GA20Ox_SUP/gdhA stack, each grown in a single growing season. The definitions for ear volume, ear length, and ear tip void are provided above. Ear fresh weight is measured as the plot average of the weight of a fresh ear at the R6 stage. Ear area is measured as the plot average of the area of an ear from a two-dimensional view by imaging the ear and including kernels and tip void in the area measurement. Typically, 10 representative ears were measured per plot. Ear diameter is a measure of the plot average of the diameter of the ear measured as the maximal "wide" axis of the ear. Each bar in FIG. 4 indicates one transformation event. Bars with double asterisks (**) indicate a statistically significant change (increase) (p-value≤0.2) as compared to both GA20Ox_SUP and gdhA single plants, whereas bars with a single asterisk (*) indicate a numerical change (decrease) as compared to both GA20Ox_SUP and gdhA single plants.

Results in FIG. 4 show that GA20Ox_SUP and gdhA single event plants had improved ear fresh weight, ear area, ear volume, ear diameter, and ear length, as well as neutral to slightly decreased ear tip void, relative to control plants, and GA20Ox_SUP/gdhA stack plants had a statistically significant increase in ear fresh weight, ear area, ear volume, ear diameter, and ear length, and a statistically significant or numerical decrease in ear tip void, relative to control plants. The average increase and/or decrease in the above ear traits in GA20Ox_SUP/gdhA stack plants was numerically greater than that of the gdhA and GA20Ox_SUP single plants, with statistically significant increases in these ear traits over one or both of the gdhA and GA20Ox_SUP single plants with some events.

These results show that GA20Ox_SUP/gdhA stack plants have enhanced ear traits, such as increased ear fresh weight, ear area, ear volume, ear diameter, and ear length, and decreased ear tip void, as compared to control plants and gdhA and/or GA20Ox_SUP single plants with statistically significant increases in ear fresh weight, ear area, ear volume, ear diameter, and ear length in GA20Ox_SUP/gdhA stack plants depending on the particular event combinations.

Example 5

Enhanced Kernels Per Ear or Single Kernel Weight of the GA20Ox_SUP/gdhA Stack Plants Positive effects on ear traits were observed when both the GA20Ox_SUP and gdhA constructs were present in the same plants. Transgenic single and stack plants, along with control plants as described above, were measured for the number of kernels per ear and single kernel weight. Definitions for kernels per ear is provided above. Single kernel weight is measured as the plot average of weight per kernel, calculated as the ratio of (sample kernel weight adjusted to a standard moisture level)/(sample kernel number). The sample kernel number ranged from 350 to 850.

Figure 5:
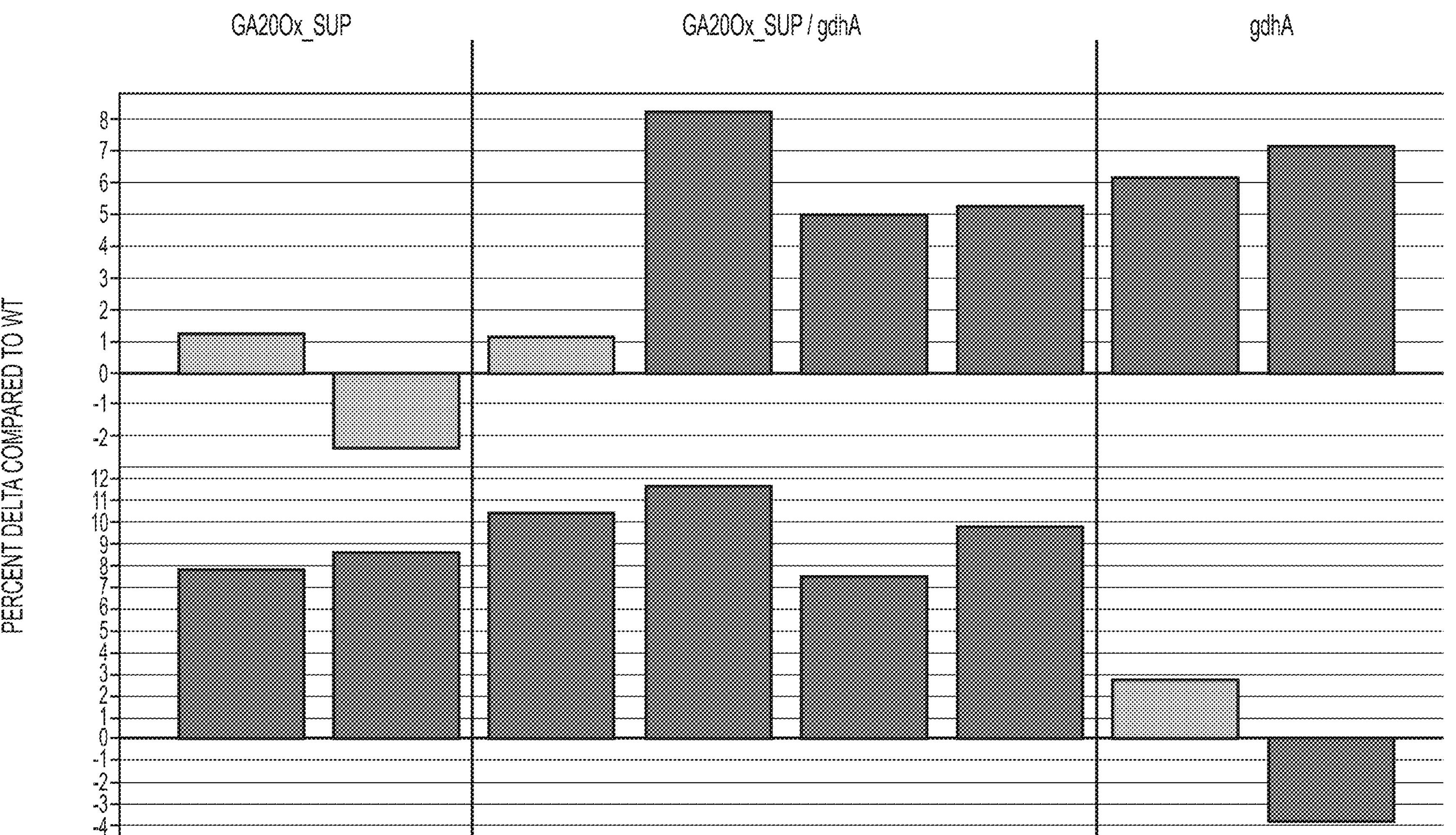

FIG. 5 shows that gdhA single plants demonstrated an increase in the number of kernels per ear relative to control plants, whereas GA20Ox_SUP single plants exhibited a slight increase or a decrease relative to control plants. However, GA20Ox_SUP/gdhA stack plants surprisingly demonstrated an increase in the number of kernels per ear relative to control plants, and the average increase was comparable to or greater than that of the gdhA single plants and was significantly greater than that of the GA20Ox_SUP single plants.

Further, FIG. 5 shows that GA20Ox_SUP single plants demonstrated an increase in single kernel weight relative to control plants, whereas gdhA single plants exhibited a slight increase or a decrease relative to control plants. However, the GA20Ox_SUP/gdhA stack plants surprisingly demonstrated an increase in single kernel weight relative to control plants, and the average increase was comparable to or greater than that of the GA20Ox_SUP single plants and was significantly greater than that of the gdhA single plants.

These results show that GA20Ox_SUP/gdhA stack plants have enhanced ear traits, such as increased number of kernels per ear and increased single kernel weight.

Example 6

Increased Yield of GA20Ox_SUP/gdhA Stack Plants

Figure 6:
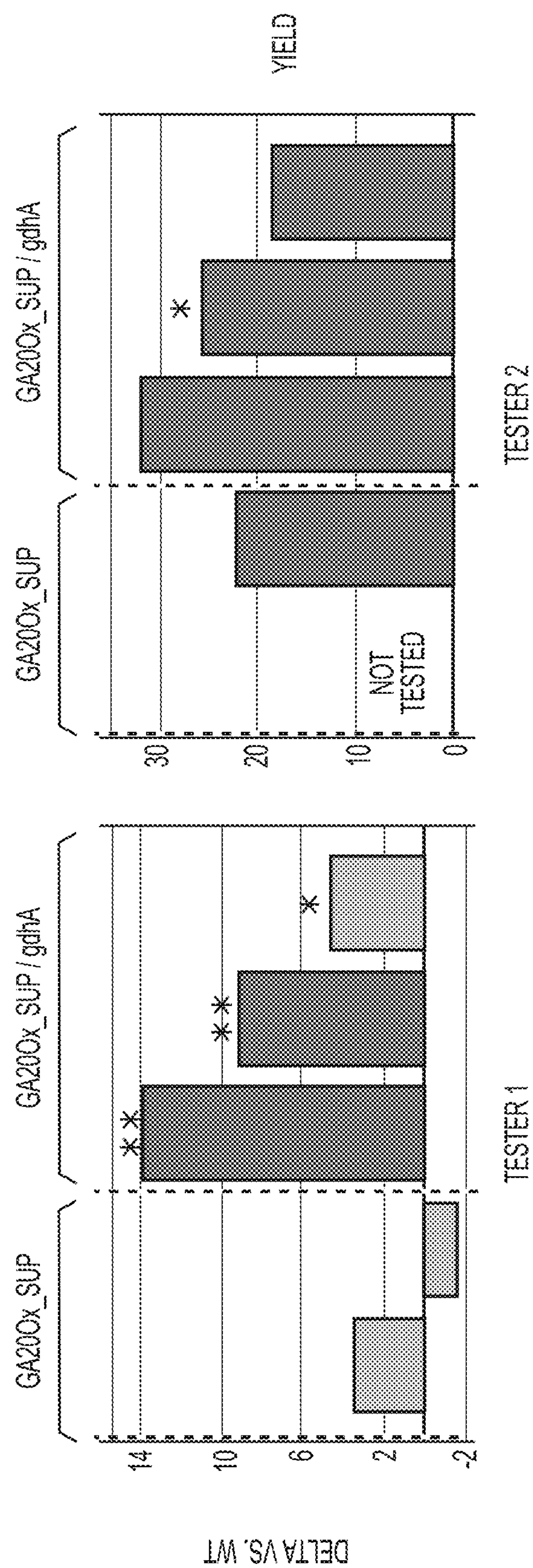
FIG. 6 shows yield measurements of GA20Ox_SUP/gdhA stack corn plants across three event-by-event combinations and GA20Ox_SUP single corn plants across two transformation events under standard agronomic conditions in the field, relative to control corn plants.

FIG. 6 shows yield results in a field trial for GA20Ox_SUP single plants and GA20Ox_SUP/gdhA stack plants. Results are shown as the percent difference (delta) in yield (bushels/acre) as compared to control plants. Dark grey bars indicate values significantly different (increased) from control plants (p-value≤0.1), and light grey bars indicate values numerically different (increased) from control plants. As shown in FIG. 6, a statistically significant or numerical increase in yield for GA20Ox_SUP/gdhA stack plants was observed relative to control plants, and the average numerical increase was greater than that of GA20Ox_SUP single plants.

Example 7

Identification of gdhA Gene Homologs

*E.coli* gdhA gene belongs to the Glu/Leu/Phe/Val dehydrogenase family. Homologs of *E.coli* gdhA protein were identified as being NADP+ glutamate dehydrogenase (GDH) proteins that belong to the 1.4.1.4 enzyme class using the ExPASy/UniProt tool. Full-length GDH enzymes identified within this enzyme class include proteins having amino acid sequences as set forth in SEQ ID NOs: 176-192.

Example 8

Generation of GA20Ox_SUP/gdhA Vector Stack Plants Using a Single Vector

Constructs and vectors were created via molecular cloning each having an expression cassette comprising a DNA sequence encoding a miRNA that targets the GA20 oxidase_3 and GA20 oxidase_5 genes in corn plants and another expression cassette comprising a DNA sequence encoding a gdhA polypeptide. Two vectors (Vector 1 and Vector 2) were constructed comprising in order a miRNA-encoding DNA sequence (SEQ ID NO: 39) encoding a miRNA having a targeting sequence (SEQ ID NO: 40) for the GA20 oxidase_3 and GA20 oxidase_5 genes, and a DNA sequence encoding an *E.coli* gdhA polypeptide (SEQ ID NO: 169), wherein the two coding sequences are each operably linked to a promoter and a terminator sequence and are separated from each other by an intergenic sequence. For each vector, the DNA sequence encoding the *E.coli* gdhA polypeptide is operably linked to an *Oryza sativa* promoter (SEQ ID NO: 170), and the miRNA-encoding DNA sequence is a rice tungro bacilliform virus (RTBV) promoter (SEQ ID NO: 65).

Corn plants were transformed via *Agrobacterium*-mediated transformation with each of Vector 1 and Vector 2 to create transgenic corn plants. Transgenic corn plants containing Vector 1 or Vector 2 were then crossed as females with male corn lines to create progeny plants comprising both the gdhA transgene and the miRNA-encoding DNA sequence for the suppression of the GA20 oxidase genes. The resulting stacked transgenic progeny plants are herein referred to as GA20Ox_SUP/gdhA vector stack plants.

Example 9

Figure 7:
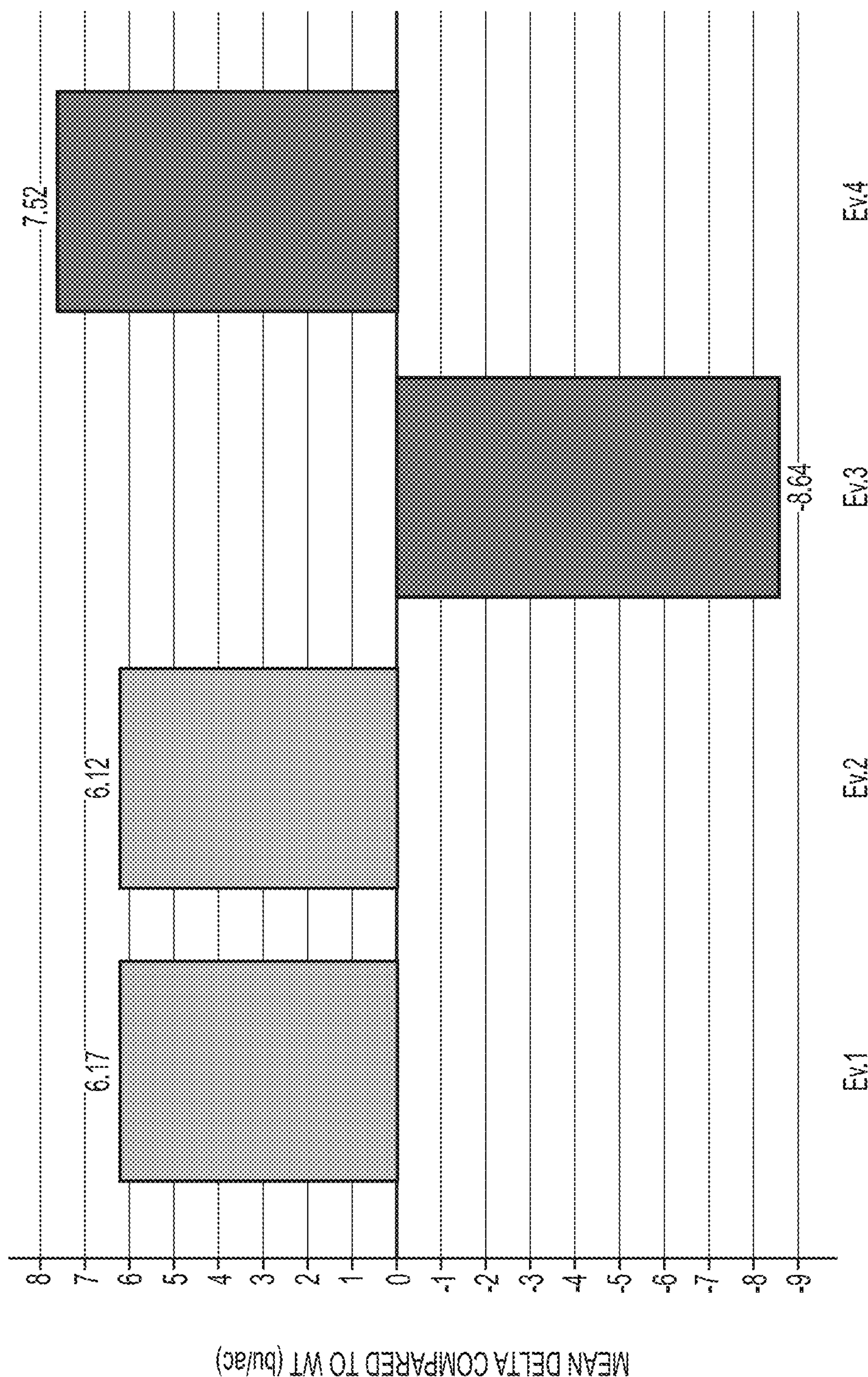
FIG. 7 shows broad acreage yield of GA20Ox_SUP/gdhA vector stack corn plants across four events, relative to control corn plants.

Increased Yield of the GA20Ox_SUP/gdhA Vector Stack Plants Compared to Control Broad acreage yield ("BAY") was measured with four events of GA20Ox_SUP/gdhA vector stack plants containing Vector 1. FIG. 7 shows BAY in one growing season across 15 locations with plants containing each of four events of the GA20Ox_SUP/gdhA vector stack from Vector 1. Results are shown as the mean difference in bushels/acre between the BAY of GA20Ox_SUP/gdhA vector stack plants and that of the non-transgenic control plants. Each bar in FIG. 7 corresponds to a single transformation event. Dark gray bars in FIG. 7 are indicative of a statistically significant positive or negative change (p-value≤0.2), and light gray bars are indicative of a numerically positive change.

As shown in FIG. 7, one of four events of the GA20Ox_SUP/gdhA vector stack from Vector 1 showed a statistically significant increase in BAY relative to control plants, and two other events of the GA20Ox_SUP/gdhA vector stack from Vector 1 showed a numerical increase in BAY relative to control plants, while a fourth event of GA20Ox_SUP/gdhA vector stack plants had a statistically significant decrease in BAY relative to control plants.

Example 10

Figure 8:
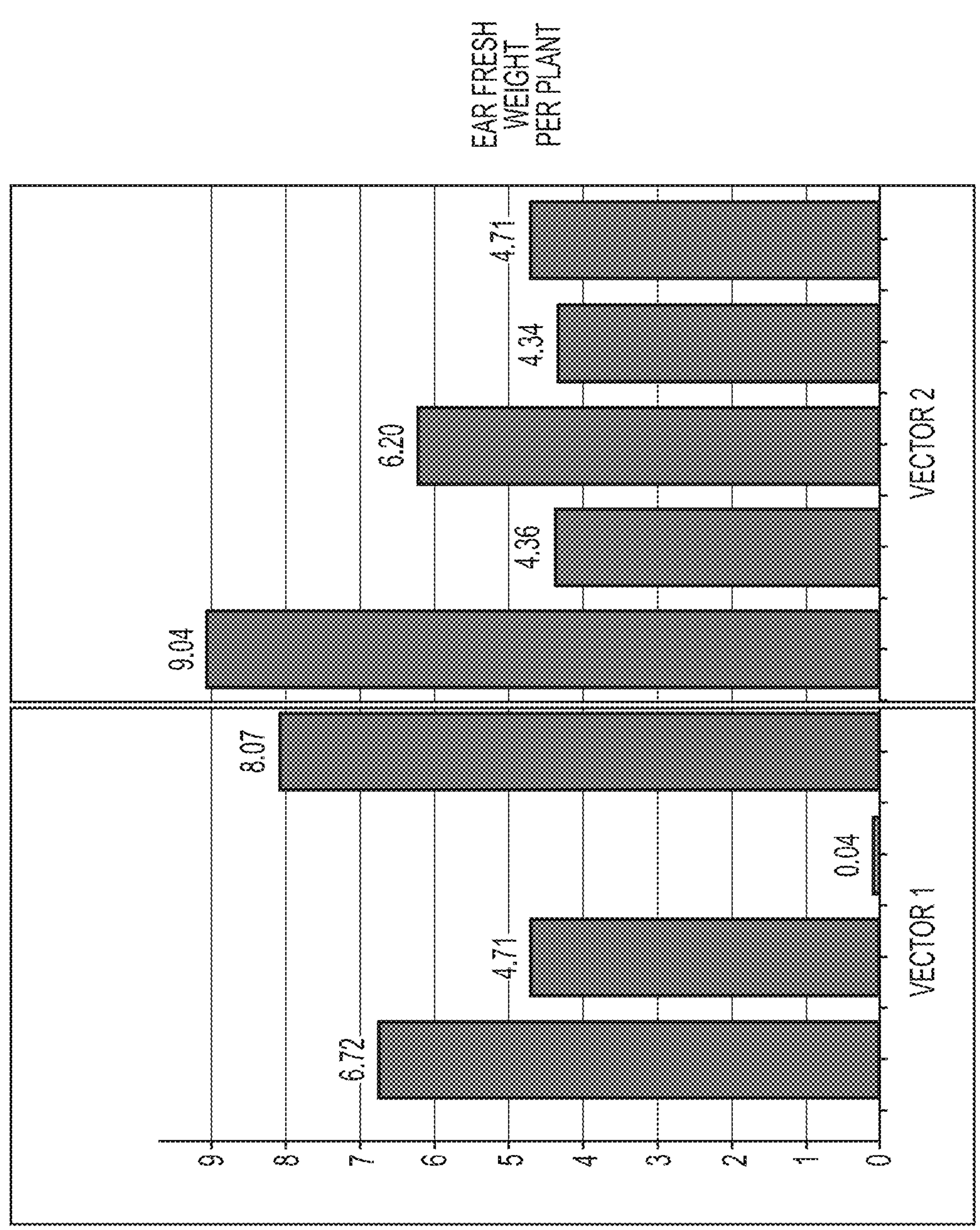
FIG. 8 shows ear fresh weight per plant of GA20Ox_SUP/gdhA vector stack corn plants containing Vector 1 or Vector 2 across four events, relative to GA20Ox_SUP single corn plants.

Increased Ear Fresh Weight of the GA20Ox_SUP/gdhA Vector Stack Plants Compared to GA20Ox_SUP Single FIG. 8 shows ear fresh weight per plant for plants containing each of the four events of GA20Ox_SUP/gdhA vector stack plants from Vector 1 or Vector 2. Results are shown as the percentage difference in ear fresh weight per plant between GA20Ox_SUP/gdhA vector stack plants and that of GA20Ox_SUP single plants. Each bar in FIG. 8 corresponds to a single transformation event. Dark gray bars in FIG. 8 are indicative of a statistically significant positive change (p-value≤0.2), and light gray bars are indicative of a numerically positive change.

As shown in the left panel of FIG. 8, plants containing three of four events of the GA20Ox_SUP/gdhA vector stack from Vector 1 showed a statistically significant increase in ear fresh weight per plant relative to GA20Ox_SUP single plants. As shown in the right panel of FIG. 8, all four events of the GA20Ox_SUP/gdhA vector stack from Vector 2 showed a statistically significant increase in ear fresh weight per plant relative to GA20Ox_SUP single plants.

Example 11

Increased Foliar Nitrogen Percentage of the GA20Ox_SUP/gdhA Vector Stack Plants As used in this example, "foliar nitrogen percentage" refers to the percentage of nitrogen ("N") content divided by the total dry weight of a leaf punch sample [% Nitrogen=100*(weight of nitrogen)/(total weight of dry sample)]. Nitrogen content was measured using a FlashEA® 1112 elemental analyzer (Thermo Fisher), and nitrogen content was calculated using the K-factor method. A constant is obtained using: K=% Th*(I−b)/p; Th=Theoretical percentage of standard, p=Weight in milligrams, I=Area integral, b=Blank area integral. Calculation of unknowns uses % Unknown=K*p/(I−b). Atropine is used to calibrate the response and check the suitability during each analysis. Acceptable results for the check samples are ±6.2% N.

Figure 9:
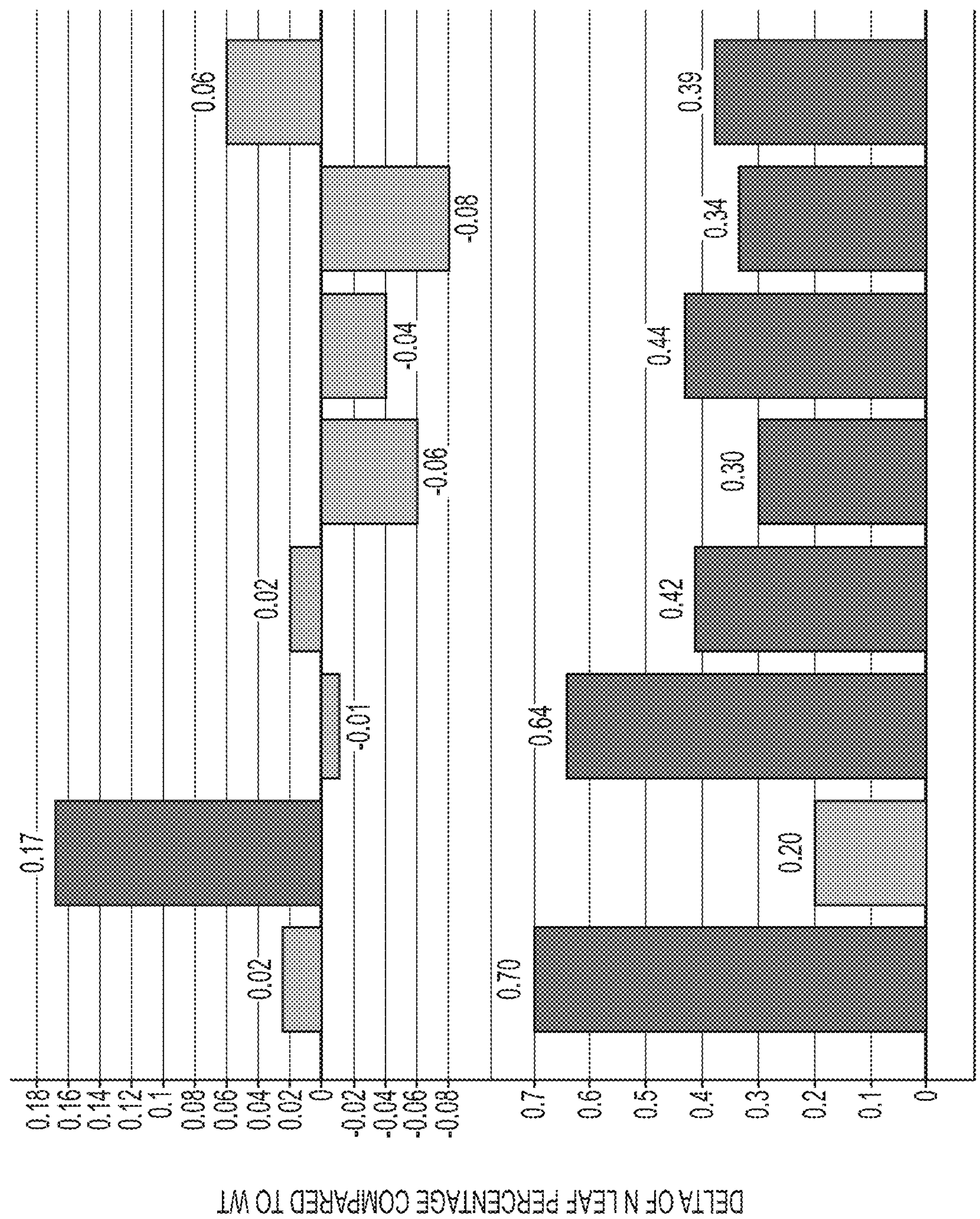
FIG. 9 shows foliar nitrogen percentage of GA20Ox_SUP/gdhA vector stack corn plants across four events and GA20Ox_SUP single corn plants across four events at the R2 or V12 developmental stage, relative to control corn plants.

FIG. 9 shows the foliar nitrogen percentage for plants containing each of four different events of the GA20Ox_SUP/gdhA vector stack from Vector 1 and for GA20Ox_SUP single plants, at the R2 or V12 developmental stage. Results are shown as the percentage difference between the foliar nitrogen percentage of GA20Ox_SUP/gdhA vector stack and GA20Ox_SUP single plants, relative to control plants. Each bar in FIG. 9 corresponds to a single transformation event. Dark gray bars in FIG. 9 are indicative of a statistically significant positive change (p-value≤0.2), and light gray bars are indicative of a numerically positive or negative change.

As shown in the top panel of FIG. 9, plants containing one out of the four events of the GA20Ox_SUP/gdhA vector stack showed a statistically significant increase in foliar nitrogen percentage at R2 stage compared to control plants, while the other three events of the GA20Ox_SUP/gdhA vector stack showed a nearly equivalent or slightly positive or negative numerical change in foliar nitrogen percentage compared to control plants, although the average increase in foliar nitrogen percentage of GA20Ox_SUP/gdhA vector stack plants at R2 stage was greater than that of the GA20Ox_SUP single plants at the R2 stage.

As shown in the bottom panel of FIG. 9, three of the four events of the GA20Ox_SUP/gdhA vector stack showed a statistically significant increase in foliar nitrogen percentage at V12 stage compared to control plants, and the other event of the GA20Ox_SUP/gdhA vector stack showed a numerical increase in foliar nitrogen percentage at V12 stage compared to control plants. The average increase in foliar nitrogen percentage for the GA20Ox_SUP/gdhA vector stack event plants at V12 stage was slightly greater than that of the GA20Ox_SUP single event plants.

Having described the present disclosure in detail, it will be apparent that modifications, variations, and equivalent aspects are possible without departing from the spirit and scope of the present disclosure as described herein and in the appended claims. Furthermore, it should be appreciated that all examples in the present disclosure are provided as non-limiting examples.

The invention claimed is:

1. A modified corn plant or a plant part thereof comprising 1) a first recombinant expression cassette comprising a transcribable DNA sequence encoding a non-coding RNA for suppression of one or more gibberellic acid 20 (GA20) oxidase genes, and 2) a second recombinant expression cassette comprising a DNA sequence encoding a glutamate dehydrogenase (GDH) polypeptide, wherein the modified corn plant is semi-dwarf and has one or more improved ear traits relative to a control corn plant that does not have the first or second recombinant expression cassettes.

2. The modified corn plant or plant part thereof of claim 1, wherein the transcribable DNA sequence comprises a sequence that is at least 80% identical or complementary to at least 15 consecutive nucleotides of one or more of SEQ ID NOs: 39, 40, and 53-56.

3. The modified corn plant or plant part thereof of claim 1, wherein the GDH polypeptide comprises an amino acid sequence that is at least 60% identical to one or more of SEQ ID NOs: 168 and 176-192.

4. The modified corn plant or plant part thereof of claim 1, wherein the DNA sequence comprised in the second recombinant expression cassette comprises a sequence that is at least 60% identical to SEQ ID NO: 169.

5. The modified corn plant or plant part thereof of claim 1, wherein the transcribable DNA sequence comprised in the first recombinant expression cassette or the DNA sequence comprised in the second recombinant expression cassette is operably linked to a heterologous plant-expressible promoter selected from the group consisting of a vascular promoter, a rice tungro bacilliform virus (RTBV) promoter, a leaf promoter, a constitutive promoter, and combinations thereof.

6. The modified corn plant or plant part thereof of claim 1, wherein the one or more improved ear traits are selected from the group consisting of ear diameter, single kernel weight, ear fresh weight, yield, grain yield estimate, ear area, ear volume, ear length, ear tip void, kernels per ear, broad acreage yield, foliar nitrogen percentage, and combinations thereof.

7. The modified corn plant or a plant part thereof of claim 1, wherein the modified corn plant comprises 1) a first transcribable DNA sequence comprising SEQ ID NO: 39, and 2) a second transcribable DNA sequence comprising SEQ ID NO: 169, wherein the modified corn plant is semi-dwarf and has one or more improved ear traits, relative to a control corn plant that does not have the first or second transcribable DNA sequence.

8. The modified corn plant or plant part thereof of claim 7, wherein the one or more improved ear traits are selected from the group consisting of ear diameter, single kernel weight, ear fresh weight, yield, grain yield estimate, ear area, ear volume, ear length, ear tip void, kernels per ear, broad acreage yield, foliar nitrogen percentage, and combinations thereof.

9. A seed or a commodity product of the modified corn plant of claim 1, wherein the seed or commodity product comprises the first and second recombinant expression cassettes.

10. A method for producing a modified corn plant, the method comprising a. introducing into a corn cell 1) a first recombinant expression cassette comprising a transcribable DNA sequence encoding a non-coding RNA for suppression of one or more GA20 oxidase genes and 2) a second recombinant expression cassette comprising a DNA sequence encoding a GDH polypeptide; and
b. regenerating or developing a modified corn plant from the corn cell, wherein the modified corn plant comprises the first and second recombinant expression cassettes, wherein the modified corn plant is semi-dwarf and has one or more improved ear traits relative to a control corn plant that does not have the first or second recombinant expression cassettes.

11. The method of claim 10, wherein the transcribable DNA sequence comprises a sequence that is at least 80% identical or complementary to at least 15 consecutive nucleotides of one or more of SEQ ID NOs: 39, 40, and 53-56.

12. The method of claim 10, wherein the GDH polypeptide comprises an amino acid sequence that is at least 60% identical to one or more of SEQ ID NOs: 168 and 176-192.

13. The method of claim 10, wherein the one or more improved ear traits are selected from the group consisting of ear diameter, single kernel weight, ear fresh weight, yield, grain yield estimate, ear area, ear volume, ear length, ear tip void, kernels per ear, broad acreage yield, foliar nitrogen percentage, and combinations thereof, relative to a control corn plant that does not have the first or second recombinant expression cassettes.

14. A method for producing a modified corn plant, the method comprising:

a. crossing a first modified corn plant with a second modified corn plant, wherein the expression or activity of one or more endogenous GA20 oxidase genes is reduced in the first modified corn plant relative to a wildtype control, and wherein the second modified corn plant comprises a recombinant expression cassette comprising a DNA sequence encoding a GDH polypeptide; and
b. producing a progeny corn plant comprising the recombinant expression cassette and has the reduced expression of the one or more endogenous GA20 oxidase genes, and
c. selecting a progeny corn plant that is semi-dwarf and has one or more improved ear traits relative to a control corn plant that does not have the first or second recombinant expression cassettes.

15. The method of claim 14, wherein the first modified corn plant and the progeny corn plant comprise a transcribable DNA sequence comprising a sequence that is at least 80% identical or complementary to at least 15 consecutive nucleotides of one or more of SEQ ID NOs: 39, 40, and 53-56.

16. The method of claim 14, wherein the GDH polypeptide comprises an amino acid sequence that is at least 60% identical to one or more of SEQ ID NOs: 168 and 176-192.

17. The method of claim 14, wherein the one or more improved ear traits are selected from the group consisting of ear diameter, single kernel weight, ear fresh weight, yield, grain yield estimate, ear area, ear volume, ear length, ear tip void, kernels per ear, broad acreage yield, foliar nitrogen percentage, and combinations thereof.

18. The modified corn plant or plant part thereof of claim 1, wherein the transcribable DNA sequence comprises a sequence that is at least 80% identical or complementary to at least 19 consecutive nucleotides of an mRNA molecule encoding an endogenous GA oxidase protein, the endogenous GA oxidase protein being at least 80% identical to SEQ ID NO: 9 or SEQ ID NO: 15.

19. The modified corn plant or plant part thereof of claim 1, wherein the non-coding RNA comprises a targeting sequence that is at least 80% identical or complementary to at least 19 consecutive nucleotides of a sequence selected from the group consisting of SEQ ID NOs: 7, 8, 13, and 14.

* * * * *

SEQUENCE LISTING

<160> NUMBER OF SEQ ID NOS: 200

<210> SEQ ID NO 1
<211> LENGTH: 1741
<212> TYPE: DNA
<213> ORGANISM: Zea mays

<400> SEQUENCE: 1

```
gacggtagtt ttcatctaaa gtttattctt cgtcacatgg gatggccgtt tgcttgtttg      60

ttgcttccgg gaggcggtgg tgaattgaag cagatcgaca agcatggctg cccactggtc     120

tcgatcgatc ggcctgccat gccatgccat gccactagag tccgtcctga ctggccgccc     180

gttcccccgt ataaaaaggc aggcaggcag gcagagcggg gacgagcaag caagcagttg     240

cagttgcagc ggcctcctcc tctgcttcct ccctcctcct cctcaccatg gtgctggctg     300

cgcacgatcc ccctcccctt gtgttcgacg ctgcccgcct gagcggcctc tccgacatcc     360

cgcagcagtt catctggccg gcggacgaga gccccacccc ggactccgcc gaggagctgg     420

ccgtgccgct catcgacctc tccggggacg ccgccgaggt ggtccggcag gtccggcgcg     480

cctgcgacct gcacggcttc ttccaggtgg tggggcacgg catcgacgcg gcgctgacgg     540

cggaggccca ccgctgcatg gacgccttct tcacgctgcc gctcccggac aagcagcgcg     600

cgcagcgccg ccagggggac agctgcggct acgccagcag cttcacgggc cggttcgcgt     660

ccaagctgcc ctggaaggag acgctgtcgt tccgctacac cgacgacgac gacggcgaca     720

agtccaagga cgtcgtggcg tcctacttcg tggacaagct gggcgagggg taccggcacc     780

acggggaggt gtacgggcgc tactgctctg agatgagccg tctgtcgctg gagctcatgg     840

aggtgctagg cgagagcctg ggcgtgggcc ggcgccactt ccggcgcttc ttccagggga     900

acgactccat catgcgcctc aactactacc cgccgtgcca gcggccctac gacacgctgg     960

gcacggggcc gcattgcgac cccacgtcgc tcaccatcct gcaccaggac gacgtgggcg    1020

gactccaggt gttcgacgcc gccacgctcg cgtggcgctc catcaggccc cgcccgggcg    1080

ccttcgtcgt caacatcggc gacaccttca tggcgctctc caacgggcgc tacaggagct    1140

gcctccaccg cgccgtcgtc aacagccggg tggcacgccg ctcgctcgcc ttcttcctgt    1200

gcccggagat ggacaaggtg gtcaggccgc ccaaggagct ggtggacgac gccaacccga    1260

gggcgtaccc ggacttcacg tggaggacgc tgctggactt caccatgagg cactacaggt    1320

cggacatgag gacgctcgag gccttctcca actggctcag caccagtagc aatggcggac    1380

agcacctgct ggagaagaag taggcatgct atttgggtat ggaagatggt ggatgtaagc    1440

aaacaaagcc aaattaagca gagtaggtta attaaggttg gctgatgatc catttaggga    1500

aggagctgat ctccctgact ccctcctcca attttctcaa ccaaatttat atagtataat    1560

aataataata aaatagcaag taatagttgt atcgtattat tattaattaa tttattagct    1620

ggtaggcaag tagtattaaa taccatttgt agtacgatgg gcgtatttct attttggcgt    1680

tttgctctgt gttttttgac gtttcctttg gatttggggg gacctcagat cagctcggcc    1740

t                                                                     1741
```

<210> SEQ ID NO 2
<211> LENGTH: 1116
<212> TYPE: DNA
<213> ORGANISM: Zea mays

<400> SEQUENCE: 2

```
atggtgctgg ctgcgcacga tccccctccc cttgtgttcg acgctgcccg cctgagcggc      60
```

```
ctctccgaca tcccgcagca gttcatctgg ccggcggacg agagccccac cccggactcc    120
gccgaggagc tggccgtgcc gctcatcgac ctctccgggg acgccgccga ggtggtccgg    180
caggtccggc gcgcctgcga cctgcacggc ttcttccagg tggtggggca cggcatcgac    240
gcggcgctga cggcggaggc ccaccgctgc atggacgcct tcttcacgct gccgctcccg    300
gacaagcagc gcgcgcagcg ccgccagggg gacagctgcg gctacgccag cagcttcacg    360
ggccggttcg cgtccaagct gccctggaag gagacgctgt cgttccgcta caccgacgac    420
gacgacggcg acaagtccaa ggacgtcgtg gcgtcctact tcgtggacaa gctgggcgag    480
gggtaccggc accacgggga ggtgtacggg cgctactgct ctgagatgag ccgtctgtcg    540
ctggagctca tggaggtgct aggcgagagc ctgggcgtgg gccggcgcca cttccggcgc    600
ttcttccagg ggaacgactc catcatgcgc ctcaactact acccgccgtg ccagcggccc    660
tacgacacgc tgggcacggg gccgcattgc gaccccacgt cgctcaccat cctgcaccag    720
gacgacgtgg gcggactcca ggtgttcgac gccgccacgc tcgcgtggcg ctccatcagg    780
ccccgcccgg gcgccttcgt cgtcaacatc ggcgacacct tcatggcgct ctccaacggg    840
cgctacagga gctgcctcca ccgcgccgtc gtcaacagcc gggtggcacg ccgctcgctc    900
gccttcttcc tgtgcccgga gatggacaag gtggtcaggc cgcccaagga gctggtggac    960
gacgccaacc cgagggcgta cccggacttc acgtggagga cgctgctgga cttcaccatg   1020
aggcactaca ggtcggacat gaggacgctc gaggccttct ccaactggct cagcaccagt   1080
agcaatggcg gacagcacct gctggagaag aagtag                             1116
```

<210> SEQ ID NO 3
<211> LENGTH: 371
<212> TYPE: PRT
<213> ORGANISM: Zea mays

<400> SEQUENCE: 3

```
Met Val Leu Ala Ala His Asp Pro Pro Pro Leu Val Phe Asp Ala Ala
1               5                   10                  15

Arg Leu Ser Gly Leu Ser Asp Ile Pro Gln Gln Phe Ile Trp Pro Ala
            20                  25                  30

Asp Glu Ser Pro Thr Pro Asp Ser Ala Glu Glu Leu Ala Val Pro Leu
        35                  40                  45

Ile Asp Leu Ser Gly Asp Ala Ala Glu Val Val Arg Gln Val Arg Arg
    50                  55                  60

Ala Cys Asp Leu His Gly Phe Phe Gln Val Val Gly His Gly Ile Asp
65                  70                  75                  80

Ala Ala Leu Thr Ala Glu Ala His Arg Cys Met Asp Ala Phe Phe Thr
                85                  90                  95

Leu Pro Leu Pro Asp Lys Gln Arg Ala Gln Arg Arg Gln Gly Asp Ser
            100                 105                 110

Cys Gly Tyr Ala Ser Ser Phe Thr Gly Arg Phe Ala Ser Lys Leu Pro
        115                 120                 125

Trp Lys Glu Thr Leu Ser Phe Arg Tyr Thr Asp Asp Asp Asp Gly Asp
    130                 135                 140

Lys Ser Lys Asp Val Val Ala Ser Tyr Phe Val Asp Lys Leu Gly Glu
145                 150                 155                 160

Gly Tyr Arg His His Gly Glu Val Tyr Gly Arg Tyr Cys Ser Glu Met
                165                 170                 175

Ser Arg Leu Ser Leu Glu Leu Met Glu Val Leu Gly Glu Ser Leu Gly
```

```
            180                 185                 190

Val Gly Arg Arg His Phe Arg Arg Phe Phe Gln Gly Asn Asp Ser Ile
        195                 200                 205

Met Arg Leu Asn Tyr Tyr Pro Pro Cys Gln Arg Pro Tyr Asp Thr Leu
    210                 215                 220

Gly Thr Gly Pro His Cys Asp Pro Thr Ser Leu Thr Ile Leu His Gln
225                 230                 235                 240

Asp Asp Val Gly Gly Leu Gln Val Phe Asp Ala Ala Thr Leu Ala Trp
                245                 250                 255

Arg Ser Ile Arg Pro Arg Pro Gly Ala Phe Val Val Asn Ile Gly Asp
            260                 265                 270

Thr Phe Met Ala Leu Ser Asn Gly Arg Tyr Arg Ser Cys Leu His Arg
        275                 280                 285

Ala Val Val Asn Ser Arg Val Ala Arg Arg Ser Leu Ala Phe Phe Leu
    290                 295                 300

Cys Pro Glu Met Asp Lys Val Val Arg Pro Pro Lys Glu Leu Val Asp
305                 310                 315                 320

Asp Ala Asn Pro Arg Ala Tyr Pro Asp Phe Thr Trp Arg Thr Leu Leu
                325                 330                 335

Asp Phe Thr Met Arg His Tyr Arg Ser Asp Met Arg Thr Leu Glu Ala
            340                 345                 350

Phe Ser Asn Trp Leu Ser Thr Ser Ser Asn Gly Gly Gln His Leu Leu
        355                 360                 365

Glu Lys Lys
    370
```

<210> SEQ ID NO 4
<211> LENGTH: 1517
<212> TYPE: DNA
<213> ORGANISM: Zea mays

<400> SEQUENCE: 4

```
caggaataaa ataagcctcc gcccggcttc gttgcatcca cgcacgcagc aagcgatcgg      60

atttcgccag catggcggcg gcggccgtgg tgttcgacgc cgaggcgctg agccgggagg     120

agcacatccc ggcgcagttc gtgtggccca ccgaggagcg ggcgccggcg ggcggcgtgg     180

aggaggtcgc catccccgtg gtcgacctcg gcgagttcct ccgccgcggg gtgctcccgc     240

gcggcgtggc ggaggcgtgc gagcgccacg gcgtcttcca ggtggtgaac cacggcgtgg     300

gcgccgcgct gctcgccgag gcctaccgct gttgcgacgc cttttacgcg ctcccgctcg     360

cggacaagca gcgcgcgcag cgccggcacg gggagaacca cggctacgcc agcagcttca     420

cgggccgctt ccactgctgc ctgccgtgga aggagacgct gtccttcaac tgccccgccg     480

gtgccgggac tgcgcgcgcc gtcgtcggct acttcgtcga cgtcctcggc gaggactacc     540

gccacatggg ggaggtgtac caggagtact gcgacgcgat gacgcgtctg gcgctggacg     600

tgacggaggt gctggcggca gcgctggggc tggaccgcgg cgcactgcgc ggcttcttcg     660

agggcggcga ctccgtcatg cggctgaacc actacccggc gtgccggcag ccgcacctga     720

cgctggggac gggcccgcac cgggacccga cgtcgctgac gctgctgcac caggacgacg     780

tgggcgggct gcaggtgcgc gccggcggcg ggccgtggcg cgcggtgcgg ccccgcgcgg     840

acgcgttcgt ggtcaacatt ggcgacacct tcgccgcgct caccgacggg cgtcacacca     900

gctgcctgca ccgcgccgtg gtgaccggcg gcggctcccg ccggtcgctc gccttcttcc     960

tcaacccgcc gctggaccgc gtcgtccgcc cgccgggcgc gctcctccag gagaacaagc    1020
```

```
aggcgggccg cccgcgcgcg ttcccggact tcacgtggcg cgagttcctc gagttcacgc   1080

agaagcacta ccggtcggac gcgggcacca tggacgcctt cgtgtcgtgg atcgcgggag   1140

gccgccgcca ccatggcgga caggaggagg gcaactgaga tcgatgcatc tctagctgta   1200

ggcagcagcg cagcagctac caagaataat ggccggcgac ggagatgcag ctacgacgca   1260

caaataaatt gagtgtttgt ggtacaataa ggacgaggac gatcaatggc gacctgtaac   1320

cggtgcagtt ttagttaatc tttcatggcg atatggcatt aaccaatcgt tggtgtaaaa   1380

tgcgtgcatg ctttgcatgc caatgttggc catgtgatgg cacagcgtga gtgtagctca   1440

cccaccgtga caacgtgcta atttcgtgtg gtcctagata ccaaggtcgt ctaatgaact   1500

tgatggattg atgattt                                                 1517
```

<210> SEQ ID NO 5
<211> LENGTH: 1107
<212> TYPE: DNA
<213> ORGANISM: Zea mays

<400> SEQUENCE: 5

```
atggcggcgg cggccgtggt gttcgacgcc gaggcgctga gccgggagga gcacatcccg     60

gcgcagttcg tgtggcccac cgaggagcgg gcgccggcgg gcggcgtgga ggaggtcgcc    120

atccccgtgg tcgacctcgg cgagttcctc cgccgcgggg tgctcccgcg cggcgtggcg    180

gaggcgtgcg agcgccacgg cgtcttccag gtggtgaacc acggcgtggg cgccgcgctg    240

ctcgccgagg cctaccgctg ttgcgacgcc ttttacgcgc tcccgctcgc ggacaagcag    300

cgcgcgcagc gccggcacgg ggagaaccac ggctacgcca gcagcttcac gggccgcttc    360

cactgctgcc tgccgtggaa ggagacgctg tccttcaact gccccgccgg tgccgggact    420

gcgcgcgccg tcgtcggcta cttcgtcgac gtcctcggcg aggactaccg ccacatgggg    480

gaggtgtacc aggagtactg cgacgcgatg acgcgtctgg cgctggacgt gacggaggtg    540

ctggcggcag cgctggggct ggaccgcggc gcactgcgcg gcttcttcga gggcggcgac    600

tccgtcatgc ggctgaacca ctacccggcg tgccggcagc cgcacctgac gctggggacg    660

ggcccgcacc gggacccgac gtcgctgacg ctgctgcacc aggacgacgt gggcgggctg    720

caggtgcgcg ccggcggcgg gccgtggcgc gcggtgcggc cccgcgcgga cgcgttcgtg    780

gtcaacattg gcgacacctt cgccgcgctc accgacgggc gtcacaccag ctgcctgcac    840

cgcgccgtgg tgaccggcgg cggctcccgc cggtcgctcg ccttcttcct caacccgccg    900

ctggaccgcg tcgtccgccc gccgggcgcg ctcctccagg agaacaagca ggcgggccgc    960

ccgcgcgcgt tcccggactt cacgtggcgc gagttcctcg agttcacgca gaagcactac   1020

cggtcggacg cgggcaccat ggacgccttc gtgtcgtgga tcgcgggagg ccgccgccac   1080

catggcggac aggaggaggg caactga                                      1107
```

<210> SEQ ID NO 6
<211> LENGTH: 368
<212> TYPE: PRT
<213> ORGANISM: Zea mays

<400> SEQUENCE: 6

```
Met Ala Ala Ala Ala Val Val Phe Asp Ala Glu Ala Leu Ser Arg Glu
1               5                   10                  15

Glu His Ile Pro Ala Gln Phe Val Trp Pro Thr Glu Glu Arg Ala Pro
            20                  25                  30
```

```
Ala Gly Gly Val Glu Glu Val Ala Ile Pro Val Val Asp Leu Gly Glu
        35                  40                  45

Phe Leu Arg Arg Gly Val Leu Pro Arg Gly Val Ala Glu Ala Cys Glu
    50                  55                  60

Arg His Gly Val Phe Gln Val Val Asn His Gly Val Gly Ala Ala Leu
65                  70                  75                  80

Leu Ala Glu Ala Tyr Arg Cys Cys Asp Ala Phe Tyr Ala Leu Pro Leu
                85                  90                  95

Ala Asp Lys Gln Arg Ala Gln Arg Arg His Gly Glu Asn His Gly Tyr
            100                 105                 110

Ala Ser Ser Phe Thr Gly Arg Phe His Cys Cys Leu Pro Trp Lys Glu
        115                 120                 125

Thr Leu Ser Phe Asn Cys Pro Ala Gly Ala Gly Thr Ala Arg Ala Val
    130                 135                 140

Val Gly Tyr Phe Val Asp Val Leu Gly Glu Asp Tyr Arg His Met Gly
145                 150                 155                 160

Glu Val Tyr Gln Glu Tyr Cys Asp Ala Met Thr Arg Leu Ala Leu Asp
                165                 170                 175

Val Thr Glu Val Leu Ala Ala Ala Leu Gly Leu Asp Arg Gly Ala Leu
            180                 185                 190

Arg Gly Phe Phe Glu Gly Gly Asp Ser Val Met Arg Leu Asn His Tyr
        195                 200                 205

Pro Ala Cys Arg Gln Pro His Leu Thr Leu Gly Thr Gly Pro His Arg
    210                 215                 220

Asp Pro Thr Ser Leu Thr Leu Leu His Gln Asp Asp Val Gly Gly Leu
225                 230                 235                 240

Gln Val Arg Ala Gly Gly Gly Pro Trp Arg Ala Val Arg Pro Arg Ala
                245                 250                 255

Asp Ala Phe Val Val Asn Ile Gly Asp Thr Phe Ala Ala Leu Thr Asp
            260                 265                 270

Gly Arg His Thr Ser Cys Leu His Arg Ala Val Val Thr Gly Gly Gly
        275                 280                 285

Ser Arg Arg Ser Leu Ala Phe Phe Leu Asn Pro Pro Leu Asp Arg Val
    290                 295                 300

Val Arg Pro Pro Gly Ala Leu Leu Gln Glu Asn Lys Gln Ala Gly Arg
305                 310                 315                 320

Pro Arg Ala Phe Pro Asp Phe Thr Trp Arg Glu Phe Leu Glu Phe Thr
                325                 330                 335

Gln Lys His Tyr Arg Ser Asp Ala Gly Thr Met Asp Ala Phe Val Ser
            340                 345                 350

Trp Ile Ala Gly Gly Arg Arg His His Gly Gly Gln Glu Glu Gly Asn
        355                 360                 365
```

<210> SEQ ID NO 7
<211> LENGTH: 1522
<212> TYPE: DNA
<213> ORGANISM: Zea mays

<400> SEQUENCE: 7

```
gcacactcgc agctcgcaca tctcatggtg tcctaagaac ggcaagagcc agctctgcct      60

agcagcagcg cacagccaca tccatggacg ccagcccgac cccaccgctc cccctccgcg     120

ccccaactcc cagcattgac ctccccgctg gcaaggacag ggccgacgcg gcggctaaca     180

aggccgcggc tgtgttcgac ctgcgccggg agcccaagat cccggagcca ttcctgtggc     240
```

```
cgcacgaaga ggcgcggccg acctcggccg cggagctgga ggtgccggtg gtggacgtgg    300
gcgtgctgcg caatggcgac ggcgcggggc tccgccgcgc cgcggcgcaa gtggcggcgg    360
cgtgcgcgac gcacgggttc ttccaggtgt gcgggcacgg cgtggacgcg gcgctggggc    420
gcgccgcgct ggacggcgcc agcgacttct tccggctgcc gctggctgag aagcagcggg    480
cccggcgcgt ccccggcacc gtgtccgggt acacgagcgc gcacgccgac cggttcgcgt    540
ccaagctccc ctggaaggag accctgtcct tcggcttcca cgacggcgcc gcggcgcccg    600
tcgtcgtgga ctacttcacc ggcaccctcg gccaagattt cgagccagtg gggcgggtgt    660
accagaggta ctgcgaggag atgaaggagc tgtcgctgac gatcatggag ctgctggagc    720
tgagcctggg cgtggagcgc ggctactacc gggagttctt cgaggacagc cgctccatca    780
tgcggtgcaa ctactacccg ccgtgcccgg tgccggagcg cacgctgggc acgggcccgc    840
actgcgaccc cacggcgctg accatcctcc tgcaggacga cgtcggcggg ctggaggtcc    900
tggtggacgg cgagtggcgc cccgtccggc ccgtcccagg cgccatggtc atcaacatcg    960
gcgacacctt catggcgctg tccaacgggc ggtacaagag ctgcctgcac cgcgcggtgg   1020
tgaaccggcg gcaggagcgg caatcgctgg ccttcttcct gtgcccgcgc gaggaccggg   1080
tggtgcgccc gccggccagc gccgcgccgc ggcagtaccc ggacttcacc tgggccgacc   1140
tcatgcgctt cacgcagcgc cactaccgcg ccgacacccg cacgctggac gccttcaccc   1200
gctggctctc ccacggcccg gcggcggcgg ctccctgcac ctaacgagcc ggccgtctct   1260
ttcgccgggg cccgcgcggg gttcgcccac gtggtgatca ggtggcagac atgtggccca   1320
cgggccccgc gccgccttcc ccatttttgg acgaccctac tgctactact actagtgtac   1380
atatgcaaaa aaatacatat atatataggt actttctcta atatttttat atataagcaa   1440
ggcggcctgg tgttcttttc tttgttttgt cgacaactgt ttgatcccat cctatggacg   1500
atggatagtt caatgtttgt ac                                            1522
```

<210> SEQ ID NO 8
<211> LENGTH: 1161
<212> TYPE: DNA
<213> ORGANISM: Zea mays

<400> SEQUENCE: 8

```
atggacgcca gcccgacccc accgctcccc ctccgcgccc caactcccag cattgacctc     60
cccgctggca aggacagggc cgacgcggcg gctaacaagg ccgcggctgt gttcgacctg    120
cgccgggagc ccaagatccc ggagccattc ctgtggccgc acgaagaggc gcggccgacc    180
tcggccgcgg agctggaggt gccggtggtg gacgtgggcg tgctgcgcaa tggcgacggc    240
gcggggctcc gccgcgccgc ggcgcaagtg gcggcggcgt gcgcgacgca cgggttcttc    300
caggtgtgcg ggcacggcgt ggacgcggcg ctggggcgcg ccgcgctgga cggcgccagc    360
gacttcttcc ggctgccgct ggctgagaag cagcgggccc ggcgcgtccc cggcaccgtg    420
tccgggtaca cgagcgcgca cgccgaccgg ttcgcgtcca agctcccctg gaaggagacc    480
ctgtccttcg gcttccacga cggcgccgcg gcgcccgtcg tcgtggacta cttcaccggc    540
accctcggcc aagatttcga gccagtgggg cgggtgtacc agaggtactg cgaggagatg    600
aaggagctgt cgctgacgat catggagctg ctggagctga gcctgggcgt ggagcgcggc    660
tactaccggg agttcttcga ggacagccgc tccatcatgc ggtgcaacta ctacccgccg    720
tgcccggtgc cggagcgcac gctgggcacg ggcccgcact gcgaccccac ggcgctgacc    780
atcctcctgc aggacgacgt cggcgggctg gaggtcctgg tggacggcga gtggcgcccc    840
```

```
gtccggcccg tcccaggcgc catggtcatc aacatcggcg acaccttcat ggcgctgtcc     900

aacgggcggt acaagagctg cctgcaccgc gcggtggtga accggcggca ggagcggcaa     960

tcgctggcct tcttcctgtg cccgcgcgag gaccgggtgg tgcgcccgcc ggccagcgcc    1020

gcgccgcggc agtacccgga cttcacctgg gccgacctca tgcgcttcac gcagcgccac    1080

taccgcgccg acacccgcac gctggacgcc ttcacccgct ggctctccca cggcccggcg    1140

gcggcggctc cctgcaccta a                                              1161
```

```
<210> SEQ ID NO 9
<211> LENGTH: 386
<212> TYPE: PRT
<213> ORGANISM: Zea mays

<400> SEQUENCE: 9

Met Asp Ala Ser Pro Thr Pro Pro Leu Pro Leu Arg Ala Pro Thr Pro
1               5                   10                  15

Ser Ile Asp Leu Pro Ala Gly Lys Asp Arg Ala Asp Ala Ala Ala Asn
            20                  25                  30

Lys Ala Ala Ala Val Phe Asp Leu Arg Arg Glu Pro Lys Ile Pro Glu
        35                  40                  45

Pro Phe Leu Trp Pro His Glu Glu Ala Arg Pro Thr Ser Ala Ala Glu
    50                  55                  60

Leu Glu Val Pro Val Val Asp Val Gly Val Leu Arg Asn Gly Asp Gly
65                  70                  75                  80

Ala Gly Leu Arg Arg Ala Ala Ala Gln Val Ala Ala Ala Cys Ala Thr
                85                  90                  95

His Gly Phe Phe Gln Val Cys Gly His Gly Val Asp Ala Ala Leu Gly
            100                 105                 110

Arg Ala Ala Leu Asp Gly Ala Ser Asp Phe Phe Arg Leu Pro Leu Ala
        115                 120                 125

Glu Lys Gln Arg Ala Arg Arg Val Pro Gly Thr Val Ser Gly Tyr Thr
    130                 135                 140

Ser Ala His Ala Asp Arg Phe Ala Ser Lys Leu Pro Trp Lys Glu Thr
145                 150                 155                 160

Leu Ser Phe Gly Phe His Asp Gly Ala Ala Ala Pro Val Val Val Asp
                165                 170                 175

Tyr Phe Thr Gly Thr Leu Gly Gln Asp Phe Glu Pro Val Gly Arg Val
            180                 185                 190

Tyr Gln Arg Tyr Cys Glu Glu Met Lys Glu Leu Ser Leu Thr Ile Met
        195                 200                 205

Glu Leu Leu Glu Leu Ser Leu Gly Val Glu Arg Gly Tyr Tyr Arg Glu
    210                 215                 220

Phe Phe Glu Asp Ser Arg Ser Ile Met Arg Cys Asn Tyr Tyr Pro Pro
225                 230                 235                 240

Cys Pro Val Pro Glu Arg Thr Leu Gly Thr Gly Pro His Cys Asp Pro
                245                 250                 255

Thr Ala Leu Thr Ile Leu Leu Gln Asp Asp Val Gly Gly Leu Glu Val
            260                 265                 270

Leu Val Asp Gly Glu Trp Arg Pro Val Arg Pro Val Pro Gly Ala Met
        275                 280                 285

Val Ile Asn Ile Gly Asp Thr Phe Met Ala Leu Ser Asn Gly Arg Tyr
    290                 295                 300

Lys Ser Cys Leu His Arg Ala Val Val Asn Arg Arg Gln Glu Arg Gln
```

```
305                 310                 315                 320

Ser Leu Ala Phe Phe Leu Cys Pro Arg Glu Asp Arg Val Val Arg Pro
                325                 330                 335

Pro Ala Ser Ala Ala Pro Arg Gln Tyr Pro Asp Phe Thr Trp Ala Asp
            340                 345                 350

Leu Met Arg Phe Thr Gln Arg His Tyr Arg Ala Asp Thr Arg Thr Leu
        355                 360                 365

Asp Ala Phe Thr Arg Trp Leu Ser His Gly Pro Ala Ala Ala Ala Pro
    370                 375                 380

Cys Thr
385


<210> SEQ ID NO 10
<211> LENGTH: 1457
<212> TYPE: DNA
<213> ORGANISM: Zea mays

<400> SEQUENCE: 10

taatcacctc atcacaggtc cccccagcct cactctcgcg ccggctcaag gtacattgcg      60

tgtcctagcc aagacacgca gctcatctca gcctcacacg cacagcaaga gcgaggcgtg     120

attcgccatg ggcggcctca ctatggacca ggccttcgtg caggcccccg agcaccgccc     180

caagcccatc gtcaccgagg ccaccggcat ccctctcatc gacctctcgc ctctggccgc     240

cagcggcggc gccgtggacg cgctggccgc cgaggtgggc gcggcgagcc gggactgggg     300

cttcttcgtg gtcgtgggcc acggcgtgcc cgcagagacc gtggcgcgcg cgacggaggc     360

gcagcgagcg ttcttcgcgc tgccggcaga gcggaaggcc gccgtgcgga ggaacgaggc     420

ggagccgctc gggtactacg agtcggagca caccaagaac gtgagggact ggaaggaggt     480

gtacgacctc gtgccgcgcg agccgccgcc gccggcagcc gtggccgacg gcgagcttgt     540

gttcgataac aagtggcccc aggatctacc gggcttcaga gaggcgctgg aggagtacgc     600

gaaagcgatg gaagagctgg cgttcaagct gctggagctg atcgcccgga gcctgaagct     660

gaggcccgac cggctgcacg gcttcttcaa ggaccagacg accttcatcc ggctgaacca     720

ctaccctcct tgcccgagcc ccgacctggc cctcggcgtg gggcggcaca aggacgccgg     780

cgccctgacc atcctgtacc aggacgacgt cggggggctc gacgtccggc ggcgctccga     840

cggcgagtgg gtccgcgtca ggcccgtgcc cgactcgttc atcatcaacg tcggcgacct     900

catccaggta cgagagcgcg gagcaccggg tgtcggtgaa ctcggcgagg gagaggttct     960

ccatgcccta cttcttcaac ccggcgacct acaccatggt ggagccggtg gaggagctgg    1020

tgagcaagga cgatccgccc aggtacgacg cctacaactg ggcgacttc ttcagcacca    1080

ggaagaacag caacttcaag aagctcaacg tggagaacat tcagatcgcg catttcaaga    1140

agagcctcgt cctcgcctaa ctactgctac tgctaggatc catgccattg ccatgtcgtc    1200

ttcagattca gagcacgcca tgtcgtcgct agcttcgtgg tagaacaaat aatgatgtgc    1260

gtgctgtgtg taagcatgga tatggatgtg aatatgtaat atgatgagca ctcctacttt    1320

ggtatgtttg ggaataacag acttgtgttg gtctggttca ttatttgtaa gaaaatcaaa    1380

aagagttagt agggcaggag gctaaccaca gtcatgctgc accacatccc tggtggaaag    1440

ctggccgggt tacgcta                                                   1457


<210> SEQ ID NO 11
<211> LENGTH: 1116
<212> TYPE: DNA
```

<213> ORGANISM: Zea mays

<400> SEQUENCE: 11

```
atgggcggcc tcactatgga ccaggccttc gtgcaggccc ccgagcaccg ccccaagccc      60
atcgtcaccg aggccaccgg catccctctc atcgacctct cgcctctggc cgccagcggc     120
ggcgccgtgg acgcgctggc cgccgaggtg ggcgcggcga gccgggactg gggcttcttc     180
gtggtcgtgg gccacggcgt gcccgcagag accgtggcgc gcgcgacgga ggcgcagcga     240
gcgttcttcg cgctgccggc agagcggaag gccgccgtgc ggaggaacga ggcggagccg     300
ctcgggtact acgagtcgga gcacaccaag aacgtgaggg actggaagga ggtgtacgac     360
ctcgtgccgc gcgagccgcc gccgccggca gccgtggccg acggcgagct tgtgttcgat     420
aacaagtggc cccaggatct accgggcttc agagaggcgc tggaggagta cgcgaaagcg     480
atggaagagc tggcgttcaa gctgctggag ctgatcgccc ggagcctgaa gctgaggccc     540
gaccggctgc acggcttctt caaggaccag acgaccttca tccggctgaa ccactaccct     600
ccttgcccga gccccgacct ggccctcggc gtggggcggc acaaggacgc cggcgccctg     660
accatcctgt accaggacga cgtcgggggg ctcgacgtcc ggcggcgctc cgacggcgag     720
tgggtccgcg tcaggcccgt gcccgactcg ttcatcatca acgtcggcga cctcatccag     780
gtacgagagc gcggagcacc gggtgtcggt gaactcggcg agggagaggt tctccatgcc     840
ctacttcttc aacccggcga cctacaccat ggtggagccg gtggaggagc tggtgagcaa     900
ggacgatccg cccaggtacg acgcctacaa ctggggcgac ttcttcagca ccaggaagaa     960
cagcaacttc aagaagctca acgtggagaa cattcagatc gcgcatttca agaagagcct    1020
cgtcctcgcc taactactgc tactgctagg atccatgcca ttgccatgtc gtcttcagat    1080
tcagagcacg ccatgtcgtc gctagcttcg tggtag                              1116
```

<210> SEQ ID NO 12
<211> LENGTH: 371
<212> TYPE: PRT
<213> ORGANISM: Zea mays

<400> SEQUENCE: 12

```
Met Gly Gly Leu Thr Met Asp Gln Ala Phe Val Gln Ala Pro Glu His
1               5                   10                  15

Arg Pro Lys Pro Ile Val Thr Glu Ala Thr Gly Ile Pro Leu Ile Asp
            20                  25                  30

Leu Ser Pro Leu Ala Ala Ser Gly Gly Ala Val Asp Ala Leu Ala Ala
        35                  40                  45

Glu Val Gly Ala Ala Ser Arg Asp Trp Gly Phe Phe Val Val Val Gly
    50                  55                  60

His Gly Val Pro Ala Glu Thr Val Ala Arg Ala Thr Glu Ala Gln Arg
65                  70                  75                  80

Ala Phe Phe Ala Leu Pro Ala Glu Arg Lys Ala Ala Val Arg Arg Asn
                85                  90                  95

Glu Ala Glu Pro Leu Gly Tyr Tyr Glu Ser Glu His Thr Lys Asn Val
            100                 105                 110

Arg Asp Trp Lys Glu Val Tyr Asp Leu Val Pro Arg Glu Pro Pro Pro
        115                 120                 125

Pro Ala Ala Val Ala Asp Gly Glu Leu Val Phe Asp Asn Lys Trp Pro
    130                 135                 140

Gln Asp Leu Pro Gly Phe Arg Glu Ala Leu Glu Glu Tyr Ala Lys Ala
145                 150                 155                 160
```

Met Glu Glu Leu Ala Phe Lys Leu Leu Glu Leu Ile Ala Arg Ser Leu
165 170 175

Lys Leu Arg Pro Asp Arg Leu His Gly Phe Phe Lys Asp Gln Thr Thr
180 185 190

Phe Ile Arg Leu Asn His Tyr Pro Pro Cys Pro Ser Pro Asp Leu Ala
195 200 205

Leu Gly Val Gly Arg His Lys Asp Ala Gly Ala Leu Thr Ile Leu Tyr
210 215 220

Gln Asp Asp Val Gly Gly Leu Asp Val Arg Arg Arg Ser Asp Gly Glu
225 230 235 240

Trp Val Arg Val Arg Pro Val Pro Asp Ser Phe Ile Ile Asn Val Gly
245 250 255

Asp Leu Ile Gln Val Arg Glu Arg Gly Ala Pro Gly Val Gly Glu Leu
260 265 270

Gly Glu Gly Glu Val Leu His Ala Leu Leu Leu Gln Pro Gly Asp Leu
275 280 285

His His Gly Gly Ala Gly Gly Gly Ala Gly Glu Gln Gly Arg Ser Ala
290 295 300

Gln Val Arg Arg Leu Gln Leu Gly Arg Leu Leu Gln His Gln Glu Glu
305 310 315 320

Gln Gln Leu Gln Glu Ala Gln Arg Gly Glu His Ser Asp Arg Ala Phe
325 330 335

Gln Glu Glu Pro Arg Pro Arg Leu Thr Thr Ala Thr Ala Arg Ile His
340 345 350

Ala Ile Ala Met Ser Ser Ser Asp Ser Glu His Ala Met Ser Ser Leu
355 360 365

Ala Ser Trp
370

<210> SEQ ID NO 13
<211> LENGTH: 1733
<212> TYPE: DNA
<213> ORGANISM: Zea mays

<400> SEQUENCE: 13
atgaggccgc gcctccctcc aaatgttccc tccctgcctt cgtctttgtc gttgctcgca 60
aactccctgt cctcccctgt tacaaatacc cccacccgcc cggacagctt ccctgcatac 120
ttgcagctcg cacatctcat ggtgtcgcag gaacgacaag agccagctgt gcctagcagc 180
agcagcagca gcgccaagcg cgcagccacg tccatggacg ccagcccggc cccgccgctc 240
ctcctccgcg cccccactcc cagccccagc attgacctcc ccgctggcaa ggacaaggcc 300
gacgcggcgg ccagcaaggc cggcgcggcc gtgttcgacc tgcgccggga gcccaagatc 360
cccgcgccat tcctgtggcc gcaggaagag gcgcggccgt cctcggccgc ggagctggag 420
gtgccgatgg tggacgtggg cgtgctgcgc aatggcgacc gcgcggggct gcggcgcgcc 480
gcggcgcagg tggccgcggc gtgcgcgacg cacgggttct tccaggtgtg cgggcacggc 540
gtggacgcgg cgctggggcg cgccgcgctg gacggcgcca gcgacttctt ccggctgccg 600
ctcgccgaga agcagcgcgc ccggcgcgtc cccggcaccg tgtccgggta cacgagcgcg 660
cacgccgacc ggttcgcggc caagctcccc tggaaggaga ccctgtcgtt cggctaccac 720
gacggcgccg cgtcgcctgt cgtcgtggac tacttcgtcg gcaccctcgg ccaggatttc 780
gagccaatgg ggtgggtgta ccagaggtac tgcgaggaga tgaaggagct gtcgctgacg 840

```
atcatggagc tgctggagct gagcctgggc gtggagctgc gcggctacta ccgggagttc     900

ttcgaggaca gccggtccat catgcggtgc aactactacc cgccgtgccc ggagccggag     960

cgcacgctgg gcacgggccc gcactgcgac cccacggcgc tcaccatcct cctgcaggac    1020

gacgtgggcg ggctggaggt gctggtggac ggtgagtggc gccccgtccg gcccgtcccg    1080

ggcgccatgg tcatcaacat cggcgacacc ttcatggcgc tgtcgaacgg gaggtacaag    1140

agctgcctgc accgcgcggt ggtgaaccag cggcgggcgc ggcggtcgct ggccttcttc    1200

ctgtgcccgc gcgaggaccg ggtggtgcgc ccgccggcca gtgctgcgcc gcggcgctac    1260

ccggacttca cctgggccga cctcatgcgc ttcacgcagc gccactaccg cgccgacacc    1320

cgcacgctgg acgccttcac ccgctggctc tcccacggcc cggcccaggc ggcggcgcct    1380

ccctgcacct agcgagccgg gccaaggccg tctctttcgc cccacgtgcg cgcccagctg    1440

ggcaggtggc cagacacgcg gcccgcgggc cccgcgccgc cttgccattt tttgacgctg    1500

gccctactgc tgtgctacta gtgtacatat gcaagagtac atatatatat atatatatac    1560

gtattttcta tatattatat ataaaagcaa ggcggcccgg tgcccttctc ttgttttgtc    1620

cacaactgtt tgatcccatt attctatgga ccatggatac ttcaatgttt gtactaagac    1680

cgtgaacgtg ggattctttt ccttcctctg tgttttttct gagaaaaatt aaa           1733


<210> SEQ ID NO 14
<211> LENGTH: 1392
<212> TYPE: DNA
<213> ORGANISM: Zea mays

<400> SEQUENCE: 14

atgaggccgc gcctccctcc aaatgttccc tccctgcctt cgtctttgtc gttgctcgca      60

aactccctgt cctcccctgt tacaaatacc cccacccgcc cggacagctt ccctgcatac     120

ttgcagctcg cacatctcat ggtgtcgcag gaacgacaag agccagctgt gcctagcagc     180

agcagcagca gcgccaagcg cgcagccacg tccatggacg ccagcccggc cccgccgctc     240

ctcctccgcg cccccactcc cagccccagc attgacctcc ccgctggcaa ggacaaggcc     300

gacgcggcgg ccagcaaggc cggcgcggcc gtgttcgacc tgcgccggga gcccaagatc     360

cccgcgccat tcctgtggcc gcaggaagag gcgcggccgt cctcggccgc ggagctggag     420

gtgccgatgg tggacgtggg cgtgctgcgc aatggcgacc gcgcggggct gcggcgcgcc     480

gcggcgcagg tggccgcggc gtgcgcgacg cacgggttct tccaggtgtg cgggcacggc     540

gtggacgcgg cgctggggcg cgccgcgctg gacggcgcca gcgacttctt ccggctgccg     600

ctcgccgaga agcagcgcgc ccggcgcgtc cccggcaccg tgtccgggta cacgagcgcg     660

cacgccgacc ggttcgcggc caagctcccc tggaaggaga ccctgtcgtt cggctaccac     720

gacggcgccg cgtcgcctgt cgtcgtggac tacttcgtcg gcaccctcgg ccaggatttc     780

gagccaatgg ggtgggtgta ccagaggtac tgcgaggaga tgaaggagct gtcgctgacg     840

atcatggagc tgctggagct gagcctgggc gtggagctgc gcggctacta ccgggagttc     900

ttcgaggaca gccggtccat catgcggtgc aactactacc cgccgtgccc ggagccggag     960

cgcacgctgg gcacgggccc gcactgcgac cccacggcgc tcaccatcct cctgcaggac    1020

gacgtgggcg ggctggaggt gctggtggac ggtgagtggc gccccgtccg gcccgtcccg    1080

ggcgccatgg tcatcaacat cggcgacacc ttcatggcgc tgtcgaacgg gaggtacaag    1140

agctgcctgc accgcgcggt ggtgaaccag cggcgggcgc ggcggtcgct ggccttcttc    1200

ctgtgcccgc gcgaggaccg ggtggtgcgc ccgccggcca gtgctgcgcc gcggcgctac    1260
```

```
ccggacttca cctgggccga cctcatgcgc ttcacgcagc gccactaccg cgccgacacc   1320

cgcacgctgg acgccttcac ccgctggctc tcccacggcc cggcccaggc ggcggcgcct   1380

ccctgcacct ag                                                       1392


<210> SEQ ID NO 15
<211> LENGTH: 463
<212> TYPE: PRT
<213> ORGANISM: Zea mays

<400> SEQUENCE: 15

Met Arg Pro Arg Leu Pro Pro Asn Val Pro Ser Leu Pro Ser Ser Leu
1               5                   10                  15

Ser Leu Leu Ala Asn Ser Leu Ser Ser Pro Val Thr Asn Thr Pro Thr
            20                  25                  30

Arg Pro Asp Ser Phe Pro Ala Tyr Leu Gln Leu Ala His Leu Met Val
        35                  40                  45

Ser Gln Glu Arg Gln Glu Pro Ala Val Pro Ser Ser Ser Ser Ser Ser
    50                  55                  60

Ala Lys Arg Ala Ala Thr Ser Met Asp Ala Ser Pro Ala Pro Pro Leu
65                  70                  75                  80

Leu Leu Arg Ala Pro Thr Pro Ser Pro Ser Ile Asp Leu Pro Ala Gly
                85                  90                  95

Lys Asp Lys Ala Asp Ala Ala Ala Ser Lys Ala Gly Ala Ala Val Phe
            100                 105                 110

Asp Leu Arg Arg Glu Pro Lys Ile Pro Ala Pro Phe Leu Trp Pro Gln
        115                 120                 125

Glu Glu Ala Arg Pro Ser Ser Ala Ala Glu Leu Glu Val Pro Met Val
    130                 135                 140

Asp Val Gly Val Leu Arg Asn Gly Asp Arg Ala Gly Leu Arg Arg Ala
145                 150                 155                 160

Ala Ala Gln Val Ala Ala Ala Cys Ala Thr His Gly Phe Phe Gln Val
                165                 170                 175

Cys Gly His Gly Val Asp Ala Ala Leu Gly Arg Ala Ala Leu Asp Gly
            180                 185                 190

Ala Ser Asp Phe Phe Arg Leu Pro Leu Ala Glu Lys Gln Arg Ala Arg
        195                 200                 205

Arg Val Pro Gly Thr Val Ser Gly Tyr Thr Ser Ala His Ala Asp Arg
    210                 215                 220

Phe Ala Ala Lys Leu Pro Trp Lys Glu Thr Leu Ser Phe Gly Tyr His
225                 230                 235                 240

Asp Gly Ala Ala Ser Pro Val Val Val Asp Tyr Phe Val Gly Thr Leu
                245                 250                 255

Gly Gln Asp Phe Glu Pro Met Gly Trp Val Tyr Gln Arg Tyr Cys Glu
            260                 265                 270

Glu Met Lys Glu Leu Ser Leu Thr Ile Met Glu Leu Leu Glu Leu Ser
        275                 280                 285

Leu Gly Val Glu Leu Arg Gly Tyr Tyr Arg Glu Phe Phe Glu Asp Ser
    290                 295                 300

Arg Ser Ile Met Arg Cys Asn Tyr Tyr Pro Pro Cys Pro Glu Pro Glu
305                 310                 315                 320

Arg Thr Leu Gly Thr Gly Pro His Cys Asp Pro Thr Ala Leu Thr Ile
                325                 330                 335

Leu Leu Gln Asp Asp Val Gly Gly Leu Glu Val Leu Val Asp Gly Glu
```

```
            340                 345                 350

Trp Arg Pro Val Arg Pro Val Pro Gly Ala Met Val Ile Asn Ile Gly
        355                 360                 365

Asp Thr Phe Met Ala Leu Ser Asn Gly Arg Tyr Lys Ser Cys Leu His
    370                 375                 380

Arg Ala Val Val Asn Gln Arg Arg Ala Arg Arg Ser Leu Ala Phe Phe
385                 390                 395                 400

Leu Cys Pro Arg Glu Asp Arg Val Val Arg Pro Pro Ala Ser Ala Ala
                405                 410                 415

Pro Arg Arg Tyr Pro Asp Phe Thr Trp Ala Asp Leu Met Arg Phe Thr
            420                 425                 430

Gln Arg His Tyr Arg Ala Asp Thr Arg Thr Leu Asp Ala Phe Thr Arg
        435                 440                 445

Trp Leu Ser His Gly Pro Ala Gln Ala Ala Ala Pro Pro Cys Thr
    450                 455                 460


<210> SEQ ID NO 16
<211> LENGTH: 1510
<212> TYPE: DNA
<213> ORGANISM: Zea mays

<400> SEQUENCE: 16

aaagagcgcg cgacggcggc ccctgggaga gccatgcgag actggaggcg gaaccgcgca     60

cgacaccaag ctgccgcgcc ggactgctgc acgcaagcgc agcgcaggac cgaccgacct    120

ccgtaggcac gcacggcgcc ggcggcatgg cggagcacct cctgtcgacg gccgtgcacg    180

acacgctgcc ggggagctac gtgcggccgg agccggagcg cccgcgcctc gcggaggtcg    240

tgaccggcgc gcgcatcccc gtcgtggacc tgggcagccc cgaccgcggc gcggtcgtgg    300

ccgccgtcgg cgacgcctgc cgctcgcacg gcttcttcca ggtcgtcaac cacgggatac    360

acgccgccct ggtcgcggcg gtgatggccg cggggcgcgg cttcttccgg ctgccccccg    420

aggagaaggc caagctctac tccgacgacc ccgccaggaa gatccggctg tccaccagct    480

tcaacgtgcg caaggagacg gtgcacaact ggcgcgacta cctccgcctg cactgccatc    540

ccctcgacga gttcctgccc gattggccgt ccaacccgcc cgatttcaag gagaccatgg    600

gcacctactg caaggaggtc cgggagctcg ggttcaggct gtacgccgcg atctcggaga    660

gcctgggcct agaggcgagc tacatgaagg aagcgctggg ggagcaggag cagcacatgg    720

cggtcaactt ctacccgccg tgcccggagc cggagctcac ctacggcctc ccggcgcaca    780

ccgaccccaa cgcgctcacc atcctgctca tggacccgga cgtcgccggc ctgcaggtgc    840

tccacgccgg ccagtgggtc gccgtcaacc cgcagcccgg cgcgctcatc atcaacatcg    900

gcgaccagct gcaggcgctg agcaacgggc agtaccggag cgtgtggcac cgcgcggtgg    960

tgaactcgga ccgggagcgc atgtccgtgg cgtcgttcct gtgcccgtgc aaccacgtcg   1020

tgctcggccc cgcgcggaag ctcgtcaccg aggacacccc ggccgtgtac aggaactaca   1080

cgtacgacaa gtactacgcc aagttctgga gcaggaacct ggaccaggag cactgcctcg   1140

agctcttcag aacctagcga atcggatacg gatggatgga tacattacat acgcgccctc   1200

tgtttttctc catgacgtta gaagaacacg ttctgcaatg tttgtccatt caaggtggta   1260

tcaatcaagg ctgtggtcgt tgcaattctt ccgctccata tacatgatta aatgctttga   1320

aagaaaaaga aaaaaaagaa acacaagtat tatggcacta ctagtgtttt taggaacaag   1380

gaaagagggg ttgcccctgc tggctatata tattaaatat aaataaaggt aaggctgtag   1440
```

```
acattggtga ataagagaaa gtatttgagt ttctctattg tcactccaga acagactcct   1500

ttgcctcgat                                                          1510


<210> SEQ ID NO 17
<211> LENGTH: 1011
<212> TYPE: DNA
<213> ORGANISM: Zea mays

<400> SEQUENCE: 17

atggcggagc acctcctgtc gacggccgtg cacgacacgc tgccggggag ctacgtgcgg     60

ccggagccgg agcgcccgcg cctcgcggag gtcgtgaccg gcgcgcgcat ccccgtcgtg    120

gacctgggca gccccgaccg cggcgcggtc gtggccgccg tcggcgacgc ctgccgctcg    180

cacggcttct tccaggtcgt caaccacggg atacacgccg ccctggtcgc ggcggtgatg    240

gccgcggggc gcggcttctt ccggctgccc cccgaggaga aggccaagct ctactccgac    300

gaccccgcca ggaagatccg gctgtccacc agcttcaacg tgcgcaagga gacggtgcac    360

aactggcgcg actacctccg cctgcactgc catcccctcg acgagttcct gcccgattgg    420

ccgtccaacc cgcccgattt caaggagacc atgggcacct actgcaagga ggtccgggag    480

ctcgggttca ggctgtacgc cgcgatctcg gagagcctgg gcctagaggc gagctacatg    540

aaggaagcgc tgggggagca ggagcagcac atggcggtca acttctaccc gccgtgcccg    600

gagccggagc tcacctacgg cctcccggcg cacaccgacc ccaacgcgct caccatcctg    660

ctcatggacc cggacgtcgc cggcctgcag gtgctccacg ccggccagtg ggtcgccgtc    720

aacccgcagc ccggcgcgct catcatcaac atcggcgacc agctgcaggc gctgagcaac    780

gggcagtacc ggagcgtgtg gcaccgcgcg gtggtgaact cggaccggga gcgcatgtcc    840

gtggcgtcgt tcctgtgccc gtgcaaccac gtcgtgctcg gccccgcgcg gaagctcgtc    900

accgaggaca ccccggccgt gtacaggaac tacacgtacg acaagtacta cgccaagttc    960

tggagcagga acctggacca ggagcactgc ctcgagctct tcagaaccta g            1011


<210> SEQ ID NO 18
<211> LENGTH: 336
<212> TYPE: PRT
<213> ORGANISM: Zea mays

<400> SEQUENCE: 18

Met Ala Glu His Leu Leu Ser Thr Ala Val His Asp Thr Leu Pro Gly
1               5                   10                  15

Ser Tyr Val Arg Pro Glu Pro Glu Arg Pro Arg Leu Ala Glu Val Val
            20                  25                  30

Thr Gly Ala Arg Ile Pro Val Val Asp Leu Gly Ser Pro Asp Arg Gly
        35                  40                  45

Ala Val Val Ala Ala Val Gly Asp Ala Cys Arg Ser His Gly Phe Phe
    50                  55                  60

Gln Val Val Asn His Gly Ile His Ala Ala Leu Val Ala Ala Val Met
65                  70                  75                  80

Ala Ala Gly Arg Gly Phe Phe Arg Leu Pro Pro Glu Glu Lys Ala Lys
                85                  90                  95

Leu Tyr Ser Asp Asp Pro Ala Arg Lys Ile Arg Leu Ser Thr Ser Phe
            100                 105                 110

Asn Val Arg Lys Glu Thr Val His Asn Trp Arg Asp Tyr Leu Arg Leu
        115                 120                 125

His Cys His Pro Leu Asp Glu Phe Leu Pro Asp Trp Pro Ser Asn Pro
```

```
    130                 135                 140

Pro Asp Phe Lys Glu Thr Met Gly Thr Tyr Cys Lys Glu Val Arg Glu
145                 150                 155                 160

Leu Gly Phe Arg Leu Tyr Ala Ala Ile Ser Glu Ser Leu Gly Leu Glu
                165                 170                 175

Ala Ser Tyr Met Lys Glu Ala Leu Gly Glu Gln Glu Gln His Met Ala
            180                 185                 190

Val Asn Phe Tyr Pro Pro Cys Pro Glu Pro Glu Leu Thr Tyr Gly Leu
        195                 200                 205

Pro Ala His Thr Asp Pro Asn Ala Leu Thr Ile Leu Leu Met Asp Pro
    210                 215                 220

Asp Val Ala Gly Leu Gln Val Leu His Ala Gly Gln Trp Val Ala Val
225                 230                 235                 240

Asn Pro Gln Pro Gly Ala Leu Ile Ile Asn Ile Gly Asp Gln Leu Gln
                245                 250                 255

Ala Leu Ser Asn Gly Gln Tyr Arg Ser Val Trp His Arg Ala Val Val
            260                 265                 270

Asn Ser Asp Arg Glu Arg Met Ser Val Ala Ser Phe Leu Cys Pro Cys
        275                 280                 285

Asn His Val Val Leu Gly Pro Ala Arg Lys Leu Val Thr Glu Asp Thr
    290                 295                 300

Pro Ala Val Tyr Arg Asn Tyr Thr Tyr Asp Lys Tyr Tyr Ala Lys Phe
305                 310                 315                 320

Trp Ser Arg Asn Leu Asp Gln Glu His Cys Leu Glu Leu Phe Arg Thr
                325                 330                 335
```

<210> SEQ ID NO 19
<211> LENGTH: 1387
<212> TYPE: DNA
<213> ORGANISM: Zea mays

<400> SEQUENCE: 19

```
gttttctttt tgaacgtaac tgacagaagc tatctgccta gctacggcgt gtcggttgct     60

tgtctcacca aagcagcgac atggaagcct gacagctcgt cgcgtcgcgc catttccacc    120

caacaaagcg gcggcgccag cacgcactgc ttctgcttgt gcgtgctcct ccgttccggg    180

cacgcctcta aagtctatac agcctcgaat ccatcccggc cgccgctcct gggggatact    240

acagcgagcc gaagcgggga tggcggagat ccctgtgatc gacctgcgcg tcgccggctc    300

ggcggccgag gagtccgcgc ggctgcgggc cgcgtgcgag cgcctgggct gcttccgggt    360

gaccggccac ggcgtgccct cggtgctcct ggcagagatg aaggccgccg tgcgcgcgct    420

cttcgacctc cccgacgacg ccaagcgccg caacgccgac gtcatcaccg gcagcggcta    480

cgtcgccccc agcccgacca acccgctcta cgaggccttc gggctcctcg acgccgccgt    540

gcccaccgac gtcgacgcct tttgcgcgct cctcgacgcg ccgcccaaca tcagggagac    600

cgtcaaggcc tacgcggaga agatgcacga tgtgatcgtt ggcgtcgccc gcgagctggc    660

gtctagcctg gggctagtcg aggagcactc gttccaggac tggccgtgcc agttccgcat    720

caacaggtac aactacacgc gggagacggt gggctcctcc ggcgtgcaga cccacacgga    780

ctcgggcttc ctcaccgtgc tccatgagga cgagtgtgtc ggcggcctcg aggtcctgga    840

cccgggcacc ggcgagttcg tgcccgtgga ccccgtcgcg ggctcctttc tcgtaaacat    900

cggcgacgtc ggcacggcgt ggagcaacgg gaggctgcac aacgtgaagc accgggtgcg    960

gtgcgtcgca cccgtgccgc gcatctccat cgccatgttc ctgctcgcac ccaaggacga   1020
```

```
cagcgtgagc gcaccggcgg cgttcgtgga cgcggaccac ccgcgcaggt acaaggtgtt   1080

caactacaac gactatcgga ggctcagact gtccaccggc gagcacgcag gcgaggcgct   1140

cgcacggatg gcggcgtgac gtggctggag ctgcaaattg gattggaagc cgagacaagc   1200

cgttagttat ttaccatgcc cgtgcgttca ccgcacacaa tcatattcaa aagccataaa   1260

ataaaaaata attttaatat cagtcaacat atggtttaaa tatcatatgg agtacaatat   1320

tccgaatttt tttttgtaat ttagtctgtc ttttgaaaaa aatgcacatc tagacctccg   1380

gatgact                                                              1387
```

```
<210> SEQ ID NO 20
<211> LENGTH: 900
<212> TYPE: DNA
<213> ORGANISM: Zea mays

<400> SEQUENCE: 20

atggcggaga tccctgtgat cgacctgcgc gtcgccggct cggcggccga ggagtccgcg     60

cggctgcggg ccgcgtgcga gcgcctgggc tgcttccggg tgaccggcca cggcgtgccc    120

tcggtgctcc tggcagagat gaaggccgcc gtgcgcgcgc tcttcgacct ccccgacgac    180

gccaagcgcc gcaacgccga cgtcatcacc ggcagcggct acgtcgcccc cagcccgacc    240

aacccgctct acgaggcctt cgggctcctc gacgccgccg tgcccaccga cgtcgacgcc    300

ttttgcgcgc tcctcgacgc gccgcccaac atcagggaga ccgtcaaggc ctacgcggag    360

aagatgcacg atgtgatcgt tggcgtcgcc cgcgagctgg cgtctagcct ggggctagtc    420

gaggagcact cgttccagga ctggccgtgc cagttccgca tcaacaggta caactacacg    480

cgggagacgg tgggctcctc cggcgtgcag acccacacgg actcgggctt cctcaccgtg    540

ctccatgagg acgagtgtgt cggcggcctc gaggtcctgg acccgggcac cggcgagttc    600

gtgcccgtgg accccgtcgc gggctccttt ctcgtaaaca tcggcgacgt cggcacggcg    660

tggagcaacg ggaggctgca caacgtgaag caccgggtgc ggtgcgtcgc acccgtgccg    720

cgcatctcca tcgccatgtt cctgctcgca cccaaggacg acagcgtgag cgcaccggcg    780

gcgttcgtgg acgcggacca cccgcgcagg tacaaggtgt tcaactacaa cgactatcgg    840

aggctcagac tgtccaccgg cgagcacgca ggcgaggcgc tcgcacggat ggcggcgtga    900
```

```
<210> SEQ ID NO 21
<211> LENGTH: 299
<212> TYPE: PRT
<213> ORGANISM: Zea mays

<400> SEQUENCE: 21

Met Ala Glu Ile Pro Val Ile Asp Leu Arg Val Ala Gly Ser Ala Ala
1               5                   10                  15

Glu Glu Ser Ala Arg Leu Arg Ala Ala Cys Glu Arg Leu Gly Cys Phe
            20                  25                  30

Arg Val Thr Gly His Gly Val Pro Ser Val Leu Leu Ala Glu Met Lys
        35                  40                  45

Ala Ala Val Arg Ala Leu Phe Asp Leu Pro Asp Asp Ala Lys Arg Arg
    50                  55                  60

Asn Ala Asp Val Ile Thr Gly Ser Gly Tyr Val Ala Pro Ser Pro Thr
65                  70                  75                  80

Asn Pro Leu Tyr Glu Ala Phe Gly Leu Leu Asp Ala Ala Val Pro Thr
                85                  90                  95
```

```
Asp Val Asp Ala Phe Cys Ala Leu Leu Asp Ala Pro Pro Asn Ile Arg
            100                 105                 110

Glu Thr Val Lys Ala Tyr Ala Glu Lys Met His Asp Val Ile Val Gly
        115                 120                 125

Val Ala Arg Glu Leu Ala Ser Ser Leu Gly Leu Val Glu Glu His Ser
    130                 135                 140

Phe Gln Asp Trp Pro Cys Gln Phe Arg Ile Asn Arg Tyr Asn Tyr Thr
145                 150                 155                 160

Arg Glu Thr Val Gly Ser Ser Gly Val Gln Thr His Thr Asp Ser Gly
                165                 170                 175

Phe Leu Thr Val Leu His Glu Asp Glu Cys Val Gly Gly Leu Glu Val
            180                 185                 190

Leu Asp Pro Gly Thr Gly Glu Phe Val Pro Val Asp Pro Val Ala Gly
        195                 200                 205

Ser Phe Leu Val Asn Ile Gly Asp Val Gly Thr Ala Trp Ser Asn Gly
    210                 215                 220

Arg Leu His Asn Val Lys His Arg Val Arg Cys Val Ala Pro Val Pro
225                 230                 235                 240

Arg Ile Ser Ile Ala Met Phe Leu Leu Ala Pro Lys Asp Asp Ser Val
                245                 250                 255

Ser Ala Pro Ala Ala Phe Val Asp Ala Asp His Pro Arg Arg Tyr Lys
            260                 265                 270

Val Phe Asn Tyr Asn Asp Tyr Arg Arg Leu Arg Leu Ser Thr Gly Glu
        275                 280                 285

His Ala Gly Glu Ala Leu Ala Arg Met Ala Ala
    290                 295
```

<210> SEQ ID NO 22
<211> LENGTH: 1496
<212> TYPE: DNA
<213> ORGANISM: Zea mays

<400> SEQUENCE: 22

```
gtcggtctct tgtctcacca aaccggcgac atggtacatg gaggccagcc cgtcgcttgg     60

cgccacaagt ctcggtgccg tccgtccgac aagcggcgcc agcgcacgct ggctgctcgt    120

gcacgcctct aaatacggcc ccggacccgc caccaagcga aggccaatcc cgtccgccgc    180

cccccaccaa ccacgaacca cgcaagcgaa cccggccggc gcggggcagc ggcgatggcg    240

gagatcccgg tgatcgacct gcgcctcgcc ggctcgtcgc ccgacgagtc ggcgcggctg    300

cgcgacgcgt gcgagcgcct gggctgcttt cgggtgaccg gccacggcgc gcccgcgggg    360

ctcctggccg acatgaaggc cgccgtgcgc gcgctcttcg acctccccga cgacgccaag    420

cgccgcaacg ccgacgtcat ccccggcagc ggctacgtcg cgccctgccc cgccaacccg    480

ctctacgagg ccttcgggct cctcgacgcc gccgcgcccg ccgacgtcga cgccttctgc    540

gcgcgcctcg acgcgccgcc caaagtcagg gagaccgtca agacctacgc ggagaagatg    600

cacgacgtga tcgtcggcgt cgccggcgag ctggccacca gcctggggct gggcctggag    660

gagcactcgt tccaggactg gccgtgccag ttccgcatca acaggtacaa ctacacgcag    720

gagacggtgg gctcctccgg cgtgcagacc cacacggact cgggcttcct caccgtgctc    780

caggaggacg agtgcgtcgg cggcctcgag gtgctggacc ccgccgccgg tgagttcgtg    840

cccgtggacc ccgtcgccgg ctccttcctc gtcaacatcg gcgacgtcgg cacggcgtgg    900

agcaacggga ggctccacaa cgtgaagcac cgggtgcggt gcgtcgcgcc cgtgccgcgc    960
```

```
atctccatcg ccatgttcct gctggcgccc aaggacgacc gcgtgagcgc cccggaggcg   1020

ttggtcgacg cgggccaccc gcgtcggtac aagccgttca actacgacga ctaccggagg   1080

ctccggctgt ccaccggcga gcgcgcaggc gaggcgctcg cgcggatggc ggcgtgatgt   1140

cgtcacgcac gtgcaagccg ttaattatag gctcgcgcat gcatacgcct acacgagagg   1200

ttgtctcgtt aagccgttct attaaaatgt gtgggggaga aagatgacta ccgtggtgcc   1260

atgtggattg ctatcgggtc tgatcaataa aatcttgcaa cacttgcacg tgcgattcca   1320

tatcctagca cgggtgggcg ccacgctagt aggtagagac cggagcggcc aaaaaatggc   1380

tacagcacca gtaggtgaac tctcaagcaa cactggctat cccacttctg acgttgtctc   1440

tctcatcact atgtatgacc agcgaatgaa gtgtttaaaa atctgacgcc gtgaaa       1496
```

```
<210> SEQ ID NO 23
<211> LENGTH: 903
<212> TYPE: DNA
<213> ORGANISM: Zea mays

<400> SEQUENCE: 23

atggcggaga tcccggtgat cgacctgcgc ctcgccggct cgtcgcccga cgagtcggcg     60

cggctgcgcg acgcgtgcga gcgcctgggc tgctttcggg tgaccggcca cggcgcgccc    120

gcggggctcc tggccgacat gaaggccgcc gtgcgcgcgc tcttcgacct ccccgacgac    180

gccaagcgcc gcaacgccga cgtcatcccc ggcagcggct acgtcgcgcc ctgccccgcc    240

aacccgctct acgaggcctt cgggctcctc gacgccgccg cgcccgccga cgtcgacgcc    300

ttctgcgcgc gcctcgacgc gccgcccaaa gtcagggaga ccgtcaagac ctacgcggag    360

aagatgcacg acgtgatcgt cggcgtcgcc ggcgagctgg ccaccagcct ggggctgggc    420

ctggaggagc actcgttcca ggactggccg tgccagttcc gcatcaacag gtacaactac    480

acgcaggaga cggtgggctc ctccggcgtg cagacccaca cggactcggg cttcctcacc    540

gtgctccagg aggacgagtg cgtcggcggc ctcgaggtgc tggaccccgc cgccggtgag    600

ttcgtgcccg tggaccccgt cgccggctcc ttcctcgtca acatcggcga cgtcggcacg    660

gcgtggagca acgggaggct ccacaacgtg aagcaccggg tgcggtgcgt cgcgcccgtg    720

ccgcgcatct ccatcgccat gttcctgctg gcgcccaagg acgaccgcgt gagcgccccg    780

gaggcgttgg tcgacgcggg ccacccgcgt cggtacaagc cgttcaacta cgacgactac    840

cggaggctcc ggctgtccac cggcgagcgc gcaggcgagg cgctcgcgcg gatggcggcg    900

tga                                                                  903
```

```
<210> SEQ ID NO 24
<211> LENGTH: 300
<212> TYPE: PRT
<213> ORGANISM: Zea mays

<400> SEQUENCE: 24

Met Ala Glu Ile Pro Val Ile Asp Leu Arg Leu Ala Gly Ser Ser Pro
1               5                   10                  15

Asp Glu Ser Ala Arg Leu Arg Asp Ala Cys Glu Arg Leu Gly Cys Phe
            20                  25                  30

Arg Val Thr Gly His Gly Ala Pro Ala Gly Leu Leu Ala Asp Met Lys
        35                  40                  45

Ala Ala Val Arg Ala Leu Phe Asp Leu Pro Asp Asp Ala Lys Arg Arg
    50                  55                  60

Asn Ala Asp Val Ile Pro Gly Ser Gly Tyr Val Ala Pro Cys Pro Ala
```

```
65                  70                  75                  80

Asn Pro Leu Tyr Glu Ala Phe Gly Leu Leu Asp Ala Ala Ala Pro Ala
                85                  90                  95

Asp Val Asp Ala Phe Cys Ala Arg Leu Asp Ala Pro Pro Lys Val Arg
            100                 105                 110

Glu Thr Val Lys Thr Tyr Ala Glu Lys Met His Asp Val Ile Val Gly
        115                 120                 125

Val Ala Gly Glu Leu Ala Thr Ser Leu Gly Leu Gly Leu Glu Glu His
    130                 135                 140

Ser Phe Gln Asp Trp Pro Cys Gln Phe Arg Ile Asn Arg Tyr Asn Tyr
145                 150                 155                 160

Thr Gln Glu Thr Val Gly Ser Ser Gly Val Gln Thr His Thr Asp Ser
                165                 170                 175

Gly Phe Leu Thr Val Leu Gln Glu Asp Glu Cys Val Gly Gly Leu Glu
            180                 185                 190

Val Leu Asp Pro Ala Ala Gly Glu Phe Val Pro Val Asp Pro Val Ala
        195                 200                 205

Gly Ser Phe Leu Val Asn Ile Gly Asp Val Gly Thr Ala Trp Ser Asn
    210                 215                 220

Gly Arg Leu His Asn Val Lys His Arg Val Arg Cys Val Ala Pro Val
225                 230                 235                 240

Pro Arg Ile Ser Ile Ala Met Phe Leu Leu Ala Pro Lys Asp Asp Arg
                245                 250                 255

Val Ser Ala Pro Glu Ala Leu Val Asp Ala Gly His Pro Arg Arg Tyr
            260                 265                 270

Lys Pro Phe Asn Tyr Asp Asp Tyr Arg Arg Leu Arg Leu Ser Thr Gly
        275                 280                 285

Glu Arg Ala Gly Glu Ala Leu Ala Arg Met Ala Ala
    290                 295                 300


<210> SEQ ID NO 25
<211> LENGTH: 1614
<212> TYPE: DNA
<213> ORGANISM: Zea mays

<400> SEQUENCE: 25

accacacgaa ttgcacatct ccacagctca cgattccaac actagctaca tatatatgta     60

gctttctagg ctactatata cactcaccac caagtgtgaa gtgtgtatat atagtgacag    120

ctactgcaat atatacatac gcgtcaccta tatattagcc aagctagcta tatgagcttg    180

gttgcggcgc caatggcgat cgtcgacgtg gccaacgccc agctgcagca agcagcagca    240

gcagctgcca agaaagacga ggacggccat gagcagcagg agtcgtccta cgactacggc    300

gcgctgatga aggcgtgag gcacctgtcg gacagcggca ttaccaggct gcccgacagg    360

tacgtcctgc ccgcgtccga ccgccccggc gtccttgccg tctcgtcgtc cgtggcgggc    420

agcggcaggg tcaagctccc tgtcgtcaac ctcgccggcc tccgcgaccc ctgccagcgc    480

gccgccgtgc tggccacgct cgacgccgcg tgccgggagt acggcttctt tcaggtggta    540

aaccacgggt tcgggagcga cgtgagcggc gggatgctgg acgtggcgca gcgcttcttc    600

gagctgccgc tggccgagcg agcgcggcac atgtcggcgg acgtgcgggc gccggtgcgc    660

tacggcacca gcttcaacca ggccaaggac gacgtgctct gctggcgcga cttcctcaag    720

ctcgtctgcc agccgctgca ggcggtgctc ccgtactggc cccagcagcc ggcggacctc    780

agggacgtgg ccaccaggta cgccacggcg agccaccggc tgttcatgga ggtcatggag    840
```

```
gcggcgctgg aggccctggg catccccacg gccggcggcg tgctcgggga gctggcagcg    900

tcgtcgtcgc acatgatgac ggtgaactgc tacccggcgt gcccgcagcc tgagctcacg    960

ctggggatgc cctcgcactc ggactacggc ctcttcacgt tcgtcctgca ggaccacgtc   1020

gagggcctcc aggtcatgca cgacggccgc tggctcacca tcgaccccat cccgggatcg   1080

ttcgtcgtca acgtcggcga ccacctagag atctacagca acgggcggta caagagcgcg   1140

ctgcaccggg tgcacgtgaa ctccacgcgg ccgcgcatct cggtggcgtc gttccacagc   1200

ctgccggcgg agcgagtgat cggccggcg ccggagctgg tggacgacga ggccggcaac    1260

ccgcggcggt acatggacac cgacttcgct accttcctcg cctacctcgc atccgcggac   1320

ggcaagaaca agaccttcct ccagtcaagg aagctgcctg ctgctgctcc tccatgcctc   1380

tagctaacta gatagctgct tattaatctg acagaataaa attaatcagt tcagcgcaca   1440

attccacaag cgaaaacaaa cctggatttg ttttaattag ctctgccctt cattattaca   1500

ttcaagctag ctcttggtca acgcatgcac acaagcttga gcattgactg gtccctttc    1560

aatcggttgc attgtactcc ctccgtacca aaattggttg tcgctatagt attt         1614
```

<210> SEQ ID NO 26
<211> LENGTH: 1212
<212> TYPE: DNA
<213> ORGANISM: Zea mays

<400> SEQUENCE: 26

```
atgagcttgg ttgcggcgcc aatggcgatc gtcgacgtgg ccaacgccca gctgcagcaa     60

gcagcagcag cagctgccaa gaaagacgag gacggccatg agcagcagga gtcgtcctac    120

gactacggcg cgctgatgaa aggcgtgagg cacctgtcgg acagcggcat taccaggctg    180

cccgacaggt acgtcctgcc cgcgtccgac cgccccggcg tccttgccgt ctcgtcgtcc    240

gtggcgggca gcggcagggt caagctccct gtcgtcaacc tcgccggcct ccgcgacccc    300

tgccagcgcg ccgccgtgct ggccacgctc gacgccgcgt gccgggagta cggcttcttt    360

caggtggtaa accacgggtt cgggagcgac gtgagcggcg ggatgctgga cgtggcgcag    420

cgcttcttcg agctgccgct ggccgagcga gcgcggcaca tgtcggcgga cgtgcgggcg    480

ccggtgcgct acggcaccag cttcaaccag gccaaggacg acgtgctctg ctggcgcgac    540

ttcctcaagc tcgtctgcca gccgctgcag gcggtgctcc cgtactggcc ccagcagccg    600

gcggacctca gggacgtggc caccaggtac gccacggcga gccaccggct gttcatggag    660

gtcatggagg cggcgctgga ggccctgggc atccccacgg ccggcggcgt gctcggggag    720

ctggcagcgt cgtcgtcgca catgatgacg gtgaactgct acccggcgtg cccgcagcct    780

gagctcacgc tggggatgcc ctcgcactcg gactacggcc tcttcacgtt cgtcctgcag    840

gaccacgtcg agggcctcca ggtcatgcac gacggccgct ggctcaccat cgaccccatc    900

ccgggatcgt tcgtcgtcaa cgtcggcgac cacctagaga tctacagcaa cgggcggtac    960

aagagcgcgc tgcaccgggt gcacgtgaac tccacgcggc cgcgcatctc ggtggcgtcg   1020

ttccacagcc tgccggcgga gcgagtgatc gggccggcgc cggagctggt ggacgacgag   1080

gccggcaacc cgcggcggta catggacacc gacttcgcta ccttcctcgc ctacctcgca   1140

tccgcggacg gcaagaacaa gaccttcctc cagtcaagga agctgcctgc tgctgctcct   1200

ccatgcctct ag                                                       1212
```

<210> SEQ ID NO 27

<211> LENGTH: 403
<212> TYPE: PRT
<213> ORGANISM: Zea mays

<400> SEQUENCE: 27

```
Met Ser Leu Val Ala Ala Pro Met Ala Ile Val Asp Val Ala Asn Ala
1               5                   10                  15

Gln Leu Gln Gln Ala Ala Ala Ala Ala Ala Lys Lys Asp Glu Asp Gly
            20                  25                  30

His Glu Gln Gln Glu Ser Ser Tyr Asp Tyr Gly Ala Leu Met Lys Gly
        35                  40                  45

Val Arg His Leu Ser Asp Ser Gly Ile Thr Arg Leu Pro Asp Arg Tyr
    50                  55                  60

Val Leu Pro Ala Ser Asp Arg Pro Gly Val Leu Ala Val Ser Ser Ser
65                  70                  75                  80

Val Ala Gly Ser Gly Arg Val Lys Leu Pro Val Val Asn Leu Ala Gly
                85                  90                  95

Leu Arg Asp Pro Cys Gln Arg Ala Ala Val Leu Ala Thr Leu Asp Ala
            100                 105                 110

Ala Cys Arg Glu Tyr Gly Phe Phe Gln Val Val Asn His Gly Phe Gly
        115                 120                 125

Ser Asp Val Ser Gly Gly Met Leu Asp Val Ala Gln Arg Phe Phe Glu
    130                 135                 140

Leu Pro Leu Ala Glu Arg Ala Arg His Met Ser Ala Asp Val Arg Ala
145                 150                 155                 160

Pro Val Arg Tyr Gly Thr Ser Phe Asn Gln Ala Lys Asp Asp Val Leu
                165                 170                 175

Cys Trp Arg Asp Phe Leu Lys Leu Val Cys Gln Pro Leu Gln Ala Val
            180                 185                 190

Leu Pro Tyr Trp Pro Gln Gln Pro Ala Asp Leu Arg Asp Val Ala Thr
        195                 200                 205

Arg Tyr Ala Thr Ala Ser His Arg Leu Phe Met Glu Val Met Glu Ala
    210                 215                 220

Ala Leu Glu Ala Leu Gly Ile Pro Thr Ala Gly Gly Val Leu Gly Glu
225                 230                 235                 240

Leu Ala Ala Ser Ser Ser His Met Met Thr Val Asn Cys Tyr Pro Ala
                245                 250                 255

Cys Pro Gln Pro Glu Leu Thr Leu Gly Met Pro Ser His Ser Asp Tyr
            260                 265                 270

Gly Leu Phe Thr Phe Val Leu Gln Asp His Val Glu Gly Leu Gln Val
        275                 280                 285

Met His Asp Gly Arg Trp Leu Thr Ile Asp Pro Ile Pro Gly Ser Phe
    290                 295                 300

Val Val Asn Val Gly Asp His Leu Glu Ile Tyr Ser Asn Gly Arg Tyr
305                 310                 315                 320

Lys Ser Ala Leu His Arg Val His Val Asn Ser Thr Arg Pro Arg Ile
                325                 330                 335

Ser Val Ala Ser Phe His Ser Leu Pro Ala Glu Arg Val Ile Gly Pro
            340                 345                 350

Ala Pro Glu Leu Val Asp Asp Glu Ala Gly Asn Pro Arg Arg Tyr Met
        355                 360                 365

Asp Thr Asp Phe Ala Thr Phe Leu Ala Tyr Leu Ala Ser Ala Asp Gly
    370                 375                 380

Lys Asn Lys Thr Phe Leu Gln Ser Arg Lys Leu Pro Ala Ala Ala Pro
```

385 390 395 400

Pro Cys Leu

<210> SEQ ID NO 28
<211> LENGTH: 1863
<212> TYPE: DNA
<213> ORGANISM: Zea mays

<400> SEQUENCE: 28
tgccaccata ccactagtgc aaggtcctag atttacactt ggtgctacac cttgcttcgc 60
ccccttcctt ccttccttcc ttccttccct ccttccttgg tctctaggca gctagcagtg 120
tggtgctgct gccggccgcc tattggccgc ctgggactgg gatccattaa ttactgcgcg 180
cgcgcggcta accaaccaat cccagcgtgc gtaatctatt gcccacatgc cgacgccgtc 240
gcacctcaac aagaacccgc gctacctgga cttccgggcg gcgcggcggg tgccggagtc 300
gcacgcctgg ccgggcctgc acgaccaccc cgtcgtggac ggcggcgcgc cgggccccga 360
cgccgtgccg gtggtggacc tgggcgccgc ggacccggcg ccggcgccgg cggcggcggt 420
ggcccgcgcc gccgagcaat ggggcgcgtt cctgctcacg ggccacggcg tccccgcgga 480
cctgctggcg cgcgtggagg accggatcgc caccatgttc gcgctgccgg ccgacgacaa 540
gatgcgcgcc gtgcgcgggc ccggcgacgc ctgcggctac ggctccccgc ccatctcctc 600
cttcttctcc aagtgcatgt ggtccgaggg ctacaccttc tcgccggcct ccctccgcgc 660
cgacctccgc aagctctggc ccaaggccgg cgacgactac accagcttct gtgatgtgat 720
ggaggagttc cacaagcaca tgcgcgccct cgcggacaag ctgctggagc tgttcctcat 780
ggcgctgggg ctcaccgacg agcaggccag cgccgtcgag gccgagcgga ggatcgccga 840
gacgatgacc gccaccatgc atctcaactg gtacccgagg tgcccggacc cgcggcgcgc 900
gctggggctg atcgcgcaca ccgactcggg cttcttcacc ttcgtgatgc agagcctcgt 960
gcccgggctg cagctcttcc gccacgcccc ggaccggtgg gtggcggtgc cggccgtgcc 1020
gggcgccttc gtcgtcaacg tgggcgacct cttccacatc ctcaccaacg gccggttcca 1080
cagcgtgtac caccgcgccg tcgtgaaccg ggacctcgac aggatctcgc tcggctactt 1140
cctcggcccg ccgccgcacg ccaaggtggc gccgctgcgc gaggccgtgc cgcccggccg 1200
ggcccccgcg taccgcgccg tcacgtggcc cgagtacatg ggcgtccgca agaaggcctt 1260
caccaccggc gcctccgcgc tcaagatggt cgccctcgcc gccgccgccg acctcgacga 1320
cgacggcgac gccgccgtcg tccatcagca gcagcagcta gtcgtctcgt cgtagccgag 1380
accgatcgcc ggagactgat gctgatgatg atgcatatat acatgagaga aatcgtcgag 1440
tagactagcc gattgcaaaa gcaaccccag ctgccgaaac ctggcatatc gatcccattc 1500
tctgctgcgc acatgtatgc atgcatgcgc ttcgtccgtt cgactcgtgt gtgcttgctt 1560
gcttgcgcgt gcagcagaac taattccgtt ccgcagctag ctgctctgct ctgctctgct 1620
ggaatgtaat taagtagtag tatatggtag tagagaaaag attagctagg cgatcgatat 1680
agatgacggg ccggggaaga agacgaatta attaagatcg atcgacgacg acgagctgtg 1740
cgtggctggc tgtgttcttc tctagcctag ttacagaggc cggctgctgc tgcttccaat 1800
cgggctgctt gtcgctactg acgatcgtta gtggatccat taactaatct ggaattctgg 1860
att 1863

<210> SEQ ID NO 29
<211> LENGTH: 1149

```
<212> TYPE: DNA
<213> ORGANISM: Zea mays

<400> SEQUENCE: 29

atgccgacgc cgtcgcacct caacaagaac ccgcgctacc tggacttccg ggcggcgcgg      60

cgggtgccgg agtcgcacgc ctggccgggc ctgcacgacc accccgtcgt ggacggcggc     120

gcgccgggcc ccgacgccgt gccggtggtg gacctgggcg ccgcggaccc ggcgccggcg     180

ccggcggcgg cggtggcccg cgccgccgag caatggggcg cgttcctgct cacgggccac     240

ggcgtccccg cggacctgct ggcgcgcgtg gaggaccgga tcgccaccat gttcgcgctg     300

ccggccgacg acaagatgcg cgccgtgcgc gggcccggcg acgcctgcgg ctacggctcc     360

ccgcccatct cctccttctt ctccaagtgc atgtggtccg agggctacac cttctcgccg     420

gcctccctcc gcgccgacct ccgcaagctc tggcccaagg ccggcgacga ctacaccagc     480

ttctgtgatg tgatggagga gttccacaag cacatgcgcg ccctcgcgga caagctgctg     540

gagctgttcc tcatggcgct ggggctcacc gacgagcagg ccagcgccgt cgaggccgag     600

cggaggatcg ccgagacgat gaccgccacc atgcatctca actggtaccc gaggtgcccg     660

gacccgcggc gcgcgctggg gctgatcgcg cacaccgact cgggcttctt caccttcgtg     720

atgcagagcc tcgtgcccgg gctgcagctc ttccgccacg ccccggaccg gtgggtggcg     780

gtgccggccg tgccgggcgc cttcgtcgtc aacgtgggcg acctcttcca catcctcacc     840

aacggccggt tccacagcgt gtaccaccgc gccgtcgtga accgggacct cgacaggatc     900

tcgctcggct acttcctcgg cccgccgccg cacgccaagg tggcgccgct gcgcgaggcc     960

gtgccgcccg gccgggcccc cgcgtaccgc gccgtcacgt ggcccgagta catgggcgtc    1020

cgcaagaagg ccttcaccac cggcgcctcc gcgctcaaga tggtcgccct cgccgccgcc    1080

gccgacctcg acgacgacgg cgacgccgcc gtcgtccatc agcagcagca gctagtcgtc    1140

tcgtcgtag                                                            1149


<210> SEQ ID NO 30
<211> LENGTH: 382
<212> TYPE: PRT
<213> ORGANISM: Zea mays

<400> SEQUENCE: 30

Met Pro Thr Pro Ser His Leu Asn Lys Asn Pro Arg Tyr Leu Asp Phe
1               5                   10                  15

Arg Ala Ala Arg Arg Val Pro Glu Ser His Ala Trp Pro Gly Leu His
            20                  25                  30

Asp His Pro Val Val Asp Gly Gly Ala Pro Gly Pro Asp Ala Val Pro
        35                  40                  45

Val Val Asp Leu Gly Ala Ala Asp Pro Ala Pro Ala Pro Ala Ala Ala
    50                  55                  60

Val Ala Arg Ala Ala Glu Gln Trp Gly Ala Phe Leu Leu Thr Gly His
65                  70                  75                  80

Gly Val Pro Ala Asp Leu Leu Ala Arg Val Glu Asp Arg Ile Ala Thr
                85                  90                  95

Met Phe Ala Leu Pro Ala Asp Asp Lys Met Arg Ala Val Arg Gly Pro
            100                 105                 110

Gly Asp Ala Cys Gly Tyr Gly Ser Pro Pro Ile Ser Ser Phe Phe Ser
        115                 120                 125

Lys Cys Met Trp Ser Glu Gly Tyr Thr Phe Ser Pro Ala Ser Leu Arg
    130                 135                 140
```

```
Ala Asp Leu Arg Lys Leu Trp Pro Lys Ala Gly Asp Asp Tyr Thr Ser
145                 150                 155                 160

Phe Cys Asp Val Met Glu Glu Phe His Lys His Met Arg Ala Leu Ala
                165                 170                 175

Asp Lys Leu Leu Glu Leu Phe Leu Met Ala Leu Gly Leu Thr Asp Glu
            180                 185                 190

Gln Ala Ser Ala Val Glu Ala Glu Arg Arg Ile Ala Glu Thr Met Thr
        195                 200                 205

Ala Thr Met His Leu Asn Trp Tyr Pro Arg Cys Pro Asp Pro Arg Arg
    210                 215                 220

Ala Leu Gly Leu Ile Ala His Thr Asp Ser Gly Phe Phe Thr Phe Val
225                 230                 235                 240

Met Gln Ser Leu Val Pro Gly Leu Gln Leu Phe Arg His Ala Pro Asp
                245                 250                 255

Arg Trp Val Ala Val Pro Ala Val Pro Gly Ala Phe Val Val Asn Val
            260                 265                 270

Gly Asp Leu Phe His Ile Leu Thr Asn Gly Arg Phe His Ser Val Tyr
        275                 280                 285

His Arg Ala Val Val Asn Arg Asp Leu Asp Arg Ile Ser Leu Gly Tyr
    290                 295                 300

Phe Leu Gly Pro Pro Pro His Ala Lys Val Ala Pro Leu Arg Glu Ala
305                 310                 315                 320

Val Pro Pro Gly Arg Ala Pro Ala Tyr Arg Ala Val Thr Trp Pro Glu
                325                 330                 335

Tyr Met Gly Val Arg Lys Lys Ala Phe Thr Thr Gly Ala Ser Ala Leu
            340                 345                 350

Lys Met Val Ala Leu Ala Ala Ala Ala Asp Leu Asp Asp Asp Gly Asp
        355                 360                 365

Ala Ala Val Val His Gln Gln Gln Gln Leu Val Val Ser Ser
    370                 375                 380
```

<210> SEQ ID NO 31
<211> LENGTH: 1439
<212> TYPE: DNA
<213> ORGANISM: Zea mays

<400> SEQUENCE: 31

```
gacctccatt ttgattatct ctatcctgta cgtgccgaga gtccttcaaa gccgacgacg      60

agacgacgat gcagtcgtcg tcgtcatcag cctcgacgcc ggctgccgct tccggcctcg     120

tcttcgatct cgggtctgcg gcgggcgtgc cggagacaca cgcgtggccg ggggtgaacg     180

agtacccgtc ggtggagtcc gctggccgcg acgtggtccc ggtggtggac atgggggtgg     240

cctgcccgga cgcgacgcgg gcgttggcgc gcgccgcaga cgagtggggc gtgtttctgc     300

tcgtcggcca cggcgtgccc cgggaagtgg cggcgcgtgc cgaggagcag gtcgcgcgcc     360

tgttcgtgct cccggctcct gacaaggccc gcgcggggcg ccgcccgggg gagcccacgg     420

ccaccggcta cggcaggccg cccctggcac tccgcttctc caagctcatg tggtccgagg     480

ggtacacgtt ccgcgccgcc accgtccgcg aagagttccg ccgcgtctgg cccgacggcg     540

gcgacgacta cctccgcttc tgcgacgtga tggaggagta cgacagagag atgagggctc     600

tcggtggcag gctgctcgac ctcttcttca tggcgctcgg cctcaccgac gtccagttcg     660

ccaccggcga gacggagcgg aggatccgcg agacctggac ggcgacgatg cacccaatcc     720

tgtgtccgga accggagcgc gccatcgggc tgacggcgca cacggactcg ggcttcatca     780
```

cgctcatcat gcagagcccc gtgcccgggc tgcagctgct ccgccgcggg ccggaccggt 840
gggtgacggt gccggcgccg ccgggcgcgc tcatcgtcat gctcggcgac ctgttccagg 900
tgctcacgaa cggccgcttc cggagcccta tccaccgcgc cgtcgtaagc cgagagcgcg 960
agcggatctc cgtgccctac ttcctctgcc cgccggagga catgacggtg gcgccgctcg 1020
cgtccgctct gctgccgggg aggaaggccg tgttccgggc cgtgacgtgg ccagagtaca 1080
tggaggtcaa gcacaaggtg ttcggcacgg atgcgccggc cctggagatg ctgcagctgc 1140
aggtggatga ggaagaacaa ggtgaaaggg ccgccaccac ctaagcccta aggaactact 1200
agctgaatcc ataaactaat aaagaattcg tgaataaggg cgttggaaga ctggacacaa 1260
cacaagagag ttgctatata tcgtatttct gaaatttaag gcaaatatct tagttaaaaa 1320
actggtatat ttaaatagac aatatatatc taaaataaag atagttcacc atttttacgg 1380
tcgaacaatg ataaagttat atattgtctg aatagtaaca aattaaagat ttccaggag 1439

<210> SEQ ID NO 32
<211> LENGTH: 1116
<212> TYPE: DNA
<213> ORGANISM: Zea mays

<400> SEQUENCE: 32
atgcagtcgt cgtcgtcatc agcctcgacg ccggctgccg cttccggcct cgtcttcgat 60
ctcgggtctg cggcgggcgt gccggagaca cacgcgtggc cgggggtgaa cgagtacccg 120
tcggtggagt ccgctggccg cgacgtggtc ccggtggtgg acatgggggt ggcctgcccg 180
gacgcgacgc gggcgttggc gcgcgccgca gacgagtggg gcgtgtttct gctcgtcggc 240
cacggcgtgc cccgggaagt ggcggcgcgt gccgaggagc aggtcgcgcg cctgttcgtg 300
ctcccggctc ctgacaaggc ccgcgcgggg cgccgccccg gggagcccac ggccaccggc 360
tacggcaggc cgcccctggc actccgcttc tccaagctca tgtggtccga ggggtacacg 420
ttccgcgccg ccaccgtccg cgaagagttc cgccgcgtct ggcccgacgg cggcgacgac 480
tacctccgct tctgcgacgt gatggaggag tacgacagag agatgagggc tctcggtggc 540
aggctgctcg acctcttctt catggcgctc ggcctcaccg acgtccagtt cgccaccggc 600
gagacggagc ggaggatccg cgagacctgg acggcgacga tgcacccaat cctgtgtccg 660
gaaccggagc gcgccatcgg gctgacggcg cacacggact cgggcttcat cacgctcatc 720
atgcagagcc ccgtgcccgg gctgcagctg ctccgccgcg ggccggaccg gtgggtgacg 780
gtgccggcgc cgccgggcgc gctcatcgtc atgctcggcg acctgttcca ggtgctcacg 840
aacggccgct tccggagccc tatccaccgc gccgtcgtaa gccgagagcg cgagcggatc 900
tccgtgccct acttcctctg cccgccggag gacatgacgg tggcgccgct cgcgtccgct 960
ctgctgccgg ggaggaaggc cgtgttccgg gccgtgacgt ggccagagta catggaggtc 1020
aagcacaagg tgttcggcac ggatgcgccg gccctggaga tgctgcagct gcaggtggat 1080
gaggaagaac aaggtgaaag ggccgccacc acctaa 1116

<210> SEQ ID NO 33
<211> LENGTH: 371
<212> TYPE: PRT
<213> ORGANISM: Zea mays

<400> SEQUENCE: 33

Met Gln Ser Ser Ser Ser Ser Ala Ser Thr Pro Ala Ala Ala Ser Gly
1 5 10 15

```
Leu Val Phe Asp Leu Gly Ser Ala Ala Gly Val Pro Glu Thr His Ala
            20                  25                  30

Trp Pro Gly Val Asn Glu Tyr Pro Ser Val Glu Ser Ala Gly Arg Asp
        35                  40                  45

Val Val Pro Val Val Asp Met Gly Val Ala Cys Pro Asp Ala Thr Arg
    50                  55                  60

Ala Leu Ala Arg Ala Ala Asp Glu Trp Gly Val Phe Leu Leu Val Gly
65                  70                  75                  80

His Gly Val Pro Arg Glu Val Ala Ala Arg Ala Glu Glu Gln Val Ala
                85                  90                  95

Arg Leu Phe Val Leu Pro Ala Pro Asp Lys Ala Arg Ala Gly Arg Arg
            100                 105                 110

Pro Gly Glu Pro Thr Ala Thr Gly Tyr Gly Arg Pro Pro Leu Ala Leu
        115                 120                 125

Arg Phe Ser Lys Leu Met Trp Ser Glu Gly Tyr Thr Phe Arg Ala Ala
    130                 135                 140

Thr Val Arg Glu Glu Phe Arg Arg Val Trp Pro Asp Gly Gly Asp Asp
145                 150                 155                 160

Tyr Leu Arg Phe Cys Asp Val Met Glu Glu Tyr Asp Arg Glu Met Arg
                165                 170                 175

Ala Leu Gly Gly Arg Leu Leu Asp Leu Phe Phe Met Ala Leu Gly Leu
            180                 185                 190

Thr Asp Val Gln Phe Ala Thr Gly Glu Thr Glu Arg Arg Ile Arg Glu
        195                 200                 205

Thr Trp Thr Ala Thr Met His Pro Ile Leu Cys Pro Glu Pro Glu Arg
    210                 215                 220

Ala Ile Gly Leu Thr Ala His Thr Asp Ser Gly Phe Ile Thr Leu Ile
225                 230                 235                 240

Met Gln Ser Pro Val Pro Gly Leu Gln Leu Leu Arg Arg Gly Pro Asp
                245                 250                 255

Arg Trp Val Thr Val Pro Ala Pro Pro Gly Ala Leu Ile Val Met Leu
            260                 265                 270

Gly Asp Leu Phe Gln Val Leu Thr Asn Gly Arg Phe Arg Ser Pro Ile
        275                 280                 285

His Arg Ala Val Val Ser Arg Glu Arg Glu Arg Ile Ser Val Pro Tyr
    290                 295                 300

Phe Leu Cys Pro Pro Glu Asp Met Thr Val Ala Pro Leu Ala Ser Ala
305                 310                 315                 320

Leu Leu Pro Gly Arg Lys Ala Val Phe Arg Ala Val Thr Trp Pro Glu
                325                 330                 335

Tyr Met Glu Val Lys His Lys Val Phe Gly Thr Asp Ala Pro Ala Leu
            340                 345                 350

Glu Met Leu Gln Leu Gln Val Asp Glu Glu Glu Gln Gly Glu Arg Ala
        355                 360                 365

Ala Thr Thr
    370


<210> SEQ ID NO 34
<211> LENGTH: 4095
<212> TYPE: DNA
<213> ORGANISM: Zea mays

<400> SEQUENCE: 34

taaatttgtg atccttgtga agttgttata tcatgaattg tgaacttgtt gcatttgtga     60
```

-continued

```
tcttttgtca actttgttgt attgtgaagt ttgatatgtt taccgatcgt attttagatt    120
tcgatcgtta ccggtgtatt ttccgcacca aacttttgtt tccgatgttt tcgaaatacc    180
gatatcgttt ccgtttctat agttaccctt ttcaatttta tttccgatta aaaatatgaa    240
aacggtaatg gttttagtgt ttatcgaccg ttttcatctc taatcatccc tgccggtgaa    300
gtttaatttt tcccttggct aaagagatgc aagctgctgt aaaatacgtt aaaacaggca    360
aggcagcccc agcagccagc atcgcgtgcc cgtctatgta catcagtgga tacgtagcat    420
ctctagtgag taatataacg attgcatttg gctggaggac gtatgttata taagtatgtc    480
atttaccagt tgcattagta tcttccctaa ctcctataat aactctcttc gtggaatgga    540
cgtagacgta tgctatataa gtattaaaaa atagtttttt aagctggtgt cctcaatttt    600
gctattgttc tcgtttttat ctttagttgt gtcacaaatt taatccgtac aacaaatcaa    660
aaataccata cccttcttat attaattttc taacataaca tttgtttaga tattttcagt    720
cgtgaaaata caattctaat tctaacgtcg tagtatcaaa tcaaaccatc cagaatttga    780
ccaagcttaa ttataaaaaa tataaaattt atgatactga atagatagca ttagatttgt    840
tatataatat atttttataa aataccattt ttatggtata aatattggta ctcctttact    900
ttaaactata gatagttttg actaaggatg caactagaat tgcatcctct tttcactgca    960
ccttcattag ttttaatatt tatttagatg ggcccttgca aactgtagat atcatctctt   1020
gcaacattct ttctatagca ccacgaaaat gtattgcggc tttgaaatta taattgaatt   1080
agttgtatca tttctttcac cgatgcgtta aattcaaaat taagtgttat atttcttcat   1140
aatttgttaa atatatagac cctataatcc accattattt actataatag catacattaa   1200
cattggtttt agcctacact acgacactcg aggcattgaa ttttcctcta tcaaagaatt   1260
atatgtgtag tagtattgtt cttgacaaaa agggggatta aaattaaact accaatattg   1320
atacttatct tatcacatcc atgaatacaa tcaacactct tacaaaagat aagatacaag   1380
attaaaaagt accatgataa tacattaaga ttattagcaa tgcattaaat taaataaatg   1440
tgcaagtgaa tcatgatttt agttttatct attttacttt taaaatatga tattctctga   1500
ctacttctaa gcataaatgt gattctaagt catgaccgat cgtgcttatt cagaaaaatg   1560
aaggagacac agatttctat aaaaaaaggt tgtcatggga ctattgggtc aaccatctta   1620
ttcatttggg aaaataagtt tagaacacat caacccattt tagatgttga gtttggccct   1680
aatggtccat tgaccttact tttgtgggtt gacatagacc atctatccca agttattgtt   1740
gtgtcacatt ccctgatatc atgaatctat attttagctt tccgttttca tatttttagt   1800
cgttacatat tttttatccg cgtactagat taaaactcta gttgttgcaa tacattttgt   1860
tcattttttt ctatttcttc tttactaaca acatattcta gttcctagct acattcttaa   1920
gtaccatagt gctataaaca ttttttatcc tacattattc cacttaagaa attgaatttt   1980
ctgcataaaa aaattatatg tccagtagtg ttgtcttata aaagcataaa gtgattaaaa   2040
ttaaaaccat tattgatatc ttatttttca aaaaaaaata taagcttata gaaagtgaat   2100
taatttcatg gtaaattaat atagtttaaa ttgaattatt agtgttatta ctatgtttat   2160
tatcaatgaa acatttttca tggttgatat aacttagtgt tacttatttt agtatttttt   2220
atataattct agttaacttt tagtttttga tttaaaaaaa cgagaattgt gtccttttgt   2280
ggagtgagta taaagaaagt aatatctgtt catcataatt tggtttttta aggtacgtga   2340
aacttgcttt atatttggac tcaagctatg tctaaataca tagtaaaaaa gcaatatttc   2400
```

-continued

```
tagaaaagac aaaacatctt ataatttaga atcaaggaaa tatatagatt ttatgtgcag   2460

tgagaagcca tttacaatgg aacgttcaac gttgggccaa tagatatttt gcgatatgat   2520

gatgggcata tttttgcatg gttgtccctc cactagctat agtttgatga tacgatacgc   2580

tgcacacacc attgggttgt accatgttag tgtagcaaca gtagaaaccc aattgtggcc   2640

gtgaaccatg ataatactag gtagagtgct agctagaggt ttcaggctat tgatgcgtga   2700

attaaacttt ctgttgtgtt gcgaggaaac gagtattgtg aaatatttga aacggttttt   2760

tttgtgaaag atttgaaacg gtatttttgt tgtgaaataa agatcaaggc taaataaatt   2820

caaactaata aaacatatta attgacggcc tgaagccccc gcccccatgg ccccatgcca   2880

tagcatcagg tcccacatga catgaggccg cgcctccctc tatgttggct ccctgccttc   2940

gccgttgtcg tcgctcccga actccctctc ctcccctgtt acaaataccc ccacccgccc   3000

ggacagcttc cctgcacact cgcagctcgc acatctcatg gtgtcctaag aacggcaaga   3060

gccagctctg cctagcagca gcgcacagcc acatccatgg acgccagccc gaccccaccg   3120

ctcccctcc gcgccccaac tcccagcatt gacctccccg ctggcaagga cagggccgac   3180

gcggcggcta acaaggccgc ggctgtgttc gacctgcgcc gggagcccaa gatcccggag   3240

ccattcctgt ggccgcacga agaggcgcgg ccgacctcgg ccgcggagct ggaggtgccg   3300

gtggtggacg tgggcgtgct gcgcaatggc gacggcgcgg ggctccgccg cgccgcggcg   3360

caagtggcgg cggcgtgcgc gacgcacggg ttcttccagg tgtgcgggca cggcgtggac   3420

gcggcgctgg ggcgcgccgc gctggacggc gccagcgact tcttccggct gccgctggct   3480

gagaagcagc gggcccggcg cgtccccggc accgtgtccg ggtacacgag cgcgcacgcc   3540

gaccggttcg cgtccaagct cccctggaag gagaccctgt ccttcggctt ccacgacggc   3600

gccgcggcgc ccgtcgtcgt ggactacttc accggcaccc tcggccaaga tttcgagcca   3660

gtggggtgag taaagaagaa gatggcgccg aatttacatt tataagtagg accagcagaa   3720

gcccctgccc ctgggggcct tagcattgca ttcgactgat gaatacgcat ggcaggcggg   3780

tgtaccagag gtactgcgag gagatgaagg agctgtcgct gacgatcatg gagctgctgg   3840

agctgagcct gggcgtggag cgcggctact accgggagtt cttcgaggac agccgctcca   3900

tcatgcggtg caactactac ccgccgtgcc cggtgccgga gcgcacgctg ggcacgggcc   3960

cgcactgcga ccccacggcg ctgaccatcc tcctgcagga cgacgtcggc gggctggagg   4020

tcctggtgga cggcgagtgg cgccccgtcc ggcccgtccc aggcgccatg gtcatcaaca   4080

tcggcgacac cttca                                                    4095
```

<210> SEQ ID NO 35
<211> LENGTH: 7404
<212> TYPE: DNA
<213> ORGANISM: Zea mays

<400> SEQUENCE: 35

```
cctattttgt gtctaatact cttcttatat taattgtttg gtcaaacttt agataaattt     60

gactaatgat gcaattaaaa ctgcatcacc tttactaagg tactgcttta tatgtttcga    120

caaaattttc aattattctc tatgtgtttt aatctttgcg ctacacctcc attgatttaa    180

atactcattt attttaaacc ataacttaaa ttatatcgga tctttgcatc ctttctatgg    240

caccatacat gaatcgatat tttggctgca aatttttaat catgttagtt ttagcatttt    300

ttcatatcca tgtgttaagt ttgaatcatg tgttgttttt atataattta ttgaaaatat    360

agatcctaaa cttcactaat acttacaaca atagcatcat catgtgtttt aatccacgcc    420
```

```
acaacactca aggcattgaa ttttcttcta ccaaagagtt gtatgtgtgt attgttcttt    480
aaaaaataga gtgattataa ttaaactacc agtattcata tgtaaaatgt atagacatct    540
aaaataaaat ttgcaaaaaa cattgttgca gactttcaat ataattaaga atgggtttta    600
gggtcatgat atatggtttg ttaaagaaac ttgttttttt ttgcaattga taaactataa    660
aatacatttt cactattgtg tgcatatgta cttggtatac atagtggcat atatcatttt    720
tgtttacttt gaggtttgaa ttatctatgt taaaattgga taacatagat acattggtgt    780
gcgtcctttg gcccatttac ttgactgagg agcaatacta taaagtaaaa catatttgga    840
tattttatct taaactccta gcataatatt gatttaatta tgaacaaata tatgtttagg    900
tgatagtttc atgggtggta aactatataa gaaggcttac catgatcttt gcaaactcta    960
ggctatgaaa gagttccatg atttgtctta gaagcataga caaaacagtg ataatgatct   1020
aaatcacact tatggcactg atgaccatat atgcaaagct aaatgcatgt taagttgtat   1080
tatatcatat gtttacaatg actatcgcat ataacgagga atacattgtc tatatagata   1140
gctattactg tagtagtgcc aaatgttgga caacatgaat cataatcttc aaacctagag   1200
aaattgtagt cagtcgtaca catatcgtct agtaagttgt ctatactttt tatttattgt   1260
atcaaatttt attgttatct tgcttgcttg tttgtttgta ccatagacac aatatggtca   1320
aaaagtggtc aatcgattcg aagaagattg caattgacga gtgctaacag ttgatccttt   1380
tgttgtgcac gctagcggag tagcatgaaa agagtaaaat atgaaattag cgttctaaac   1440
tgtttgtgct ataggtactt cgtatttaat ggagtgacta actataggaa ggtgagagct   1500
cagaagtcag caccctcaca cagagttcta gagttagtgg tcatcgaacc acgacaaact   1560
acatgatgag cagaagaggc aacatcaaga ctatgatcaa tagtttcggg tcaatgaatg   1620
acatcgtgat gagtatttat ctaactatat agaacaacaa cacatgatgt tttaagtaag   1680
ttcaactgat cttctattgc tatctttaag tatttaacgt agcgaataat gttttatcta   1740
tttcattcat aaataatgtt gtgacaaaag gggataacca tcacttttac catgttctag   1800
ataccacaac catctccacc atcataatgg gttcttcatt ggtgcttgga cctcaaataa   1860
tcatatctat agccaactta gctcaattct aataaaatta ggcaacttgg cttcattgta   1920
gcaaaaatag ccaacttagc tcaattttat ctaaacttag ctaatctagc acaacttaga   1980
tcaatattag gaaaaactaa tcaatctaat ctagctcaac tatagcgaaa gatagatatt   2040
gtagcataac ttagtagatc tatctcaaat tttagcaaaa actaatcaat ttagataaac   2100
tctataaaat tttaatcatt atgacttatt tccaactaat tgtaacttgc atgattttta   2160
tgttccttct ttataattag caacacctaa agacacgaat gatgaggggt ctaacgcatt   2220
cattaaccag ttgttaaata atactctagg tagatgataa gaactctaat tattctatga   2280
atctaagcta aaagatgttt aatatttaag tattggtgtt tattatgtta tttagaacga   2340
ttcatgttac ttaaagattt gttatgattt ttaaatatga ttatgataat ttatgtggtg   2400
tggattaact tgtgaacata tgtgatgtag atgaatatgt atgttgtgga tggaaccata   2460
tgaatatata tacacactca tatactattc gttggtgtag gtaaagcttc atccatcggt   2520
aattactaaa tggtcttcag tcattaccac taggtgaagc ttcacacgac cgataattat   2580
tgaagaacgc tcattaattt ccggtaatgg cttattggcc ttcactagtc ggtgaaaatt   2640
agctattttt ataccaataa aaattagcta atatatgtaa accaggtcta atttttatgg   2700
gcctcttacc gaccaaaatt gattagatta ttgttacaat agttttagtc aaaagctagc   2760
```

-continued

```
tatgctataa aaattttgaa ttaaagtgag tttcgtaata aaaattgcat acttttaaaa   2820
taaaataatt aaaaaacagt ttttagaaat acaatcaaac accttatgct ataaaaaaat   2880
tgtaatgtac ctacaaatat ataatacttt actttaaaat aggcctgtgc cttctcggct   2940
ctatatgggc tgcctccaac gaagcgccat ggccatgggc tccactgtgt cgggtcccac   3000
atgaggccgc gcctccctcc aaatgttccc tccctgcctt cgtctttgtc gttgctcgca   3060
aactccctgt cctcccctgt tacaaatacc cccacccgcc cggacagctt ccctgcatac   3120
ttgcagctcg cacatctcat ggtgtcgcag gaacgacaag agccagctgt gcctagcagc   3180
agcagcagca gcgccaagcg cgcagccacg tccatggacg ccagcccggc cccgccgctc   3240
ctcctccgcg cccccactcc cagccccagc attgacctcc ccgctggcaa ggacaaggcc   3300
gacgcggcgg ccagcaaggc cggcgcggcc gtgttcgacc tgcgccggga gcccaagatc   3360
cccgcgccat tcctgtggcc gcaggaagag gcgcggccgt cctcggccgc ggagctggag   3420
gtgccgatgg tggacgtggg cgtgctgcgc aatggcgacc gcgcggggct gcggcgcgcc   3480
gcggcgcagg tggccgcggc gtgcgcgacg cacgggttct tccaggtgtg cgggcacggc   3540
gtggacgcgg cgctggggcg cgccgcgctg gacggcgcca gcgacttctt ccggctgccg   3600
ctcgccgaga agcagcgcgc ccggcgcgtc cccggcaccg tgtccgggta cacgagcgcg   3660
cacgccgacc ggttcgcggc caagctcccc tggaaggaga ccctgtcgtt cggctaccac   3720
gacggcgccg cgtcgcctgt cgtcgtggac tacttcgtcg gcaccctcgg ccaggatttc   3780
gagccaatgg ggtaagtaag gtagtaagaa ggagcgccgg tttacattta ccgcacgtcg   3840
gcgtgcggtc gagtcgggac tcgggagacg tatgaacccc cgtcccgtcc catgcatgtg   3900
tggcaggtgg gtgtaccaga ggtactgcga ggagatgaag gagctgtcgc tgacgatcat   3960
ggagctgctg gagctgagcc tgggcgtgga gctgcgcggc tactaccggg agttcttcga   4020
ggacagccgg tccatcatgc ggtgcaacta ctacccgccg tgcccggagc cggagcgcac   4080
gctgggcacg ggcccgcact gcgaccccac ggcgctcacc atcctcctgc aggacgacgt   4140
gggcgggctg gaggtgctgg tggacggtga gtggcgcccc gtccggcccg tcccgggcgc   4200
catggtcatc aacatcggcg acaccttcat ggtaacgaaa cgaaagcgct cgctcctctg   4260
ttttccttgg ccgctcttgt cctgtgtgta tattcagttg agctctctct gtgctgttat   4320
ttcccgaatc ctagtggacc taaacgggca ggttattaca gcacgcacac gtaggcatgt   4380
catgtagcta gtacatacat agcgatgccg atgcaaatgc aatagagaca tgcgttcgag   4440
ttggttccta tctcggcggg ctacggcagg tacacgcggc cgcggcgcgc tctctctagt   4500
ctatccgcgg ccgcgcccag gccgatcgag gcttccgggg gagagttgcg acaagagaac   4560
ggaccgaggg ggtcggctag cggtagcaag ttccctgttg gtttgtggcg ttggagcgtt   4620
gcggagaggc ttgcgcggcg gcggggacgt cgacggggac gtggcgggga gacgatacga   4680
tgggtgccgg gcaggtttcc gaattccaaa cgtttttgtg gcgtgcgtcc atggggcgcc   4740
cccaaacttc ggacgtttcc ggcgctccaa caaatcttct cgcttcacac gtcaccgtcg   4800
tcccggattc atttgcctcg tcgctccacc attcgctgct ctcctctcca cgtactctta   4860
ccctgacctt tgggaaagaa ctgaacattc gagatgcaca acagttcaaa tataacatat   4920
gcagcacaag atcgttcgac tgctatccga caagccaaca acgtgcccag tagaactgaa   4980
tgtacctgtg atttccagca ctaacttaca gcaacgttgt gaaaaaacaa aaacgaaaac   5040
aaacggcaga aaaaacagat gtattgttct acagttacac caaatatttt ctggtccttt   5100
cagcaccaac aagagccata cgcatatcta gaagacaaaa ttcctctaat ttcaccccta   5160
```

```
cgtggtagca gttcctcctc aacacagttc acgtgctagc gtcgagttct ttgggccgcc   5220

acatcgactt ctcgacgcag agcaggccct cgctgccctt ggtgtaggtc atccgcacct   5280

cccactgcac ggacttggcc atgctctcca gctcatttat cgtgtccgcg gtgtccctca   5340

cgatcagctt gccctgtggc ctcagtacac ggtcgacctc ggcgaaaact gcagccagtt   5400

tgcatctgta aacaggcaac acagattttt agtatctaaa acactgcagg caaacgccac   5460

aggttttagt cgcaagaagc aataaaagca tgcaaacaat gctacgtgta cgtatcaaag   5520

gaacatgtca aaactcgttg catgaacgat cattgatgtt tccttgctga actagtcaca   5580

tcagtctgct tcaacttctg ggtttcacta gtagatatac cagaagggta gaataatgtg   5640

aagagcaaga aatacagacc tctttctgag ctttgagaac agatggtccg cgtgcagaag   5700

gtcatacgtt cttgggtaag tgctgaaaga ctcgcaccag tcatggtaca tgccaaacaa   5760

accgcgctcg tagatgatgg gcagcgtgtc tggtgaatcg atcggcacga tattcatgac   5820

ccagaccttt tggtccctca gagctgcagc aaaactgcca tgcaacaatg taaagcatta   5880

gtcaagaaga aggtgtacag tgcatttctc cttgtcaaca gtcttcagta acaaaaaaaa   5940

agtgttatgc ttgactgaat ctttcaaaga aatatgcttg atgacttatg gtggacaagt   6000

tgcctgttat agtgttatgt tttaattaac tatgtgccag cttgggtaac tagtagttat   6060

gtagtgtgat ctgaattacc aaaatataaa taaataaata aacatgccca agaaactacg   6120

aaaaccattt acttaccctc catagacagc tctcatgtcc atgacatttc tcactttgga   6180

ccagtcaatt cccatgccat tcacatacga tttacttaca acccgtttcc agtgggcatt   6240

atctgcctca aaatcttcat ttgcaggctt tccatagaca ccaaccttgg aaccatcaat   6300

ccagaaaggg gtcttctcaa gcctttgcgg ccataactct ggccattttg atcctcggac   6360

ttttgagcca ccaggcagtt tgtgcatgca tgcttccaac ggtacattcc tgcaaatcaa   6420

aaggctgtgt aagcaaagca gagaagcact tttctccatt gaaaatatac tcttctcaaa   6480

gaaccgaaac cataccaagc agcatctgca tcatcagatt ccttgcacaa tggcgggctg   6540

ttttcagatc ttttctcata gcaaatattg tccattggtt tctgatatat gaccatacca   6600

acttggttta acttatcctt agtcttgttg accatcttcc agcacatgga ctttgtcaaa   6660

gtagacatgg ctgaaaaggg tatgtggcca catgttatgt tagaaataaa attcaatttt   6720

gaacagttgg tccatagcat gtattttgaa caaatgcaat ccttctccat ccatgaaaga   6780

agttgaccct tcatacttag gattattcag tactttcact catgtctgct gaatttgttc   6840

tcttggtagt tgctatacaa gaaaggggga agtacagagt agctaaactt atacaagcta   6900

tagtctgata tttgtatgaa acataaattt tggtatggat gtcttattaa aatgggaggt   6960

tgtataatat ttttctagcc tacctcaact tgcttgagac taaaaggctt tgttgttgtt   7020

gttgaggctg tatggtgctt tgactttaca aatcaagtta tcagctaccc tacttatgga   7080

tatacacctc tcataaaatg atggtaagaa gtttcgatat gtcacattaa cataagaact   7140

tcattcagtt agggtacaac gaagttaagt agttacggaa ataccattcc aaatctcaac   7200

atcctctggg agcttttggt aaacaggagt ggcagaccag acaaagtaac caccagggcg   7260

taacaagcgg ttcaattcca gcaaaagcat gccacctaaa agtagcgagc cagcaataag   7320

attcagttct atagcaaatc aataaatgaa aggaggacat gtcaatatgt aaccagcagg   7380

acaaaccttc gatgtgccaa ggga                                          7404
```

<210> SEQ ID NO 36

<211> LENGTH: 1788
<212> TYPE: DNA
<213> ORGANISM: Zea mays

<400> SEQUENCE: 36

```
aatcccagcg tgcgtaatct attgcccaca tgccgacgcc gtcgcacctc aacaagaacc     60
cgcgctacct ggacttccgg gcggcgcggc gggtgccgga gtcgcacgcc tggccgggcc    120
tgcacgacca ccccgtcgtg gacggcggcg cgcccgggccc cgacgccgtg ccggtggtgg   180
acctgggcgc cgcggacccg gcgccggcgc cggcggcggc ggtggcccgc gccgccgagc    240
aatggggcgc gttcctgctc acgggccacg gcgtccccgc ggacctgctg gcgcgcgtgg    300
aggaccggat cgccaccatg ttcgcgctgc cggccgacga caagatgcgc gccgtgcgcg    360
ggcccggcga cgcctgcggc tacggctccc cgcccatctc ctccttcttc tccaagtgca    420
tgtggtccga gggctacacc ttctcgccgg cctccctccg cgccgacctc cgcaagctct    480
ggcccaaggc cggcgacgac tacaccagct tctggtacgt tgcgttgcgt gcttgtgtgc    540
gcgcacacct gccgaccgcg gccacaccgt acgcaaccca cgcgtacgta cgtgcgctag    600
ctacctgctt cgctcgcttc gctcctctcg cctcgccatg catatgcacg tacggccgta    660
caggtacagc agcaggtcac acgcacgaac gcacgcacgc accagcaccg atatgataca    720
tcatcgacgt gtcgtccccc cgtctaaggc catgcatgca tgcaagcacg cctagctagc    780
ccttttggct tgctagctga cgaggggagc taggacgagc atacttactg tgcgcgtcat    840
gctcaattgc tcacactata ctactacttg ttactacagt gatgtgatgg aggagttcca    900
caagcacatg cgcgccctcg cggacaagct gctggagctg ttcctcatgg cgctggggct    960
caccgacgag caggccagcg ccgtcgaggc cgagcggagg atcgccgaga cgatgaccgc   1020
caccatgcat ctcaactggt gggtatatat tattgtctgt catgttgtcg tcgtcgtacg   1080
cgttgcggtt gggtgtacat gtatataaca caaacaacaa aaaactaacg ccgtgccgac   1140
gacgacgacg atcatcaggt acccgaggtg cccggacccg cggcgcgcgc tggggctgat   1200
cgcgcacacc gactcgggct tcttcacctt cgtgatgcag agcctcgtgc ccggctgca    1260
gctcttccgc cacgccccgg accggtgggt ggcggtgccg gccgtgccgg gcgccttcgt   1320
cgtcaacgtg ggcgacctct tccacatcct caccaacggc cggttccaca gcgtgtacca   1380
ccgcgccgtc gtgaaccggg acctcgacag gatctcgctc ggctacttcc tcggcccgcc   1440
gccgcacgcc aaggtggcgc cgctgcgcga ggccgtgccg cccggccggg cccccgcgta   1500
ccgcgccgtc acgtggcccg agtacatggg cgtccgcaag aaggccttca ccaccggcgc   1560
ctccgcgctc aagatggtcg ccctcgccgc cgccgccgac ctcgacgacg acggcgacgc   1620
cgccgtcgtc catcagcagc agcagctagt cgtctcgtcg tagccgagac cgatcgccgg   1680
agactgatgc tgatgatgat gcatatatac atgagagaaa tcgtcgagta gactagccga   1740
ttgcaaaagc aaccccagct gccgaaacct ggcatatcga tcccattc                1788
```

<210> SEQ ID NO 37
<211> LENGTH: 1698
<212> TYPE: DNA
<213> ORGANISM: Zea mays

<400> SEQUENCE: 37

```
cgtgccgaga gtccttcaaa gccgacgacg agacgacgat gcagtcgtcg tcgtcatcag     60
cctcgacgcc ggctgccgct tccggcctcg tcttcgatct cgggtctgcg gcgggcgtgc    120
cggagacaca cgcgtggccg ggggtgaacg agtacccgtc ggtggagtcc gctggccgcg    180
```

```
acgtggtccc ggtggtggac atgggggtgg cctgcccgga cgcgacgcgg gcgttggcgc    240

gcgccgcaga cgagtggggc gtgtttctgc tcgtcggcca cggcgtgccc cgggaagtgg    300

cggcgcgtgc cgaggagcag gtcgcgcgcc tgttcgtgct cccggctcct gacaaggccc    360

gcgcggggcg ccgccccggg gagcccacgg ccaccggcta cggcaggccg cccctggcac    420

tccgcttctc caagctcatg tggtccgagg ggtacacgtt ccgcgccgcc accgtccgcg    480

aagagttccg ccgcgtctgg cccgacggcg gcgacgacta cctccgcttc tggtacgtac    540

gagcgccatg tcacgtgctt gtgctttcat gcctcgtacc gtcgtcgtgc tgtacgtgtt    600

atgtttatcg gccggtacgt cacgcgtgct acactggtta acgacgtgag cgtgcccacg    660

ttgactgcat gcatgtgcat gcgcgcgccc agcgacgtga tggaggagta cgacagagag    720

atgagggctc tcggtggcag gctgctcgac ctcttcttca tggcgctcgg cctcaccgac    780

gtccagttcg ccaccggcga gacggagcgg aggatccgcg agacctggac ggcgacgatg    840

cacccaatcc tgtacgtacg tcaaaaacga atatctgacc aatgcaaacg tttttctgca    900

atgccagtca tccactcatc ctgtacgtac ctctggactc tgcttgtcca tctactgatg    960

acacgtatgg taggtacccc aggtgtccgg aaccggagcg cgccatcggg ctgacggcgc   1020

acacggactc gggcttcatc acgctcatca tgcagagccc cgtgcccggg ctgcagctgc   1080

tccgccgcgg gccggaccgg tgggtgacgg tgccggcgcc gccgggcgcg ctcatcgtca   1140

tgctcggcga cctgttccag gtgctcacga acggccgctt ccggagccct atccaccgcg   1200

ccgtcgtaag ccgagagcgc gagcggatct ccgtgcccta cttcctctgc ccgccggagg   1260

acatgacggt ggcgccgctc gcgtccgctc tgctgccggg gaggaaggcc gtgttccggg   1320

ccgtgacgtg gccagagtac atggaggtca agcacaaggt gttcggcacg gatgcgccgg   1380

ccctggagat gctgcagctg caggtggatg aggaagaaca aggtgaaagg gccgccacca   1440

cctaagccct aaggaactac tagctgaatc cataaactaa taaagaattc gtgaataagg   1500

gcgttggaag actggacaca acacaagaga gttgctatat atcgtatttc tgaaatttaa   1560

ggcaaatatc ttagttaaaa aactggtata tttaaataga caatatatat ctaaaataaa   1620

gatagttcac catttttacg gtcgaacaat gataaagtta tatattgtct gaatagtaac   1680

aaattaaaga tttccagg                                                 1698
```

<210> SEQ ID NO 38
<211> LENGTH: 4095
<212> TYPE: DNA
<213> ORGANISM: Zea mays

<400> SEQUENCE: 38

```
cggtctaagt gaccgtttga gagaggaaaa gggttgaaag agacccggtc tttgtgacca     60

cctcaacggg gagtaggttt ataagaaccg aacctcggta aaacgaatca ccgtgtcatc    120

cgccttattt gcttgtgatt tgttttcgcc ctctctttcg gactcgttta tatttctaac    180

gctaaccccg acttgtagtt gtgcttaaag tttgtaaatt tcagattcgc cctattcacc    240

ccctctaggc gactttcata taaatattgg gagaaatatg aaaaacaaat gaaggtcgaa    300

cgagtcagag acaccataaa aaagaggtcg tcttaactag ggtgctaaac ctcaacattg    360

tagtagatct tagtactgag tttgacatct ttgacaccaa caagatggtg atacgttact    420

ttctacgtta acttgggtag gtatatcgac tatagtggcc tataacacta ggctatgtaa    480

tatgatattg tgttgagtct ttataaacat gatttttttt aaaaaaaaga gctaaaataa    540
```

```
aaaatagaaa tcgacggtac gatgcaagtt cttctcaaga caaccaaacg caccccttgcc    600
cctttattga aattgaagta tgtgctttat caaatgttta aatactaatt ataagtatta    660
aatataattt aattataata ctaattatat agataaagac taaataacaa gacaaattta    720
ttaaatataa ttaattcatt attaacaaat acttaatgta gcacgatcga atcatggact    780
aattagtctt gatagactcg tcttaccatt taatcataat tagttttgta tactgtttat    840
aatatttcta actagctagt attaaacttt tgatgtaacc taactaaagt ttagtcacgc    900
caatacataa ggactcggat cgttcgatca cccatgacat cacgtatact aagagcatct    960
ccaaaagctc tccagaagtc tcccctaaat ctattttttt gggaaaaaca caaaaacatg   1020
tctccaacag ttcccttaaa gcgcccccaa ctttttcata gcccttaaaa ctccctcatt   1080
tgtagctaca aatgaggggt tttttgggct ccccagaaac aaactgttga tttaagggat   1140
ctgttggaga aaggattaaa atttaccctc acttattatt tagatgtccc ttaaaactga   1200
ttttgaggag tcgttttatg tagagctctt ggagatgctc taacacaccg agcacaaccg   1260
catcatcaat caaaacaacc caaagtttgt tcggtacaag tcatcagcct gtgtacacac   1320
atcagcctcg gccccgggag aagcgctagc aaacaaggtt cacctaaaaa tccatccaga   1380
ttcattgaat ccaaccagca caaacgtccc atttattaat cacctcatca caggtccccc   1440
cagcctcact ctcgcgccgg ctcaaggtac attgcgtgtc ctagccaaga cacgcagctc   1500
atctcagcct cacacgcaca gcaagagcga ggcgtgattc gccatgggcg gcctcactat   1560
ggaccaggcc ttcgtgcagg cccccgagca ccgccccaag cccatcgtca ccgaggccac   1620
cggcatccct ctcatcgacc tctcgcctct ggccgccagc ggcggcgccg tggacgcgct   1680
ggccgccgag gtgggcgcgg cgagccggga ctggggcttc ttcgtggtcg tgggccacgg   1740
cgtgcccgca gagaccgtgg cgcgcgcgac ggaggcgcag cgagcgttct tcgcgctgcc   1800
ggcagagcgg aaggccgccg tgcggaggaa cgaggcggag ccgctcgggt actacgagtc   1860
ggagcacacc aagaacgtga gggactggaa ggaggtgtac gacctcgtgc cgcgcgagcc   1920
gccgccgccg gcagccgtgg ccgacggcga gcttgtgttc gataacaagt ggccccagga   1980
tctaccgggc ttcaggtgac gaaattaact atatatccct ttcgatcata gttgcgttaa   2040
taaattaagg gaatcgtgag cgtacgtacg taagtttccg cagagaggcg ctggaggagt   2100
acgcgaaagc gatggaagag ctggcgttca agctgctgga gctgatcgcc cggagcctga   2160
agctgaggcc cgaccggctg cacggcttct tcaaggacca gacgaccttc atccggctga   2220
accactaccc tccttgcccg agccccgacc tggccctcgg cgtggggcgg cacaaggacg   2280
ccggcgccct gaccatcctg taccaggacg acgtcggggg gctcgacgtc cggcggcgct   2340
ccgacggcga gtgggtccgc gtcaggcccg tgcccgactc gttcatcatc aacgtcggcg   2400
acctcatcca ggtacgtgcc cacctgatga actgagctga acgtaggttg catgcactgc   2460
atgtgtatag gcttctcaga tcgcttcgtg tggcgtaagg tgtggagcaa cgacaggtac   2520
gagagcgcgg agcaccgggt gtcggtgaac tcggcgaggg agaggttctc catgccctac   2580
ttcttcaacc cggcgaccta caccatggtg gagccggtgg aggagctggt gagcaaggac   2640
gatccgccca ggtacgacgc ctacaactgg ggcgacttct tcagcaccag gaagaacagc   2700
aacttcaaga agctcaacgt ggagaacatt cagatcgcgc atttcaagaa gagcctcgtc   2760
ctcgcctaac tactgctact gctaggatcc atgccattgc catgtcgtct tcagattcag   2820
agcacgccat gtcgtcgcta gcttcgtggt agaacaaata atgatgtgcg tgctgtgtgt   2880
aagcatggat atggatgtga atatgtaata tgatgagcac tcctactttg gtatgtttgg   2940
```

```
gaataacaga cttgtgttgg tctggttcat tatttgtaag aaaatcaaaa agagttagta   3000

gggcaggagg ctaaccacag tcatgctgca ccacatccct ggtggaaagc tggccgggtt   3060

acgctacgct cgtgcagcca gattactgca gggccgggat atgcttccgg tggaaggaag   3120

gggacggtgg ctgaggacca tggggctgga gcctgggaga gaggtcgagc tagaagaaag   3180

ggggagagag aagacgcaca acgaagatgg gtcagccagg gatttcgacc caagggggag   3240

ctagtggatt ttgggagaaa acagaaaaga gaaaagagaa aagaagaaaa atttgttggt   3300

gtgaacacaa ggttgatttg tcttttctta tttggattga tgatgagtcg tggactaacc   3360

gacccgtgag ctattgtgtc gtataatcat gtctctcggt ttctggtgtg caggtttgaa   3420

gcacagagac ggtggtcgac gcaaaggtga acgtcatgca ggttcgtgcc gatggaccgg   3480

gagcagtgaa agacgagcgt tgggacttga acaagggacc agagtcgccg gatgactagc   3540

cgcagtggct gacgcctgga acacgcatag acgtgaggac gtggtagagc aggtgaaaat   3600

cgcctagagg gggggggggt gaatagacaa aacctaaaaa ttataaactt tgaacacaaa   3660

ctttacctga ggttaccgtt agaacgagta ttaatgaaat cggagtgcgg aaggcaagtt   3720

cttcttgcta cgagttgctt aatcaatatt gataactttg ggagtcaact caaaatgatc   3780

acaagcaaaa gaactagaga gagaggagag gaagaatcaa ctcgcaaagt aatgatcaac   3840

acaaatgaac acaatgattt atttctcgag gtttggttcc gaagaaccta ctccccgttc   3900

aggagtccac ataggacatg tctctttcaa ccctttctct ctctcaaatg gtcacataga   3960

ctggttcagt tgagagcacc tagagggggg tgaataggtg atcttgtaaa atcaaacact   4020

aatagccaca aaacttagtt taaagtgtta gtacggctaa gtagctttga agcgagttat   4080

tgtgaacaca acaat                                                    4095
```

```
<210> SEQ ID NO 39
<211> LENGTH: 21
<212> TYPE: DNA
<213> ORGANISM: Artificial Sequence
<220> FEATURE:
<223> OTHER INFORMATION: suppression oligo

<400> SEQUENCE: 39

ctccatcatg cggtgcaact a                                               21


<210> SEQ ID NO 40
<211> LENGTH: 21
<212> TYPE: RNA
<213> ORGANISM: Artificial Sequence
<220> FEATURE:
<223> OTHER INFORMATION: suppression oligo

<400> SEQUENCE: 40

uaguugcacc gcaugaugga g                                               21


<210> SEQ ID NO 41
<211> LENGTH: 19
<212> TYPE: DNA
<213> ORGANISM: Artificial Sequence
<220> FEATURE:
<223> OTHER INFORMATION: suppression oligo

<400> SEQUENCE: 41

ggtactgcga ggagatgaa                                                  19


<210> SEQ ID NO 42
```

<211> LENGTH: 21
<212> TYPE: RNA
<213> ORGANISM: Artificial Sequence
<220> FEATURE:
<223> OTHER INFORMATION: suppression oligo

<400> SEQUENCE: 42
uucaucuccu cgcaguaccu a 21

<210> SEQ ID NO 43
<211> LENGTH: 19
<212> TYPE: DNA
<213> ORGANISM: Artificial Sequence
<220> FEATURE:
<223> OTHER INFORMATION: suppression oligo

<400> SEQUENCE: 43
caggcgccat ggtcatcaa 19

<210> SEQ ID NO 44
<211> LENGTH: 21
<212> TYPE: RNA
<213> ORGANISM: Artificial Sequence
<220> FEATURE:
<223> OTHER INFORMATION: suppression oligo

<400> SEQUENCE: 44
uugaugacca uggcgccugg a 21

<210> SEQ ID NO 45
<211> LENGTH: 19
<212> TYPE: DNA
<213> ORGANISM: Artificial Sequence
<220> FEATURE:
<223> OTHER INFORMATION: suppression oligo

<400> SEQUENCE: 45
tcatgcggtg caactacta 19

<210> SEQ ID NO 46
<211> LENGTH: 21
<212> TYPE: RNA
<213> ORGANISM: Artificial Sequence
<220> FEATURE:
<223> OTHER INFORMATION: suppression oligo

<400> SEQUENCE: 46
uaguaguugc accgcaugau a 21

<210> SEQ ID NO 47
<211> LENGTH: 19
<212> TYPE: DNA
<213> ORGANISM: Artificial Sequence
<220> FEATURE:
<223> OTHER INFORMATION: suppression oligo

<400> SEQUENCE: 47
tcgctcgcct tcttcctca 19

<210> SEQ ID NO 48
<211> LENGTH: 21
<212> TYPE: RNA
<213> ORGANISM: Artificial Sequence
<220> FEATURE:
<223> OTHER INFORMATION: suppression oligo

<400> SEQUENCE: 48

```
ugaggaagaa ggcgagcgac a                                              21


<210> SEQ ID NO 49
<211> LENGTH: 19
<212> TYPE: DNA
<213> ORGANISM: Artificial Sequence
<220> FEATURE:
<223> OTHER INFORMATION: suppression oligo

<400> SEQUENCE: 49

tccaacgggc ggtacaaga                                                 19


<210> SEQ ID NO 50
<211> LENGTH: 21
<212> TYPE: RNA
<213> ORGANISM: Artificial Sequence
<220> FEATURE:
<223> OTHER INFORMATION: suppression oligo

<400> SEQUENCE: 50

ucuuguaccg cccguuggac c                                              21


<210> SEQ ID NO 51
<211> LENGTH: 19
<212> TYPE: DNA
<213> ORGANISM: Artificial Sequence
<220> FEATURE:
<223> OTHER INFORMATION: suppression oligo

<400> SEQUENCE: 51

gcatcaacag gtacaacta                                                 19


<210> SEQ ID NO 52
<211> LENGTH: 21
<212> TYPE: RNA
<213> ORGANISM: Artificial Sequence
<220> FEATURE:
<223> OTHER INFORMATION: suppression oligo

<400> SEQUENCE: 52

uaguuguacc uguugaugcg a                                              21


<210> SEQ ID NO 53
<211> LENGTH: 19
<212> TYPE: DNA
<213> ORGANISM: Artificial Sequence
<220> FEATURE:
<223> OTHER INFORMATION: suppression oligo

<400> SEQUENCE: 53

tggacgatgg atagttcaa                                                 19


<210> SEQ ID NO 54
<211> LENGTH: 21
<212> TYPE: RNA
<213> ORGANISM: Artificial Sequence
<220> FEATURE:
<223> OTHER INFORMATION: suppression oligo

<400> SEQUENCE: 54

uugaacuauc caucguccau c                                              21


<210> SEQ ID NO 55
<211> LENGTH: 19
<212> TYPE: DNA
```

<213> ORGANISM: Artificial Sequence
<220> FEATURE:
<223> OTHER INFORMATION: suppression oligo

<400> SEQUENCE: 55
tggaccatgg atacttcaa 19

<210> SEQ ID NO 56
<211> LENGTH: 21
<212> TYPE: RNA
<213> ORGANISM: Artificial Sequence
<220> FEATURE:
<223> OTHER INFORMATION: suppression oligo

<400> SEQUENCE: 56
uugaaguauc caugguccau c 21

<210> SEQ ID NO 57
<211> LENGTH: 19
<212> TYPE: DNA
<213> ORGANISM: Artificial Sequence
<220> FEATURE:
<223> OTHER INFORMATION: suppression oligo

<400> SEQUENCE: 57
gcaaggtcct agatttaca 19

<210> SEQ ID NO 58
<211> LENGTH: 21
<212> TYPE: RNA
<213> ORGANISM: Artificial Sequence
<220> FEATURE:
<223> OTHER INFORMATION: suppression oligo

<400> SEQUENCE: 58
uguaaaucua ggaccuugca a 21

<210> SEQ ID NO 59
<211> LENGTH: 19
<212> TYPE: DNA
<213> ORGANISM: Artificial Sequence
<220> FEATURE:
<223> OTHER INFORMATION: suppression oligo

<400> SEQUENCE: 59
cagagtacat ggaggtcaa 19

<210> SEQ ID NO 60
<211> LENGTH: 21
<212> TYPE: RNA
<213> ORGANISM: Artificial Sequence
<220> FEATURE:
<223> OTHER INFORMATION: suppression oligo

<400> SEQUENCE: 60
uugaccucca uguacucugg a 21

<210> SEQ ID NO 61
<211> LENGTH: 19
<212> TYPE: DNA
<213> ORGANISM: Artificial Sequence
<220> FEATURE:
<223> OTHER INFORMATION: suppression oligo

<400> SEQUENCE: 61
ccatgcccta cttcttcaa 19

<210> SEQ ID NO 62
<211> LENGTH: 21
<212> TYPE: RNA
<213> ORGANISM: Artificial Sequence
<220> FEATURE:
<223> OTHER INFORMATION: suppression oligo

<400> SEQUENCE: 62
uugaagaagu agggcaugga a 21

<210> SEQ ID NO 63
<211> LENGTH: 19
<212> TYPE: DNA
<213> ORGANISM: Artificial Sequence
<220> FEATURE:
<223> OTHER INFORMATION: suppression oligo

<400> SEQUENCE: 63
acatggcggt caacttcta 19

<210> SEQ ID NO 64
<211> LENGTH: 21
<212> TYPE: RNA
<213> ORGANISM: Artificial Sequence
<220> FEATURE:
<223> OTHER INFORMATION: suppression oligo

<400> SEQUENCE: 64
uagaaguuga ccgccaugug a 21

<210> SEQ ID NO 65
<211> LENGTH: 726
<212> TYPE: DNA
<213> ORGANISM: Rice tungro bacilliform virus

<400> SEQUENCE: 65
tcctacaaaa gggagtagta atatttaatg agcttgaagg aggatatcaa ctctctccaa 60
ggtttattgg agacctttat gctcatggtt ttattaaaca aataaacttc acaaccaagg 120
ttcctgaagg gctaccgcca atcatagcgg aaaaacttca agactataag ttccctggat 180
caaataccgt cttaatagaa cgagagattc ctcgctggaa cttcaatgaa atgaaaagag 240
aaacacagat gaggaccaac ttatatatct tcaagaatta tcgctgtttc tatggctatt 300
caccattaag gccatacgaa cctataactc ctgaagaatt tgggtttgat tactacagtt 360
gggaaaatat ggttgatgaa gacgaaggag aagttgtata catctccaag tatactaaga 420
ttatcaaagt cactaaagag catgcatggg cttggccaga acatgatgga gacacaatgt 480
cctgcaccac atcaatagaa gatgaatgga tccatcgtat ggacaatgct taaagaagct 540
ttatcaaaag caactttaag tacgaatcaa taaagaagga ccagaagata taaagcggga 600
acatcttcac atgctaccac atggctagca tctttacttt agcatctcta ttattgtaag 660
agtgtataat gaccagtgtg cccctggact ccagtatata aggagcacca gagtagtgta 720
atagat 726

<210> SEQ ID NO 66
<211> LENGTH: 165
<212> TYPE: DNA
<213> ORGANISM: Rice tungro bacilliform virus

<400> SEQUENCE: 66

-continued

```
acgaatcaat aaagaaggac cagaagatat aaagctggaa catcttcaca tgctaccaca      60

tggctagcat ctttacttta gcatctctat tattgtaaga gtgtataatg accagtgtgc     120

ccctggactc cagtatataa ggagcaccag agtagtgtaa tagat                     165


<210> SEQ ID NO 67
<211> LENGTH: 2000
<212> TYPE: DNA
<213> ORGANISM: Zea mays

<400> SEQUENCE: 67

ctgcaatata tacaccaaaa gtattataaa ctgtcatata tatgaccaaa accttttttat     60

tttagaaaag tatattaatc atggtatatt aatcaaagtt gttgttgggg ctgcaaaaat     120

catacccttc ttccacaagc tgttccttga actgcaggta ctcaggaact ctcagctcct     180

caacagcgag ctcactgacg ttgaccctca catactccca gacaccaggc ctagggcgga     240

tggcaagtgc aacccatggg gggatgacaa tcgcctcctg taagataata gagctagaat     300

gattaaagaa ggtgcacact acaaaaggaa cagtgctgtc cagcgagatc tgaatctgat     360

gcaaacctga gctgccctca ggacatcctc aaaagcacca tccttgagct tctcgcgctc     420

agcctcaggg atcgcattgt tgtactcggc aatgatctgg tggggctgca gcataccctt     480

tccaaggttt ttcagcctgc gcaaaacgat gtgccaaata acatcagact atgccagatc     540

tataaactca tcaaacatat acaatttcaa gaaatagttt agacgtatga tcagcagtca     600

gtagcgtggg aacatatgca acatagcgaa gaggcacaac agcaaattca ttcgaaaaaa     660

tgaaaacaaa gattcctctc ttttaactga acttctcgaa accccctttca tgcctacaca    720

tccgatctag tcagatgcct atgcgttcat gctgaacaga acgtgtcaga actaagcata     780

aactggttag caagcattat cgtattcgat agaccctttta gtaacaagct atacattggg    840

taagttcaga ctccaatcat tctgttcaga aacatcgtat tgaatataaa actaaagaac     900

acacatgcag gtgcagccag atctaacagc agtttacagt cggtactaaa aaaagcatgg     960

tgtatgtatg tatcatcagt atccagtact aggtttcgac aaaatcctgg atgctaatta    1020

aatactcatc ttattaggga acacaggaac attatgtcta cagcattgaa tgatggccac    1080

atcatgctag atctaacaat acataaatatg atggaactgg tcttaaaaag tcgcattcgc   1140

tcaaataata cccgtagcaa aataaatgta aacttgcaga cgaagcgggg gaaatgaggg    1200

cagacctggt gaagacggcg acaagctcat tggggtgggc agagagtgag tcgccaatgc    1260

gctccctgac gctgtggagg cggctcagga cacggtcacc tgcaccttcc cccattgctg    1320

tcctcttcct ggatcctcag gcctgcacag cgaaaccgaa acggaagcgg aagcttcagt    1380

cagcagagaa aactgaaacc gaaaaacggt tcagatccgt tgacataaaa gctgcgatga    1440

catcctaaaa ctaaaacccc tccagcaaga cataaaccca actgccaaca accagtcttt    1500

taagtctcga cacacccttg acgctgcgcc acgaaactat attgcaggca agaaaccaac    1560

agaacctaac tctggaaggg gggaaagaaa cggcagacag gagcaagacc caaaaaaaaa    1620

cgactcagat cctggtacta tagtcctagt acctagacca gaaagaagaa acaaccaata    1680

caacaagagg catacaagaa ctgaatcgat gaactgaaac gcttcagagg accgaggaat    1740

ggcggagaag ggaggcgcct atttatacag atctgacgag agaaccgaac aaaaacacat    1800

cgatgggaac catggagaag aaaagggctg gccgcatggc accaatggcc tcggcctcca    1860

aaaagccgtt gaatccaaag caggcgagga cgaagcgtga cgcggcaggg tacttctcta    1920

gaaaagcacg gcatcagcaa ggtggggggg ctggggttcc ttattgcagg caatcacgag    1980
```

gtgattagca caaacggaag 2000

<210> SEQ ID NO 68
<211> LENGTH: 2000
<212> TYPE: DNA
<213> ORGANISM: Oryza sativa

<400> SEQUENCE: 68
ctgaaatata catcagagat attacaatga catatatatc gataaaagaa aaataataaa 60
attaagtttt aaattttaag aatatatgtt tttagtatcc caattatgca gatttcatac 120
ccttcttcca caagctgttc cttgaactgc aagtactcgg ggactgtcag caactcaaca 180
gcgagctcgc tcacattgac cctcacatac tcccagacac cgggcctcgg gcggatggca 240
agggcaaccc atggggagat aacaatcccc tcctgcatga taaaaaacaa ttacaagtta 300
agttagagca agcggtagag taaagatgga tctctgtgat gcaatgaaat ctgaatctga 360
ttcaaacctg tgcactcctc aggacatcct caaaagcacc gtccttcagc ttctcacgat 420
cagcctcaga gattgcgttg ttgtactcag caatgatctg gtgggcctga agcattccct 480
ttccgaggtt aaccagcctg cgcaaataac agtgtcaaca aaaatatcag gccagatcta 540
tcaactcagc ctataaatat ctcaataaga taattttagc acttgagcat ttgcgcataa 600
taagaaaatt tgctattagc cacttaaaaa gaccatatat gatctgtttg cattgagatg 660
aattaaaaat ttcattgtag atatgaaatg attagttttg accatttaat tggacttaat 720
gaaatatgcg cgataatcag atctacgcgc tcgcgccaat agatctagta agatgtaggt 780
tttttatttt ttttgtgaaa ctttgctacc acaacaagca tctgtaccag tgcagaattc 840
attacttgta ttcagtttgt aaaccgtata tataatataa ataacatgca catgcagtca 900
gatctagcac taccagtcca cagtaatcca aaactacatt tgtatatttc atcattattc 960
agtagtacta ggtttgtaca aaatcttggc tgcagaaggc cgcacttaaa tattcattct 1020
aatcagaaac ttaaaaaaaa agtgactaca aaatgattgc atccaattca gtaaatatga 1080
gccattcctg gccagatcta acaatctcaa caacaaagat cctatatgaa catctccttc 1140
taaaagaaaa tacagtaaca tctgaaggca gtagactaga aaccaacaaa atctaatgct 1200
gggaaatcac taaatcagca cgaacctggt gaagacggcg acgagctcat tggggtgggc 1260
ggagagggag tcgccgatgc gctccctgac gctgtggagg cggctcagga cgcggtcgcc 1320
ggcagcttcc cccattgctc tcctcttcct cttggctcct caagcctgcg tgcacaacca 1380
accaccatca tcagatacat ccagacccag tcaacacaat cactccagga aaaaaaaaag 1440
tcaagccata aaccccaacc aaaaaccacg cctttgacaa acactggaag aaaaagaaaa 1500
tcgcagcttt ttcacaagca atctagaaga aaagaaaaag aaaagactac atagcagcta 1560
taattgactg agaagcatac aggaatcaaa caatggagaa ggggagggag gaagaacaat 1620
gatgctccag gctgaggacc gaggaactgg gtgaagcggg gtaggcgcgt atttatgcag 1680
atctgaggag agaaaccacc aaaacaatcc gatggtttca acgaaaaaga tcgtcgcttc 1740
ttgctgcacc agctcaccca tagccgttga gatcgaagct aagctagcag cagcaaagct 1800
ggaacgaaga gtgacgcatt caagctcctc tcctctcctc tcctctcctc cggagcacga 1860
ggccagcatg ggatggattg gggtttcttg ttggccatgg caaaggagga ggtcattaac 1920
gttgacacgg cgtaatttaa ttaaatctta tcttaaaata tgatttaagt ggtagtaaca 1980
aggaagatta atactatgaa 2000

<210> SEQ ID NO 69
<211> LENGTH: 2000
<212> TYPE: DNA
<213> ORGANISM: Oryza sativa

<400> SEQUENCE: 69
gctgtttaag aaaaacagaa gtaaaattca gtcactgtta ttttgcttca gttataatct 60
gcaaatcgtc gttctggtac ttactgtcca tcaacaagct gttccttgaa tgccaagtac 120
tcagaaacac tcagctcttc cactgccaac tcacttacat tcacccgaat gtagtcccag 180
acaccaggcc ttggcctgat ggccagtgca acccagggcg gcagcacaat ggcttcctac 240
atacagtcaa ggaagtaagt tagaaagact ggtatttgac tttgagttga ctatcataac 300
catcctggct cattgccaaa tttacctgag cagcccggag aatgtcttca aagggagcat 360
atttctcttt gtcagcttcg atcaaggcat cgaactccgc aagcagctgg tgacgctgga 420
gcattccctt tccctggtta acatacctgc atagagtgat atttaagaaa tagaaccaat 480
gcttagatct cacatccttt ctgcggctga actatgttaa tggcactacc acataaacct 540
gatttttact tcttattttt aagaccacat gatctgtact taatctagct atgaacaaac 600
aatatttcaa catcatctaa gattcatgac tcaagacaaa aatgttagag ctcatcacag 660
attattatag ataccatcat taaaactaaa gagatgcata accttgtcag ctaagaattt 720
gtaacatact aacatgttat cgtttcacat ctgggttgac taagaactaa ccaactgtat 780
ggataaaatc attgaaaact caaaacaatt agtagcaggt tccaagaaga cacaagatat 840
tatattgaga tcttcaccta gagaagagtg caatcaactc attgggatga gacgagaagg 900
tggcaccgag gcgttcgcgg agactgtgga ggcgagctag cttggcagcc atgactcaat 960
ttcaggaact gcaaagaaag gttacactta gcaacacgta ccaaaaccac tcacttgcac 1020
aagaataatt agtcaacagc catcactaag cattgcaaga ctatctctga acaggaaagc 1080
catgctaaat caacactaat aacatcacac aaaagcattg gaagatcaaa acataactaa 1140
aaacagctgt ttcatctaca caactgaaag catctatggt ttacgaagca gagtgcgagt 1200
actgattcaa aataaatcaa cctgaaccaa tatactctga caatgttttc aaagggataa 1260
aagaaccagc tttatcaaat ggatttgttg ggttttagta agtatcattg agataccgat 1320
ggcatatctc aaactttgca aaattataat ggcatggttc caaattaccc tttagtatta 1380
gcaccagtta gatcctaatt cctaaatccg ataggacaga gcgaaagatc cctggagata 1440
tgaagatttg gctacagatt aagcagagcc aacatgaagt tccgaatatt atgaatccgc 1500
aagcggggag atcaaagaga agaatacgga aggtcgcgac tccatgaaag aatccaacca 1560
aaaacccaaa gatttttctc agttcaaaaa aaaaaaaccc ttcatttttg gttcgccatc 1620
caccgacagg caccaagaca ttcctcagga agcaaaaaag attaagcaga acaagtgata 1680
agcaagacac agtatcaacg gactacgagt cgagaaaatc actgaggcgc gattcttact 1740
gcaccaagta aaaaaaaatt tgggggcaaa aagaactctg caatggggcg gagcaacgtg 1800
gcagcaaaac taaaggtcga ggatttgagg ttttttgccg gttttcctcg aaaccccgaa 1860
tccgctcata gtaaacccac taaactgcag cagaaacccc cctcttggtt cagatttacc 1920
gaaagcagta aacccaagaa catgtcagca aaaactcctg caagattcag ctgacgaccc 1980
accaaagaat cgcaagaaat 2000

<210> SEQ ID NO 70
<211> LENGTH: 2000

<212> TYPE: DNA
<213> ORGANISM: Oryza sativa

<400> SEQUENCE: 70

```
tggcggacgc gccacgcaca aacacaaacc tgcacacccc tgtgtcagag gaggagaggc      60
caagaaagga aatcgagtgg aggaagtgag gagcggcgga gacgtaggag gaggaggggg     120
agatggaaat ggaaagccgc gcgagagagg aggcgcgtgc tggatgggag gaggaggagg     180
aggtggtggg tttgtgtttg gagagacgag cgagagaggc gaagcattta aagggaggaa     240
gagggggaga gagagagaga gagagagaga gagagagaga gagagagaaa ggaggaatat     300
aataaagggt ggtgcacctg ccaactgcta tgctcaccaa cactttgtac acacccagtt     360
acaccccct gcctttatta tttccagtgc agtaataact tcaacaatta ttgaaatgaa     420
aatggaatta atggagttag tatcggatta gcgacacgct tgccgagctt ctagacggtg     480
cgattatttc agcgggaacg actttctgta ggtgaattta atagaggagt gttttaaatc     540
cactcgacgt tgtaatagct ggtttaattc gtttgtactg tcgagtagtt atccaaaatc     600
aattttggat atttaaaaga aaaaaaaaca gatccgaagt attggaccta ctggcaaata     660
ggaattttgc tatatatagg tgtgcgttca tttataatgg agtagcatgg agttttatta     720
atccagtaaa tgttttcatt gatttaatta atataacgaa tttcgcttga ggccatattt     780
gttaaacgct tttatctcta tcatcattca tcctaccagt aaagagcacc ggagatcgca     840
cttcatttaa atatatgtcc atgttggata aaccatagtt tattatagtg ttcttttata     900
tgttttgtgg ggaatttaga ttgtttaata tggcatacat atccatccat cattattata     960
ttctaacaca actggataag tgttctaaac tattgtagaa taactttgta gtatgatcga    1020
tcttgtggaa taaaaaaagt ctgacaataa cctttcataa aggaatatga atacccgtaa    1080
tcaacgcatc aaatcattca cggtgtacgc ctagcgaatt cgttggcgag tgctcgtgcg    1140
gccgtgggct cgctgtgatg catgcatggc tctctggcta cgtcgagata gcgattagta    1200
gcaaaattaa gcaagccact tattaattaa tctttggaga tatcatatga ttaaggcatt    1260
aattcgtacg tactcgtcgt cagcgttttc tgcaaagtcc actacagttt tttctttctt    1320
tgctgaaaat gctgatgtgt tggagatgga gtgacgtgca caacctgccg ccacgtggat    1380
ggttgctgga gcctacgtgt catcttaatt tgaacaaaaa aaaaagagga ataatacatc    1440
aatacatttt cgaatttcag ttctgccatt gaccagtaat acacatgtcg gcctcacatt    1500
ttaccctgat cttagtaacg ggtggtcgcc tggtcggtca ctgaaaaaag ttcaggaaat    1560
tatagtcaaa ctgaaacgaa catattcact ccttaaaaaa actaaatctt tttatatatt    1620
tgtgatattg taaaatagct acgggataat gatatagata tatatagtga taagggatag    1680
atggatcgag atatggagtt gtgctttctt taatttccac tacttgggct accatattat    1740
ggtagttggt atgaaaagat acacagcagt atagtgatgt gatcaatgac atgtatatct    1800
cacatgctcc catgttggag tcaaattttg ctagactaaa atccaattcc aagcagtccc    1860
tagccaagaa caaacaaaat tcagtgaggt cactgctgca ccaaggactg catgcatgca    1920
ggagaagggc attttctctt ttttcttttg gagactcgat tcaattcggt cggtcggtcg    1980
caatggtcag cttaattaaa                                                2000
```

<210> SEQ ID NO 71
<211> LENGTH: 2000
<212> TYPE: DNA
<213> ORGANISM: Oryza sativa

<400> SEQUENCE: 71

```
tgtgaaaggt ggcggcacca gcttagccgc agcttctctc gtcgtctccc tgaaacgaga      60
gggaggaagt tggtagcgtg atatatttag gcatgtcatc tcttgtataa gaagtcttat     120
ctgtgctaat tcacacggtt ctctaatctc tctccattct gtttttgtaa attggttcag     180
tagatagcgt agggttatgc ttatatatac tccgtgaagt atatatttaa aaattagtca     240
cacgtaaagt actatacatg ttttatcgtc taataacaat aaaaacacta atcataaaat     300
ttttttaaat aatacgaatg gttaaacgtt gaatatgaac cgtgcaaaac tatatttatt     360
ttgtaacaga gaaaatattt cacattaatt agattgttgt tttatggaag gttggagagc     420
tgcgccgccg ttgcgcagac ctaggaggct gcttataagt tataatcaat caattcacgg     480
atgccggctg ggacgcggcc catcgtccgg gaagacgaca actcaacgca aaaagccgat     540
atgcctccaa attgccattg ccacctctac ggctgtttat actgctccaa atcaaaagcg     600
tccatggaag aatctagtat ttcccgcaaa gacgatgatg atatgcagga ttggatatat     660
agggggttgt tgcatgattg ctagaactcc cgtttccgaa gttgttcgtc catttttaaa     720
gctgccaaat aggaatttat tttgttttca agtgtaatag agttctgtcc agatgagtga     780
attataattt ggttcacatt ttatttgcta agtttcagtt tgaacattct caaataactt     840
ttttcttcac tttttaaccg agtaacttag ttattttttc cgtttggacc acccaacaat     900
ttgttgctaa gtgcatctca cccgtcaaat aattcctttg aatccaaatt caattatatc     960
ccaaaaataa aaaacttctg aattccacat caattcaaac cccaaccatt ttaatttctc    1020
tccatatttt ccatttctct atttttacct ttctcttttt tccatctatt tatttttttc    1080
cttttctatt tctttctttc tccttccttt ctctgtttcc ttcttcttct cctcggctag    1140
gcccgagcca gcccgtgccg cctcgcgcca accctgtgcc gccttacgcc gcgcttgcgt    1200
gcgctcgcgc ccacctcgtg cccaacccgc gcacgccaca cgcacacacg aggacgatcg    1260
acggacgaat gcaatcatat ccccttcctt actcagctag aaggctcaag aaccgcaact    1320
ttgatctctt ccaccctctc aaatccgccc caacccctgc tgactcaatc gccattaccg    1380
gaggaaaaat ccccgaaacc ctattaccgg cgccactaac agagctccaa aattcgtcgc    1440
ataattcgaa aatattctga aattgaaggt aaaaatggaa tctacatgcg aagtactccc    1500
tttcccctcc aatccgtcac tggaacgccg ccggcgccgc ctcccgctgc cactgccctg    1560
tttggccgcc gacagccgca cggcgcgccg ctgctccagg ccgccctagc ttcaaccacc    1620
gccacctttg gctccgcctc cctcctctta tgctcaccaa gcccgcctcc ctcgccggag    1680
atcgccggaa ccaccgccgc catggccgcc accgcctcct gcttctggcc gccgccgcca    1740
gcctcgccac cggcgcctat gccaccgccg accacggaaa cggagtccct acaccttggg    1800
gaccacaaaa ccggcggcat ccctcccaaa accggcctcc tccaccgccg gcgttcgtgg    1860
gattccggcc agttctgtgc agagcgagag aagaagagga aaaatagatt ttcctattga    1920
aagataaatc agaaaattcc tttttctttt cctatcaagt tgaccatccg tttgacctca    1980
aaatcaaaat ctgagaccta                                                2000
```

<210> SEQ ID NO 72
<211> LENGTH: 786
<212> TYPE: DNA
<213> ORGANISM: Zea mays

<400> SEQUENCE: 72

```
gacatggagg tggaaggcct gacgtagata gagaagatgc tcttagcttt cattgtcttt      60
```

```
cttttgtagt catctgattt acctctctcg tttatacaac tggtttttta aacactcctt    120

aacttttcaa attgtctctt tctttaccct agactagata attttaatgg tgattttgct    180

aatgtggcgc catgttagat agaggtaaaa tgaactagtt aaaagctcag agtgataaat    240

caggctctca aaaattcata aactgttttt taaatatcca aatattttta catggaaaat    300

aataaaattt agtttagtat taaaaaattc agttgaatat agttttgtct tcaaaaatta    360

tgaaactgat cttaattatt tttccttaaa accgtgctct atctttgatg tctagtttga    420

gacgattata taattttttt tgtgcttaac tacgacgagc tgaagtacgt agaaatacta    480

gtggagtcgt gccgcgtgtg cctgtagcca ctcgtacgct acagcccaag cgctagagcc    540

caagaggccg gaggtggaag gcgtcgcggc actatagcca ctcgccgcaa gagcccaaga    600

gaccggagct ggaaggatga gggtctgggt gttcacgaat tgcctggagg caggaggctc    660

gtcgtccgga gccacaggcg tggagacgtc cgggataagg tgagcagccg ctgcgatagg    720

ggcgcgtgtg aaccccgtcg cgccccacgg atggtataag aataaaggca ttccgcgtgc    780

aggatt                                                               786
```

<210> SEQ ID NO 73
<211> LENGTH: 1160
<212> TYPE: DNA
<213> ORGANISM: Zea mays

<400> SEQUENCE: 73

```
atgtgctggt gccccataag gtaggcacct aggtctgtgt ttgaagcatc gacagatttg     60

taaacatgtt cctatgaacc tatttctgat tgataatttg tcaaaactca tcatttgtct    120

tcatccttgc ctgcttgcgt tcacgtgaca aagtacgtgt atgtcttcgg cctttgctgt    180

gtatgtttcg cattgcttag atgtggtgaa agaacatcag aagatgcatt gatggcgtgc    240

ttaaaccagt gatgtgctcc aggtgttcct gcagtctgca gagatattta ctcttgtagt    300

cttgttgaca gcacagttgt atgtgatttc ttggatgtaa tgtaaaccaa atgaaagata    360

ggaacagttc gtcctcttcc gtatacgaag gtcactgtat catttgtcgt ggcacaagat    420

gatctgcagg caggactgca acatggtttc ttggactgtc ctgaatgccc gttcttgttc    480

tttagttgag ccagagcagc agcctggtgt cggtgcctga gacctgacga agcacacggc    540

aaacaaacaa gtcgcagcag ctagcagggg cgttgccatc gccacaagcc cccaagagac    600

ccgccgagga aaagaaaaaa aaactacggc cgccgttgcc aagccgagcg tgcgaaccga    660

tccacggatg ggagatcaga gatcacccac cgcaggcggg cggcagtggc tggcgaggtg    720

cgtccacaga acctgctgca ggtccctgtc cgtcccggcg accccttttc taggcgagca    780

actccccatg gcagagctgc acgcagcagg gcccgtcgtt ggttgcagct ttaacccttt    840

ttgttttaac catacaatgc agagtcgcag aggtgaaaca ggacggaaat tacagaaaag    900

atggtggtgt gccagcagcc ccagcatgaa gaagatcagg acaaaagaaa agcttgtgat    960

tggtgacagc aacaggattg gattggagcc aagctaggca gtgagaggca ggcagcaaga   1020

cgcgtcagcc actgaaatcc agagggcaac ctcggcctca caactcatat ccccttgtgc   1080

tgttgcgcgc cgtggttagc caggtgtgct gcaggcctcc tccttgttta tatatgggag   1140

atgctctcac cctctaaggt                                                1160
```

<210> SEQ ID NO 74
<211> LENGTH: 1532
<212> TYPE: DNA

<213> ORGANISM: Oryza sativa

<400> SEQUENCE: 74

```
tagtcctcta atatatgaaa ttttgatata ggtaaagaag ggtattgcaa ggataagaat      60
gtaaaaagaa ataagagtaa tccttaccga taatagtatt ccttctctac cgttaaaagt     120
taaacctgtg cgtgtagcat tttaatccag gatctatcga atccgtccct cgttggcgtg     180
ggcgacgaac acgtgcagaa gaagctttcc ccagaaagca cctcaccgcc tcgccgtctg     240
gcagactggc acgcggggcc ctaccctcgc tgcgcctggg cccgtccgcc ttctgcacac     300
tgtcacgccc ccacccgctc gccgcctcgc gcctctctct ccgcctccgc cgcggccgcc     360
cgacgtgata gcgacacgta ggactcgcca aacacaaaaa atccatcgcg atttttggaa     420
ttttgttaca aaccaaatcc cgcattagag atttaatttg atttaattta attacgtagg     480
agtaccagat aaggagatcg agttaaaaaa gctaacggcg cggcgtggtt atctccgaat     540
cggctgtggc tccccgcgtc ggcgtcggcg cggcggcggc gcgccggccg aaccctggcc     600
gtcggatcgg gcgtcgtcct gggccccacg cgccacgggc ggctgtcgtt tgctcctcgg     660
agcggggtgg gcccaccatg gccaccacca caggtcgcgg tcgcggctga cctggcggtg     720
gtcccgtgct cgcggtgttt ttttttttc actctctttc tctcggtgga cagtagcggg     780
ggccgcggcc cgcgggggca gagattgcaa aaacagcgga aacggaagat tgcaaaattg     840
caactgcttt cctgttttta attcgggatc aaaaagattc tttcgtcggg gtccccgtgc     900
cattgttgta ttgcgcgtag gtccttgctt gtaaaagata atctccttaa ttttttcttt     960
gtactactag tgtatatgca gtaagaatat accatgagta aaatgaacca caaaactaat    1020
tacgatatac cattctcatg tagacgttct cttttctttt gctagtcata cgtgcatata    1080
taaccaaaca aaaaaatgtt tgaagtactc ctatccaatt tattactcca gtagacaaca    1140
aaagaaaatg tttgaagtaa taactgatcc atggtacagt agggttgtcg tcaatcttgt    1200
gtttctttca ttccattgta cttacaatcg tactccagct agcacagcac aatgggctta    1260
agctttggac cccaaattct gatcttgtcg gggacccgta cgaaaatact cccgtagaga    1320
tgcagatacc gtcacaacct acaaccaacg aatgttaaga aaacaaaggg aaaaaaaaag    1380
aggcgaattc ggaggagaaa aaacggtggc taaaatatag tgcgggtgtg gggacgcgac    1440
gcgagcgacg aaagaggaga gaggatgggt tggcctgccc ccccctcccc tgtctataaa    1500
tgcagaggcg ccgagtgccc tagtcgccgc tc                                  1532
```

<210> SEQ ID NO 75
<211> LENGTH: 841
<212> TYPE: DNA
<213> ORGANISM: Oryza sativa

<400> SEQUENCE: 75

```
tcgaggtcat tcatatgctt gagaagagag tcgggatagt ccaaaataaa acaaaggtaa      60
gattacctgg tcaaaagtga aaacatcagt taaaaggtgg tataaagtaa aatatcggta     120
ataaaaggtg gcccaaagtg aaatttactc ttttctacta ttataaaaat tgaggatgtt     180
tttgtcggta ctttgatacg tcatttttgt atgaattggt ttttaagttt attcgctttt     240
ggaaatgcat atctgtattt gagtcgggtt ttaagttcgt ttgcttttgt aaatacagag     300
ggatttgtat aagaaatatc tttagaaaaa cccatatgct aatttgacat aatttttgag     360
aaaaatatat attcaggcga attctcacaa tgaacaataa taagattaaa atagctttcc     420
cccgttgcag cgcatgggta ttttttctag taaaaataaa agataaactt agactcaaaa     480
```

```
catttacaaa aacaacccct aaagttccta aagcccaaag tgctatccac gatccatagc    540

aagcccagcc caacccaacc caacccaacc caccccagtc cagccaactg gacaatagtc    600

tccacacccc cccactatca ccgtgagttg tccgcacgca ccgcacgtct cgcagccaaa    660

aaaaaaaaga aagaaaaaaa agaaaaagaa aaaacagcag gtgggtccgg gtcgtggggg    720

ccggaaacgc gaggaggatc gcgagccagc gacgaggccg gccctccctc cgcttccaaa    780

gaaacgcccc ccatcgccac tatatacata cccccccctc tcctcccatc cccccaaccc    840

t                                                                    841
```

<210> SEQ ID NO 76
<211> LENGTH: 1392
<212> TYPE: DNA
<213> ORGANISM: Oryza sativa

<400> SEQUENCE: 76

```
ctcgaggtca ttcatatgct tgagaagaga gtcgggatag tccaaaataa aacaaaggta     60

agattacctg gtcaaaagtg aaaacatcag ttaaaaggtg gtataagtaa aatatcggta    120

ataaaaggtg gcccaaagtg aaatttactc ttttctacta ttataaaaat tgaggatgtt    180

ttgtcggtac tttgatacgt catttttgta tgaattggtt tttaagttta ttcgcgattt    240

tggaaatgca tatctgtatt tgagtcgggt tttaagttcg tttgcttttg taaatacaga    300

gggatttgta taagaaatat ctttaaaaaa acccatatgc taatttgaca taatttttga    360

gaaaaatata tattcaggcg aattctcaca atgaacaata ataagattaa aatagcttgc    420

ccccgttgca gcgatgggta tttttttctag taaaataaaa gataaactta gactcaaaac    480

atttacaaaa acaaccccta aagtcctaaa gcccaaagtg ctatgcacga tccatagcaa    540

gcccagccca acccaaccca acccaaccca ccccagtgca gccaactggc aaatagtctc    600

cacaccccgg cactatcacc gtgagttgtc cgcaccaccg cacgtctcgc agccaaaaaa    660

aaaaaaagaa agaaaaaaaa gaaaaagaaa aaacagcagg tgggtccggg tcgtgggggc    720

cggaaaagcg aggaggatcg cgagcagcga cgaggccggc cctccctccg cttccaaaga    780

aacgcccccc atcgccacta tatacatacc ccccctctc ctcccatccc cccaacccta    840

ccaccaccac caccaccacc tcctcccccc tcgctgccgg acgacgagct cctccccccct    900

ccccctccgc cgccgccggt aaccaccccg cgtccctctc ctctttcttt ctccgttttt    960

tttttccgtc tcgtctcgat ctttggcctt ggtagtttgg gggcgagagg cggcttcgtc   1020

gcccagatcg gtgcgcggga ggggcgggat ctcgcggctg ggtctcggcg tgcggccgga   1080

tcctcgcggg gaatggggct ctcggatgta gatctgatcc gccgttgttg ggggagatga   1140

tggggcgttt aaaatttcgc catgctaaac aagatcagga agaggggaaa agggcactat   1200

ggtttatatt tttatatatt tctgctgctg ctcgtcaggc ttagatgtgc tagatctttc   1260

tttcttcttt ttgtgggtag aatttgaatc cctcagcatt gttcatcggt agtttttctt   1320

ttcatgattt gtgacaaatg cagcctcgtg cggagctttt ttgtaggtag aagatggctg   1380

acgccgagga ta                                                       1392
```

<210> SEQ ID NO 77
<211> LENGTH: 743
<212> TYPE: DNA
<213> ORGANISM: Oryza sativa

<400> SEQUENCE: 77

```
gaattcccgg acctccatgc ctacatcaac taatttgatt ccttgagttt acgtttagtg      60

atatgtctat ttttagagct tgttggggct tcggcctcag ctctagccag ccaaacatgt     120

tctaccaagt accctatgtt ggcatgatat agtgatgcat tataacaata aatgagcgag     180

ggattgctgg ctgaaaaagc tatactagct gcatttggtt atagttaacc gaactattaa     240

ttgcgtgtac aacaaaataa aaaaaatgca tgttgcacat tctttcatta acattatgtt     300

ttggtagtgt gaattagaaa tttgattgac agtagatcga caaacatagt ttcaatatgc     360

ttaagttagt tatgacttta acatatcagt ctccttgata ttttcgtttt agattcgtct     420

ctctactagt gtgtatgtcc accttccata gcagtgaagg gttccattcc atccctggta     480

aaaaaaaatc aaccactact atttatttcc taaaaagcaa aatgataaaa tatcattttt     540

ttaataaaaa taaaaaaatt ttggggtaca taattgatgt tgccccttgg gattaacctt     600

aaaaaagggc gaattttcta gggtttggcc aagttttgca atgcaccaaa ttattcccct     660

tgggccggcc gccaccccaa aaaaaacccc aacccccaac tttccattga aggccgggcc     720

cccttaaatc ctcatccccc caa                                             743
```

```
<210> SEQ ID NO 78
<211> LENGTH: 144
<212> TYPE: DNA
<213> ORGANISM: Oryza sativa

<400> SEQUENCE: 78

taaaaaaggg cgaattttct agggtttggc caagttttgc aatgcaccaa attattcccc      60

ttgggccggc cgccacccca aaaaaaaccc caacccccaa ctttccattg aaggccgggc     120

ccccttaaat cctcatcccc ccaa                                            144
```

```
<210> SEQ ID NO 79
<211> LENGTH: 612
<212> TYPE: DNA
<213> ORGANISM: Cauliflower mosaic virus

<400> SEQUENCE: 79

ggtccgattg agacttttca acaaagggta atatccggaa acctcctcgg attccattgc      60

ccagctatct gtcactttat tgtgaagata gtggaaaagg aaggtggctc ctacaaatgc     120

catcattgcg ataaaggaaa ggccatcgtt gaagatgcct ctgccgacag tggtcccaaa     180

gatggacccc cacccacgag gagcatcgtg gaaaaagaag acgttccaac cacgtcttca     240

aagcaagtgg attgatgtga tggtccgatt gagacttttc aacaaagggt aatatccgga     300

aacctcctcg gattccattg cccagctatc tgtcacttta ttgtgaagat agtggaaaag     360

gaaggtggct cctacaaatg ccatcattgc gataaaggaa aggccatcgt tgaagatgcc     420

tctgccgaca gtggtcccaa agatggaccc ccacccacga ggagcatcgt ggaaaaagaa     480

gacgttccaa ccacgtcttc aaagcaagtg gattgatgtg atatctccac tgacgtaagg     540

gatgacgcac aatcccacta tccttcgcaa gacccttcct ctatataagg aagttcattt     600

catttggaga gg                                                         612
```

```
<210> SEQ ID NO 80
<211> LENGTH: 837
<212> TYPE: DNA
<213> ORGANISM: Coix lacryma-jobi

<400> SEQUENCE: 80

agcagactcg cattatcgat ggagctctac caaactggcc ctaggcatta acctaccatg      60
```

```
gatcacatcg taaaaaaaaa accctaccat ggatcctatc tgttttcttt ttgccctgaa    120

agagtgaagt catcatcata tttaccatgg cgcgcgtagg agcgcttcgt cgaagaccca    180

taggggggcg gtactcgcac cgtggttgtt tcctgttatg taatatcgga tgggggagca    240

gtcggctagg ttggtcccat cggtactggt cgtcccctag tgcgctagat gcgcgatgtt    300

tgtcctcaaa aactcttttc ttcttaataa caatcatacg caaatttttt gcgtattcga    360

gaaaaaaaga agattctatc tgtttttttt ttgaaatggc tccaatttat aggaggagcc    420

cgtttaacgg cgtcgacaaa tctaacggac accaaccagc gaatgagcga acccaccagc    480

gccaagctag ccaagcgaag cagacggccg agacgctgac acccttgcct tggcgcggca    540

tctccgtcgc tggctcgctg gctctggccc cttcgcgaga gttccggtcc acctccacct    600

gtgtcggttt ccaactccgt tccgccttcg cgtgggactt gttccgttca tccgttggcg    660

gcatccggaa attgcgtggc gtagagcacg gggccctcct ctcacacggc acggaaccgt    720

cacgagctca cggcaccggc agcacggcgg ggattccttc cccaccaccg ctccttccct    780

ttcccttcct cgcccgccat cataaatagc cacccctccc agcttccttc gccacat       837
```

<210> SEQ ID NO 81
<211> LENGTH: 947
<212> TYPE: DNA
<213> ORGANISM: Oryza sativa

<400> SEQUENCE: 81

```
aatccgaaaa gtttctgcac cgttttcacg tcctaactaa caatataggg aacgtgtgct     60

aaatataaaa tgagacctta tatatgtagc gctgataact agaactatgt aagaaaaact    120

catccaccta ctttagtggc aatcgggcta aataaaaaag agtcgctaca ctagtttcgt    180

tttccttagt aattaagtgg gaaaatgaaa tcattattgc ttagaatata cgttcacatc    240

tctgtcatga agttaaatta ttcgaggtag ccataattgt catcaaactc ttcttgaata    300

aaaaaatctt tctagctgaa ctcaatgggt aaagagagat attttttttt aaaaaaaaat    360

agaatgaaga tattctgaac gtatcggcaa agatttaaac atataattat ataattttat    420

agtttgtgca ttcgttatat cgcacgtcat taaggacatg tcttactcca tctcaatttt    480

tatttagtaa ttaaagacaa ttgacttatt tttattattt atctttttttc gattagatgc    540

aaggtactta cgcacacact ttgtgctcat gtgcatgtgt gagtgcacct cctcaataca    600

cgttcaacta gcgacacatc tccaatatca ctcgcctatt taatacattt aggtagcaat    660

atctgaattc aagcactcca ccatcaccag accactttta ataatatcta aaatacaaaa    720

aataatttta cagaatagca tgaaaagtat gaaacgaact atttaggttt ttcacataca    780

aaaaaaaaaa gaattttgct cgtgcgcgag cgccaatctc ccatattggg cacacaggca    840

acaacagagt ggctgcccac agaacaaccc acaaaaaacg atgatctaac ggaggacagc    900

aagtccgcaa caacctttta acagcaggct ttgcggccag gagagag                  947
```

<210> SEQ ID NO 82
<211> LENGTH: 721
<212> TYPE: DNA
<213> ORGANISM: Mirabilis mosaic caulimovirus

<400> SEQUENCE: 82

```
tggagattca gaaaaatctc catcaacaaa taatccaagt aaggattaat ggattgatca     60

acatccttac cgctatgggt aagattgatg aaaagtcaaa aacaaaaatc aattatgcac    120
```

```
accagcatgt gttgatcacc agctattgtg ggacaccaat ttcgtccaca gacatcaaca    180

tcttatcgtc ctttgaagat aagataataa tgttgaagat aagagtggga gccaccacta    240

aaacattgct ttgtcaaaag ctaaaaaaga tgatgcccga cagccacttg tgtgaagcat    300

gtgaagccgg tccctccact aagaaaatta gtgaagcatc ttccagtggt ccctccactc    360

acagctcaat cagtgagcaa caggacgaag gaaatgacgt aagccatgac gtctaatccc    420

acaagaattt ccttatataa ggaacacaaa tcagaaggaa gagatcaatc gaaatcaaaa    480

tcggaatcga aatcaaaatc ggaatcgaaa tctctcatct ctctctacct tctctctaaa    540

aaacacttag atgtgtgagt aatcacccac ttggggttgt aatatgtagt agtaaataag    600

ggaaccttag ggtataccat tgttgtaata ttattttcag tatcaataaa ataatctttc    660

agtttatctt atattcattt gtgtgacacc gtattcccat aaaaccgatc ctaatctctc    720

c                                                                    721
```

<210> SEQ ID NO 83
<211> LENGTH: 352
<212> TYPE: DNA
<213> ORGANISM: Peanut chlorotic streak caulimovirus

<400> SEQUENCE: 83

```
acagagggat ttctctgaag atcatgtttg ccagctatgc gaacaatcat cgggagatct     60

tgagccaatc aaagaggagt gatgtagacc taaagcaata atggagccat gacgtaaggg    120

cttacgccat tacgaaataa ttaaaggctg atgtgacctg tcggtctctc agaaccttta    180

ctttttatat ttggcgtgta tttttaaatt tccacggcaa tgacgatgtg acctgtgcat    240

ccgctttgcc tataaataag ttttagtttg tattgatcga cacgatcgag aagacacggc    300

catttggacg atcatttgag agtctaaaag aacgagtctt gtaatatgtt tt            352
```

<210> SEQ ID NO 84
<211> LENGTH: 1648
<212> TYPE: DNA
<213> ORGANISM: Sorghum bicolor

<400> SEQUENCE: 84

```
cactcgcaca tctcatggtg tcccaagaac ggcaagagcc agcactgcct ctgcctagca     60

acagcagcag cgccaagcga gcagccgcgt ccatggacgc cagcagcccg gccccgccgc    120

tcctcctccg cgcccccact cccagtccca gcattgacct ccccgctgcc gctggcaagg    180

ccgcggccgt gttcgacctg cggcgggagc ccaagatccc ggcgccattc ctgtggccgc    240

acgaggaggc gcgcccgacc tcggccgcgg agctggaggt tccggtggtg gacgtgggcg    300

tgctgcgcaa tggcgaccgc gcggggctgc ggcgcgccgc ggcgcaggtg gcctcggcgt    360

gcgcgacgca cgggttcttc caggtgtgcg ggcacggcgt ggacgcggcc ctggggcgcg    420

ccgcgctgga cggcgccagc gacttcttcc ggctgccgct ggccgacaag cagcgcgccc    480

ggcgcgtccc cggcaccgtg tccgggtaca cgagcgcgca cgccgaccgg ttcgcgtcca    540

agctccccctg gaaggagacc ctgtccttcg gcttccacga cggcgccgcg tcgcccgtcg    600

tcgtggacta cttcaccggc accctcggcc aagatttcga gccaatgggg cgggtgtacc    660

agaggtactg cgagaagatg aaggagctgt cgctgacgat catggagctg ctggagctga    720

gcctgggcgt ggagcgcggc tactaccggg agttcttcga ggacagccgc tccatcatgc    780

ggtgcaacta ctacccgccg tgcccggagc cggagcgcac gctgggcacg ggcccgcact    840

gcgaccctac ggcgctgacc atcctcctgc aggacgacgt cggcgggctg gaggtgctgg    900
```

```
tggacggcga gtggcgcccc gtccggcccg tcccaggcgc catggtcatc aacatcggcg    960
acaccttcat ggcgctgtcg aacgggcggt acaagagctg cctgcaccgc gcggtggtga   1020
accagcggca ggagcggcgg tcgctggcct tcttcctgtg cccgcgcgag gaccgggtgg   1080
tgcggccgcc ggccagcagc gccacgccgc ggcagtaccc ggacttcacc tgggccgacc   1140
tcatgcgctt cacgcagcgc cactaccgcg ccgacacccg cacgctggac gccttcaccc   1200
gctggctctc ccacggccca gtcccagccc aggaggcggc ggctccctgc acctagcgag   1260
cgagcgagcc gggccaaaca aacaaggggc aaaggccatc tctttcgccg gggcccgcgc   1320
gcggggttcg cccacgtgcg cgcccaggtg ggcgctggcc gcgggcaggt ggcggacatg   1380
tggcctgcgg gccccgcgcc gccttcccat ttttggacgc tgccgcgcat gccgcatgcg   1440
tgcgtcgacg gccctactac ttctactact gctactgcga ctactagtgt acatacgcaa   1500
aaatacatat atacgtattt tctatatata tatatataag caaggcggcc ccccggtgac   1560
cttttctttg tttttgtcga caactgtgtt ttgatcccat tctagctgtt ctatggacca   1620
tggatggttc gttcaatgtt tgtacgta                                      1648
```

<210> SEQ ID NO 85
<211> LENGTH: 1242
<212> TYPE: DNA
<213> ORGANISM: Sorghum bicolor

<400> SEQUENCE: 85

```
atggtgtccc aagaacggca agagccagca ctgcctctgc ctagcaacag cagcagcgcc     60
aagcgagcag ccgcgtccat ggacgccagc agcccggccc cgccgctcct cctccgcgcc    120
cccactccca gtcccagcat tgacctcccc gctgccgctg gcaaggccgc ggccgtgttc    180
gacctgcggc gggagcccaa gatcccggcg ccattcctgt ggccgcacga ggaggcgcgc    240
ccgacctcgg ccgcggagct ggaggttccg gtggtggacg tgggcgtgct gcgcaatggc    300
gaccgcgcgg ggctgcggcg cgccgcggcg caggtggcct cggcgtgcgc gacgcacggg    360
ttcttccagg tgtgcgggca cggcgtggac gcggccctgg ggcgcgccgc gctggacggc    420
gccagcgact tcttccggct gccgctggcc gacaagcagc gcgcccggcg cgtccccggc    480
accgtgtccg ggtacacgag cgcgcacgcc gaccggttcg cgtccaagct cccctggaag    540
gagaccctgt ccttcggctt ccacgacggc gccgcgtcgc ccgtcgtcgt ggactacttc    600
accggcaccc tcggccaaga tttcgagcca atggggcggg tgtaccagag gtactgcgag    660
aagatgaagg agctgtcgct gacgatcatg gagctgctgg agctgagcct gggcgtggag    720
cgcggctact accgggagtt cttcgaggac agccgctcca tcatgcggtg caactactac    780
ccgccgtgcc cggagccgga gcgcacgctg ggcacgggcc cgcactgcga ccctacggcg    840
ctgaccatcc tcctgcagga cgacgtcggc gggctggagg tgctggtgga cggcgagtgg    900
cgccccgtcc ggcccgtccc aggcgccatg gtcatcaaca tcggcgacac cttcatggcg    960
ctgtcgaacg ggcggtacaa gagctgcctg caccgcgcgg tggtgaacca gcggcaggag   1020
cggcggtcgc tggccttctt cctgtgcccg cgcgaggacc gggtggtgcg gccgccggcc   1080
agcagcgcca cgccgcggca gtacccggac ttcacctggg ccgacctcat gcgcttcacg   1140
cagcgccact accgcgccga cacccgcacg ctggacgcct tcacccgctg gctctcccac   1200
ggcccagtcc cagcccagga ggcggcggct ccctgcacct ag                      1242
```

<210> SEQ ID NO 86

```
<211> LENGTH: 413
<212> TYPE: PRT
<213> ORGANISM: Sorghum bicolor

<400> SEQUENCE: 86

Met Val Ser Gln Glu Arg Gln Glu Pro Ala Leu Pro Leu Pro Ser Asn
1               5                   10                  15

Ser Ser Ser Ala Lys Arg Ala Ala Ala Ser Met Asp Ala Ser Ser Pro
            20                  25                  30

Ala Pro Pro Leu Leu Leu Arg Ala Pro Thr Pro Ser Pro Ser Ile Asp
        35                  40                  45

Leu Pro Ala Ala Ala Gly Lys Ala Ala Ala Val Phe Asp Leu Arg Arg
    50                  55                  60

Glu Pro Lys Ile Pro Ala Pro Phe Leu Trp Pro His Glu Glu Ala Arg
65                  70                  75                  80

Pro Thr Ser Ala Ala Glu Leu Glu Val Pro Val Val Asp Val Gly Val
                85                  90                  95

Leu Arg Asn Gly Asp Arg Ala Gly Leu Arg Arg Ala Ala Ala Gln Val
            100                 105                 110

Ala Ser Ala Cys Ala Thr His Gly Phe Phe Gln Val Cys Gly His Gly
        115                 120                 125

Val Asp Ala Ala Leu Gly Arg Ala Ala Leu Asp Gly Ala Ser Asp Phe
    130                 135                 140

Phe Arg Leu Pro Leu Ala Asp Lys Gln Arg Ala Arg Arg Val Pro Gly
145                 150                 155                 160

Thr Val Ser Gly Tyr Thr Ser Ala His Ala Asp Arg Phe Ala Ser Lys
                165                 170                 175

Leu Pro Trp Lys Glu Thr Leu Ser Phe Gly Phe His Asp Gly Ala Ala
            180                 185                 190

Ser Pro Val Val Val Asp Tyr Phe Thr Gly Thr Leu Gly Gln Asp Phe
        195                 200                 205

Glu Pro Met Gly Arg Val Tyr Gln Arg Tyr Cys Glu Lys Met Lys Glu
    210                 215                 220

Leu Ser Leu Thr Ile Met Glu Leu Leu Glu Leu Ser Leu Gly Val Glu
225                 230                 235                 240

Arg Gly Tyr Tyr Arg Glu Phe Phe Glu Asp Ser Arg Ser Ile Met Arg
                245                 250                 255

Cys Asn Tyr Tyr Pro Pro Cys Pro Glu Pro Glu Arg Thr Leu Gly Thr
            260                 265                 270

Gly Pro His Cys Asp Pro Thr Ala Leu Thr Ile Leu Leu Gln Asp Asp
        275                 280                 285

Val Gly Gly Leu Glu Val Leu Val Asp Gly Glu Trp Arg Pro Val Arg
    290                 295                 300

Pro Val Pro Gly Ala Met Val Ile Asn Ile Gly Asp Thr Phe Met Ala
305                 310                 315                 320

Leu Ser Asn Gly Arg Tyr Lys Ser Cys Leu His Arg Ala Val Val Asn
                325                 330                 335

Gln Arg Gln Glu Arg Arg Ser Leu Ala Phe Phe Leu Cys Pro Arg Glu
            340                 345                 350

Asp Arg Val Val Arg Pro Pro Ala Ser Ser Ala Thr Pro Arg Gln Tyr
        355                 360                 365

Pro Asp Phe Thr Trp Ala Asp Leu Met Arg Phe Thr Gln Arg His Tyr
    370                 375                 380

Arg Ala Asp Thr Arg Thr Leu Asp Ala Phe Thr Arg Trp Leu Ser His
```

```
385                 390                 395                 400

Gly Pro Val Pro Ala Gln Glu Ala Ala Ala Pro Cys Thr
                405                 410


<210> SEQ ID NO 87
<211> LENGTH: 12906
<212> TYPE: DNA
<213> ORGANISM: Sorghum bicolor

<400> SEQUENCE: 87

cactcgcaca tctcatggtg tcccaagaac ggcaagagcc agcactgcct ctgcctagca     60

acagcagcag cgccaagcga gcagccgcgt ccatggacgc cagcagcccg gccccgccgc    120

tcctcctccg cgcccccact cccagtccca gcattgacct ccccgctgcc gctggcaagg    180

ccgcggccgt gttcgacctg cggcgggagc ccaagatccc ggcgccattc ctgtggccgc    240

acgaggaggc gcgcccgacc tcggccgcgg agctggaggt tccggtggtg gacgtgggcg    300

tgctgcgcaa tggcgaccgc gcggggctgc ggcgcgccgc ggcgcaggtg gcctcggcgt    360

gcgcgacgca cgggttcttc caggtgtgcg ggcacggcgt ggacgcggcc ctggggcgcg    420

ccgcgctgga cggcgccagc gacttcttcc ggctgccgct ggccgacaag cagcgcgccc    480

ggcgcgtccc cggcaccgtg tccgggtaca cgagcgcgca cgccgaccgg ttcgcgtcca    540

agctcccctg gaaggagacc ctgtccttcg gcttccacga cggcgccgcg tcgcccgtcg    600

tcgtggacta cttcaccggc accctcggcc aagatttcga gccaatgggg taagcgaagc    660

accgatttac atttaccgcg cgtcggcccc tgaggcctgg gtcttagtct tagcactgca    720

tatacggtcg gtagctctgg atatgatacg tatatatgaa accccgttcc aatcccatgc    780

acggtgtaca caggcgggtg taccagaggt actgcgagaa gatgaaggag ctgtcgctga    840

cgatcatgga gctgctggag ctgagcctgg gcgtggagcg cggctactac cgggagttct    900

tcgaggacag ccgctccatc atgcggtgca actactaccc gccgtgcccg gagccggagc    960

gcacgctggg cacgggcccg cactgcgacc ctacggcgct gaccatcctc ctgcaggacg   1020

acgtcggcgg gctggaggtg ctggtggacg gcgagtggcg ccccgtccgg cccgtcccag   1080

gcgccatggt catcaacatc ggcgacacct tcatggtaac ccctgctctg tttttttcttg  1140

tcctcctctt gtcctgtgtg tgtgtatatt cacttctctc tgttttttttg ccccgaatcc  1200

tagtggacct aactggacgg attacagcac gcacacgtag gcatgtcatg tagcagcagt   1260

ctgcagcact gtagtactta gcgatgcaat agagacatgc gttccagtcg gttccatctc   1320

ggtgggctac agctacagtc ctacacggac gcggctcgta gtcgtaggga cgggcgcgtt   1380

ctctgtatcc acacacggct gcgcccaggc cgaggcttcc gccgcgggaa agttgcgaca   1440

acagaacggg gtttgtgccg ttggagcgtt gcggagaggc agaggcttgg ggggacgggg   1500

gcgcgatacg ctgcgatggg tgggtgaccg aggcgacgct ttcggcgggg gcccgggcct   1560

gcccaggtgc gcgcggcctc gtcgccttcc cctgtttttt tgatgccgcc gctcggtcct   1620

cggtgttctg gctccgcccg cccgctcgct gggtgcccat cccatctgat ccgatccgct   1680

ccgctccgcg gtggcggtcc tatgcgatgc cgccgcacga gcgcgggggg ccgccccgtgg  1740

aggagtagaa agtggtacaa ggttggttgg aacttggaat tgtggggggt tactgctgct   1800

ggtggctgct gctttgcaac ttgccaggct gctgcctgtt gcccccccgcg ttttctagcc  1860

gtttccgctc gcgatccggc acgcggcgcc cacaccgggg ctccagctcg gccccttggc   1920

cgtgtaggta gcaggcactt gcatctgtcc gttcgacacg atgattcttg tgcactgtgt   1980
```

-continued

```
acgtatgtac taacccttc tggtatgatg tacgcatggc atgcaggcgc tgtcgaacgg   2040
gcggtacaag agctgcctgc accgcgcggt ggtgaaccag cggcaggagc ggcggtcgct   2100
ggccttcttc ctgtgcccgc gcgaggaccg ggtggtgcgg ccgccggcca gcagcgccac   2160
gccgcggcag tacccggact tcacctgggc cgacctcatg cgcttcacgc agcgccacta   2220
ccgcgccgac acccgcacgc tggacgcctt cacccgctgg ctctcccacg gcccagtccc   2280
agcccaggag gcggcggctc cctgcaccta gcgagcgagc gagccgggcc aaacaaacaa   2340
ggggcaaagg ccatctcttt cgccggggcc cgcgcgcggg gttcgcccac gtgcgcgccc   2400
aggtgggcgc tggccgcggg caggtggcgg acatgtggcc tgcgggcccc gcgccgcctt   2460
cccatttttg gacgctgccg cgcatgccgc atgcgtgcgt cgacggccct actacttcta   2520
ctactgctac tgcgactact agtgtacata cgcaaaaata catatatacg tattttctat   2580
atatatatat ataagcaagg cggccccccg gtgacctttt ctttgttttt gtcgacaact   2640
gtgttttgat cccattctag ctgttctatg gaccatggat ggttcgttca atgtttgtac   2700
gtactccacg taaccaaact actctagtgg actagtagat cgggctcatg tgatgaaact   2760
ggaccgacgc ggacgtcacg tgcgtcaccc gcgtctggta gcggtagcgc acgagcgccg   2820
aatgtttcct gggcccgcaa gagaatcgct tctcatctcc tctcaccatg aatggggaaa   2880
aatgctgcgt cgaaagttcc agacgtttcc aaattccaaa cggttttgtg gcgtccgatc   2940
catggggcgc cccaaacttc caagacgttt tcaggttcca aatcttcgtg ctccacatca   3000
ccttcttccc agattcattt gcctcgtcgc ttgctctcct gtgttattca cgggtcccac   3060
tgttgccccg tctgcgagaa agaaatttat tagagttgaa gcattcgaca tttcgactga   3120
ctgattgtta gtatcactaa attttgtgca catgtttctt tggtcattca tctctggata   3180
ttttttttag ataatggata taaatatcgg gcctctacat ctgaggaagt acacagccaa   3240
ttattttcat ctctggacat gggacgatgg aagaggcaga tagatttagg agacccttca   3300
attcagaatt tcaggtgcac aaggcctgcc tggcttgccc ggattcttgt ttcggacatg   3360
accaactagg ccgcactact tgcactgata gctggagaaa aaacaaaact ttgcaaacag   3420
caggattatc tacaagggaa actccatcca cgtgaaccag catttcaggg agagatgcga   3480
caaaaaaaaa gaggcggcaa caaaaaaatc ttactgcaat tttatctctg cattgaacct   3540
cttccaacca tgccgcatcc tgtactgttt tgtatctttc ccggtggtcc gttgcgttct   3600
cacgcagttg ataacatgca gtcacgcacc accgaatcca gtgtactagg ggtagtgact   3660
tgtcacgcgg aacaacaggt cggtagcacc aagcaagtcg ctgtagactt gggcgtttaa   3720
caacgacttg cacaacagtt caaatatagc atatgcaatt atgcacaaga ttgttcgact   3780
gctatccgac aaactgaaga agctgcccaa ttgaacagaa tgtaccagtg atttccagca   3840
cactatctta cagcagcgtt gagaatgaaa caacaaatgg gggaaaacag atgtgtatta   3900
ttctacagtt acaccaaaga gtttgtcctt tcagcatcaa caagaatcat atgcatatct   3960
agtgacaaaa attcctctaa ttttacccta cttggtaaca gttctcttca acacatatat   4020
ttcacgtgct tgcatcgagt tccttgggcc gccacatcga cttctcgacg caaagcaagc   4080
cctcgttgcc cttggtgtag gtcattcgca cctcccactg cagggacttg gccatgcttt   4140
ccagttcgtt tattgtgtcc gcagtgtccc tcacaatcag tttgccttgg ggcctcagta   4200
cacgatcaac ctcggcaaaa actgccatca atttgcatct gtaaacaagc aacacagatt   4260
tagcatctgt aaacaccaca ggtttcattg caagaagcat aaagcatgca aacatgctac   4320
ttgtacatgt caaagaaaca tgtcaaactc aaacacatga aaatcattat tattgttttc   4380
```

-continued

```
ttgctgaact gatcacatta gttggtttca atttctgagt tccactagta atctatacca   4440
gaaggataga ataatgtcaa gaacaagaga tacaaacctc tttgtgagct ttgagaatag   4500
atggtccgcg tgcagaaggt cataagttct tgggtaagtg ctcaaagact cgcaccagtc   4560
atggtacata ccaaacaaac cacgctcgta aatgatgggc agtgtgtctg gtgaatcaat   4620
cggcacaata ttcatgaccc agaccttttg gtccctcaga gctgcagcaa aactgccatg   4680
caacgatgta aagcattagt aaaaatattg ggttttttaa accaaaacca agaaagataa   4740
ttcctccagc ttaactgaaa gaaagaaaga aaaaaactgc ttaatgactt atggtggaca   4800
agttgcctgt tatgttttat gatagctatg tgccagcttg gctaactggt agttatgtag   4860
tgtgatctga attaccaaaa aagagaagaa aaaaaaatca tgcccaagaa actgagaaag   4920
acacccattt acttaccctc catacacagc tctcatgtcc attacatttc tcactttgga   4980
ccagtcaatt cccatgccat tcacatacga tttacttaca accctttcc agtgagcatt   5040
atctgcctcg aaatcttcat ttgcaggctt tccatagacc ccaaccttgg aaccatcaat   5100
ccagaaagga gtcttctcaa gcctttgtgg ccaaaactct ggccattttg accctcgaac   5160
tttcgagcca acaggcagtt tgtgcatgca tgcttccaaa ggtacattcc tgcaaatcaa   5220
aagattgtgt aagcaaagca gaggaagcac ttcgccgcat tgaaaatacg ttcttctcaa   5280
agaaacaaaa ccataccaag ctgcatctgc atcatcagat tccttgcaca atggtgggtt   5340
gttttcggat cttttctcat agcaaatgtt gtccattggt ttctgaaata tgaccatacc   5400
aacttgattt aacttatcct tagtcttgtt gaccatcttc cagcacatgg actttgtcaa   5460
agtggacatc gctgaaaaga ttaaggggtc atatgttatg atagaaataa aattcaattt   5520
tgcactgttg gtacatagca tctgttttga acaaatgcaa tccttcctta tccatgaaag   5580
aagttaaccc ctgatactta ggattattca gtactttcac tcatgaactg ctgaatttgt   5640
tctgccagta gttgctatac tagaaatgtt cagtgtacca aacataaatt tggtacgggt   5700
tccttattaa agatgggagg ctgtatggta tttcgacgta acaaatcaag ttagcagcta   5760
ccctacttat ggatatacac ttctcaaaat gaatatacat agttttgata ggtgacatta   5820
attaatataa gaacttcatg cagttagggt gaaactaaac taagcagtta cggaaatacc   5880
attccaaatc tcaacatcct ctgggagctt ttggtaaaca ggagtggcag accagacaaa   5940
gtaaccacca gggcgtaaca agcggttcaa ttccagcaaa agcatgccac ctaaaaggag   6000
tcagtaataa gattcagttc tatagcaaat caataaatga aaggaagaca tgtcaccaac   6060
aagacaaacc ttcaatgtgc caagggaccc tgcagcgagc gcaatgaatg acatcaaaga   6120
ctctgctggg gtatggaagt ctcttggtgc ccatcacagc tgatattgct ggaattcccc   6180
tttctaatgc aaattgtact tgagcttcat gctcatcttt cggagcaaaa gacatggtaa   6240
gcacatctct atcaaacatg tagcctccaa agctggcaac tccacaaccg acatctagaa   6300
tgacgcggct tcgtttgccc catgcaatat caggcagtgc ctgtgaatga cagtttaatc   6360
agcatatgat gaaagcaagt gtgataatat caagttcaaa gatgcaacat gaaactttca   6420
taatcatgga cagtactaag cttgcttgat agattaatgt atggatgaga ctaaaaaaaa   6480
ggaaagttgt atccatcaga acgagaggct gaaaacacat ggctggctgt gaaagcctga   6540
tgtcgtttag tctagcataa acaaactgtc ctcagcatgt agatttccat agggtggcat   6600
ttgacaaatt atgattgtgg actagcgaat caatcactga ttctcaaaag tgtgagacag   6660
atgagttcaa gtctaagggg tgactaatat gggatgctgg gatgatgatg atgatatata   6720
```

-continued

```
cctgctgaat agtatcaata tagtggaggg caccattctt gaactgagtc ccacccccag   6780
ggaacaggag gtagtcacct gatactttaa cccaattttg atgtcccttg tactctgcga   6840
gcctagtgtg aggaacattg ctgtaccata cctgcaaaaa gcagcacaag atggtaataa   6900
gtaaacagag atcttggtca gctaaagatg attcagtgtc gtacaattta gaatagacag   6960
aatcaccttg tccctgctcc ttggccactc aattgggcgt ttatatcctt ctgggagtgg   7020
aacaaggcag gtaggaggct cctcagggca atgcctctca cgatgttcat aatgtttagt   7080
agttcgaagc ttcttgatag ccttctcgtt gtcaaggcaa ggtatgtaat ctgtcgaggc   7140
actgctatta catagtttcc aggaatagct agtcgcatca cctgaagact ttgatgacgc   7200
ttggacttcc ttttcattct tggactctgc agcctgtgtg gggaatgaac cattctgggt   7260
atttgactcc ttcagaagct ctgattgggc cccatcagga aatacctcgt tggagtttga   7320
gctctgatcc ttctctccat ttcttccac cttctcttct atctgaggtt gctcctcctg    7380
agtggcatca ccttcaggct tctcttcttg atcatccttg ctctctccat caggtttttc   7440
atcaccactc tcatttgtga tttcatcatc tttcttctcc ccactcttct ccccgtcacc   7500
atcgttcttc atgtcatctg accgcccttc tgattttcca tttgcatcat caaacatatc   7560
cttggtctca gctttctctg tcggcacttc cggctccttc tcttcaggct tctcctctgg   7620
cttctcagtg aacttctctt ccatcgtggc atccttgtta ttcggctcct ccggcatcgt   7680
ggcatcattg ttgtcggtgt cctcaaattt ctcagaacct tcaccagcat tgtcctgtga   7740
ggccccaaaa ttgacaggcg caggctgctg cttcaccacc ggcttcttat tcgaggagat   7800
ctccagcggg aagacagtgg acgaggtcat catccacgcg ccgaccaggc agagcgccac   7860
aaagacgacg accgtggtgg tcgtgcagaa cgacgacgac gtcgaggacg gccggcggcc   7920
gtccatcttc ccacctcggc caaatgccat tagtgcctgg cgaacatgta ccagagcacc   7980
gaccttcacg cgatttatct ccaccaacta ctgctggacc aagaaccccc aaaaaaatcg   8040
cacctttgtc tgctttgtgc tgctacagcc gcgcggcacc tgaagcaaac cacaaaaaaa   8100
acttaaatcg ccgcggacat aaatcaaggt gctggatcta aagaacaaac gctggatcta   8160
ctcaagcaac aacggaagga agatccgcta ttggtgctag tattagcttc ttgtttccta   8220
gtactacagc ggctctttcc cagtataaga acacgggaaa acgcggagaa atccccccttc  8280
gtggccaaac atggaaagaa aattagtaaa gcgtgtgctt taaaaccccc tcgttctgtt   8340
ccttccgcgg agagctaccg catcttccaa ttgagctggt tctcagctgg gcgcaaaacg   8400
cgcactaatc aatgtccgat tccatccaca aagaaaaaaa agacgggaac agctaatcca   8460
gcagctcgct cgctagctag ctagctcatc ggcggaagga cggaaccagc tttgctggat   8520
ccaggacagc aagagtgtgc aaggagaaag aacggagcag caatgcggat tgcggaggcg   8580
gtggattggt acctcgccgg aaccgaccgg agtggtcgcg gtggccctcc gcgcggatct   8640
cgaagaggag cgaggaaggg gaaggcggat gcgcgtcctt gggttctctg ccaccgcact   8700
gggcctcgcc gcgttataaa ggcgggcggg cgggcgggca gcgcagtgtg agtggagtgc   8760
aatctgttgt gtagtgtgtg aagaggcgga agcggaagcg gaggagatgg gttcgcatta   8820
gacgaccgta cgtaattata cgctatacta gtacttgggt tagattactc gggagatctt   8880
ggccaaaatg tccggtctga gtgtttggta gttttatgga tttgcccttt taagatgttg   8940
gtatttctcc gggagcttag aaagaagaaa tggcgatgct ttaggccttg tttagatgcg   9000
aaaaaaattt ggatttcgct actgtggcat ttttatttgt ttgtagcaaa tattgtccaa   9060
acacggacta actaagattc atctcgcgat ttacagttaa actgtacaat tagtttttat   9120
```

```
tttcatttat atttaatgtt tcatggatgt gtcgaaagat acgatatgat agaaaatttt   9180
gaaaactttt tagttattga ggttaactaa acaatgcctt aattgagaat ttactcgagc   9240
aaaaagagtt aggtcagtct cagtggagag tttcatggtg ttgtttccaa gactgccata   9300
tcatgtgaaa tgaaatgaaa cttggttgaa acactcactc tcaatggaga gtttcatttt   9360
atagtttcat gggcatttaa tttcaatact catagagagt tgatatcgtg ccaactcatt   9420
tcttctctct cttcttaaat acacagtcat atcatcaaaa aaaatcctat gtagcaacat   9480
atttaatgca aataaaactc atatggtgga ctgtaggagt agcattaggc caagggcaca   9540
cacacggtca cggtgtgagt gcgacggtgc gagtgggccc gcggcggtag taagtgcgtg   9600
cgcgcccggc gccccccctcc gcggcgacga cgcagcggca gcgcgtcgtc cagtgcaccg   9660
tctgctgttc ggcgctgcgg gtcctccgcg ccacggcgca gtgaaccggg cgcgtgcatc   9720
ccgggagcgg cggcttggca ctcccctgct tgtcggtggc ggccgtcggc atcgctcggc   9780
cccggagcgt cacgaggctg ctgattggga gcgagagcga gtagtggggc tggttgggga   9840
caatcccatt cccacccggc ccaccaggct gggactggcc cactagtcac tagtgggtgg   9900
ctcatgggtg tgggtgggct ggctaatgcc gcctgcccaa caaccaaccc aacccctgtg   9960
gacgctggta ccggtagttg ccgcgccatg gtggactgct gccgcctgat gcctttgcct  10020
gccacgctcc acgagttgag gcgcaccaaa ctgtgctgtg ctcctgattt gtgctaatcg  10080
gccgacgcgt accattcttt ctttctttcg tctacgcgca gagaggccgg ttgactgttt  10140
cttcgttgga gggccatgtt gactcgtact aataataaaa ataataatac taggttgact  10200
ttttcaattc caacgcagca gtgcaaagct gcccacctat gagcacaggt ccttttttaa  10260
ctccgttttt gtacgtacac acgtactgtc cagcctgtgt ctaataatct taccaaaaac  10320
ctgtcatctc actatcaacc aatcaggctc tccgcctgtt cgtcgaggaa cagcagttgt  10380
tttccctact ccaacataga gtacactatg gacgcacatt accatgccag cttgagctta  10440
gcattgccca ccgttggata actgccatgc cattctcagg ccctgtttag ttcccatcta  10500
aaaatttttc atccattcca tcgaatcttt ggacacatgc atggaacatt aaatgtagat  10560
aaaaaaataa actaattaca cagtttagtt gagaatcgcg agacgaatct tttaagtcta  10620
gttactccat aattagcctt aagtgctaca gtaatccaca tatactaatg acagattaat  10680
tatgcttaat aaatttgtct tacagtttcc tgacgagcta tgtaatttgt tttttttatta  10740
gtttctaaaa acccctcccg acatccttcc gacatatccg atgtgacaac caaaaaattt  10800
tcatcttcaa tctaaacagg ccctcactct catcatctca tgccggggca gcaggtccgt  10860
cgtcaggtct gtcgtcccgt cccgtgccgt ctgaagcaac aggcgagaga aacgccgttc  10920
catcggtttg ccgagcgtgc agaggataga gctatactcg atccggagag gattgtgaaa  10980
cgaagcacgg ttaagcagtg ccgcgcacgt gctgctctgc tcctggatcc gatccagatc  11040
gactcggggc gtctcggcct cagcggcgat ggcaatcatc gcgcgcgctg ctggagctgg  11100
acgttttcgt cttgcattgc aggaggcgga acagaacgga gaaagccacg gcgcgctttg  11160
ccgacgccac gcgctgacac gagggacccg ttcagcggcc agcacgcagc ctaatcatgc  11220
ctgtcggggg gagctcatcc gttcctgaat ttgggtcatg ctccagtatc aggtattcag  11280
gtactagtac tcctgagcca tgtgctgcga caaaaaagcg aggctcctgt agtagagcct  11340
tgtttactta caaaattttt tacattctca gttatattaa atcttgtgac acatgcataa  11400
agcattaaat atacataaaa gaaataatta tttacacagt tacttataat ttgcgaaacg  11460
```

```
aatcttttaa gactggttag tttatgatta gataatattt attaaataca aatgaaagta  11520

atattattta tattttgcaa aaagtaaata agacctaggt agctaggcca acgtgagcat  11580

gtcggacccg gaccggttcg ttctacggcg cgtcccgcaa acctgcagcc aggtagtagt  11640

agtacaccgt gcacgggaga ggtgcgccat gcatgctcgg gcaaaagatc atagagaaag  11700

gtgcagcgtt tcagttgcac acctgaccga gtgacgcctc gccttgtttg gctttgttcc  11760

caaaattttt taaaattcct catcacatta aatctttgaa cgaatatatg gagcattaaa  11820

tataaataaa agaaataatt aatcatacaa tttgtctgta atttgcgaga cgaatctttt  11880

gagcctagtt agtttataat taaataatat ttgttaaata caaacgaaaa tgctacgtta  11940

gccaaaacta aaatttttct ccaaacgtga cccagcacct tccgatcaat catcactcag  12000

cgggtcacgt cagaagatca gatggacctt gccgtccggg cctgtctctc ggcctcctcc  12060

ccatctggaa cgaacagagg tccagtcctg tttcgagtcg agctgagtcg atcagatggg  12120

cctaaatagg ccgaagacgt aggcaaaggg cccgctgatt tatctgattc ttctaggacc  12180

gtgcatgcgc ggatgggcct aggtggaaac ccaacagatg tgaggcttca aagaggaaga  12240

agtccgttac acatggagag ttagtctata atgggataat atttaccaca aacaaataaa  12300

aatactacag tagcgaaatc caaaattttt cacatctaaa caaggcccta gatgttttgt  12360

cagtgccaga ccagagaaaa tctcgtcttc tgctgtcaat agctttgatg attcctggcg  12420

gcagaggtaa agcttgcctg ggccttgttt agttccgaaa agtgaaaagt tttcggtact  12480

gtagcacttt tgtttgttcg tgacaaatat catccaatta tggactaact agaattaaaa  12540

gattcgtctc gtgatctaca gctaaactgt gtaattagtt tttgttttcg tctatattta  12600

atgtttcatg catgtgccac aagattcgat gtgacggaga attttgaaaa ttttttggtt  12660

ttcagagtga actaaacaag gcccagatgt aattgaccat gccatcgagc gcgagttgac  12720

tagagtgagt cggccctgat ggttaagtag tgcagactgc caagtggaca accgtctatc  12780

aactttgcag agtggggcga atgcactgag gatgttggag aggggcaagc caaggtaaac  12840

ttgaggaaag atgcttgttg acactgtagt atgtgaacaa tcctgtttaa ttttgtgtcc  12900

tcgacg                                                              12906
```

<210> SEQ ID NO 88
<211> LENGTH: 1790
<212> TYPE: DNA
<213> ORGANISM: Setaria italica

<400> SEQUENCE: 88

```
tctcatggtg tcccaagcac agcaagagcc agctctgcct cacagcagca gcaccgccaa     60

gcgcgcagcc gcgtcactca tggacgcccg cccggcccag cctctcctcc tccgcgcccc    120

gactcccagc attgacctcc ccgcgtccaa gccggacagg gccgccgcgg cggccggcaa    180

ggccgccgcc gcctccgtgt tcgacctgcg gcgggagccc aagatcccgg cgccattcgt    240

gtggccgcac gacgacgcgc ggccggcgtc ggcggcggag ctggacgtgc cgttggtgga    300

cgtgggcgtg ctgcgcaatg gcgaccgcgc ggggctgcgg cgcgctgcgg cgcaggtggc    360

cgcggcgtgc gcgacgcacg ggttcttcca ggtgtgcggg cacggcgtgg gcgcggacct    420

ggcgcgcgcg gcgctggacg gcgccagtga cttcttccgg ctgccgctgg cggagaagca    480

gcgcgcccgg cgcgtcccgg ggaccgtgtc cgggtacacg agcgcgcacg ccgaccggtt    540

cgcgtccaag ctcccctgga aggagaccct ctccttcggg ttccacgacg gcgccgcgtc    600

gcccgtcgtc gtcgactact tcgccggcac cctcgggcag gacttcgagg cagtggggcg    660
```

```
ggtgtaccag aggtactgcg aggagatgaa ggctctgtcg ctgacgatca tggagctcct    720
ggagctgagc ctgggcgtgg agcgcggcta ctaccgcgac ttcttcgagg acagccgctc    780
catcatgcgg tgcaactact acccgccgtg cccggagccg gagcgcacgc tgggcacggg    840
cccgcactgc gaccccaccg cgctgaccat cctcctccag gacgacgtcg gcgggctcga    900
ggtcctcgtc gacggcgact ggcgccccgt ccgccccgtc cccggcgcca tggtcatcaa    960
catcggcgac accttcatgg ctctgtccaa cgggcggtac aagagctgcc tgcaccgggc   1020
ggtggtgaac cagcggcagg agcggcggtc gctggccttc ttcctgtgcc cgcgcgagga   1080
ccgggtggtg cgcccgccgg ccagcggcgc cgtcggcgag gcgcccccgcc gctacccgga   1140
cttcacctgg gccgacctca tgcgcttcac gcagcgccac taccgcgccg acacccgcac   1200
gctggacgcc ttcacacgct ggctctccca cggcccggcc caggacgcgc cagtggcggc   1260
ggcggcttcc acctagctag cggcgcggat ccgaccgagc ccattgacga cgccgtccct   1320
ttccgccgcc gccggggccc gcgcgggggt tcaccccacg tgcgcgccca ggtgggcgag   1380
gtggcggcct cgtggcccgc gggccccgcg ccgccttccc atttttgggc gctgccgccc   1440
cgcgcgcatg ccggatgcgt gcgtccacgg cctactgctg ctactagtgt acatatacaa   1500
acatacatat atacgtagta taaatatata agcaagcggc ccggtgcccc ttttcgtttt   1560
cttgttttgt cgatcacaat ctctggattc gatggatgga taaatgtttg tacgcatgca   1620
tgtagatggg ctcatgaaat ttcagaatct ggaacggacg aggagctcac gtgcctcttc   1680
cgtgtctggt agcggtagct gcgtgccaaa tgtctggtgg gcccaaagaa attctagtgc   1740
cacccgtccg gatccggcat ccgaaagttc ccgacggttc gacacccgaa               1790
```

<210> SEQ ID NO 89
<211> LENGTH: 1272
<212> TYPE: DNA
<213> ORGANISM: Setaria italica

<400> SEQUENCE: 89

```
atggtgtccc aagcacagca agagccagct ctgcctcaca gcagcagcac cgccaagcgc     60
gcagccgcgt cactcatgga cgcccgcccg gcccagcctc tcctcctccg cgccccgact    120
cccagcattg acctccccgc gtccaagccg gacagggccg ccgcggcggc cggcaaggcc    180
gccgccgcct ccgtgttcga cctgcggcgg gagcccaaga tcccggcgcc attcgtgtgg    240
ccgcacgacg acgcgcggcc ggcgtcggcg gcggagctgg acgtgccgtt ggtggacgtg    300
ggcgtgctgc gcaatggcga ccgcgcgggg ctgcggcgcg ctgcggcgca ggtggccgcg    360
gcgtgcgcga cgcacgggtt cttccaggtg tgcgggcacg gcgtgggcgc ggacctggcg    420
cgcgcggcgc tggacggcgc cagtgacttc ttccggctgc cgctggcgga gaagcagcgc    480
gcccggcgcg tcccggggac cgtgtccggg tacacgagcg cgcacgccga ccggttcgcg    540
tccaagctcc cctggaagga gaccctctcc ttcgggttcc acgacggcgc cgcgtcgccc    600
gtcgtcgtcg actacttcgc cggcaccctc gggcaggact tcgaggcagt ggggcgggtg    660
taccagaggt actgcgagga gatgaaggct ctgtcgctga cgatcatgga gctcctggag    720
ctgagcctgg gcgtggagcg cggctactac cgcgacttct tcgaggacag ccgctccatc    780
atgcggtgca actactaccc gccgtgcccg gagccggagc gcacgctggg cacgggcccg    840
cactgcgacc ccaccgcgct gaccatcctc ctccaggacg acgtcggcgg gctcgaggtc    900
ctcgtcgacg gcgactggcg ccccgtccgc cccgtccccg gcgccatggt catcaacatc    960
```

```
ggcgacacct tcatggctct gtccaacggg cggtacaaga gctgcctgca ccgggcggtg   1020

gtgaaccagc ggcaggagcg gcggtcgctg gccttcttcc tgtgcccgcg cgaggaccgg   1080

gtggtgcgcc cgccggccag cggcgccgtc ggcgaggcgc cccgccgcta cccggacttc   1140

acctgggccg acctcatgcg cttcacgcag cgccactacc gcgccgacac ccgcacgctg   1200

gacgccttca cacgctggct ctcccacggc ccggcccagg acgcgccagt ggcggcggcg   1260

gcttccacct ag                                                       1272


<210> SEQ ID NO 90
<211> LENGTH: 423
<212> TYPE: PRT
<213> ORGANISM: Setaria italica

<400> SEQUENCE: 90

Met Val Ser Gln Ala Gln Gln Glu Pro Ala Leu Pro His Ser Ser Ser
1               5                   10                  15

Thr Ala Lys Arg Ala Ala Ala Ser Leu Met Asp Ala Arg Pro Ala Gln
            20                  25                  30

Pro Leu Leu Leu Arg Ala Pro Thr Pro Ser Ile Asp Leu Pro Ala Ser
        35                  40                  45

Lys Pro Asp Arg Ala Ala Ala Ala Ala Gly Lys Ala Ala Ala Ala Ser
    50                  55                  60

Val Phe Asp Leu Arg Arg Glu Pro Lys Ile Pro Ala Pro Phe Val Trp
65                  70                  75                  80

Pro His Asp Asp Ala Arg Pro Ala Ser Ala Ala Glu Leu Asp Val Pro
                85                  90                  95

Leu Val Asp Val Gly Val Leu Arg Asn Gly Asp Arg Ala Gly Leu Arg
            100                 105                 110

Arg Ala Ala Ala Gln Val Ala Ala Ala Cys Ala Thr His Gly Phe Phe
        115                 120                 125

Gln Val Cys Gly His Gly Val Gly Ala Asp Leu Ala Arg Ala Ala Leu
    130                 135                 140

Asp Gly Ala Ser Asp Phe Phe Arg Leu Pro Leu Ala Glu Lys Gln Arg
145                 150                 155                 160

Ala Arg Arg Val Pro Gly Thr Val Ser Gly Tyr Thr Ser Ala His Ala
                165                 170                 175

Asp Arg Phe Ala Ser Lys Leu Pro Trp Lys Glu Thr Leu Ser Phe Gly
            180                 185                 190

Phe His Asp Gly Ala Ala Ser Pro Val Val Val Asp Tyr Phe Ala Gly
        195                 200                 205

Thr Leu Gly Gln Asp Phe Glu Ala Val Gly Arg Val Tyr Gln Arg Tyr
    210                 215                 220

Cys Glu Glu Met Lys Ala Leu Ser Leu Thr Ile Met Glu Leu Leu Glu
225                 230                 235                 240

Leu Ser Leu Gly Val Glu Arg Gly Tyr Tyr Arg Asp Phe Phe Glu Asp
                245                 250                 255

Ser Arg Ser Ile Met Arg Cys Asn Tyr Tyr Pro Pro Cys Pro Glu Pro
            260                 265                 270

Glu Arg Thr Leu Gly Thr Gly Pro His Cys Asp Pro Thr Ala Leu Thr
        275                 280                 285

Ile Leu Leu Gln Asp Asp Val Gly Gly Leu Glu Val Leu Val Asp Gly
    290                 295                 300

Asp Trp Arg Pro Val Arg Pro Val Pro Gly Ala Met Val Ile Asn Ile
305                 310                 315                 320
```

```
Gly Asp Thr Phe Met Ala Leu Ser Asn Gly Arg Tyr Lys Ser Cys Leu
                325                 330                 335

His Arg Ala Val Val Asn Gln Arg Gln Glu Arg Arg Ser Leu Ala Phe
            340                 345                 350

Phe Leu Cys Pro Arg Glu Asp Arg Val Val Arg Pro Pro Ala Ser Gly
        355                 360                 365

Ala Val Gly Glu Ala Pro Arg Arg Tyr Pro Asp Phe Thr Trp Ala Asp
    370                 375                 380

Leu Met Arg Phe Thr Gln Arg His Tyr Arg Ala Asp Thr Arg Thr Leu
385                 390                 395                 400

Asp Ala Phe Thr Arg Trp Leu Ser His Gly Pro Ala Gln Asp Ala Pro
                405                 410                 415

Val Ala Ala Ala Ala Ser Thr
            420
```

<210> SEQ ID NO 91
<211> LENGTH: 2888
<212> TYPE: DNA
<213> ORGANISM: Setaria italica

<400> SEQUENCE: 91

```
tctcatggtg tcccaagcac agcaagagcc agctctgcct cacagcagca gcaccgccaa     60

gcgcgcagcc gcgtcactca tggacgcccg cccggcccag cctctcctcc tccgcgcccc    120

gactcccagc attgacctcc ccgcgtccaa gccggacagg gccgccgcgg cggccggcaa    180

ggccgccgcc gcctccgtgt tcgacctgcg gcgggagccc aagatcccgg cgccattcgt    240

gtggccgcac gacgacgcgc ggccggcgtc ggcggcggag ctggacgtgc cgttggtgga    300

cgtgggcgtg ctgcgcaatg gcgaccgcgc ggggctgcgg cgcgctgcgg cgcaggtggc    360

cgcggcgtgc gcgacgcacg ggttcttcca ggtgtgcggg cacggcgtgg gcgcggacct    420

ggcgcgcgcg gcgctggacg gcgccagtga cttcttccgg ctgccgctgg cggagaagca    480

gcgcgcccgg cgcgtcccgg ggaccgtgtc cgggtacacg agcgcgcacg ccgaccggtt    540

cgcgtccaag ctcccctgga aggagaccct ctccttcggg ttccacgacg gcgccgcgtc    600

gcccgtcgtc gtcgactact tcgccggcac cctcgggcag gacttcgagg cagtggggta    660

agtatgtagg aatgaacttg gcacgcattg catccacatg gcgtgctgat cgaacgagct    720

gagccaaccg gcatgcacac atggcgtggc aggcgggtgt accagaggta ctgcgaggag    780

atgaaggctc tgtcgctgac gatcatggag ctcctggagc tgagcctggg cgtggagcgc    840

ggctactacc gcgacttctt cgaggacagc cgctccatca tgcggtgcaa ctactacccg    900

ccgtgcccgg agccggagcg cacgctgggc acgggcccgc actgcgaccc caccgcgctg    960

accatcctcc tccaggacga cgtcggcggg ctcgaggtcc tcgtcgacgg cgactggcgc   1020

cccgtccgcc ccgtccccgg cgccatggtc atcaacatcg gcgacacctt catggtacgg   1080

ccgccgctaa tccatccttt tgttgctctt atctcctctg gcgagtgcga gtaacgaaag   1140

cgctagctcc cctgctcctt gtcctgctct gtttcccaag tcctaatgga gctaaccggg   1200

cagactgcaa cacgcacgcg taggcatgtc acgtagccac cacttgcact gtgctgcgca   1260

gcgacgacgc aacgcggacg tgcgttcgag tcggttccat ctcggcgccg ctacacgcgg   1320

ccgcggctcc tagcctccta gggctccctg atccctatcc ccgagccctt ccgcgggaaa   1380

agttcgttgg cgacggcaga ggagagccga cgggtccgtg ccgttggagc gtggcggcag   1440

gagaggccgg gagggtgttt tgttgcgttg cgcggcggcg cggaggatgc gatggcgcgg   1500
```

```
gcgggcggcg ctttcggcgg tggcccccgc gacccacgtg cgcgcgcggt ctcgtcgcct   1560
tccctgtttt ggtgccacct ctctgtgtcc gggaatgggt tggcttagcg gcgaccgaga   1620
ccgggcggtg gtctggcctg ctcccggcgc ccatcccgcc tggtctctca tcctgctcct   1680
cctatgcgcg agggggcctg tagcggctgg agtacaagca gattggttgg gttgggttgc   1740
tgctgcttgg ctgttgcccg cccgctttct agccgtttcc gctcgccatc cggcacgcgg   1800
cgcccacgcc ggggctccag ctcggcccct ttggccgtgt gggtggcagg caccctgca    1860
tcgtctcgtg cgtccggttt ccgcgcctgg ccccccgcct tgaggtttcc ctgtgctttt   1920
gacaagactt tcgtagatat atgtgtgtgt atgtgtgtgt gtgcgtgcgc gcgtgtgtgt   1980
atatatatat ataaataaat aacatctgtg aatgatggat tacacgtgta gctgaccggc   2040
tgattgtgtt cgcgtgtgtg tcttcgatgc attgcaggct ctgtccaacg ggcggtacaa   2100
gagctgcctg caccgggcgg tggtgaacca gcggcaggag cggcggtcgc tggccttctt   2160
cctgtgcccg cgcgaggacc gggtggtgcg cccgccggcc agcggcgccg tcggcgaggc   2220
gccccgccgc tacccggact tcacctgggc cgacctcatg cgcttcacgc agcgccacta   2280
ccgcgccgac acccgcacgc tggacgcctt cacacgctgg ctctcccacg gcccggccca   2340
ggacgcgcca gtggcggcgg cggcttccac ctagctagcg gcgcggatcc gaccgagccc   2400
attgacgacg ccgtcccttt ccgccgccgc cggggcccgc gcgggggttc accccacgtg   2460
cgcgcccagg tgggcgaggt ggcggcctcg tggcccgcgg gccccgcgcc gccttcccat   2520
ttttgggcgc tgccgccccg cgcgcatgcc ggatgcgtgc gtccacggcc tactgctgct   2580
actagtgtac atatacaaac atacatatat acgtagtata aatatataag caagcggccc   2640
ggtgcccctt ttcgttttct tgttttgtcg atcacaatct ctggattcga tggatggata   2700
aatgtttgta cgcatgcatg tagatgggct catgaaattt cagaatctgg aacggacgag   2760
gagctcacgt gcctcttccg tgtctggtag cggtagctgc gtgccaaatg tctggtgggc   2820
ccaaagaaat tctagtgcca cccgtccgga tccggcatcc gaaagttccc gacggttcga   2880
cacccgaa                                                            2888
```

<210> SEQ ID NO 92
<211> LENGTH: 1567
<212> TYPE: DNA
<213> ORGANISM: Oryza sativa

<400> SEQUENCE: 92

```
tgcccagaca gctcgccctg cacacacaca cacactcaca ctcacacacg ctctcaactc     60
actcccgctc aacacagcgc tcacttctca tctccaatct catggtggcc gagcacccca    120
cgccaccaca gccgcaccaa ccaccgccca tggactccac cgccggctct ggcattgccg    180
ccccggcggc ggcggcggtg tgcgacctga ggatggagcc caagatcccg gagccattcg    240
tgtggccgaa cggcgacgcg aggccggcgt cggcggcgga gctggacatg cccgtggtcg    300
acgtgggcgt gctccgcgac ggcgacgccg aggggctgcg ccgcgccgcg gcgcaggtgg    360
ccgccgcgtg cgccacgcac gggttcttcc aggtgtccga gcacggcgtc gacgccgctc    420
tggcgcgcgc cgcgctcgac ggcgccagcg acttcttccg cctcccgctc gccgagaagc    480
gccgcgcgcg ccgcgtcccg ggcaccgtgt ccggctacac cagcgcccac gccgaccgct    540
tcgcctccaa gctcccatgg aaggagaccc tctccttcgg cttccacgac cgcgccgccg    600
cccccgtcgt cgccgactac ttctccagca ccctcggccc cgacttcgcg ccaatgggga    660
```

```
gggtgtacca gaagtactgc gaggagatga aggagctgtc gctgacgatc atggaactcc     720

tggagctgag cctgggcgtg gagcgaggct actacaggga gttcttcgcg gacagcagct     780

caatcatgcg gtgcaactac tacccgccat gcccggagcc ggagcggacg ctcggcacgg     840

gcccgcactg cgaccccacc gccctcacca tcctcctcca ggacgacgtc ggcggcctcg     900

aggtcctcgt cgacggcgaa tggcgccccg tcagccccgt ccccggcgcc atggtcatca     960

acatcggcga caccttcatg gcgctgtcga acgggaggta taagagctgc ctgcacaggg    1020

cggtggtgaa ccagcggcgg gagcggcggt cgctggcgtt cttcctgtgc ccgcgggagg    1080

acagggtggt gcggccgccg ccgagcgccg ccacgccgca gcactacccg gacttcacct    1140

gggccgacct catgcgcttc acgcagcgcc actaccgcgc cgacacccgc acgctcgacg    1200

ccttcacgcg ctggctcgcg ccgccggccg ccgacgccgc cgcgacggcg caggtcgagg    1260

cggccagctg atcgccgaac ggaacgaaac ggaacgaaca gaagccgatt tttggcgggg    1320

cccacgccca cgtgaggccc cacgtggaca gtgggcccgg gcggaggtgg cacccacgtg    1380

gaccgcgggc cccgcgccgc cttccaattt tggaccctac cgctgtacat attcatatat    1440

tgcaagaaga agcaaaacgt acgtgtgggt tgggttgggc ttctctctat tactaaaaaa    1500

aatataatgg aacgacggat gaatggatgc ttatttattt atctaaattg aattcgaatt    1560

cggctca                                                              1567


<210> SEQ ID NO 93
<211> LENGTH: 1170
<212> TYPE: DNA
<213> ORGANISM: Oryza sativa

<400> SEQUENCE: 93

atggtggccg agcaccccac gccaccacag ccgcaccaac caccgcccat ggactccacc      60

gccggctctg gcattgccgc cccggcggcg gcggcggtgt gcgacctgag gatggagccc     120

aagatcccgg agccattcgt gtggccgaac ggcgacgcga ggccggcgtc ggcggcggag     180

ctggacatgc ccgtggtcga cgtgggcgtg ctccgcgacg gcgacgccga ggggctgcgc     240

cgcgccgcgg cgcaggtggc cgccgcgtgc gccacgcacg ggttcttcca ggtgtccgag     300

cacggcgtcg acgccgctct ggcgcgcgcc gcgctcgacg gcgccagcga cttcttccgc     360

ctcccgctcg ccgagaagcg ccgcgcgcgc cgcgtcccgg gcaccgtgtc cggctacacc     420

agcgcccacg ccgaccgctt cgcctccaag ctcccatgga aggagaccct ctccttcggc     480

ttccacgacc gcgccgccgc ccccgtcgtc gccgactact tctccagcac cctcggcccc     540

gacttcgcgc caatggggag ggtgtaccag aagtactgcg aggagatgaa ggagctgtcg     600

ctgacgatca tggaactcct ggagctgagc ctgggcgtgg agcgaggcta ctacagggag     660

ttcttcgcgg acagcagctc aatcatgcgg tgcaactact acccgccatg cccggagccg     720

gagcggacgc tcggcacggg cccgcactgc gaccccaccg ccctcaccat cctcctccag     780

gacgacgtcg gcggcctcga ggtcctcgtc gacggcgaat ggcgccccgt cagccccgtc     840

cccggcgcca tggtcatcaa catcggcgac accttcatgg cgctgtcgaa cgggaggtat     900

aagagctgcc tgcacagggc ggtggtgaac cagcggcggg agcggcggtc gctggcgttc     960

ttcctgtgcc cgcgggagga cagggtggtg cggccgccgc cgagcgccgc cacgccgcag    1020

cactacccgg acttcacctg ggccgacctc atgcgcttca cgcagcgcca ctaccgcgcc    1080

gacacccgca cgctcgacgc cttcacgcgc tggctcgcgc cgccggccgc cgacgccgcc    1140

gcgacggcgc aggtcgaggc ggccagctga                                     1170
```

<210> SEQ ID NO 94
<211> LENGTH: 389
<212> TYPE: PRT
<213> ORGANISM: Oryza sativa

<400> SEQUENCE: 94

```
Met Val Ala Glu His Pro Thr Pro Pro Gln Pro His Gln Pro Pro Pro
1               5                   10                  15

Met Asp Ser Thr Ala Gly Ser Gly Ile Ala Ala Pro Ala Ala Ala Ala
            20                  25                  30

Val Cys Asp Leu Arg Met Glu Pro Lys Ile Pro Glu Pro Phe Val Trp
        35                  40                  45

Pro Asn Gly Asp Ala Arg Pro Ala Ser Ala Ala Glu Leu Asp Met Pro
    50                  55                  60

Val Val Asp Val Gly Val Leu Arg Asp Gly Asp Ala Glu Gly Leu Arg
65                  70                  75                  80

Arg Ala Ala Ala Gln Val Ala Ala Ala Cys Ala Thr His Gly Phe Phe
                85                  90                  95

Gln Val Ser Glu His Gly Val Asp Ala Ala Leu Ala Arg Ala Ala Leu
            100                 105                 110

Asp Gly Ala Ser Asp Phe Phe Arg Leu Pro Leu Ala Glu Lys Arg Arg
        115                 120                 125

Ala Arg Arg Val Pro Gly Thr Val Ser Gly Tyr Thr Ser Ala His Ala
    130                 135                 140

Asp Arg Phe Ala Ser Lys Leu Pro Trp Lys Glu Thr Leu Ser Phe Gly
145                 150                 155                 160

Phe His Asp Arg Ala Ala Ala Pro Val Val Ala Asp Tyr Phe Ser Ser
                165                 170                 175

Thr Leu Gly Pro Asp Phe Ala Pro Met Gly Arg Val Tyr Gln Lys Tyr
            180                 185                 190

Cys Glu Glu Met Lys Glu Leu Ser Leu Thr Ile Met Glu Leu Leu Glu
        195                 200                 205

Leu Ser Leu Gly Val Glu Arg Gly Tyr Tyr Arg Glu Phe Phe Ala Asp
    210                 215                 220

Ser Ser Ser Ile Met Arg Cys Asn Tyr Tyr Pro Pro Cys Pro Glu Pro
225                 230                 235                 240

Glu Arg Thr Leu Gly Thr Gly Pro His Cys Asp Pro Thr Ala Leu Thr
                245                 250                 255

Ile Leu Leu Gln Asp Asp Val Gly Gly Leu Glu Val Leu Val Asp Gly
            260                 265                 270

Glu Trp Arg Pro Val Ser Pro Val Pro Gly Ala Met Val Ile Asn Ile
        275                 280                 285

Gly Asp Thr Phe Met Ala Leu Ser Asn Gly Arg Tyr Lys Ser Cys Leu
    290                 295                 300

His Arg Ala Val Val Asn Gln Arg Arg Glu Arg Arg Ser Leu Ala Phe
305                 310                 315                 320

Phe Leu Cys Pro Arg Glu Asp Arg Val Val Arg Pro Pro Pro Ser Ala
                325                 330                 335

Ala Thr Pro Gln His Tyr Pro Asp Phe Thr Trp Ala Asp Leu Met Arg
            340                 345                 350

Phe Thr Gln Arg His Tyr Arg Ala Asp Thr Arg Thr Leu Asp Ala Phe
        355                 360                 365

Thr Arg Trp Leu Ala Pro Pro Ala Ala Asp Ala Ala Ala Thr Ala Gln
```

370 375 380

Val Glu Ala Ala Ser
385

<210> SEQ ID NO 95
<211> LENGTH: 3140
<212> TYPE: DNA
<213> ORGANISM: Oryza sativa

<400> SEQUENCE: 95
tgcccagaca gctcgccctg cacacacaca cacactcaca ctcacacacg ctctcaactc 60
actcccgctc aacacagcgc tcacttctca tctccaatct catggtggcc gagcacccca 120
cgccaccaca gccgcaccaa ccaccgccca tggactccac cgccggctct ggcattgccg 180
ccccggcggc ggcggcggtg tgcgacctga ggatggagcc caagatcccg gagccattcg 240
tgtggccgaa cggcgacgcg aggccggcgt cggcggcgga gctggacatg cccgtggtcg 300
acgtgggcgt gctccgcgac ggcgacgccg aggggctgcg ccgcgccgcg gcgcaggtgg 360
ccgccgcgtg cgccacgcac gggttcttcc aggtgtccga gcacggcgtc gacgccgctc 420
tggcgcgcgc cgcgctcgac ggcgccagcg acttcttccg cctcccgctc gccgagaagc 480
gccgcgcgcg ccgcgtcccg ggcaccgtgt ccggctacac cagcgcccac gccgaccgct 540
tcgcctccaa gctcccatgg aaggagaccc tctccttcgg cttccacgac cgcgccgccg 600
cccccgtcgt cgccgactac ttctccagca ccctcggccc cgacttcgcg ccaatggggt 660
aattaaaacg atggtggacg acattgcatt tcaaattcaa aacaaattca aaacacaccg 720
accgagatta tgctgaattc aaacgcgttt gtgcgcgcag gagggtgtac cagaagtact 780
gcgaggagat gaaggagctg tcgctgacga tcatggaact cctggagctg agcctgggcg 840
tggagcgagg ctactacagg gagttcttcg cggacagcag ctcaatcatg cggtgcaact 900
actacccgcc atgcccggag ccggagcgga cgctcggcac gggcccgcac tgcgacccca 960
ccgccctcac catcctcctc caggacgacg tcggcggcct cgaggtcctc gtcgacggcg 1020
aatggcgccc cgtcagcccc gtccccggcg ccatggtcat caacatcggc gacaccttca 1080
tggtaaacca tctcctattc tcctctcctc tgttctcctc tgcttcgaag caacagaaca 1140
agtaattcaa gctttttttt ctctctcgcg cgaaattgac gagaaaaata agatcgtggt 1200
aggggcgggg ctttcagctg aaagcgggaa gaaaccgacc tgacgtgatt tctctgttcc 1260
aatcacaaac aatggaatgc ccactcctc catgtgttat gatttatctc acatcttata 1320
gttaatagga gtaagtaaca agctactttt ttcatattat agttcgtttg attttttttt 1380
tttaaagttt ttttagtttt atccaaattt attgaaaaac ttagcaacgt ttataatacc 1440
aaattagtct catttagttt aatattgtat atattttgat aatatattta tgttatatta 1500
aaaatattac tatatttttc tataaacatt attaaaagcc atttataata taaaatggaa 1560
ggagtaatta atatggatct cccccgacat gagaatattt tccgatggtg tgacgacgcc 1620
atgtaagctt cggtgggcct ggacggccag aggtgccaac agccacgtcc aacaacccct 1680
gggtcccccc ctaacactcc aaacagtagt gagtagtgtc tcgtcgcgtt ttagtatttg 1740
atgacaaaca aagtgtgagt tgagttagcc accaccaact tgcacacgag cacatacatt 1800
tgtgtccatt ctcgccagtc acttccatct ctagtcctaa ctcctatcta gcgatgtaag 1860
cggataattt catcatccgt atataaacct gtttgttata gttaatttcc tatataatac 1920
tataacagta tacattttaa aagaaaacaa aattaggata aacaggccct gctcctatcc 1980

```
atccatggca cttggaagga ccagactcgg tcatgccatg ccaagccaag atatgggtta   2040
tggaagagta gagaagagga gagatgagag ataagcatgc gttctcctcc tcgttggatg   2100
tgtattttgg agggatttgt gtagtagtag cagcggcgcc gcggggacgg atgcggatgg   2160
tggcgctttc ggtggcgttt tcccgggggg gttttggttt ggcgcttggg ggggatggca   2220
tggcgcggcg tgcggctgca cgccacacac acgcgcgcgc acgcacgtac gtcgtcgtcg   2280
ccgcgggcgg acggtagctt agggtggtgt gttccgcgcg cgggcgcgga ttgttccatg   2340
ccgatcgatt tggcgccacc ctcgccgcgg ctcttgtcgc gtcgtgcgcc tctctcgcgc   2400
ggtttgtcct tgtcgcgttg ctcagccggc gacgggggca cggacattgg cgatgtagcc   2460
ctgcacgtgt cggcctctcc gttgatgaat gatgatgtat gtatgtattt ttttttgtct   2520
gaaggaattt gtggggaatt gttgtgtgtg caggcgctgt cgaacgggag gtataagagc   2580
tgcctgcaca gggcggtggt gaaccagcgg cgggagcggc ggtcgctggc gttcttcctg   2640
tgcccgcggg aggacagggt ggtgcggccg ccgccgagcg ccgccacgcc gcagcactac   2700
ccggacttca cctgggccga cctcatgcgc ttcacgcagc gccactaccg cgccgacacc   2760
cgcacgctcg acgccttcac gcgctggctc gcgccgccgg ccgccgacgc cgccgcgacg   2820
gcgcaggtcg aggcggccag ctgatcgccg aacggaacga aacggaacga acagaagccg   2880
atttttggcg gggcccacgc ccacgtgagg ccccacgtgg acagtgggcc cgggcggagg   2940
tggcacccac gtggaccgcg ggccccgcgc cgccttccaa ttttggaccc taccgctgta   3000
catattcata tattgcaaga agaagcaaaa cgtacgtgtg ggttgggttg ggcttctctc   3060
tattactaaa aaaaatataa tggaacgacg gatgaatgga tgcttattta tttatctaaa   3120
ttgaattcga attcggctca                                                3140

<210> SEQ ID NO 96
<211> LENGTH: 1170
<212> TYPE: DNA
<213> ORGANISM: Triticum aestivum

<400> SEQUENCE: 96

atggacacca gccctgcaac tcccctgctc ctccagcctc ctgctcccag cattgacccg     60
ttcgccgcca aggcggccgt caacaagggc ggcggcgcgg caaccgcggt gtacgacctc    120
cggagggagc cgaagatccc cgccccgttc gtgtggccgc acgccgaggt gcgccccacc    180
acggcccagg agctggccgt gccggtggtg gacgtgggcg tgctgcgcaa tggcgacgcc    240
gcggggctcc gccgcgccgt ggcgcaggtg gccgcggcgt gcgccacgca cgggttcttc    300
caggtgtccg ggcacggcgt ggacgaggcc ctggcgcgcg cggcgctgga cggcgcgagc    360
ggcttcttcc ggctgccgct ggccgagaag cagcgcgcgc ggcgcgtccc ggggaccgtg    420
tccgggtaca cgagcgcgca cgccgaccgg ttcgcctcca agctcccctg gaaggagacc    480
ctctccttcg gcttccacga ccgcgccggc gccgcgcccg tcgtggtgga ctacttcacc    540
agcaccctcg ggccggacta cgagccaatg ggagggtgt accaggagta ctgcgggaag    600
atgaaggagc tgtcgctgag gatcatggag ctgctggagc tgagccaggg cgtggagaag    660
cgcgggtact accgggagtt cttcgcggac agcagctcca tcatgcggtg caactactac    720
ccgccgtgcc cggagccgga gcgcacgctg ggcacgggcc cgcactgcga ccccacggcg    780
ctcaccatcc tactgcagga cgacgtgggc gggctggagg tcctcgtcga cggcgactgg    840
cgccccgtcc gccccgtccc cggcgccatg gtcatcaaca tcggcgacac cttcatggcg    900
ctgtcgaacg ggcggtacaa gagctgcctg caccgcgcgg tggtgaaccg gcggcaggag    960
```

```
cggcggtcgc tggccttctt cctgtgcccg cgcgaggacc gcgtggtgcg gccgccgccg   1020

ggcctgagga gcccgcggcg gtacccggac ttcacctggg ctgacctcat gcgcttcacg   1080

cagcgccact accgcgccga cacgcgcacc ctcgacgcct tcacccagtg gttctcctcc   1140

tcctcctcct cggcccagga ggcggcctga                                    1170


<210> SEQ ID NO 97
<211> LENGTH: 389
<212> TYPE: PRT
<213> ORGANISM: Triticum aestivum

<400> SEQUENCE: 97

Met Asp Thr Ser Pro Ala Thr Pro Leu Leu Leu Gln Pro Pro Ala Pro
1               5                   10                  15

Ser Ile Asp Pro Phe Ala Ala Lys Ala Ala Val Asn Lys Gly Gly Gly
            20                  25                  30

Ala Ala Thr Ala Val Tyr Asp Leu Arg Arg Glu Pro Lys Ile Pro Ala
        35                  40                  45

Pro Phe Val Trp Pro His Ala Glu Val Arg Pro Thr Thr Ala Gln Glu
    50                  55                  60

Leu Ala Val Pro Val Val Asp Val Gly Val Leu Arg Asn Gly Asp Ala
65                  70                  75                  80

Ala Gly Leu Arg Arg Ala Val Ala Gln Val Ala Ala Ala Cys Ala Thr
                85                  90                  95

His Gly Phe Phe Gln Val Ser Gly His Gly Val Asp Glu Ala Leu Ala
            100                 105                 110

Arg Ala Ala Leu Asp Gly Ala Ser Gly Phe Phe Arg Leu Pro Leu Ala
        115                 120                 125

Glu Lys Gln Arg Ala Arg Arg Val Pro Gly Thr Val Ser Gly Tyr Thr
    130                 135                 140

Ser Ala His Ala Asp Arg Phe Ala Ser Lys Leu Pro Trp Lys Glu Thr
145                 150                 155                 160

Leu Ser Phe Gly Phe His Asp Arg Ala Gly Ala Ala Pro Val Val Val
                165                 170                 175

Asp Tyr Phe Thr Ser Thr Leu Gly Pro Asp Tyr Glu Pro Met Gly Arg
            180                 185                 190

Val Tyr Gln Glu Tyr Cys Gly Lys Met Lys Glu Leu Ser Leu Arg Ile
        195                 200                 205

Met Glu Leu Leu Glu Leu Ser Gln Gly Val Glu Lys Arg Gly Tyr Tyr
    210                 215                 220

Arg Glu Phe Phe Ala Asp Ser Ser Ser Ile Met Arg Cys Asn Tyr Tyr
225                 230                 235                 240

Pro Pro Cys Pro Glu Pro Glu Arg Thr Leu Gly Thr Gly Pro His Cys
                245                 250                 255

Asp Pro Thr Ala Leu Thr Ile Leu Leu Gln Asp Asp Val Gly Gly Leu
            260                 265                 270

Glu Val Leu Val Asp Gly Asp Trp Arg Pro Val Arg Pro Val Pro Gly
        275                 280                 285

Ala Met Val Ile Asn Ile Gly Asp Thr Phe Met Ala Leu Ser Asn Gly
    290                 295                 300

Arg Tyr Lys Ser Cys Leu His Arg Ala Val Val Asn Arg Arg Gln Glu
305                 310                 315                 320

Arg Arg Ser Leu Ala Phe Phe Leu Cys Pro Arg Glu Asp Arg Val Val
                325                 330                 335
```

```
Arg Pro Pro Pro Gly Leu Arg Ser Pro Arg Arg Tyr Pro Asp Phe Thr
            340                 345                 350

Trp Ala Asp Leu Met Arg Phe Thr Gln Arg His Tyr Arg Ala Asp Thr
        355                 360                 365

Arg Thr Leu Asp Ala Phe Thr Gln Trp Phe Ser Ser Ser Ser Ser Ser
    370                 375                 380

Ala Gln Glu Ala Ala
385


<210> SEQ ID NO 98
<211> LENGTH: 3050
<212> TYPE: DNA
<213> ORGANISM: Triticum aestivum

<400> SEQUENCE: 98

ctcatggtgc tccagaccgc tcagcaagaa ccatccctga cgcgtccgcc tcactgcagc      60

gtcgccagcg cgcgctcgcc ggcggccatg gacaccagcc ctgcaactcc cctgctcctc     120

cagcctcctg ctcccagcat tgacccgttc gccgccaagg cggccgtcaa caagggcggc     180

ggcgcggcaa ccgcggtgta cgacctccgg agggagccga agatccccgc cccgttcgtg     240

tggccgcacg ccgaggtgcg ccccaccacg gcccaggagc tggccgtgcc ggtggtggac     300

gtgggcgtgc tgcgcaatgg cgacgccgcg gggctccgcc gcgccgtggc gcaggtggcc     360

gcggcgtgcg ccacgcacgg gttcttccag gtgtccgggc acggcgtgga cgaggccctg     420

gcgcgcgcgg cgctggacgg cgcgagcggc ttcttccggc tgccgctggc cgagaagcag     480

cgcgcgcggc gcgtcccggg gaccgtgtcc gggtacacga gcgcgcacgc cgaccggttc     540

gcctccaagc tcccctggaa ggagaccctc tccttcggct tccacgaccg cgccggcgcc     600

gcgcccgtcg tggtggacta cttcaccagc accctcgggc cggactacga gccaatgggg     660

taatatatcc acccgcccac acccctatcc ggccagcacg aatccatccc cgccactgca     720

tttttttcct tttgtttccg cgcgaccgta cgttcgatcg gcgcccacgt acgtacgtgc     780

gtacgcagta gcagtacttg aagccgccgt actacgtgct gagtagtgac aactgaacac     840

gtgcaggagg gtgtaccagg agtactgcgg gaagatgaag gagctgtcgc tgaggatcat     900

ggagctgctg gagctgagcc agggcgtgga gaagcgcggg tactaccggg agttcttcgc     960

ggacagcagc tccatcatgc ggtgcaacta ctacccgccg tgcccggagc cggagcgcac    1020

gctgggcacg ggcccgcact gcgaccccac ggcgctcacc atcctactgc aggacgacgt    1080

gggcgggctg gaggtcctcg tcgacggcga ctggcgcccc gtccgccccg tccccggcgc    1140

catggtcatc aacatcggcg acaccttcat ggtaattact cctctctcag cgttgctttc    1200

gctgattaat tgcagaaaca gtagtcaact acccatgctc tgttccgctg tgctctgctt    1260

cccaacgagc gaaccggccc ataaaaactg ccttgctgtc ttggaaccaa gaggaaaggg    1320

accgtgggag cctaccgaca cgacgtgatt gcactctgct tcctaacaag cgagccgccg    1380

gtagggctat caccgtaagg gctcctttga ttcaaaggaa tttcttagga tttctgaagg    1440

attgaaatcc ttaggatttt ttcctatgtt ggtacttcga ttcataggat tgaatcccat    1500

aggatttttt tcctatgaaa tcttctgtac tacatttcat aggaaatcta acatccactc    1560

caaccttttt ttatatttcc tttgtttttc atgtgccatc aaacactcct tgttaatcct    1620

ataggattca agtgggcatg ccactccaat cctatacttt tcccattcct acgttttcaa    1680

aatcctacga atcaaagagg ccctaaagct gctgacatga cgtgattttt tttttctttt    1740
```

```
ctttctttct ttctcagctc caatcaacgc tggttattag atcattagag tggacaggtt   1800
gaattaacat gcagtagtta gtagttagca gccacaaacg ggtcccgttc tctgaagtct   1860
gaactgacat aagtcctgat catcgaccat tctttgcttc ctaggacgat gcctgttgga   1920
acttgcgtcc aatgcccgtt agggagtggt aattgtcatc acttttagac tcgtcgattc   1980
cactgatgaa gacgtagcac atggatgagc caacgtatcc gtttctagtg gtctcgaaaa   2040
gtagggtttc attcattcta tctatctatc cgtccgtcca aaagggctgc gatgcgagca   2100
cttgagtcgg agccaatcag agcgcgagaa aagatagggg gggtagcaag ccatgtcgga   2160
ggggcgtttg cttccggcag gtttggattc ttgtggtagg cgggcggctc tgtacagtag   2220
cggcggtgac ggtgaggtgg cggcgctttc ggtggcgggc caacccaggt gcatgcacgc   2280
gcgctcgtcg ttttcccgcc tgaatctgcc gctgcgccca tggcaagggg gtgggtgctg   2340
ccgccgggcg atggagtaga tcacggtcgc cgtcgggctc ggccagttga tcacggttcg   2400
ttcgtgcggt actaggttcc cccacggcac tgtgactgca tcgttccggc cctcgccatt   2460
ggcgatcggg caatctcctg ttcatccgtc gctgttgatt cctcggccac gatagaccat   2520
gcgcgtgccg gtcgtcgccc cgtcgcgctc gcttcacgtg ctcgtcgcgt ggctcccgtc   2580
ccacacgagg ccgccgcttt ctgacccagt ggagcgcgtg atttacagtt tatatatgtc   2640
gctgcatttt tctttttgtg tgctgctcat tttgcttgga cggagaccgg gaacgattag   2700
ccacggatct aacgcgttgt tgcttgtttt caatgcatgc atgcaggcgc tgtcgaacgg   2760
gcggtacaag agctgcctgc accgcgcggt ggtgaaccgg cggcaggagc ggcggtcgct   2820
ggccttcttc ctgtgcccgc gcgaggaccg cgtggtgcgg ccgccgccgg gcctgaggag   2880
cccgcggcgg tacccggact tcacctgggc tgacctcatg cgcttcacgc agcgccacta   2940
ccgcgccgac acgcgcaccc tcgacgcctt cacccagtgg ttctcctcct cctcctcctc   3000
ggcccaggag gcggcctgat tctgctctgc cacgaaacga tcggtccaca              3050
```

```
<210> SEQ ID NO 99
<211> LENGTH: 1486
<212> TYPE: DNA
<213> ORGANISM: Hordeum vulgare

<400> SEQUENCE: 99

gaccagtagc atatagtttt tcttgtgttt gccatggtgg acgtgtcgaa ctttgtagaa     60
gccaatggca atgcagcagt atcgattcct gccatggaag ttgctgggag tcctcacgtc    120
ccgttcgttc ctcgggacgc gaacgcgaca gacagcaaga atgccaagga cgtcctcgac    180
ctctggcggc agcagaaaca aatcccggct cccttcatct ggccccacgc cgacgcgcgg    240
ccgtcgtcga tcttggagct ggacgtgccc gtggtcgaca tcggcgcggc cctgcacagc    300
gccgccggga tggcccgcgc cgcggcgcag gtggccgagg catgcgcgag ccacggcttc    360
ttccaggtga ccgggcacgg cgtcgacccc gcgctggccc aagcagcgct cgacggcgca    420
gcggacttct tccgcctgcc gctcgccacc aagcagcgcg cccgccgatc cccggggacc    480
gtcaaagggt acgcctccgc ccacgccgac cgcttcgccg ccaagcttcc ctggaaggag    540
actctctcct tcatccacaa ccacgtccac gaggacgtcg gcgcccgcgc aagcagtcac    600
gtcgtcgact acttcacctc cgcccttggc gacgacttca tgcacctagg ggaggtgtac    660
caggagtact gtgaggcgat ggaggacgcg tcgctggcga taatggaggt gctgggggtg    720
agcctggggc tggggagagg gtactacagg gacttcttcg ccgacggcag ctccatcatg    780
aggtgcaact actacccgcg gtgcccggag ccggaccgga cgctggggac ggggccgcac    840
```

```
tgcgacccgt cggcgctgac catcctgctg caggacggcg aggtggacgg gctccaggtg    900
ctcgtcgacg gcgcatggcg ctccgtgcgg cccaagcccg gcgagctcgt cgtaaacatc    960
ggcgacacct tcatggcgct gtcgaacggc cggtacaaga gctgcctcca ccgcgcggtg   1020
gtgcaccggg agaaggagcg ccggtcgctg gcctacttcc tcgccccgcg ggaggaccgg   1080
gtggttcgcc cgccgccttc gccggcgccg gcgccgcggc tctacccgga cttcacctgg   1140
gcggagctca tgcgattcac gcagcgccac taccgcgccg acgcccgcac gctcgacgcc   1200
ttcgcgtgct ggctcgacct gcccagctgc cccaccacgc cccaggccca agggactgtc   1260
tagtgtctgt gatgtatcat ctgtctcagc tgttgtatac gaccacttgt gtctgctagc   1320
tctgcgcttg tgtttcttat gtgagctaac taactaaata gtgtgtatat ttcttgccgc   1380
gccttatgca agccctagtc tagaacatgt aataattaac ttaagcatat acgttgatct   1440
ttggtgtatt tttcatattt ccttcataat gaataatcta ttatgc                  1486
```

<210> SEQ ID NO 100
<211> LENGTH: 1230
<212> TYPE: DNA
<213> ORGANISM: Hordeum vulgare

<400> SEQUENCE: 100

```
atggtggacg tgtcgaactt tgtagaagcc aatggcaatg cagcagtatc gattcctgcc     60
atggaagttg ctgggagtcc tcacgtcccg ttcgttcctc gggacgcgaa cgcgacagac    120
agcaagaatg ccaaggacgt cctcgacctc tggcggcagc agaaacaaat cccggctccc    180
ttcatctggc cccacgccga cgcgcggccg tcgtcgatct tggagctgga cgtgcccgtg    240
gtcgacatcg gcgcggccct gcacagcgcc gccgggatgg cccgcgccgc ggcgcaggtg    300
gccgaggcat gcgcgagcca cggcttcttc caggtgaccg ggcacggcgt cgaccccgcg    360
ctggcccaag cagcgctcga cggcgcagcg gacttcttcc gcctgccgct cgccaccaag    420
cagcgcgccc gccgatcccc ggggaccgtc aaagggtacg cctccgccca cgccgaccgc    480
ttcgccgcca agcttccctg gaaggagact ctctccttca tccacaacca cgtccacgag    540
gacgtcggcg cccgcgcaag cagtcacgtc gtcgactact tcacctccgc ccttggcgac    600
gacttcatgc acctagggga ggtgtaccag gagtactgtg aggcgatgga ggacgcgtcg    660
ctggcgataa tggaggtgct gggggtgagc ctggggctgg ggagagggta ctacagggac    720
ttcttcgccg acggcagctc catcatgagg tgcaactact acccgcggtg cccggagccg    780
gaccggacgc tggggacggg gccgcactgc gacccgtcgg cgctgaccat cctgctgcag    840
gacggcgagg tggacgggct ccaggtgctc gtcgacggcg catggcgctc cgtgcggccc    900
aagcccggcg agctcgtcgt aaacatcggc gacaccttca tggcgctgtc gaacggccgg    960
tacaagagct gcctccaccg cgcggtggtg caccgggaga aggagcgccg gtcgctggcc   1020
tacttcctcg ccccgcggga ggaccgggtg gttcgcccgc cgccttcgcc ggcgccggcg   1080
ccgcggctct acccggactt cacctgggcg gagctcatgc gattcacgca gcgccactac   1140
cgcgccgacg cccgcacgct cgacgccttc gcgtgctggc tcgacctgcc cagctgcccc   1200
accacgcccc aggcccaagg gactgtctag                                    1230
```

<210> SEQ ID NO 101
<211> LENGTH: 409
<212> TYPE: PRT
<213> ORGANISM: Hordeum vulgare

<400> SEQUENCE: 101

```
Met Val Asp Val Ser Asn Phe Val Glu Ala Asn Gly Asn Ala Ala Val
1               5                   10                  15

Ser Ile Pro Ala Met Glu Val Ala Gly Ser Pro His Val Pro Phe Val
            20                  25                  30

Pro Arg Asp Ala Asn Ala Thr Asp Ser Lys Asn Ala Lys Asp Val Leu
        35                  40                  45

Asp Leu Trp Arg Gln Gln Lys Gln Ile Pro Ala Pro Phe Ile Trp Pro
    50                  55                  60

His Ala Asp Ala Arg Pro Ser Ser Ile Leu Glu Leu Asp Val Pro Val
65                  70                  75                  80

Val Asp Ile Gly Ala Ala Leu His Ser Ala Ala Gly Met Ala Arg Ala
                85                  90                  95

Ala Ala Gln Val Ala Glu Ala Cys Ala Ser His Gly Phe Phe Gln Val
            100                 105                 110

Thr Gly His Gly Val Asp Pro Ala Leu Ala Gln Ala Ala Leu Asp Gly
        115                 120                 125

Ala Ala Asp Phe Phe Arg Leu Pro Leu Ala Thr Lys Gln Arg Ala Arg
    130                 135                 140

Arg Ser Pro Gly Thr Val Lys Gly Tyr Ala Ser Ala His Ala Asp Arg
145                 150                 155                 160

Phe Ala Ala Lys Leu Pro Trp Lys Glu Thr Leu Ser Phe Ile His Asn
                165                 170                 175

His Val His Glu Asp Val Gly Ala Arg Ala Ser Ser His Val Val Asp
            180                 185                 190

Tyr Phe Thr Ser Ala Leu Gly Asp Asp Phe Met His Leu Gly Glu Val
        195                 200                 205

Tyr Gln Glu Tyr Cys Glu Ala Met Glu Asp Ala Ser Leu Ala Ile Met
    210                 215                 220

Glu Val Leu Gly Val Ser Leu Gly Leu Gly Arg Gly Tyr Tyr Arg Asp
225                 230                 235                 240

Phe Phe Ala Asp Gly Ser Ser Ile Met Arg Cys Asn Tyr Tyr Pro Arg
                245                 250                 255

Cys Pro Glu Pro Asp Arg Thr Leu Gly Thr Gly Pro His Cys Asp Pro
            260                 265                 270

Ser Ala Leu Thr Ile Leu Leu Gln Asp Gly Glu Val Asp Gly Leu Gln
        275                 280                 285

Val Leu Val Asp Gly Ala Trp Arg Ser Val Arg Pro Lys Pro Gly Glu
    290                 295                 300

Leu Val Val Asn Ile Gly Asp Thr Phe Met Ala Leu Ser Asn Gly Arg
305                 310                 315                 320

Tyr Lys Ser Cys Leu His Arg Ala Val Val His Arg Glu Lys Glu Arg
                325                 330                 335

Arg Ser Leu Ala Tyr Phe Leu Ala Pro Arg Glu Asp Arg Val Val Arg
            340                 345                 350

Pro Pro Pro Ser Pro Ala Pro Ala Pro Arg Leu Tyr Pro Asp Phe Thr
        355                 360                 365

Trp Ala Glu Leu Met Arg Phe Thr Gln Arg His Tyr Arg Ala Asp Ala
    370                 375                 380

Arg Thr Leu Asp Ala Phe Ala Cys Trp Leu Asp Leu Pro Ser Cys Pro
385                 390                 395                 400

Thr Thr Pro Gln Ala Gln Gly Thr Val
                405
```

<210> SEQ ID NO 102
<211> LENGTH: 1423
<212> TYPE: DNA
<213> ORGANISM: Sorghum bicolor

<400> SEQUENCE: 102

```
cctctcatca caggccccag cctcactctt ctcacagcaa gacatcgcag cctcacaacc      60
acacagcaac gtgatcgcca tgggcgggct caccatggag caggccttcg tgcaggcccc     120
cgagcaccgc cccaagccca ccgtcaccga ggccaccggc atcctggtca tcgacctctc     180
gcctctcacc gccagcgaca ccgacgcggc cgcggtggac gcgctggccg ccgaggtggg     240
cgcggcgagc cgggactggg gcttcttcgt ggtggttggc cacggcgtgc ccgcggagac     300
cgtggcgcgc gcgacggcgg cgcagcgcgc gttcttcgcg ctgccggcgg agcggaaggc     360
cgccgtgcgg aggagcgagg cggagccgct cgggtactac gagtcggagc acaccaagaa     420
cgtcagggac tggaaggagg tgttcgacct cgtcccgcgc gatccgccgc cgccagcagc     480
cgtggccgac ggcgagctcg tcttcaagaa caagtggccc caggatctgc cgggcttcag     540
agaggcgctg gaggagtacg cggcagcgat ggaggagctg tcgttcaagc tgctggagct     600
gatcgcccgg agcttgaagc tgaggcccga ccggctgcac ggcttcttca aggaccagac     660
gacgttcatc cggctgaacc actaccctcc atgcccgagc ccggacctgg cgctgggagt     720
ggggcggcac aaggacgcgg gggcgctgac catcctgtac caggacgaag tgggcgggct     780
ggacgtccgg cggcgctcct ccgacggcgg cggcggcgag tgggtgcggg tgaggcccgt     840
gccggagtcg ttcgtcatca acgtcggcga cctcgtccag gtgtggagca acgacaggta     900
cgagagcgcg gagcaccggg tgtcggtgaa ctcggcgagg gagaggttct ccatgcccta     960
cttcttcaac ccggcgagct acaccatggt ggagccggtg gaggagctgg tgagcgacga    1020
cgacccgccc aggtacgacg cctacagctg gggcgagttc ttcagcacca ggaagaacag    1080
caacttcaag aagctcagcg tggagaacat tcagatcgcg catttcaaga agaccctcgt    1140
cctcgcctag ataagcagca ggatactaca ggtctacagg actaggacaa gccgatcgag    1200
gtgaccggcc gtcgtcttca gattcagtat atgcgtgtcg ccgttcgtgt tagaacaaat    1260
taataatgtg cgcgctgtgt gctgtgtgtg tggagtaaaa aaaaactaaa catggatgtg    1320
catgttcaaa aaaaaaaaca tggatgcgag tatgtttggg aataataaca ggcttgtgac    1380
ggtctggttt atttgcaaat tcaaaccgaa ttggttgatc ttc                      1423
```

<210> SEQ ID NO 103
<211> LENGTH: 1071
<212> TYPE: DNA
<213> ORGANISM: Sorghum bicolor

<400> SEQUENCE: 103

```
atgggcgggc tcaccatgga gcaggccttc gtgcaggccc ccgagcaccg ccccaagccc      60
accgtcaccg aggccaccgg catcctggtc atcgacctct cgcctctcac cgccagcgac     120
accgacgcgg ccgcggtgga cgcgctggcc gccgaggtgg gcgcggcgag ccgggactgg     180
ggcttcttcg tggtggttgg ccacggcgtg cccgcggaga ccgtggcgcg cgcgacggcg     240
gcgcagcgcg cgttcttcgc gctgccggcg gagcggaagg ccgccgtgcg gaggagcgag     300
gcggagccgc tcgggtacta cgagtcggag cacaccaaga acgtcaggga ctggaaggag     360
gtgttcgacc tcgtcccgcg cgatccgccg ccgccagcag ccgtggccga cggcgagctc     420
```

```
gtcttcaaga acaagtggcc ccaggatctg ccgggcttca gagaggcgct ggaggagtac    480

gcggcagcga tggaggagct gtcgttcaag ctgctggagc tgatcgcccg gagcttgaag    540

ctgaggcccg accggctgca cggcttcttc aaggaccaga cgacgttcat ccggctgaac    600

cactaccctc catgcccgag cccggacctg gcgctgggag tggggcggca caaggacgcg    660

ggggcgctga ccatcctgta ccaggacgaa gtgggcgggc tggacgtccg gcggcgctcc    720

tccgacggcg gcggcggcga gtgggtgcgg gtgaggcccg tgccggagtc gttcgtcatc    780

aacgtcggcg acctcgtcca ggtgtggagc aacgacaggt acgagagcgc ggagcaccgg    840

gtgtcggtga actcggcgag ggagaggttc tccatgccct acttcttcaa cccggcgagc    900

tacaccatgg tggagccggt ggaggagctg gtgagcgacg acgacccgcc caggtacgac    960

gcctacagct ggggcgagtt cttcagcacc aggaagaaca gcaacttcaa gaagctcagc   1020

gtggagaaca ttcagatcgc gcatttcaag aagaccctcg tcctcgccta g            1071
```

```
<210> SEQ ID NO 104
<211> LENGTH: 356
<212> TYPE: PRT
<213> ORGANISM: Sorghum bicolor

<400> SEQUENCE: 104

Met Gly Gly Leu Thr Met Glu Gln Ala Phe Val Gln Ala Pro Glu His
1               5                   10                  15

Arg Pro Lys Pro Thr Val Thr Glu Ala Thr Gly Ile Leu Val Ile Asp
            20                  25                  30

Leu Ser Pro Leu Thr Ala Ser Asp Thr Asp Ala Ala Ala Val Asp Ala
        35                  40                  45

Leu Ala Ala Glu Val Gly Ala Ala Ser Arg Asp Trp Gly Phe Phe Val
    50                  55                  60

Val Val Gly His Gly Val Pro Ala Glu Thr Val Ala Arg Ala Thr Ala
65                  70                  75                  80

Ala Gln Arg Ala Phe Phe Ala Leu Pro Ala Glu Arg Lys Ala Ala Val
                85                  90                  95

Arg Arg Ser Glu Ala Glu Pro Leu Gly Tyr Tyr Glu Ser Glu His Thr
            100                 105                 110

Lys Asn Val Arg Asp Trp Lys Glu Val Phe Asp Leu Val Pro Arg Asp
        115                 120                 125

Pro Pro Pro Pro Ala Ala Val Ala Asp Gly Glu Leu Val Phe Lys Asn
    130                 135                 140

Lys Trp Pro Gln Asp Leu Pro Gly Phe Arg Glu Ala Leu Glu Glu Tyr
145                 150                 155                 160

Ala Ala Ala Met Glu Glu Leu Ser Phe Lys Leu Leu Glu Leu Ile Ala
                165                 170                 175

Arg Ser Leu Lys Leu Arg Pro Asp Arg Leu His Gly Phe Phe Lys Asp
            180                 185                 190

Gln Thr Thr Phe Ile Arg Leu Asn His Tyr Pro Pro Cys Pro Ser Pro
        195                 200                 205

Asp Leu Ala Leu Gly Val Gly Arg His Lys Asp Ala Gly Ala Leu Thr
    210                 215                 220

Ile Leu Tyr Gln Asp Glu Val Gly Gly Leu Asp Val Arg Arg Arg Ser
225                 230                 235                 240

Ser Asp Gly Gly Gly Gly Glu Trp Val Arg Val Arg Pro Val Pro Glu
                245                 250                 255

Ser Phe Val Ile Asn Val Gly Asp Leu Val Gln Val Trp Ser Asn Asp
```

```
            260                 265                 270

Arg Tyr Glu Ser Ala Glu His Arg Val Ser Val Asn Ser Ala Arg Glu
        275                 280                 285

Arg Phe Ser Met Pro Tyr Phe Phe Asn Pro Ala Ser Tyr Thr Met Val
    290                 295                 300

Glu Pro Val Glu Glu Leu Val Ser Asp Asp Asp Pro Pro Arg Tyr Asp
305                 310                 315                 320

Ala Tyr Ser Trp Gly Glu Phe Phe Ser Thr Arg Lys Asn Ser Asn Phe
                325                 330                 335

Lys Lys Leu Ser Val Glu Asn Ile Gln Ile Ala His Phe Lys Lys Thr
            340                 345                 350

Leu Val Leu Ala
        355


<210> SEQ ID NO 105
<211> LENGTH: 1499
<212> TYPE: DNA
<213> ORGANISM: Sorghum bicolor

<400> SEQUENCE: 105

cctctcatca caggccccag cctcactctt ctcacagcaa gacatcgcag cctcacaacc      60

acacagcaac gtgatcgcca tgggcgggct caccatggag caggccttcg tgcaggcccc     120

cgagcaccgc cccaagccca ccgtcaccga ggccaccggc atcctggtca tcgacctctc     180

gcctctcacc gccagcgaca ccgacgcggc cgcggtggac gcgctggccg ccgaggtggg     240

cgcggcgagc cgggactggg gcttcttcgt ggtggttggc cacggcgtgc ccgcggagac     300

cgtggcgcgc gcgacggcgg cgcagcgcgc gttcttcgcg ctgccggcgg agcggaaggc     360

cgccgtgcgg aggagcgagg cggagccgct cgggtactac gagtcggagc acaccaagaa     420

cgtcagggac tggaaggagg tgttcgacct cgtcccgcgc gatccgccgc cgccagcagc     480

cgtggccgac ggcgagctcg tcttcaagaa caagtggccc caggatctgc cgggcttcag     540

gtgacgaaat caacttatct tttcgatcat attttaccat ttaatagttt aacaataatt     600

gaactttttt ttgcagagag gcgctggagg agtacgcggc agcgatggag gagctgtcgt     660

tcaagctgct ggagctgatc gcccggagct tgaagctgag gcccgaccgg ctgcacggct     720

tcttcaagga ccagacgacg ttcatccggc tgaaccacta ccctccatgc ccgagcccgg     780

acctggcgct gggagtgggg cggcacaagg acgcgggggc gctgaccatc ctgtaccagg     840

acgaagtggg cgggctggac gtccggcggc gctcctccga cggcggcggc ggcgagtggg     900

tgcgggtgag gcccgtgccg gagtcgttcg tcatcaacgt cggcgacctc gtccaggtgt     960

ggagcaacga caggtacgag agcgcggagc accgggtgtc ggtgaactcg gcgagggaga    1020

ggttctccat gccctacttc ttcaacccgg cgagctacac catggtggag ccggtggagg    1080

agctggtgag cgacgacgac ccgcccaggt acgacgccta cagctggggc gagttcttca    1140

gcaccaggaa gaacagcaac ttcaagaagc tcagcgtgga gaacattcag atcgcgcatt    1200

tcaagaagac cctcgtcctc gcctagataa gcagcaggat actacaggtc tacaggacta    1260

ggacaagccg atcgaggtga ccggccgtcg tcttcagatt cagtatatgc gtgtcgccgt    1320

tcgtgttaga acaaattaat aatgtgcgcg ctgtgtgctg tgtgtgtgga gtaaaaaaaa    1380

actaaacatg gatgtgcatg ttcaaaaaaa aaaacatgga tgcgagtatg tttgggaata    1440

ataacaggct tgtgacggtc tggtttattt gcaaattcaa accgaattgg ttgatcttc     1499
```

<210> SEQ ID NO 106
<211> LENGTH: 1490
<212> TYPE: DNA
<213> ORGANISM: Setaria italica

<400> SEQUENCE: 106

```
accccacaca cacacccgca ctgcatgcgg cgtcctagct aatcagtcgc tgctggcagc     60
ctcacaagtc acacaactcc gacgcaggaa agctcgatcc atcgccatgg gcggcttctc    120
catggatcag tccttcgtgc aggcccccga gcaccgcccc aagcccaccg tcaccgaggc    180
cacgggcatc ccgctcatcg acctctcgcc actcaccggc ggtggcggcg gcgacgcggc    240
cgccgtggac gcgctggccg ccgaggtggg cgcggcgagc cgggactggg gcttcttcgt    300
ggtggtgggg cacggtgtgc cggcggagac cgtggcgcgc gccacggagg cgcagcgcgc    360
gttcttcgcc ctgccggcgg agcggaaagc cgccgtgcgg aggagcgagg cggagccgct    420
cgggtactac gagtcggagc acaccaagaa cgtcagggac tggaaggagg tgtacgacct    480
cgtcccgggc gggcttcagc cgccgatagc cgtggccgac ggcgaggtcg tgttcgaaaa    540
caagtggccc gaagacctgc cgggattcag agaggcgttg gaggagtaca tgcaagcgat    600
ggaagagctg gcattcaaga tactggagct gatcgcccgg agcctgaacc tgaggcctga    660
cagactgcac ggcttcttca aggaccagac caccttcatc cggctcaacc actaccctcc    720
ctgcccgagc ccgacctcg ccctcggcgt cggccggcac aaggacgccg gagcactgac    780
catcctctac caggacgacg tcggcgggct cgacgtccgg cgccgttccg acggcgattg    840
ggtccgcgtc aagcctgtcc ccgactcctt catcatcaac gtcggcgacc tcatccaggt    900
ttggagcaac gacaggtacg agagcgcgga gcaccgggtt acggtgaact cggccaagga    960
gaggttctcc aggccctact tcttcaaccc ggcgggctac accatggtgg agccggtgga   1020
ggagctggtg agcgaggagg acccgccccg gtacgacgcc tacaactggg gcaacttctt   1080
cagcaccagg aagaacagca acttcaagaa gctgagcgtg gagaacatcc agatcgcgca   1140
tttcaagagg agcgtcgccg cctaggatac gcacagaaag atcccatatg ctgacttgct   1200
gatgaggcga caggcggccg tgtcgtcttc agattcagag actgggagta aacatttgtg   1260
cggtgttctg taatcgtgat gtgacgagaa ctttagatat atgtttggaa ataacagcct   1320
tgtgttggtc tggcttatcc gcaaagtcaa gattttcttc tacattttgg gattattgtt   1380
ggtaagcatt aagcaacgtc cagttcttac ttcttagctc gatcagtgga cgtaggaccg   1440
gcctctgatg acaagggtga tttatgagaa atgtcatgta tatatgttcc              1490
```

<210> SEQ ID NO 107
<211> LENGTH: 1059
<212> TYPE: DNA
<213> ORGANISM: Setaria italica

<400> SEQUENCE: 107

```
atgggcggct tctccatgga tcagtccttc gtgcaggccc ccgagcaccg ccccaagccc     60
accgtcaccg aggccacggg catcccgctc atcgacctct cgccactcac cggcggtggc    120
ggcggcgacg cggccgccgt ggacgcgctg gccgccgagg tgggcgcggc gagccgggac    180
tggggcttct tcgtggtggt ggggcacggt gtgccggcgg agaccgtggc gcgcgccacg    240
gaggcgcagc gcgcgttctt cgccctgccg gcggagcgga aagccgccgt gcggaggagc    300
gaggcggagc cgctcgggta ctacgagtcg gagcacacca agaacgtcag ggactggaag    360
gaggtgtacg acctcgtccc gggcgggctt cagccgccga tagccgtggc cgacggcgag    420
```

```
gtcgtgttcg aaaacaagtg gcccgaagac ctgccgggat tcagagaggc gttggaggag     480

tacatgcaag cgatggaaga gctggcattc aagatactgg agctgatcgc ccggagcctg     540

aacctgaggc ctgacagact gcacggcttc ttcaaggacc agaccacctt catccggctc     600

aaccactacc ctccctgccc gagccccgac ctcgccctcg gcgtcggccg gcacaaggac     660

gccggagcac tgaccatcct ctaccaggac gacgtcggcg ggctcgacgt ccggcgccgt     720

tccgacggcg attgggtccg cgtcaagcct gtccccgact ccttcatcat caacgtcggc     780

gacctcatcc aggtttggag caacgacagg tacgagagcg cggagcaccg ggttacggtg     840

aactcggcca aggagaggtt ctccaggccc tacttcttca acccggcggg ctacaccatg     900

gtggagccgg tggaggagct ggtgagcgag gaggacccgc cccggtacga cgcctacaac     960

tggggcaact tcttcagcac caggaagaac agcaacttca agaagctgag cgtggagaac    1020

atccagatcg cgcatttcaa gaggagcgtc gccgcctag                           1059
```

<210> SEQ ID NO 108
<211> LENGTH: 352
<212> TYPE: PRT
<213> ORGANISM: Setaria italica

<400> SEQUENCE: 108

```
Met Gly Gly Phe Ser Met Asp Gln Ser Phe Val Gln Ala Pro Glu His
1               5                   10                  15

Arg Pro Lys Pro Thr Val Thr Glu Ala Thr Gly Ile Pro Leu Ile Asp
            20                  25                  30

Leu Ser Pro Leu Thr Gly Gly Gly Gly Gly Asp Ala Ala Ala Val Asp
        35                  40                  45

Ala Leu Ala Ala Glu Val Gly Ala Ala Ser Arg Asp Trp Gly Phe Phe
    50                  55                  60

Val Val Val Gly His Gly Val Pro Ala Glu Thr Val Ala Arg Ala Thr
65                  70                  75                  80

Glu Ala Gln Arg Ala Phe Phe Ala Leu Pro Ala Glu Arg Lys Ala Ala
                85                  90                  95

Val Arg Arg Ser Glu Ala Glu Pro Leu Gly Tyr Tyr Glu Ser Glu His
            100                 105                 110

Thr Lys Asn Val Arg Asp Trp Lys Glu Val Tyr Asp Leu Val Pro Gly
        115                 120                 125

Gly Leu Gln Pro Pro Ile Ala Val Ala Asp Gly Glu Val Val Phe Glu
    130                 135                 140

Asn Lys Trp Pro Glu Asp Leu Pro Gly Phe Arg Glu Ala Leu Glu Glu
145                 150                 155                 160

Tyr Met Gln Ala Met Glu Glu Leu Ala Phe Lys Ile Leu Glu Leu Ile
                165                 170                 175

Ala Arg Ser Leu Asn Leu Arg Pro Asp Arg Leu His Gly Phe Phe Lys
            180                 185                 190

Asp Gln Thr Thr Phe Ile Arg Leu Asn His Tyr Pro Pro Cys Pro Ser
        195                 200                 205

Pro Asp Leu Ala Leu Gly Val Gly Arg His Lys Asp Ala Gly Ala Leu
    210                 215                 220

Thr Ile Leu Tyr Gln Asp Asp Val Gly Gly Leu Asp Val Arg Arg Arg
225                 230                 235                 240

Ser Asp Gly Asp Trp Val Arg Val Lys Pro Val Pro Asp Ser Phe Ile
                245                 250                 255

Ile Asn Val Gly Asp Leu Ile Gln Val Trp Ser Asn Asp Arg Tyr Glu
```

```
            260                 265                 270

Ser Ala Glu His Arg Val Thr Val Asn Ser Ala Lys Glu Arg Phe Ser
        275                 280                 285

Arg Pro Tyr Phe Phe Asn Pro Ala Gly Tyr Thr Met Val Glu Pro Val
    290                 295                 300

Glu Glu Leu Val Ser Glu Glu Asp Pro Pro Arg Tyr Asp Ala Tyr Asn
305                 310                 315                 320

Trp Gly Asn Phe Phe Ser Thr Arg Lys Asn Ser Asn Phe Lys Lys Leu
                325                 330                 335

Ser Val Glu Asn Ile Gln Ile Ala His Phe Lys Arg Ser Val Ala Ala
            340                 345                 350


<210> SEQ ID NO 109
<211> LENGTH: 1886
<212> TYPE: DNA
<213> ORGANISM: Setaria italica

<400> SEQUENCE: 109

accccacaca cacacccgca ctgcatgcgg cgtcctagct aatcagtcgc tgctggcagc      60

ctcacaagtc acacaactcc gacgcaggaa agctcgatcc atcgccatgg gcggcttctc     120

catggatcag tccttcgtgc aggcccccga gcaccgcccc aagcccaccg tcaccgaggc     180

cacgggcatc ccgctcatcg acctctcgcc actcaccggc ggtggcggcg gcgacgcggc     240

cgccgtggac gcgctggccg ccgaggtggg cgcggcgagc cgggactggg gcttcttcgt     300

ggtggtgggg cacggtgtgc cggcggagac cgtggcgcgc gccacggagg cgcagcgcgc     360

gttcttcgcc ctgccggcgg agcggaaagc cgccgtgcgg aggagcgagg cggagccgct     420

cgggtactac gagtcggagc acaccaagaa cgtcagggac tggaaggagg tgtacgacct     480

cgtcccgggc gggcttcagc cgccgatagc cgtggccgac ggcgaggtcg tgttcgaaaa     540

caagtggccc gaagacctgc cgggattcag gtgaatcaac ttgcgcatat tgttgtttct     600

ggcattgcat atgatcgtcg tgccagtatg ttttgacaat atttttgttt tcatattttt     660

ggtgaagatg ggaaaatctt tgttgaaata atcagggaat tttcacatct ttttttaatc     720

aaagatagaa taggttcggt tactgaattt tgatgatgga cagaaaaagc tgtgttttca     780

ctttccatct cagcgatgtt tttttgtgga tgaattctcc taaatttttg tcttttcatg     840

ttaaaacttg aacgggaatt ctcgcagaga ggcgttggag gagtacatgc aagcgatgga     900

agagctggca ttcaagatac tggagctgat cgcccggagc ctgaacctga ggcctgacag     960

actgcacggc ttcttcaagg accagaccac cttcatccgg ctcaaccact accctccctg    1020

cccgagcccc gacctcgccc tcggcgtcgg ccggcacaag gacgccggag cactgaccat    1080

cctctaccag gacgacgtcg gcgggctcga cgtccggcgc cgttccgacg gcgattgggt    1140

ccgcgtcaag cctgtccccg actccttcat catcaacgtc ggcgacctca tccaggtaca    1200

acaaacaaaa acacacgtca ttctcaaatc ttttcgtgct gttaatgctc attcacgaat    1260

tgatatctta catgaacgac tgagactttt tcaggtttgg agcaacgaca ggtacgagag    1320

cgcggagcac cgggttacgg tgaactcggc caaggagagg ttctccaggc cctacttctt    1380

caacccggcg ggctacacca tggtggagcc ggtggaggag ctggtgagcg aggaggaccc    1440

gccccggtac gacgcctaca actggggcaa cttcttcagc accaggaaga acagcaactt    1500

caagaagctg agcgtggaga acatccagat cgcgcatttc aagaggagcg tcgccgccta    1560

ggatacgcac agaaagatcc catatgctga cttgctgatg aggcgacagg cggccgtgtc    1620
```

```
gtcttcagat tcagagactg ggagtaaaca tttgtgcggt gttctgtaat cgtgatgtga   1680

cgagaacttt agatatatgt ttggaaataa cagccttgtg ttggtctggc ttatccgcaa   1740

agtcaagatt ttcttctaca ttttgggatt attgttggta agcattaagc aacgtccagt   1800

tcttacttct tagctcgatc agtggacgta ggaccggcct ctgatgacaa gggtgattta   1860

tgagaaatgt catgtatata tgttcc                                         1886
```

<210> SEQ ID NO 110
<211> LENGTH: 1379
<212> TYPE: DNA
<213> ORGANISM: Oryza sativa

<400> SEQUENCE: 110

```
aagccacacg cacacacaca cacacgctga cacacgagac gaacacttgt gctacagctt     60

ctcgccacca gctactgatc gaccatgggc ggcctctcca tggaccaggc gttcgtgcag    120

gcccccgagc accgccccaa ggcgtccgtc gccgaggccg acggcatccc ggtcatcgac    180

ctctcccctc tcctcgccgc cggcgatggc gacgccgacg gggtggacgc gctcgcggcg    240

gaggtcggga gggcgagccg ggactggggc ttcttcgtgg tggtgcgcca cggtgtgccc    300

gcggaggcgg tggcgcgcgc ggcggaggcg cagaggacgt tcttcgcgct gccgccggag    360

cggagggcgg ccgtggcgcg gagcgaggcg gcgccgatgg ggtactacgc gtccgagcac    420

accaagaacg tcagggactg gaaggaggtg ttcgacctcg tcccgcgcca gacgccgccg    480

ccgccgacga ccgccgtggc cgacggcgac ctggtgttcg acaacaagtg gcccgacgac    540

ctgccgggat tcagggaggc aatggaggag tacggcgaag cggtggagga gctggcgttc    600

aagctgctgg agctgatcgc caggagcctc ggcctgagac ccgaccgcct ccatggcttc    660

ttcaaggacg accagaccac cttcatccgg ctcaaccact accctccctg cccgagcccc    720

gacctcgccc tcggcgtcgg ccgccacaag gacgccggcg cgctcaccgt gctctaccag    780

gacgatgtcg gcggcctcga cgtccgccgc cgatccgacg gcgagtgggt gcgcgtcagg    840

cccgtccctc actccttcat catcaacgtc ggcgacatca tccaggtgtg gagcaatgac    900

aggtacgaga gcgcggagca ccgggtggcg gtgaacgtgg agaaggagag gttctccatc    960

cctttcttct tcaacccggc gggccacacc atggtggagc cactggagga ggtcgtgagc   1020

gacgagagcc cggccaggta caacccctac aactggggcg aattcttcag caccaggaag   1080

aacagcaact tcaagaagct ggacgtggag aacgtccaga tcacgcattt caggaagaat   1140

taacgcgccg gctagatcat gttcagtaaa ttttcagatg atgatgcgtg gacaaccata   1200

tagcctttgc gtcataagtt aataatgtct gtgacagtat atcatgtaaa caatcgtatg   1260

atgtggcttc tctatctgcc ggtgatggta atgtgacatt gtagaagagg gtttgtgaga   1320

tacttccttc acttaacttt tacgaatgaa tatagacaac cacaacatcc ttgtcgtga    1379
```

<210> SEQ ID NO 111
<211> LENGTH: 1059
<212> TYPE: DNA
<213> ORGANISM: Oryza sativa

<400> SEQUENCE: 111

```
atgggcggcc tctccatgga ccaggcgttc gtgcaggccc ccgagcaccg ccccaaggcg     60

tccgtcgccg aggccgacgg catcccggtc atcgacctct cccctctcct cgccgccggc    120

gatggcgacg ccgacggggt ggacgcgctc gcggcggagg tcgggagggc gagccgggac    180

tggggcttct tcgtggtggt gcgccacggt gtgcccgcgg aggcggtggc gcgcgcggcg    240
```

```
gaggcgcaga ggacgttctt cgcgctgccg ccggagcgga gggcggccgt ggcgcggagc    300

gaggcggcgc cgatggggta ctacgcgtcc gagcacacca agaacgtcag ggactggaag    360

gaggtgttcg acctcgtccc gcgccagacg ccgccgccgc cgacgaccgc cgtggccgac    420

ggcgacctgg tgttcgacaa caagtggccc gacgacctgc cgggattcag ggaggcaatg    480

gaggagtacg gcgaagcggt ggaggagctg gcgttcaagc tgctggagct gatcgccagg    540

agcctcggcc tgagacccga ccgcctccat ggcttcttca aggacgacca gaccaccttc    600

atccggctca accactaccc tccctgcccg agccccgacc tcgccctcgg cgtcggccgc    660

cacaaggacg ccggcgcgct caccgtgctc taccaggacg atgtcggcgg cctcgacgtc    720

cgccgccgat ccgacggcga gtgggtgcgc gtcaggcccg tccctcactc cttcatcatc    780

aacgtcggcg acatcatcca ggtgtggagc aatgacaggt acgagagcgc ggagcaccgg    840

gtggcggtga acgtggagaa ggagaggttc tccatccctt tcttcttcaa cccggcgggc    900

cacaccatgg tggagccact ggaggaggtc gtgagcgacg agagcccggc caggtacaac    960

ccctacaact ggggcgaatt cttcagcacc aggaagaaca gcaacttcaa gaagctggac   1020

gtggagaacg tccagatcac gcatttcagg aagaattaa                          1059
```

<210> SEQ ID NO 112
<211> LENGTH: 352
<212> TYPE: PRT
<213> ORGANISM: Oryza sativa

<400> SEQUENCE: 112

```
Met Gly Gly Leu Ser Met Asp Gln Ala Phe Val Gln Ala Pro Glu His
1               5                   10                  15

Arg Pro Lys Ala Ser Val Ala Glu Ala Asp Gly Ile Pro Val Ile Asp
            20                  25                  30

Leu Ser Pro Leu Leu Ala Ala Gly Asp Gly Asp Ala Asp Gly Val Asp
        35                  40                  45

Ala Leu Ala Ala Glu Val Gly Arg Ala Ser Arg Asp Trp Gly Phe Phe
    50                  55                  60

Val Val Val Arg His Gly Val Pro Ala Glu Ala Val Ala Arg Ala Ala
65                  70                  75                  80

Glu Ala Gln Arg Thr Phe Phe Ala Leu Pro Pro Glu Arg Arg Ala Ala
                85                  90                  95

Val Ala Arg Ser Glu Ala Ala Pro Met Gly Tyr Tyr Ala Ser Glu His
            100                 105                 110

Thr Lys Asn Val Arg Asp Trp Lys Glu Val Phe Asp Leu Val Pro Arg
        115                 120                 125

Gln Thr Pro Pro Pro Pro Thr Thr Ala Val Ala Asp Gly Asp Leu Val
    130                 135                 140

Phe Asp Asn Lys Trp Pro Asp Asp Leu Pro Gly Phe Arg Glu Ala Met
145                 150                 155                 160

Glu Glu Tyr Gly Glu Ala Val Glu Glu Leu Ala Phe Lys Leu Leu Glu
                165                 170                 175

Leu Ile Ala Arg Ser Leu Gly Leu Arg Pro Asp Arg Leu His Gly Phe
            180                 185                 190

Phe Lys Asp Asp Gln Thr Thr Phe Ile Arg Leu Asn His Tyr Pro Pro
        195                 200                 205

Cys Pro Ser Pro Asp Leu Ala Leu Gly Val Gly Arg His Lys Asp Ala
    210                 215                 220
```

```
Gly Ala Leu Thr Val Leu Tyr Gln Asp Asp Val Gly Gly Leu Asp Val
225                 230                 235                 240

Arg Arg Arg Ser Asp Gly Glu Trp Val Arg Val Arg Pro Val Pro His
                245                 250                 255

Ser Phe Ile Ile Asn Val Gly Asp Ile Ile Gln Val Trp Ser Asn Asp
            260                 265                 270

Arg Tyr Glu Ser Ala Glu His Arg Val Ala Val Asn Val Glu Lys Glu
        275                 280                 285

Arg Phe Ser Ile Pro Phe Phe Phe Asn Pro Ala Gly His Thr Met Val
    290                 295                 300

Glu Pro Leu Glu Glu Val Val Ser Asp Glu Ser Pro Ala Arg Tyr Asn
305                 310                 315                 320

Pro Tyr Asn Trp Gly Glu Phe Phe Ser Thr Arg Lys Asn Ser Asn Phe
                325                 330                 335

Lys Lys Leu Asp Val Glu Asn Val Gln Ile Thr His Phe Arg Lys Asn
            340                 345                 350


<210> SEQ ID NO 113
<211> LENGTH: 2027
<212> TYPE: DNA
<213> ORGANISM: Oryza sativa

<400> SEQUENCE: 113

aagccacacg cacacacaca cacacgctga cacacgagac gaacacttgt gctacagctt     60

ctcgccacca gctactgatc gaccatgggc ggcctctcca tggaccaggc gttcgtgcag    120

gcccccgagc accgccccaa ggcgtccgtc gccgaggccg acggcatccc ggtcatcgac    180

ctctcccctc tcctcgccgc cggcgatggc gacgccgacg gggtggacgc gctcgcggcg    240

gaggtcggga gggcgagccg ggactggggc ttcttcgtgg tggtgcgcca cggtgtgccc    300

gcggaggcgg tggcgcgcgc ggcggaggcg cagaggacgt tcttcgcgct gccgccggag    360

cggagggcgg ccgtggcgcg gagcgaggcg gcgccgatgg ggtactacgc gtccgagcac    420

accaagaacg tcagggactg gaaggaggtg ttcgacctcg tcccgcgcca gacgccgccg    480

ccgccgacga ccgccgtggc cgacggcgac ctggtgttcg acaacaagtg gcccgacgac    540

ctgccgggat tcaggtcagg tcaccacatc gatcgatcgt cttcttcatc ctcgcatcaa    600

ttcagttcaa cctcatcgaa ttcttgagca gggaggcaat ggaggagtac ggcgaagcgg    660

tggaggagct ggcgttcaag ctgctggagc tgatcgccag gagcctcggc ctgagacccg    720

accgcctcca tggcttcttc aaggacgacc agaccacctt catccggctc aaccactacc    780

ctccctgccc gagccccgac ctcgccctcg gcgtcggccg ccacaaggac gccggcgcgc    840

tcaccgtgct ctaccaggac gatgtcggcg gcctcgacgt ccgccgccga tccgacggcg    900

agtgggtgcg cgtcaggccc gtccctcact ccttcatcat caacgtcggc gacatcatcc    960

aggtactttt ttttttgagc agctacatat ttatcaacaa attttcttct aacaatttat   1020

cggacataaa tatattacaa tgaaagaata attgtatcat aacttgtgtg tccttatatg   1080

taagttttag aaatcctata gtaacatggt attttcgcga aagcggagat tgtgagaccg   1140

tatcttttca cccatgcgcg tcatatgatt tttttttctt gccaacttaa ataaatttca   1200

aagtaaatct aatagattaa aattatgtga aacttacata taagttttct acggtaacac   1260

gctattttca cgaaacggag gtcgttccaa gttgaatgaa tcttgaagta aatctaacga   1320

tttaaaatta tgtgcataca cgttatatta cagttatata caagttataa tataattaca   1380

ctacaattat aacggtattc atagttgaca aacttttaaa agagaattag ttaataaata   1440
```

```
tataacaaca ttgtagttta attgttacta tttgacatca tttttatttg cattttgaat   1500
ttgactgaaa aaattgagag tgcgcttgtc caggtgtgga gcaatgacag gtacgagagc   1560
gcggagcacc gggtggcggt gaacgtggag aaggagaggt tctccatccc tttcttcttc   1620
aacccggcgg gccacaccat ggtggagcca ctggaggagg tcgtgagcga cgagagcccg   1680
gccaggtaca acccctacaa ctggggcgaa ttcttcagca ccaggaagaa cagcaacttc   1740
aagaagctgg acgtggagaa cgtccagatc acgcatttca ggaagaatta acgcgccggc   1800
tagatcatgt tcagtaaatt ttcagatgat gatgcgtgga caaccatata gcctttgcgt   1860
cataagttaa taatgtctgt gacagtatat catgtaaaca atcgtatgat gtggcttctc   1920
tatctgccgg tgatggtaat gtgacattgt agaagagggt ttgtgagata cttccttcac   1980
ttaactttta cgaatgaata tagacaacca caacatcctt gtcgtga                 2027
```

<210> SEQ ID NO 114
<211> LENGTH: 1747
<212> TYPE: DNA
<213> ORGANISM: Triticum aestivum

<400> SEQUENCE: 114

```
tcactcaagg ccacaacaca ctcgccagtc catcgccacc atacgtgaca acttgagtta     60
cttgatctgt tgctcatcga tctcgacatc gccatgggcg gcctctccat ggaccaggcc    120
ttcgtgcagg cccccgagca tcgcaccaag gcgaacctcg ccgacgcggc cggcatcccg    180
gtcatcgacc tctcccctct cgccgccggc gacaaggccg gcctggacgc cctcgcggcc    240
gaggtgggca gggcgagccg tgactggggg ttcttcgtgg tggtgcgcca cggcgtgccg    300
gcggagacgg tggcgcgggc gctggaggcg cagagggcct tcttcgcgct gcccgcggac    360
cggaaggcgg ccgtgcggag ggacgaggcg gcgccgctgg ggtactacga gtcggagcac    420
accaagaacg tcagggactg gaaggaggtg ttcgacctcg tcccccgcga gccgccgccg    480
cctgccgcgg ttgccgacgg cgagctcatg ttcgagaaca agtggcccga ggacctgccg    540
gggttcagag aggctctcga agagtacgag aaagcgatgg aggagctggc gttcaagctg    600
ctggagctga tcgcccggag cctgggactg agaccggacc ggctgcacgg cttcttcaag    660
gaccagacca ccttcatccg gctgaaccac tacccgccct gccccagccc cgacctcgcc    720
ctcggcgtcg gtcgccacaa ggacgccggc gcgctcacca tcctctacca ggacgacgtc    780
ggcgggctcg acgtccggcg ccgctccgac ggcgagtggg tgcgcgtcag gcctgtcccg    840
gactcctacg tcatcaacgt cggcgacatc atccaggtgt ggagcaacga caggtacgag    900
agcgcggagc acagggtgtc ggtgaactcg cacaaggaga ggttctccat gccctacttc    960
ttcgaccccg ggagcgacgc catgatcgag ccgttggagg agatggtgag cgacgaaagg   1020
ccggccaggt acgacgccta caactggggc aacttcttca gcaccaggaa gaacagcaac   1080
ttcaggaagc tcgccgtcga aaacgtccag atcgcacact tcagaaagga ccgaccttaa   1140
atgaaggatc cctcatgaat tcatgatcct tccgctctcc tcagtgatcc tagtgctaca   1200
actacaagca tctccccgtt tgtagtaatc atatataaat aagtattccc tccgtaaact   1260
aatataagag catttaaaac actactctag tgatctaaat gctcttatat tagtttacag   1320
agagagtatt gtgtattaat aatgactttc tctgtttcaa aataagtgat gacgtggttt   1380
tagttcaatt ttttttagag aggaggcatc tgacgggcct taaactgagg accttagagt   1440
acaaacaagg ttcgacgaaa gtaagtttaa gggatacaag gccgtagcca acaaaacgcg   1500
```

acgcagcgcg caatctaaaa tcagcgtgct gtcaaggtag ctggagacgt ccatgccgtt 1560
aatctctctc aagaagctcg ccgaagctca gtgcaccttg cgtgcactct tgtgaagagc 1620
accttcacgt gtcctttgtc ctgagatttt gtcaacagtt tccatgactg caagaaaaac 1680
actagtttgt ataatagctc agcgggatgt cgaatgaatt gcccctcaat caaagcttta 1740
tttctag 1747

<210> SEQ ID NO 115
<211> LENGTH: 1047
<212> TYPE: DNA
<213> ORGANISM: Triticum aestivum

<400> SEQUENCE: 115
atgggcggcc tctccatgga ccaggccttc gtgcaggccc ccgagcatcg caccaaggcg 60
aacctcgccg acgcggccgg catcccggtc atcgacctct cccctctcgc cgccggcgac 120
aaggccggcc tggacgccct cgcggccgag gtgggcaggg cgagccgtga ctgggggttc 180
ttcgtggtgg tgcgccacgg cgtgccggcg gagacggtgg cgcgggcgct ggaggcgcag 240
agggccttct tcgcgctgcc cgcggaccgg aaggcggccg tgcggaggga cgaggcggcg 300
ccgctggggt actacgagtc ggagcacacc aagaacgtca gggactggaa ggaggtgttc 360
gacctcgtcc cccgcgagcc gccgccgcct gccgcggttg ccgacggcga gctcatgttc 420
gagaacaagt ggcccgagga cctgccgggg ttcagagagg ctctcgaaga gtacgagaaa 480
gcgatggagg agctggcgtt caagctgctg gagctgatcg cccggagcct gggactgaga 540
ccggaccggc tgcacggctt cttcaaggac cagaccacct tcatccggct gaaccactac 600
ccgccctgcc ccagccccga cctcgccctc ggcgtcggtc gccacaagga cgccggcgcg 660
ctcaccatcc tctaccagga cgacgtcggc gggctcgacg tccggcgccg ctccgacggc 720
gagtgggtgc gcgtcaggcc tgtcccggac tcctacgtca tcaacgtcgg cgacatcatc 780
caggtgtgga gcaacgacag gtacgagagc gcggagcaca gggtgtcggt gaactcgcac 840
aaggagaggt tctccatgcc ctacttcttc gaccccggga gcgacgccat gatcgagccg 900
ttggaggaga tggtgagcga cgaaaggccg gccaggtacg acgcctacaa ctggggcaac 960
ttcttcagca ccaggaagaa cagcaacttc aggaagctcg ccgtcgaaaa cgtccagatc 1020
gcacacttca gaaaggaccg accttaa 1047

<210> SEQ ID NO 116
<211> LENGTH: 348
<212> TYPE: PRT
<213> ORGANISM: Triticum aestivum

<400> SEQUENCE: 116

Met Gly Gly Leu Ser Met Asp Gln Ala Phe Val Gln Ala Pro Glu His
1 5 10 15

Arg Thr Lys Ala Asn Leu Ala Asp Ala Ala Gly Ile Pro Val Ile Asp
20 25 30

Leu Ser Pro Leu Ala Ala Gly Asp Lys Ala Gly Leu Asp Ala Leu Ala
35 40 45

Ala Glu Val Gly Arg Ala Ser Arg Asp Trp Gly Phe Phe Val Val Val
50 55 60

Arg His Gly Val Pro Ala Glu Thr Val Ala Arg Ala Leu Glu Ala Gln
65 70 75 80

Arg Ala Phe Phe Ala Leu Pro Ala Asp Arg Lys Ala Ala Val Arg Arg
85 90 95

```
Asp Glu Ala Ala Pro Leu Gly Tyr Tyr Glu Ser Glu His Thr Lys Asn
            100                 105                 110

Val Arg Asp Trp Lys Glu Val Phe Asp Leu Val Pro Arg Glu Pro Pro
        115                 120                 125

Pro Pro Ala Ala Val Ala Asp Gly Glu Leu Met Phe Glu Asn Lys Trp
    130                 135                 140

Pro Glu Asp Leu Pro Gly Phe Arg Glu Ala Leu Glu Glu Tyr Glu Lys
145                 150                 155                 160

Ala Met Glu Glu Leu Ala Phe Lys Leu Leu Glu Leu Ile Ala Arg Ser
                165                 170                 175

Leu Gly Leu Arg Pro Asp Arg Leu His Gly Phe Phe Lys Asp Gln Thr
            180                 185                 190

Thr Phe Ile Arg Leu Asn His Tyr Pro Pro Cys Pro Ser Pro Asp Leu
        195                 200                 205

Ala Leu Gly Val Gly Arg His Lys Asp Ala Gly Ala Leu Thr Ile Leu
    210                 215                 220

Tyr Gln Asp Asp Val Gly Gly Leu Asp Val Arg Arg Arg Ser Asp Gly
225                 230                 235                 240

Glu Trp Val Arg Val Arg Pro Val Pro Asp Ser Tyr Val Ile Asn Val
                245                 250                 255

Gly Asp Ile Ile Gln Val Trp Ser Asn Asp Arg Tyr Glu Ser Ala Glu
            260                 265                 270

His Arg Val Ser Val Asn Ser His Lys Glu Arg Phe Ser Met Pro Tyr
        275                 280                 285

Phe Phe Asp Pro Gly Ser Asp Ala Met Ile Glu Pro Leu Glu Glu Met
    290                 295                 300

Val Ser Asp Glu Arg Pro Ala Arg Tyr Asp Ala Tyr Asn Trp Gly Asn
305                 310                 315                 320

Phe Phe Ser Thr Arg Lys Asn Ser Asn Phe Arg Lys Leu Ala Val Glu
                325                 330                 335

Asn Val Gln Ile Ala His Phe Arg Lys Asp Arg Pro
            340                 345
```

<210> SEQ ID NO 117
<211> LENGTH: 1863
<212> TYPE: DNA
<213> ORGANISM: Triticum aestivum

<400> SEQUENCE: 117

```
tcactcaagg ccacaacaca ctcgccagtc catcgccacc atacgtgaca acttgagtta     60

cttgatctgt tgctcatcga tctcgacatc gccatgggcg gcctctccat ggaccaggcc    120

ttcgtgcagg cccccgagca tcgcaccaag gcgaacctcg ccgacgcggc cggcatcccg    180

gtcatcgacc tctcccctct cgccgccggc gacaaggccg gcctggacgc cctcgcggcc    240

gaggtgggca gggcgagccg tgactggggg ttcttcgtgg tggtgcgcca cggcgtgccg    300

gcggagacgg tggcgcgggc gctggaggcg cagagggcct tcttcgcgct gcccgcggac    360

cggaaggcgg ccgtgcggag ggacgaggcg gcgccgctgg ggtactacga gtcggagcac    420

accaagaacg tcagggactg gaaggaggtg ttcgacctcg tcccccgcga gccgccgccg    480

cctgccgcgg ttgccgacgg cgagctcatg ttcgagaaca agtggcccga ggacctgccg    540

gggttcaggt acggtcatca actcaatcaa ttctgcgacc ccgagagaaa tggttcacta    600

ttattcgtgg ttcatacgta tgattcagac gttaatctcg atgcaaattg atttgtgcat    660
```

```
gcagagaggc tctcgaagag tacgagaaag cgatggagga gctggcgttc aagctgctgg    720
agctgatcgc ccggagcctg ggactgagac cggaccggct gcacggcttc ttcaaggacc    780
agaccacctt catccggctg aaccactacc cgccctgccc cagccccgac ctcgccctcg    840
gcgtcggtcg ccacaaggac gccggcgcgc tcaccatcct ctaccaggac gacgtcggcg    900
ggctcgacgt ccggcgccgc tccgacggcg agtgggtgcg cgtcaggcct gtcccggact    960
cctacgtcat caacgtcggc gacatcatcc aggtgtggag caacgacagg tacgagagcg   1020
cggagcacag ggtgtcggtg aactcgcaca aggagaggtt ctccatgccc tacttcttcg   1080
accccgggag cgacgccatg atcgagccgt tggaggagat ggtgagcgac gaaaggccgg   1140
ccaggtacga cgcctacaac tggggcaact tcttcagcac caggaagaac agcaacttca   1200
ggaagctcgc cgtcgaaaac gtccagatcg cacacttcag aaaggaccga ccttaaatga   1260
aggatccctc atgaattcat gatccttccg ctctcctcag tgatcctagt gctacaacta   1320
caagcatctc cccgtttgta gtaatcatat ataaataagt attccctccg taaactaata   1380
taagagcatt taaaacacta ctctagtgat ctaaatgctc ttatattagt ttacagagag   1440
agtattgtgt attaataatg actttctctg tttcaaaata agtgatgacg tggttttagt   1500
tcaatttttt ttagagagga ggcatctgac gggccttaaa ctgaggacct tagagtacaa   1560
acaaggttcg acgaaagtaa gtttaaggga tacaaggccg tagccaacaa aacgcgacgc   1620
agcgcgcaat ctaaaatcag cgtgctgtca aggtagctgg agacgtccat gccgttaatc   1680
tctctcaaga agctcgccga agctcagtgc accttgcgtg cactcttgtg aagagcacct   1740
tcacgtgtcc tttgtcctga gattttgtca acagtttcca tgactgcaag aaaaacacta   1800
gtttgtataa tagctcagcg ggatgtcgaa tgaattgccc ctcaatcaaa gctttatttc   1860
tag                                                                 1863
```

<210> SEQ ID NO 118
<211> LENGTH: 349
<212> TYPE: PRT
<213> ORGANISM: Hordeum vulgare

<400> SEQUENCE: 118

```
Met Gly Gly Leu Ser Met Gly Gln Ala Phe Val Gln Ala Pro Glu His
1               5                   10                  15

Arg Thr Lys Pro Thr Leu Ala Asp Ala Asp Gly Ile Pro Val Ile Asp
            20                  25                  30

Leu Ser Pro Leu Ala Ala Gly Asp Glu Ala Gly Val Asp Ala Leu Ala
        35                  40                  45

Ala Glu Val Gly Arg Ala Ser Arg Asp Trp Gly Phe Phe Val Val Val
    50                  55                  60

Arg His Gly Val Pro Ala Glu Thr Val Ala Arg Ala Leu Glu Ala Gln
65                  70                  75                  80

Arg Ala Phe Phe Ala Leu Pro Ala Glu Arg Lys Ala Ala Val Arg Arg
                85                  90                  95

Asp Glu Ala Ala Pro Leu Gly Tyr Tyr Glu Ser Glu His Thr Lys Asn
            100                 105                 110

Val Arg Asp Trp Lys Glu Val Phe Asp Phe Val Pro Arg Glu Pro Pro
        115                 120                 125

Pro Pro Ala Ala Val Ala Asp Gly Glu Leu Val Phe Glu Asn Lys Trp
    130                 135                 140

Pro Glu Asp Leu Pro Gly Phe Arg Val Ala Phe Glu Glu Tyr Ala Lys
145                 150                 155                 160
```

```
Ala Met Glu Glu Leu Ala Phe Lys Leu Leu Glu Leu Ile Ala Arg Ser
                165                 170                 175

Leu Gly Leu Thr Pro Asp Arg Leu Asn Gly Phe Phe Lys Asp His Gln
            180                 185                 190

Thr Thr Phe Ile Arg Leu Asn His Tyr Pro Pro Cys Pro Ser Pro Asp
        195                 200                 205

Leu Ala Leu Gly Val Gly Arg His Lys Asp Ala Gly Ala Leu Thr Val
    210                 215                 220

Leu Tyr Gln Asp Asp Val Gly Gly Leu Asp Val Arg His Arg Ser Asp
225                 230                 235                 240

Gly Glu Trp Val Arg Val Arg Pro Val Pro Asp Ser Tyr Val Ile Asn
                245                 250                 255

Val Gly Asp Ile Ile Gln Val Trp Ser Asn Asp Arg Tyr Glu Ser Ala
            260                 265                 270

Glu His Arg Val Ser Val Asn Ser Asp Lys Glu Arg Phe Ser Met Pro
        275                 280                 285

Tyr Phe Phe Asn Pro Gly Ser Asp Ala Met Val Glu Pro Leu Glu Glu
    290                 295                 300

Met Val Ser Asp Glu Arg Pro Ala Arg Tyr Asp Ala Tyr Asn Trp Gly
305                 310                 315                 320

His Phe Phe Ser Thr Arg Lys Asn Ser Asn Phe Lys Lys Leu Asp Val
                325                 330                 335

Glu Asn Val Gln Ile Ala His Phe Arg Lys Leu His Leu
            340                 345


<210> SEQ ID NO 119
<211> LENGTH: 1963
<212> TYPE: DNA
<213> ORGANISM: Sorghum bicolor

<400> SEQUENCE: 119

tataaatacc acgccatgta cttctctgct tctacacttc tccagcttct ctcatgccat      60

accactagtg caaggtccta gatttacact tggtgctaca gcttcttcct ccctccctcc     120

cctctctagg cagctagcac gcagcgcagc acacgaaaca tctattgacc ggccgcctcc     180

gccggggatc cataattact atactaccaa tcggccagcg tcatgccgac gccgtcgcac     240

ctcgcgaacc cgcgctactt cgacttccgt gcggcgcggc gggtgccgga gacgcacgcc     300

tggccggggc tgcacgacca ccccgtcgtg gacggcggcg cgccggggcc agacgccgtc     360

cccgtggtgg acctcgcggg ggcggcggac gagccgagag ccgcggtggt ggcccaagtg     420

gcgcgcgccg ccgagcaatg gggcgcgttc ctgctcacgg ggcacggcgt ccccgcggag     480

ctgctggcgc gcgtcgagga ccggatcgcc accatgttcg cgctgccagc ggacgacaag     540

atgcgcgccg tgcgcgggcc tggcgacgcc tgcggctacg gctccccgcc catctcctcc     600

ttcttctcca agtgcatgtg gtcggaggga tacaccttct cgccggccaa cctccgcgcc     660

gacctccgca agctctggcc taaggccggc gacgactaca ccagcttctg tgatgtgatg     720

gaggagttcc acaagcacat gcgtgccctc gcggacaagc tgctggagct gttcctcatg     780

gcgctggggc tcaccgacga gcaggtcggc ggcgtggagg cggagcggag gatcgccgag     840

acgatgaccg ccaccatgca cctcaactgg taccctcggt gcccggaccc gcgccgcgcg     900

ctggggctga tcgcgcacac cgactcgggc ttcttcacct tcgtgctgca gagcctcgtc     960

ccggggctgc agctcttccg ccacgccccg gaccggtggg tggcggtgcc ggcggtaccg    1020
```

ggcgccttcg tcgtcaacgt gggcgacctc ttccacatcc tcaccaacgg ccggttccac 1080
agcgtgtacc accgcgccgt cgtgaaccgg gacctcgaca ggatatctct cggctacttc 1140
ctcggcccgc cgccgcacgc caaggtggcg ccgctaaggg aggccgtgcc gcccggccgc 1200
acccccgcgt accgcgccgt cacgtggccc gagtacatgg gcgtccgcaa gaaggccttc 1260
accaccggcg catccgcgct caagatggtc gccctcgccg ccgccgccgc cgccgccgac 1320
ctcgacgatg acgccggtgc tggcgccgcc gccgaacctg tcgtccatca gcagctactc 1380
gtctcgtcgt agccgatcga tcgccggatc ggtcgagact gatgatgatg atgcatatat 1440
actcgtcgat ggagtagaca gactaatcaa gcaaccctga aactatgaat gcatgcgtgc 1500
gcttcgtgct tgcttgcgca tgcagctagc aggcttcatt ccgttccgca gctgctctgc 1560
tccaacctgc tctgctggat tgatgtatat ggtagaagaa ttaagagatc gatggatgac 1620
ggaggaagaa gaagacgaag acgacgatga ggaaaaggac acgctgtacg tagctggttc 1680
ttctagtcta gtttacagca ggccgggcgg ccggctgctg cttccaatcg agtttgtcgt 1740
tactgacgat tgttagtgga tcgattaact aatctggaat tctggattat taatataatg 1800
catgtggttt ggcatctggc gtaaagcagg taatggtacc tagccagtag ccagtagcca 1860
ggctggtcaa tgataggtct ataccctgat cctgtactgt tgtttctttc ggtctttctg 1920
agagagaaaa aaaacgaata tatggcgtac tcaattcatc aaa 1963

<210> SEQ ID NO 120
<211> LENGTH: 1170
<212> TYPE: DNA
<213> ORGANISM: Sorghum bicolor

<400> SEQUENCE: 120
atgccgacgc cgtcgcacct cgcgaacccg cgctacttcg acttccgtgc ggcgcggcgg 60
gtgccggaga cgcacgcctg gccggggctg cacgaccacc ccgtcgtgga cggcggcgcg 120
ccggggccag acgccgtccc cgtggtggac ctcgcggggg cggcggacga gccgagagcc 180
gcggtggtgg cccaagtggc gcgcgccgcc gagcaatggg gcgcgttcct gctcacgggg 240
cacggcgtcc ccgcggagct gctggcgcgc gtcgaggacc ggatcgccac catgttcgcg 300
ctgccagcgg acgacaagat gcgcgccgtg cgcgggcctg gcgacgcctg cggctacggc 360
tccccgccca tctcctcctt cttctccaag tgcatgtggt cggagggata caccttctcg 420
ccggccaacc tccgcgccga cctccgcaag ctctggccta aggccggcga cgactacacc 480
agcttctgtg atgtgatgga ggagttccac aagcacatgc gtgccctcgc ggacaagctg 540
ctggagctgt tcctcatggc gctggggctc accgacgagc aggtcggcgg cgtggaggcg 600
gagcggagga tcgccgagac gatgaccgcc accatgcacc tcaactggta ccctcggtgc 660
ccggacccgc gccgcgcgct ggggctgatc gcgcacaccg actcgggctt cttcaccttc 720
gtgctgcaga gcctcgtccc ggggctgcag ctcttccgcc acgccccgga ccggtgggtg 780
gcggtgccgg cggtaccggg cgccttcgtc gtcaacgtgg gcgacctctt ccacatcctc 840
accaacggcc ggttccacag cgtgtaccac cgcgccgtcg tgaaccggga cctcgacagg 900
atatctctcg gctacttcct cggcccgccg ccgcacgcca aggtggcgcc gctaagggag 960
gccgtgccgc ccggccgcac cccgcgtac cgcgccgtca cgtggcccga gtacatgggc 1020
gtccgcaaga aggccttcac caccggcgca tccgcgctca agatggtcgc cctcgccgcc 1080
gccgccgccg ccgccgacct cgacgatgac gccggtgctg gcgccgccgc cgaacctgtc 1140
gtccatcagc agctactcgt ctcgtcgtag 1170

<210> SEQ ID NO 121
<211> LENGTH: 389
<212> TYPE: PRT
<213> ORGANISM: Sorghum bicolor

<400> SEQUENCE: 121

```
Met Pro Thr Pro Ser His Leu Ala Asn Pro Arg Tyr Phe Asp Phe Arg
1               5                   10                  15

Ala Ala Arg Arg Val Pro Glu Thr His Ala Trp Pro Gly Leu His Asp
            20                  25                  30

His Pro Val Val Asp Gly Gly Ala Pro Gly Pro Asp Ala Val Pro Val
        35                  40                  45

Val Asp Leu Ala Gly Ala Ala Asp Glu Pro Arg Ala Ala Val Val Ala
    50                  55                  60

Gln Val Ala Arg Ala Ala Glu Gln Trp Gly Ala Phe Leu Leu Thr Gly
65                  70                  75                  80

His Gly Val Pro Ala Glu Leu Leu Ala Arg Val Glu Asp Arg Ile Ala
                85                  90                  95

Thr Met Phe Ala Leu Pro Ala Asp Asp Lys Met Arg Ala Val Arg Gly
            100                 105                 110

Pro Gly Asp Ala Cys Gly Tyr Gly Ser Pro Pro Ile Ser Ser Phe Phe
        115                 120                 125

Ser Lys Cys Met Trp Ser Glu Gly Tyr Thr Phe Ser Pro Ala Asn Leu
    130                 135                 140

Arg Ala Asp Leu Arg Lys Leu Trp Pro Lys Ala Gly Asp Asp Tyr Thr
145                 150                 155                 160

Ser Phe Cys Asp Val Met Glu Glu Phe His Lys His Met Arg Ala Leu
                165                 170                 175

Ala Asp Lys Leu Leu Glu Leu Phe Leu Met Ala Leu Gly Leu Thr Asp
            180                 185                 190

Glu Gln Val Gly Gly Val Glu Ala Glu Arg Arg Ile Ala Glu Thr Met
        195                 200                 205

Thr Ala Thr Met His Leu Asn Trp Tyr Pro Arg Cys Pro Asp Pro Arg
    210                 215                 220

Arg Ala Leu Gly Leu Ile Ala His Thr Asp Ser Gly Phe Phe Thr Phe
225                 230                 235                 240

Val Leu Gln Ser Leu Val Pro Gly Leu Gln Leu Phe Arg His Ala Pro
                245                 250                 255

Asp Arg Trp Val Ala Val Pro Ala Val Pro Gly Ala Phe Val Val Asn
            260                 265                 270

Val Gly Asp Leu Phe His Ile Leu Thr Asn Gly Arg Phe His Ser Val
        275                 280                 285

Tyr His Arg Ala Val Val Asn Arg Asp Leu Asp Arg Ile Ser Leu Gly
    290                 295                 300

Tyr Phe Leu Gly Pro Pro Pro His Ala Lys Val Ala Pro Leu Arg Glu
305                 310                 315                 320

Ala Val Pro Pro Gly Arg Thr Pro Ala Tyr Arg Ala Val Thr Trp Pro
                325                 330                 335

Glu Tyr Met Gly Val Arg Lys Lys Ala Phe Thr Thr Gly Ala Ser Ala
            340                 345                 350

Leu Lys Met Val Ala Leu Ala Ala Ala Ala Ala Ala Ala Asp Leu Asp
        355                 360                 365

Asp Asp Ala Gly Ala Gly Ala Ala Ala Glu Pro Val Val His Gln Gln
```

370 375 380

Leu Leu Val Ser Ser
385

<210> SEQ ID NO 122
<211> LENGTH: 2321
<212> TYPE: DNA
<213> ORGANISM: Sorghum bicolor

<400> SEQUENCE: 122

```
tataaatacc acgccatgta cttctctgct tctacacttc tccagcttct ctcatgccat     60
accactagtg caaggtccta gatttacact tggtgctaca gcttcttcct ccctccctcc    120
cctctctagg cagctagcac gcagcgcagc acacgaaaca tctattgacc ggccgcctcc    180
gccggggatc cataattact atactaccaa tcggccagcg tcatgccgac gccgtcgcac    240
ctcgcgaacc cgcgctactt cgacttccgt gcggcgcggc gggtgccgga gacgcacgcc    300
tggccggggc tgcacgacca ccccgtcgtg gacggcggcg cgccggggcc agacgccgtc    360
cccgtggtgg acctcgcggg ggcggcggac gagccgagag ccgcggtggt ggcccaagtg    420
gcgcgcgccg ccgagcaatg gggcgcgttc ctgctcacgg ggcacggcgt ccccgcggag    480
ctgctggcgc gcgtcgagga ccggatcgcc accatgttcg cgctgccagc ggacgacaag    540
atgcgcgccg tgcgcgggcc tggcgacgcc tgcggctacg gctccccgcc catctcctcc    600
ttcttctcca agtgcatgtg gtcggaggga tacaccttct cgccggccaa cctccgcgcc    660
gacctccgca agctctggcc taaggccggc gacgactaca ccagcttctg gtacgtgcac    720
ccgccggccg cgcgccgcca cacaccgtac ccacacacgt gcgcgctcgc gcctagctac    780
tagtagctgc tttgctttgc ttacctttga ttctcgcctt tgccatgcat atgcatgatg    840
cacgtacagg tactgcaggt acaacatgtc acacgcacgc acgcacgcac aacccatagt    900
ccgatacgat acatcatcga tcgacgtgtc gtcaccgtct aaggccatgc atgcatgcaa    960
gcacacgcct agaccttttt agcatgctgg ctgacgagga gtatactagc taataagcta   1020
cttgtcactg cgcgtcttgc ttaattacac tagtgcatat ttctacagtg atgtgatgga   1080
ggagttccac aagcacatgc gtgccctcgc ggacaagctg ctggagctgt tcctcatggc   1140
gctggggctc accgacgagc aggtcggcgg cgtggaggcg gagcggagga tcgccgagac   1200
gatgaccgcc accatgcacc tcaactggta ccctcggtgc ccggacccgc gccgcgcgct   1260
ggggctgatc gcgcacaccg actcgggctt cttcaccttc gtgctgcaga gcctcgtccc   1320
ggggctgcag ctcttccgcc acgccccgga ccggtgggtg gcggtgccgg cggtaccggg   1380
cgccttcgtc gtcaacgtgg gcgacctctt ccacatcctc accaacggcc ggttccacag   1440
cgtgtaccac cgcgccgtcg tgaaccggga cctcgacagg atatctctcg gctacttcct   1500
cggcccgccg ccgcacgcca aggtggcgcc gctaagggag gccgtgccgc ccggccgcac   1560
ccccgcgtac cgcgccgtca cgtggcccga gtacatgggc gtccgcaaga aggccttcac   1620
caccggcgca tccgcgctca agatggtcgc cctcgccgcc gccgccgccg ccgccgacct   1680
cgacgatgac gccggtgctg gcgccgccgc cgaacctgtc gtccatcagc agctactcgt   1740
ctcgtcgtag ccgatcgatc gccggatcgg tcgagactga tgatgatgat gcatatatac   1800
tcgtcgatgg agtagacaga ctaatcaagc aaccctgaaa ctatgaatgc atgcgtgcgc   1860
ttcgtgcttg cttgcgcatg cagctagcag gcttcattcc gttccgcagc tgctctgctc   1920
caacctgctc tgctggattg atgtatatgg tagaagaatt aagagatcga tggatgacgg   1980
```

```
aggaagaaga agacgaagac gacgatgagg aaaaggacac gctgtacgta gctggttctt   2040

ctagtctagt ttacagcagg ccgggcggcc ggctgctgct tccaatcgag tttgtcgtta   2100

ctgacgattg ttagtggatc gattaactaa tctggaattc tggattatta atataatgca   2160

tgtggtttgg catctggcgt aaagcaggta atggtaccta gccagtagcc agtagccagg   2220

ctggtcaatg ataggtctat accctgatcc tgtactgttg tttctttcgg tctttctgag   2280

agagaaaaaa aacgaatata tggcgtactc aattcatcaa a                       2321
```

<210> SEQ ID NO 123
<211> LENGTH: 1796
<212> TYPE: DNA
<213> ORGANISM: Setaria italica

<400> SEQUENCE: 123

```
actagtgcaa ggtcctagat ttacacttgg tgcttgcttg tttcttccta gttgctactg     60

gtagcacgca gtggctggct ggccgtaatc tattgtctgg gctcgatcgg tgattaggaa    120

gtagccaaag caagctaagg ccgccgccgc cgccgccatg ccgacgccgt cgcacctcaa    180

gaacccgctc tacttcgact tccgcgccgc gcggcgggtg ccggagtccc acgcctggcc    240

ggggctcgac gaccaccccg tggtggacgg cggcggcgcg ccggggtccc cggacgccgt    300

gccggtggtg gacctgcgcg agccgggcgc cgcggcggtg gcccgcgtgg cgcgcgccgc    360

cgagcagtgg ggcgcgttcc tgctcaccgg ccacggcgtc cccgcggagc tcctggcgcg    420

cgtcgaggac cgcgtcgcgt gcatgttcgc gctgccggcc gccgacaaga tgcgcgccgt    480

gcgcgggccg gggacgcct gcggctacgg ctcgccgccc atctcctcct tcttctccaa    540

gtgcatgtgg tccgagggct acaccttctc gccggcctcc ctccgccgcg acctccgcaa    600

gctctggccc aaggccggcg acgactacga cagcttctgt gacgtgatgg aggagttcca    660

caaggagatg cgcgccctcg ccgacaggct cctggagctg ttcctcaggg cgctcgggct    720

caccggcgag caggtcggcg ccgtcgaggc ggagcggagg atcggcgaga cgatgaccgc    780

caccatgcac ctcaactggt atccgaggtg cccggacccg cggcgcgcgc tggggctgat    840

cgcgcacacg gactcgggct tcttcacctt cgtgctgcag agcctcgtgc cggggctgca    900

gctgttccgg cacggcccca accggtgggt ggcggtgccg gccgtgccgg gcgccttcgt    960

cgtcaacgtc ggcgacctct tccacatcct cacgaacggc cgcttccaca gcgtgtacca   1020

ccgcgccgtc gtcaaccggg acctcgaccg gatatcgctc ggctacttcc tcggcccgcc   1080

gccccacgcc aaggtggcgc cgctccggga ggtcgtgccg ccgggccggg cccccgccta   1140

ccgcgccgtc acgtggcccg agtacatggg cgtccgcaag aaggccttca ccaccggcgc   1200

ctccgcgctc aagatggtcg ccgccgccgc cgccgccacc gaatccgacg acaccgacgc   1260

agccgccgcc gccgttcacc agccgccggt cgtcgtctca tcgtagccga tcgatcgccg   1320

gaaacacaga cgatgcatac cgtaccccga gcaatctaat caaaacaagg catccattct   1380

cgcgcgcatg cagcggccag ccgggcttcc gcagctgctc ggcctcctct gctggctgtg   1440

gaaatggaaa attttaatct gagatgaaga cgaagacgaa gacgaaacgg agaggaaaag   1500

gacatgctgt agctgtttct tctagttgcg caggccgctc ccagtcgagt ttgtcgttac   1560

tgacgattat tactctgatg aaaactaatc tgaattaatg catgtagttt ggcaatttgg   1620

tactaaaggt aggcacctag ccaggctggt caatgatagg tctataacct gatcctgttc   1680

tctgttgttt tcctttgtct gagaaaaaat ggaaataatt gatccggccg gacgggtgta   1740

ctgataggtg atgctgaatt gctgatgcaa gaggttgcga gctgcagtga gcagca       1796
```

<210> SEQ ID NO 124
<211> LENGTH: 1149
<212> TYPE: DNA
<213> ORGANISM: Setaria italica

<400> SEQUENCE: 124

```
atgccgacgc cgtcgcacct caagaacccg ctctacttcg acttccgcgc cgcgcggcgg      60
gtgccggagt cccacgcctg gccggggctc gacgaccacc ccgtggtgga cggcggcggc     120
gcgccggggt ccccggacgc cgtgccggtg gtggacctgc gcgagccggg cgccgcggcg     180
gtggcccgcg tggcgcgcgc cgccgagcag tggggcgcgt tcctgctcac cggccacggc     240
gtccccgcgg agctcctggc gcgcgtcgag gaccgcgtcg cgtgcatgtt cgcgctgccg     300
gccgccgaca agatgcgcgc cgtgcgcggg ccgggggacg cctgcggcta cggctcgccg     360
cccatctcct ccttcttctc caagtgcatg tggtccgagg gctacacctt ctcgccggcc     420
tccctccgcc gcgacctccg caagctctgg cccaaggccg gcgacgacta cgacagcttc     480
tgtgacgtga tggaggagtt ccacaaggag atgcgcgccc tcgccgacag gctcctggag     540
ctgttcctca gggcgctcgg gctcaccggc gagcaggtcg gcgccgtcga ggcggagcgg     600
aggatcggcg agacgatgac cgccaccatg cacctcaact ggtatccgag gtgcccggac     660
ccgcggcgcg cgctggggct gatcgcgcac acggactcgg gcttcttcac cttcgtgctg     720
cagagcctcg tgccggggct gcagctgttc cggcacggcc ccaaccggtg ggtggcggtg     780
ccggccgtgc cgggcgcctt cgtcgtcaac gtcggcgacc tcttccacat cctcacgaac     840
ggccgcttcc acagcgtgta ccaccgcgcc gtcgtcaacc gggacctcga ccggatatcg     900
ctcggctact tcctcggccc gccgccccac gccaaggtgg cgccgctccg ggaggtcgtg     960
ccgccgggcc gggcccccgc ctaccgcgcc gtcacgtggc ccgagtacat gggcgtccgc    1020
aagaaggcct tcaccaccgg cgcctccgcg ctcaagatgg tcgccgccgc cgccgccgcc    1080
accgaatccg acgacaccga cgcagccgcc gccgccgttc accagccgcc ggtcgtcgtc    1140
tcatcgtag                                                            1149
```

<210> SEQ ID NO 125
<211> LENGTH: 382
<212> TYPE: PRT
<213> ORGANISM: Setaria italica

<400> SEQUENCE: 125

```
Met Pro Thr Pro Ser His Leu Lys Asn Pro Leu Tyr Phe Asp Phe Arg
1               5                   10                  15

Ala Ala Arg Arg Val Pro Glu Ser His Ala Trp Pro Gly Leu Asp Asp
            20                  25                  30

His Pro Val Val Asp Gly Gly Gly Ala Pro Gly Ser Pro Asp Ala Val
        35                  40                  45

Pro Val Val Asp Leu Arg Glu Pro Gly Ala Ala Ala Val Ala Arg Val
    50                  55                  60

Ala Arg Ala Ala Glu Gln Trp Gly Ala Phe Leu Leu Thr Gly His Gly
65                  70                  75                  80

Val Pro Ala Glu Leu Leu Ala Arg Val Glu Asp Arg Val Ala Cys Met
                85                  90                  95

Phe Ala Leu Pro Ala Ala Asp Lys Met Arg Ala Val Arg Gly Pro Gly
            100                 105                 110

Asp Ala Cys Gly Tyr Gly Ser Pro Pro Ile Ser Ser Phe Phe Ser Lys
```

```
        115                 120                 125

Cys Met Trp Ser Glu Gly Tyr Thr Phe Ser Pro Ala Ser Leu Arg Arg
    130                 135                 140

Asp Leu Arg Lys Leu Trp Pro Lys Ala Gly Asp Asp Tyr Asp Ser Phe
145                 150                 155                 160

Cys Asp Val Met Glu Glu Phe His Lys Glu Met Arg Ala Leu Ala Asp
                165                 170                 175

Arg Leu Leu Glu Leu Phe Leu Arg Ala Leu Gly Leu Thr Gly Glu Gln
            180                 185                 190

Val Gly Ala Val Glu Ala Glu Arg Arg Ile Gly Glu Thr Met Thr Ala
        195                 200                 205

Thr Met His Leu Asn Trp Tyr Pro Arg Cys Pro Asp Pro Arg Arg Ala
    210                 215                 220

Leu Gly Leu Ile Ala His Thr Asp Ser Gly Phe Phe Thr Phe Val Leu
225                 230                 235                 240

Gln Ser Leu Val Pro Gly Leu Gln Leu Phe Arg His Gly Pro Asn Arg
                245                 250                 255

Trp Val Ala Val Pro Ala Val Pro Gly Ala Phe Val Val Asn Val Gly
            260                 265                 270

Asp Leu Phe His Ile Leu Thr Asn Gly Arg Phe His Ser Val Tyr His
        275                 280                 285

Arg Ala Val Val Asn Arg Asp Leu Asp Arg Ile Ser Leu Gly Tyr Phe
    290                 295                 300

Leu Gly Pro Pro Pro His Ala Lys Val Ala Pro Leu Arg Glu Val Val
305                 310                 315                 320

Pro Pro Gly Arg Ala Pro Ala Tyr Arg Ala Val Thr Trp Pro Glu Tyr
                325                 330                 335

Met Gly Val Arg Lys Lys Ala Phe Thr Thr Gly Ala Ser Ala Leu Lys
            340                 345                 350

Met Val Ala Ala Ala Ala Ala Ala Thr Glu Ser Asp Asp Thr Asp Ala
        355                 360                 365

Ala Ala Ala Ala Val His Gln Pro Pro Val Val Val Ser Ser
    370                 375                 380


<210> SEQ ID NO 126
<211> LENGTH: 2146
<212> TYPE: DNA
<213> ORGANISM: Setaria italica

<400> SEQUENCE: 126

actagtgcaa ggtcctagat ttacacttgg tgcttgcttg tttcttccta gttgctactg      60

gtagcacgca gtggctggct ggccgtaatc tattgtctgg gctcgatcgg tgattaggaa     120

gtagccaaag caagctaagg ccgccgccgc cgccgccatg ccgacgccgt cgcacctcaa     180

gaacccgctc tacttcgact tccgcgccgc gcggcgggtg ccggagtccc acgcctggcc     240

ggggctcgac gaccaccccg tggtggacgg cggcggcgcg ccggggtccc cggacgccgt     300

gccggtggtg gacctgcgcg agccgggcgc cgcggcggtg gcccgcgtgg cgcgcgccgc     360

cgagcagtgg ggcgcgttcc tgctcaccgg ccacggcgtc cccgcggagc tcctggcgcg     420

cgtcgaggac cgcgtcgcgt gcatgttcgc gctgccggcc gccgacaaga tgcgcgccgt     480

gcgcgggccg ggggacgcct gcggctacgg ctcgccgccc atctcctcct tcttctccaa     540

gtgcatgtgg tccgagggct acaccttctc gccggcctcc ctccgccgcg acctccgcaa     600

gctctggccc aaggccggcg acgactacga cagcttctgg tacgtcgtcg tctatagcta     660
```

```
gtagctagcc gccggcacac gtgcgcctga cctgctccgc catgcatggt gcacgtatgc    720

agatcgatca cacgcaccga tcgatcgacg tgtcccggtc aaggccatgc atgcatgcaa    780

gcaaccaaca gcacgcctcc tgatactgct tgttgcttac accgttggta tgtgcctgtt    840

gcctacagtg acgtgatgga ggagttccac aaggagatgc gcgccctcgc cgacaggctc    900

ctggagctgt tcctcagggc gctcgggctc accggcgagc aggtcggcgc cgtcgaggcg    960

gagcggagga tcggcgagac gatgaccgcc accatgcacc tcaactggta tgtgccatgc   1020

catgaccacc tgcgtctatg aactaacgga agcttccatc gcgtgtccat gacgatttag   1080

aagctgtagt ccagagcttg agacaaacga aacgaagctt acatggtggc gtgacgtgtc   1140

gcgtgcaggt atccgaggtg cccggacccg cggcgcgcgc tggggctgat cgcgcacacg   1200

gactcgggct tcttcacctt cgtgctgcag agcctcgtgc cggggctgca gctgttccgg   1260

cacggcccca accggtgggt ggcggtgccg gccgtgccgg gcgccttcgt cgtcaacgtc   1320

ggcgacctct tccacatcct cacgaacggc cgcttccaca gcgtgtacca ccgcgccgtc   1380

gtcaaccggg acctcgaccg gatatcgctc ggctacttcc tcggcccgcc gccccacgcc   1440

aaggtggcgc cgctccggga ggtcgtgccg ccgggccggg cccccgccta ccgcgccgtc   1500

acgtggcccg agtacatggg cgtccgcaag aaggccttca ccaccggcgc ctccgcgctc   1560

aagatggtcg ccgccgccgc cgccgccacc gaatccgacg acaccgacgc agccgccgcc   1620

gccgttcacc agccgccggt cgtcgtctca tcgtagccga tcgatcgccg gaaacacaga   1680

cgatgcatac cgtaccccga gcaatctaat caaaacaagg catccattct cgcgcgcatg   1740

cagcggccag ccgggcttcc gcagctgctc ggcctcctct gctggctgtg gaaatggaaa   1800

attttaatct gagatgaaga cgaagacgaa gacgaaacgg agaggaaaag gacatgctgt   1860

agctgtttct tctagttgcg caggccgctc ccagtcgagt ttgtcgttac tgacgattat   1920

tactctgatg aaaactaatc tgaattaatg catgtagttt ggcaatttgg tactaaaggt   1980

aggcacctag ccaggctggt caatgatagg tctataacct gatcctgttc tctgttgttt   2040

tcctttgtct gagaaaaaat ggaaataatt gatccggccg gacgggtgta ctgataggtg   2100

atgctgaatt gctgatgcaa gaggttgcga gctgcagtga gcagca                  2146
```

<210> SEQ ID NO 127
<211> LENGTH: 1933
<212> TYPE: DNA
<213> ORGANISM: Oryza sativa

<400> SEQUENCE: 127

```
actactcatt ccactattgt aaagtcatag aaaaaattta tatagagaga aaaaattagt     60

gttgttattg ttactggctt tctgccagac gagacgagcg agcgcgcgag tgtgttgctc    120

tctggtcatc gtcgtcgtcg tcgcgatgcc gacgccgtcg cacttgaaga acccgctctg    180

cttcgacttc cgggcggcga ggcgggtgcc ggagacgcac gcgtggccgg ggctggacga    240

ccacccggtg gtggacggcg gcggcggcgg cggcgaggac gcggtgccgg tggtggacgt    300

cggggcgggc gacgcggcgg cgcgggtggc gcgggcggcg gagcagtggg gcgcgttcct    360

tctggtcggg cacggcgtgc cggcggcgct gctgtcgcgc gtcgaggagc gcgtcgcccg    420

cgtgttctcc ctgccggcgt cggagaagat gcgcgccgtc cgcggccccg gcgagccctg    480

cggctacggc tcgccgccca tctcctcctt cttctccaag ctcatgtggt ccgagggcta    540

caccttctcc ccttcctccc tccgctccga gctccgccgc ctctggccca agtccggcga    600
```

```
cgactacctc ctcttctgtg acgtgatgga ggagtttcac aaggagatgc ggcggctagc    660

cgacgagttg ctgaggttgt tcttgagggc gctggggctc accggcgagg aggtcgccgg    720

agtcgaggcg gagaggagga tcggcgagag gatgacggcg acggtgcacc tcaactggta    780

cccgaggtgc ccggagccgc ggcgagcgct ggggctcatc gcgcacacgg actcgggctt    840

cttcaccttc gtgctccaga gcctcgtccc ggggctgcag ctgttccgtc gagggcccga    900

ccggtgggtg gcggtgccgg cggtggcggg ggccttcgtc gtcaacgtcg gcgacctctt    960

ccacatcctc accaacggcc gcttccacag cgtctaccac cgcgccgtcg tgaaccgcga   1020

ccgcgaccgg gtctcgctcg gctacttcct cggcccgccg ccggacgccg aggtggcgcc   1080

gctgccggag gccgtgccgg ccggccggag ccccgcctac cgcgctgtca cgtggccgga   1140

gtacatggcc gtccgcaaga aggccttcgc caccggcggc tccgccctca agatggtctc   1200

caccgacgcc gccgccgccg ccgacgaaca cgacgacgtc gccgccgccg ccgacgtcca   1260

cgcataagct atagctacta gctacctcga tctcacgcaa aaaaaaaaag aaacaattaa   1320

tagagcaaaa aaaaaaagaa gagaaaatgg tggtacttgt gtttaaggtt tcctccatgc   1380

aaaatggttt gcatgcatgc atgcaaagct agcatctgca gctgcaagaa ttacaagagc   1440

agagaagcag acagctagat ggagataatt aattaattaa ttaatctaat taagcatgca   1500

ataattaaga ttattattct gatttcagaa ctgaaaaaaa aagtgtggtt aattaattat   1560

tggttaggct taattttatc tagatgtaga aaaagaatca agatcttcaa gcaagagaga   1620

agaggatcga agaagaagga aaagaaaacg aaaaggacat gctgtgttgt ctcttctagt   1680

tgtaccctgg ctgctgatta agtgctttgt tttgttgctg caagcttgtc gttactgatt   1740

attagttagt tatgcatcta attgattaaa ctaatctgtt tggcattttg gctcgagcta   1800

agctatagcc aggctggtca atgataggaa cttgtacaat ttaagcaatt gaacctgatc   1860

ctgtactggc atgtatgtat atatgcaagt gatgagaacc actagctagt atagctagac   1920

atgtatttgt ata                                                      1933
```

<210> SEQ ID NO 128
<211> LENGTH: 1122
<212> TYPE: DNA
<213> ORGANISM: Oryza sativa

<400> SEQUENCE: 128

```
atgccgacgc cgtcgcactt gaagaacccg ctctgcttcg acttccgggc ggcgaggcgg     60

gtgccggaga cgcacgcgtg gccggggctg gacgaccacc cggtggtgga cggcggcggc    120

ggcggcggcg aggacgcggt gccggtggtg gacgtcgggg cgggcgacgc ggcggcgcgg    180

gtggcgcggg cggcggagca gtggggcgcg ttccttctgg tcgggcacgg cgtgccggcg    240

gcgctgctgt cgcgcgtcga ggagcgcgtc gcccgcgtgt tctccctgcc ggcgtcggag    300

aagatgcgcg ccgtccgcgg ccccggcgag ccctgcggct acggctcgcc gcccatctcc    360

tccttcttct ccaagctcat gtggtccgag ggctacacct tctccccttc ctccctccgc    420

tccgagctcc gccgcctctg gcccaagtcc ggcgacgact acctcctctt ctgtgacgtg    480

atggaggagt ttcacaagga gatgcggcgg ctagccgacg agttgctgag gttgttcttg    540

agggcgctgg ggctcaccgg cgaggaggtc gccggagtcg aggcggagag gaggatcggc    600

gagaggatga cggcgacggt gcacctcaac tggtacccga ggtgcccgga gccgcggcga    660

gcgctggggc tcatcgcgca cacggactcg ggcttcttca ccttcgtgct ccagagcctc    720

gtcccggggc tgcagctgtt ccgtcgaggg cccgaccggt gggtggcggt gccggcggtg    780
```

```
gcgggggcct tcgtcgtcaa cgtcggcgac ctcttccaca tcctcaccaa cggccgcttc    840

cacagcgtct accaccgcgc cgtcgtgaac cgcgaccgcg accgggtctc gctcggctac    900

ttcctcggcc cgccgccgga cgccgaggtg gcgccgctgc cggaggccgt gccggccggc    960

cggagccccg cctaccgcgc tgtcacgtgg ccggagtaca tggccgtccg caagaaggcc   1020

ttcgccaccg gcggctccgc cctcaagatg gtctccaccg acgccgccgc cgccgccgac   1080

gaacacgacg acgtcgccgc cgccgccgac gtccacgcat aa                      1122


<210> SEQ ID NO 129
<211> LENGTH: 373
<212> TYPE: PRT
<213> ORGANISM: Oryza sativa

<400> SEQUENCE: 129

Met Pro Thr Pro Ser His Leu Lys Asn Pro Leu Cys Phe Asp Phe Arg
1               5                   10                  15

Ala Ala Arg Arg Val Pro Glu Thr His Ala Trp Pro Gly Leu Asp Asp
            20                  25                  30

His Pro Val Val Asp Gly Gly Gly Gly Gly Gly Glu Asp Ala Val Pro
        35                  40                  45

Val Val Asp Val Gly Ala Gly Asp Ala Ala Ala Arg Val Ala Arg Ala
    50                  55                  60

Ala Glu Gln Trp Gly Ala Phe Leu Leu Val Gly His Gly Val Pro Ala
65                  70                  75                  80

Ala Leu Leu Ser Arg Val Glu Glu Arg Val Ala Arg Val Phe Ser Leu
                85                  90                  95

Pro Ala Ser Glu Lys Met Arg Ala Val Arg Gly Pro Gly Glu Pro Cys
            100                 105                 110

Gly Tyr Gly Ser Pro Pro Ile Ser Ser Phe Phe Ser Lys Leu Met Trp
        115                 120                 125

Ser Glu Gly Tyr Thr Phe Ser Pro Ser Ser Leu Arg Ser Glu Leu Arg
    130                 135                 140

Arg Leu Trp Pro Lys Ser Gly Asp Asp Tyr Leu Leu Phe Cys Asp Val
145                 150                 155                 160

Met Glu Glu Phe His Lys Glu Met Arg Arg Leu Ala Asp Glu Leu Leu
                165                 170                 175

Arg Leu Phe Leu Arg Ala Leu Gly Leu Thr Gly Glu Glu Val Ala Gly
            180                 185                 190

Val Glu Ala Glu Arg Arg Ile Gly Glu Arg Met Thr Ala Thr Val His
        195                 200                 205

Leu Asn Trp Tyr Pro Arg Cys Pro Glu Pro Arg Arg Ala Leu Gly Leu
    210                 215                 220

Ile Ala His Thr Asp Ser Gly Phe Phe Thr Phe Val Leu Gln Ser Leu
225                 230                 235                 240

Val Pro Gly Leu Gln Leu Phe Arg Arg Gly Pro Asp Arg Trp Val Ala
                245                 250                 255

Val Pro Ala Val Ala Gly Ala Phe Val Val Asn Val Gly Asp Leu Phe
            260                 265                 270

His Ile Leu Thr Asn Gly Arg Phe His Ser Val Tyr His Arg Ala Val
        275                 280                 285

Val Asn Arg Asp Arg Asp Arg Val Ser Leu Gly Tyr Phe Leu Gly Pro
    290                 295                 300

Pro Pro Asp Ala Glu Val Ala Pro Leu Pro Glu Ala Val Pro Ala Gly
```

```
305                 310                 315                 320

Arg Ser Pro Ala Tyr Arg Ala Val Thr Trp Pro Glu Tyr Met Ala Val
                325                 330                 335

Arg Lys Lys Ala Phe Ala Thr Gly Gly Ser Ala Leu Lys Met Val Ser
            340                 345                 350

Thr Asp Ala Ala Ala Ala Ala Asp Glu His Asp Asp Val Ala Ala Ala
        355                 360                 365

Ala Asp Val His Ala
    370


<210> SEQ ID NO 130
<211> LENGTH: 2040
<212> TYPE: DNA
<213> ORGANISM: Oryza sativa

<400> SEQUENCE: 130

actactcatt ccactattgt aaagtcatag aaaaaattta tatagagaga aaaaattagt      60

gttgttattg ttactggctt tctgccagac gagacgagcg agcgcgcgag tgtgttgctc     120

tctggtcatc gtcgtcgtcg tcgcgatgcc gacgccgtcg cacttgaaga acccgctctg     180

cttcgacttc cgggcggcga ggcgggtgcc ggagacgcac gcgtggccgg ggctggacga     240

ccacccggtg gtggacggcg gcggcggcgg cggcgaggac gcggtgccgg tggtggacgt     300

cggggcgggc gacgcggcgg cgcgggtggc gcgggcggcg gagcagtggg gcgcgttcct     360

tctggtcggg cacggcgtgc cggcggcgct gctgtcgcgc gtcgaggagc gcgtcgcccg     420

cgtgttctcc ctgccggcgt cggagaagat gcgcgccgtc cgcggccccg gcgagccctg     480

cggctacggc tcgccgccca tctcctcctt cttctccaag ctcatgtggt ccgagggcta     540

caccttctcc ccttcctccc tccgctccga gctccgccgc ctctggccca agtccggcga     600

cgactacctc ctcttctggt atatatacat atatactctc ccatgcattc catgcacata     660

cactctacgt atatatctac ctctacgtat atatctacgt attgatctac gtataatata     720

cgcagtgacg tgatggagga gtttcacaag gagatgcggc ggctagccga cgagttgctg     780

aggttgttct tgagggcgct ggggctcacc ggcgaggagg tcgccggagt cgaggcggag     840

aggaggatcg gcgagaggat gacggcgacg gtgcacctca actggtaccc gaggtgcccg     900

gagccgcggc gagcgctggg gctcatcgcg cacacggact cgggcttctt caccttcgtg     960

ctccagagcc tcgtcccggg gctgcagctg ttccgtcgag ggcccgaccg gtgggtggcg    1020

gtgccggcgg tggcgggggc cttcgtcgtc aacgtcggcg acctcttcca catcctcacc    1080

aacggccgct tccacagcgt ctaccaccgc gccgtcgtga accgcgaccg cgaccgggtc    1140

tcgctcggct acttcctcgg cccgccgccg gacgccgagg tggcgccgct gccggaggcc    1200

gtgccggccg gccggagccc cgcctaccgc gctgtcacgt ggccggagta catggccgtc    1260

cgcaagaagg ccttcgccac cggcggctcc gccctcaaga tggtctccac cgacgccgcc    1320

gccgccgccg acgaacacga cgacgtcgcc gccgccgccg acgtccacgc ataagctata    1380

gctactagct acctcgatct cacgcaaaaa aaaaaagaaa caattaatag agcaaaaaaa    1440

aaaagaagag aaaatggtgg tacttgtgtt taaggtttcc tccatgcaaa atggtttgca    1500

tgcatgcatg caaagctagc atctgcagct gcaagaatta caagagcaga gaagcagaca    1560

gctagatgga gataattaat taattaatta atctaattaa gcatgcaata attaagatta    1620

ttattctgat ttcagaactg aaaaaaaaag tgtggttaat taattattgg ttaggcttaa    1680

ttttatctag atgtagaaaa agaatcaaga tcttcaagca agagagaaga ggatcgaaga    1740
```

agaaggaaaa gaaaacgaaa aggacatgct gtgttgtctc ttctagttgt accctggctg 1800
ctgattaagt gctttgtttt gttgctgcaa gcttgtcgtt actgattatt agttagttat 1860
gcatctaatt gattaaacta atctgtttgg cattttggct cgagctaagc tatagccagg 1920
ctggtcaatg ataggaactt gtacaattta agcaattgaa cctgatcctg tactggcatg 1980
tatgtatata tgcaagtgat gagaaccact agctagtata gctagacatg tatttgtata 2040

<210> SEQ ID NO 131
<211> LENGTH: 1332
<212> TYPE: DNA
<213> ORGANISM: Hordeum vulgare

<400> SEQUENCE: 131
acactcactc ctcaatccat ccgtctccac cattgctcgc tagctcgagc tctactagct 60
agcactgcaa agtcagccgg gccggagttg atttggtcct tgttagcttg accgatcgta 120
tacgtatcgc caggatgccg acgccgtcgc acctgagcaa ggacccgcac tacttcgact 180
tccgggcggc gcggcgggtg ccggagacac acgcgtggcc ggggctgcac gaccacccgg 240
tggtggacgg cggcggcgcg ggcggagggc cggacgcggt gccggtggtg gacatgcgcg 300
acccgtgcgc cgcggaggcg gtggcgctgg ccgcgcagga ctggggcgcc ttcctcttgc 360
agggccacgg cgtcccgttg gagctgctgg cccgcgtgga ggccgcgata gcgggcatgt 420
tcgcgctgcc ggcgtcggag aagatgcgcg ccgtgcggcg gcccggcgac tcgtgcggct 480
acgggtcgcc gcccatctcc tccttcttct ccaagtgcat gtggtccgag ggctacacct 540
tctccccggc caacctccgc tccgacctcc gcaagctctg gcccaaggcc ggccacgact 600
accgccactt ctgtgccgtg atggaggagt tccacaggga gatgcgcgtt ctggccgaca 660
agctgctgga gctgttcctg gtggccctcg ggctcaccgg cgagcaggtc gccgccgtcg 720
agtcggagca caagatcgcc gagaccatga ccgccacaat gcacctcaac tggtacccca 780
agtgcccgga cccgaagcga gcgctgggcc tgatcgcgca cacggactcg ggcttcttca 840
ccttcgtgct ccagagcctg gtgcccgggc tgcagctgtt ccggcacggc cccgaccgtt 900
gggtgacggt gcccgccgtg ccgggcgcca tggtcgtcaa cgtcggcgac ctcttccaca 960
tcctcaccaa tggccgcttc cacagcgtct accaccgcgc cgtcgtcaac cgcgacagcg 1020
accggatatc gctggggtac ttcctcggcc cgcccgccca cgttaaggtg gcgccgctca 1080
gggaggccct cgccggcacg cccgctgcct accgcgccgt cacgtggccc gagtacatgg 1140
gcgtgcgcaa gaaggccttc accaccggcg cctccgcgct caagatggtc gccatctcca 1200
ccgacgacgc cgccgacgtc ctccccgacg tcctctcgtc gtagatcggc gccggccatc 1260
acccggccgg ccaagagacc gatctataca aacaattagt gaacaaaaaa aaaaaaaaaa 1320
aaaaaaaaaa aa 1332

<210> SEQ ID NO 132
<211> LENGTH: 1110
<212> TYPE: DNA
<213> ORGANISM: Hordeum vulgare

<400> SEQUENCE: 132
atgccgacgc cgtcgcacct gagcaaggac ccgcactact tcgacttccg ggcggcgcgg 60
cgggtgccgg agacacacgc gtggccgggg ctgcacgacc acccggtggt ggacggcggc 120
ggcgcgggcg gagggccgga cgcggtgccg gtggtggaca tgcgcgaccc gtgcgccgcg 180

```
gaggcggtgg cgctggccgc gcaggactgg ggcgccttcc tcttgcaggg ccacggcgtc    240

ccgttggagc tgctggcccg cgtggaggcc gcgatagcgg gcatgttcgc gctgccggcg    300

tcggagaaga tgcgcgccgt gcggcggccc ggcgactcgt gcggctacgg gtcgccgccc    360

atctcctcct tcttctccaa gtgcatgtgg tccgagggct acaccttctc cccggccaac    420

ctccgctccg acctccgcaa gctctggccc aaggccggcc acgactaccg ccacttctgt    480

gccgtgatgg aggagttcca cagggagatg cgcgttctgg ccgacaagct gctggagctg    540

ttcctggtgg ccctcgggct caccggcgag caggtcgccg ccgtcgagtc ggagcacaag    600

atcgccgaga ccatgaccgc cacaatgcac ctcaactggt accccaagtg cccggacccg    660

aagcgagcgc tgggcctgat cgcgcacacg gactcgggct tcttcacctt cgtgctccag    720

agcctggtgc ccgggctgca gctgttccgg cacggccccg accgttgggt gacggtgccc    780

gccgtgccgg gcgccatggt cgtcaacgtc ggcgacctct tccacatcct caccaatggc    840

cgcttccaca gcgtctacca ccgcgccgtc gtcaaccgcg acagcgaccg gatatcgctg    900

gggtacttcc tcggcccgcc cgcccacgtt aaggtggcgc cgctcaggga ggccctcgcc    960

ggcacgcccg ctgcctaccg cgccgtcacg tggcccgagt acatgggcgt gcgcaagaag   1020

gccttcacca ccggcgcctc cgcgctcaag atggtcgcca tctccaccga cgacgccgcc   1080

gacgtcctcc ccgacgtcct ctcgtcgtag                                    1110
```

<210> SEQ ID NO 133
<211> LENGTH: 369
<212> TYPE: PRT
<213> ORGANISM: Hordeum vulgare

<400> SEQUENCE: 133

```
Met Pro Thr Pro Ser His Leu Ser Lys Asp Pro His Tyr Phe Asp Phe
1               5                   10                  15

Arg Ala Ala Arg Arg Val Pro Glu Thr His Ala Trp Pro Gly Leu His
            20                  25                  30

Asp His Pro Val Val Asp Gly Gly Gly Ala Gly Gly Gly Pro Asp Ala
        35                  40                  45

Val Pro Val Val Asp Met Arg Asp Pro Cys Ala Ala Glu Ala Val Ala
    50                  55                  60

Leu Ala Ala Gln Asp Trp Gly Ala Phe Leu Leu Gln Gly His Gly Val
65                  70                  75                  80

Pro Leu Glu Leu Leu Ala Arg Val Glu Ala Ala Ile Ala Gly Met Phe
                85                  90                  95

Ala Leu Pro Ala Ser Glu Lys Met Arg Ala Val Arg Arg Pro Gly Asp
            100                 105                 110

Ser Cys Gly Tyr Gly Ser Pro Pro Ile Ser Ser Phe Phe Ser Lys Cys
        115                 120                 125

Met Trp Ser Glu Gly Tyr Thr Phe Ser Pro Ala Asn Leu Arg Ser Asp
    130                 135                 140

Leu Arg Lys Leu Trp Pro Lys Ala Gly His Asp Tyr Arg His Phe Cys
145                 150                 155                 160

Ala Val Met Glu Glu Phe His Arg Glu Met Arg Val Leu Ala Asp Lys
                165                 170                 175

Leu Leu Glu Leu Phe Leu Val Ala Leu Gly Leu Thr Gly Glu Gln Val
            180                 185                 190

Ala Ala Val Glu Ser Glu His Lys Ile Ala Glu Thr Met Thr Ala Thr
        195                 200                 205
```

```
Met His Leu Asn Trp Tyr Pro Lys Cys Pro Asp Pro Lys Arg Ala Leu
    210                 215                 220

Gly Leu Ile Ala His Thr Asp Ser Gly Phe Phe Thr Phe Val Leu Gln
225                 230                 235                 240

Ser Leu Val Pro Gly Leu Gln Leu Phe Arg His Gly Pro Asp Arg Trp
                245                 250                 255

Val Thr Val Pro Ala Val Pro Gly Ala Met Val Val Asn Val Gly Asp
            260                 265                 270

Leu Phe His Ile Leu Thr Asn Gly Arg Phe His Ser Val Tyr His Arg
        275                 280                 285

Ala Val Val Asn Arg Asp Ser Asp Arg Ile Ser Leu Gly Tyr Phe Leu
    290                 295                 300

Gly Pro Pro Ala His Val Lys Val Ala Pro Leu Arg Glu Ala Leu Ala
305                 310                 315                 320

Gly Thr Pro Ala Ala Tyr Arg Ala Val Thr Trp Pro Glu Tyr Met Gly
                325                 330                 335

Val Arg Lys Lys Ala Phe Thr Thr Gly Ala Ser Ala Leu Lys Met Val
            340                 345                 350

Ala Ile Ser Thr Asp Asp Ala Ala Asp Val Leu Pro Asp Val Leu Ser
        355                 360                 365

Ser
```

<210> SEQ ID NO 134
<211> LENGTH: 1653
<212> TYPE: DNA
<213> ORGANISM: Triticum aestivum
<220> FEATURE:
<221> NAME/KEY: misc_feature
<222> LOCATION: (1594)..(1600)
<223> OTHER INFORMATION: n is a, c, g, or t
<220> FEATURE:
<221> NAME/KEY: misc_feature
<222> LOCATION: (1641)..(1641)
<223> OTHER INFORMATION: n is a, c, g, or t

<400> SEQUENCE: 134

```
cacgagatcc atccgtctcc accattgctc gctagctcga gctcctagct agtactgcaa     60

agtcagccgg ggagttgatt tggtccttct tggcttgacc gatcgtacgt gccgccagga    120

tgccgacgcc ggcgcacctg agcaaggacc cgcgctactt cgacttccgg gcggcgcggc    180

gggtgccgga gacgcacgcg tggcccgggc tgcacgacca ccccgtggtg gacggcagcg    240

gcgcgggcgg agggccggac gcggtgccgg tggtggacat gcgcgacccg tgcgcggcgg    300

aggcggtggc gctggcggcg caggactggg gcgccttcct cctggagggc cacggcgtcc    360

cgttggagct gctggcgcgc gtggaggccg cgatcgcggg catgttcgcg ctgccggcgt    420

cggagaagat gcgcgccgtg cggcggcccg gcgactcgtg cggctacggg tcgccgccca    480

tctcctcctt cttctccaag tgcatgtggt ccgagggcta caccttctcc ccggccaacc    540

tccgctccga cctccgcaag ctctggccca aggccggcca cgactaccgc cacttctgcg    600

ccgtgatgga ggagttccac agggagatgc gcgcgctggc cgacaagctg ctggagctgt    660

tcctggtggc cctcgggctc accggcgagc aggtcgccgc cgtcgagtcc gagcagaaga    720

tcgccgagac catgaccgcc acaatgcacc tcaactggta ccccaagtgc ccggacccga    780

agcgggcgct gggcctgatc gcgcacacgg actcgggctt cttcaccttc gtgctgcaga    840

gccttgtgcc cgggctgcag ctgttccggc acggccccga ccggtgggtg acggtgcccg    900

ccgtgccggg ggccatggtc gtcaacgtcg gcgacctctt ccagatcctc accaacggcc    960
```

```
gcttccacag cgtctaccac cgcgccgtcg tcaaccgcga cagcgaccgg atatcgctcg   1020
gctacttcct cggcccgccc gcccacgtca aggtggcgcc gctcagggag gccctggccg   1080
gcacgcccgc cgcctaccgc gccgtcacgt ggcccgagta catgggcgtg cgcaagaagg   1140
ccttcaccac cggcgcctcc gcgctcaaga tggtcgccat ctccactgac aacgacgccg   1200
ccaaccacac ggacgacctg atctcgtcgt agatcggcgc cggccatcac cggccggcca   1260
agggatcgat ctacacacac aattagtgaa caaaaaaatg ccagagatgg tgcatggtgg   1320
gctggtagct tagctgaggt agctaggagg aagagcgcgc gtgcggctgt cgttcgtgcg   1380
gctgttcccg caaaaaaaaa aaaggtttcc tccatatatg tctccatgca gaactgcaga   1440
tgctggtggt ggatgcgtcc atgcagcagg gaacgaacta attgtaagaa aatcaagcaa   1500
acttagttct acatctgtaa ttaagtatgc atgccacttg gtttaattca attcaagtgc   1560
agaaaaaatt atgatgggaa aaaaaaagac atgnnnnnnn aaaaaaaaaa aaaaaaaaaa   1620
aaaaaaaaaa aaaaaaaaaa naaaaaaaaa aaa                                1653
```

<210> SEQ ID NO 135
<211> LENGTH: 1113
<212> TYPE: DNA
<213> ORGANISM: Triticum aestivum

<400> SEQUENCE: 135

```
atgccgacgc cggcgcacct gagcaaggac ccgcgctact tcgacttccg ggcggcgcgg     60
cgggtgccgg agacgcacgc gtggcccggg ctgcacgacc accccgtggt ggacggcagc    120
ggcgcgggcg gagggccgga cgcggtgccg gtggtggaca tgcgcgaccc gtgcgcggcg    180
gaggcggtgg cgctggcggc gcaggactgg ggcgccttcc tcctggaggg ccacggcgtc    240
ccgttggagc tgctggcgcg cgtggaggcc gcgatcgcgg gcatgttcgc gctgccggcg    300
tcggagaaga tgcgcgccgt gcggcggccc ggcgactcgt gcggctacgg gtcgccgccc    360
atctcctcct tcttctccaa gtgcatgtgg tccgagggct acaccttctc cccggccaac    420
ctccgctccg acctccgcaa gctctggccc aaggccggcc acgactaccg ccacttctgc    480
gccgtgatgg aggagttcca cagggagatg cgcgcgctgg ccgacaagct gctggagctg    540
ttcctggtgg ccctcgggct caccggcgag caggtcgccg ccgtcgagtc cgagcagaag    600
atcgccgaga ccatgaccgc cacaatgcac ctcaactggt accccaagtg cccggacccg    660
aagcgggcgc tgggcctgat cgcgcacacg gactcgggct tcttcacctt cgtgctgcag    720
agccttgtgc ccgggctgca gctgttccgg cacggccccg accggtgggt gacggtgccc    780
gccgtgccgg gggccatggt cgtcaacgtc ggcgacctct tccagatcct caccaacggc    840
cgcttccaca gcgtctacca ccgcgccgtc gtcaaccgcg acagcgaccg gatatcgctc    900
ggctacttcc tcggcccgcc cgcccacgtc aaggtggcgc cgctcaggga ggccctggcc    960
ggcacgcccg ccgcctaccg cgccgtcacg tggcccgagt acatgggcgt gcgcaagaag   1020
gccttcacca ccggcgcctc cgcgctcaag atggtcgcca tctccactga caacgacgcc   1080
gccaaccaca cggacgacct gatctcgtcg tag                                1113
```

<210> SEQ ID NO 136
<211> LENGTH: 370
<212> TYPE: PRT
<213> ORGANISM: Triticum aestivum

<400> SEQUENCE: 136

```
Met Pro Thr Pro Ala His Leu Ser Lys Asp Pro Arg Tyr Phe Asp Phe
1               5                   10                  15

Arg Ala Ala Arg Arg Val Pro Glu Thr His Ala Trp Pro Gly Leu His
            20                  25                  30

Asp His Pro Val Val Asp Gly Ser Gly Ala Gly Gly Gly Pro Asp Ala
        35                  40                  45

Val Pro Val Val Asp Met Arg Asp Pro Cys Ala Ala Glu Ala Val Ala
    50                  55                  60

Leu Ala Ala Gln Asp Trp Gly Ala Phe Leu Leu Glu Gly His Gly Val
65                  70                  75                  80

Pro Leu Glu Leu Leu Ala Arg Val Glu Ala Ala Ile Ala Gly Met Phe
                85                  90                  95

Ala Leu Pro Ala Ser Glu Lys Met Arg Ala Val Arg Arg Pro Gly Asp
            100                 105                 110

Ser Cys Gly Tyr Gly Ser Pro Pro Ile Ser Ser Phe Phe Ser Lys Cys
        115                 120                 125

Met Trp Ser Glu Gly Tyr Thr Phe Ser Pro Ala Asn Leu Arg Ser Asp
    130                 135                 140

Leu Arg Lys Leu Trp Pro Lys Ala Gly His Asp Tyr Arg His Phe Cys
145                 150                 155                 160

Ala Val Met Glu Glu Phe His Arg Glu Met Arg Ala Leu Ala Asp Lys
                165                 170                 175

Leu Leu Glu Leu Phe Leu Val Ala Leu Gly Leu Thr Gly Glu Gln Val
            180                 185                 190

Ala Ala Val Glu Ser Glu Gln Lys Ile Ala Glu Thr Met Thr Ala Thr
        195                 200                 205

Met His Leu Asn Trp Tyr Pro Lys Cys Pro Asp Pro Lys Arg Ala Leu
    210                 215                 220

Gly Leu Ile Ala His Thr Asp Ser Gly Phe Phe Thr Phe Val Leu Gln
225                 230                 235                 240

Ser Leu Val Pro Gly Leu Gln Leu Phe Arg His Gly Pro Asp Arg Trp
                245                 250                 255

Val Thr Val Pro Ala Val Pro Gly Ala Met Val Val Asn Val Gly Asp
            260                 265                 270

Leu Phe Gln Ile Leu Thr Asn Gly Arg Phe His Ser Val Tyr His Arg
        275                 280                 285

Ala Val Val Asn Arg Asp Ser Asp Arg Ile Ser Leu Gly Tyr Phe Leu
    290                 295                 300

Gly Pro Pro Ala His Val Lys Val Ala Pro Leu Arg Glu Ala Leu Ala
305                 310                 315                 320

Gly Thr Pro Ala Ala Tyr Arg Ala Val Thr Trp Pro Glu Tyr Met Gly
                325                 330                 335

Val Arg Lys Lys Ala Phe Thr Thr Gly Ala Ser Ala Leu Lys Met Val
            340                 345                 350

Ala Ile Ser Thr Asp Asn Asp Ala Ala Asn His Thr Asp Asp Leu Ile
        355                 360                 365

Ser Ser
    370
```

<210> SEQ ID NO 137
<211> LENGTH: 1884
<212> TYPE: DNA
<213> ORGANISM: Triticum aestivum

<400> SEQUENCE: 137

```
tatatataca gctccttgta cttctctcgt tcttacactc actcctcaat ccatccgtct     60
ccaccattgc tcgctagctc gagctcctag ctagtactgc aaagtcagcc ggggagttga    120
tttggtcctt cttggcttga ccgatcgtac gtgccgccag gatgccgacg ccggcgcacc    180
tgagcaagga cccgcgctac ttcgacttcc gggcggcgcg gcgggtgccg gagacgcacg    240
cgtggcccgg gctgcacgac caccccgtgg tggacggcag cggcgcgggc ggagggccgg    300
acgcggtgcc ggtggtggac atgcgcgacc cgtgcgcggc ggaggcggtg gcgctggcgg    360
cgcaggactg ggcgcccttc ctcctggagg gccacggcgt cccgttggag ctgctggcgc    420
gcgtggaggc cgcgatcgcg ggcatgttcg cgctgccggc gtcggagaag atgcgcgccg    480
tgcggcggcc cggcgactcg tgcggctacg ggtcgccgcc catctcctcc ttcttctcca    540
agtgcatgtg gtccgagggc tacaccttct ccccggccaa cctccgctcc gacctccgca    600
agctctggcc caaggccggc cacgactacc gccacttctg gtacgtacgc cggccgccga    660
tgcgcatata cacgtcatag tacggcacct acctaactgg ctctggccaa ccgtccgtac    720
acacgtgaag gggcgacgtg tccgactccg accatgcatg catgcacgcg cgcgaaactt    780
gttactcctg ttctgctatg gcagcagcta gccgcgtgtg tccgttcgta ggagtagtta    840
cttacacagt tacacttacg ccgtccgtcg tgttcctcga cgtgcagcgc cgtgatggag    900
gagttccaca gggagatgcg cgcgctggcc gacaagctgc tggagctgtt cctggtggcc    960
ctcgggctca ccggcgagca ggtcgccgcc gtcgagtccg agcagaagat cgccgagacc   1020
atgaccgcca caatgcacct caactggtac gttccactac tactccagta gtacaagtac   1080
aatatataga atacaaatgg cagcagccac gacgacacgt actccaccat gcagcaaagc   1140
atatattgtc ggtgcggcgg ttgacacgga gttgtgtcgt gtcgttgatt cacaggtacc   1200
ccaagtgccc ggacccgaag cgggcgctgg gcctgatcgc gcacacggac tcgggcttct   1260
tcaccttcgt gctgcagagc cttgtgcccg ggctgcagct gttccggcac ggccccgacc   1320
ggtgggtgac ggtgcccgcc gtgccggggg ccatggtcgt caacgtcggc gacctcttcc   1380
agatcctcac caacggccgc ttccacagcg tctaccaccg cgccgtcgtc aaccgcgaca   1440
gcgaccggat atcgctcggc tacttcctcg gcccgcccgc ccacgtcaag gtggcgccgc   1500
tcagggaggc cctggccggc acgcccgccg cctaccgcgc cgtcacgtgg cccgagtaca   1560
tgggcgtgcg caagaaggcc ttcaccaccg gcgcctccgc gctcaagatg gtcgccatct   1620
ccactgacaa cgacgccgcc aaccacacgg acgacctgat ctcgtcgtag atcggcgccg   1680
gccatcaccg gccggccaag ggatcgatct acacacacaa ttagtgaaca aaaaaatgcc   1740
agagatggtg catggtgggc tggtagctta gctgaggtag ctaggaggaa gagcgcgcgt   1800
gcggctgtcg ttcgtgcggc tgttcccgca aaaaaaaaaa ggtttcctcc atatakgtcc   1860
ccakscaaaa tsgmaawgct gggg                                          1884
```

<210> SEQ ID NO 138
<211> LENGTH: 20
<212> TYPE: RNA
<213> ORGANISM: Artificial Sequence
<220> FEATURE:
<223> OTHER INFORMATION: suppression oligo

<400> SEQUENCE: 138

```
acggguucuu ccaggugugc                                                 20
```

<210> SEQ ID NO 139

<211> LENGTH: 20
<212> TYPE: RNA
<213> ORGANISM: Artificial Sequence
<220> FEATURE:
<223> OTHER INFORMATION: suppression oligo

<400> SEQUENCE: 139
cacggguucu uccaggugug 20

<210> SEQ ID NO 140
<211> LENGTH: 20
<212> TYPE: RNA
<213> ORGANISM: Artificial Sequence
<220> FEATURE:
<223> OTHER INFORMATION: suppression oligo

<400> SEQUENCE: 140
cauugaccuc cccgcuggca 20

<210> SEQ ID NO 141
<211> LENGTH: 20
<212> TYPE: RNA
<213> ORGANISM: Artificial Sequence
<220> FEATURE:
<223> OTHER INFORMATION: suppression oligo

<400> SEQUENCE: 141
ccagcgggga ggucaaugcu 20

<210> SEQ ID NO 142
<211> LENGTH: 20
<212> TYPE: RNA
<213> ORGANISM: Artificial Sequence
<220> FEATURE:
<223> OTHER INFORMATION: suppression oligo

<400> SEQUENCE: 142
cccagcauug accuccccgc 20

<210> SEQ ID NO 143
<211> LENGTH: 20
<212> TYPE: RNA
<213> ORGANISM: Artificial Sequence
<220> FEATURE:
<223> OTHER INFORMATION: suppression oligo

<400> SEQUENCE: 143
cgcgcucgug uacccggaca 20

<210> SEQ ID NO 144
<211> LENGTH: 20
<212> TYPE: RNA
<213> ORGANISM: Artificial Sequence
<220> FEATURE:
<223> OTHER INFORMATION: suppression oligo

<400> SEQUENCE: 144 cuccccggcgc aggucgaaca 20

<210> SEQ ID NO 145
<211> LENGTH: 20
<212> TYPE: RNA
<213> ORGANISM: Artificial Sequence
<220> FEATURE:
<223> OTHER INFORMATION: suppression oligo

<400> SEQUENCE: 145
guguacccgg acacggugcc 20

<210> SEQ ID NO 146
<211> LENGTH: 20
<212> TYPE: RNA
<213> ORGANISM: Artificial Sequence
<220> FEATURE:
<223> OTHER INFORMATION: suppression oligo

<400> SEQUENCE: 146
ugcagggaag cuguccgggc 20

<210> SEQ ID NO 147
<211> LENGTH: 20
<212> TYPE: RNA
<213> ORGANISM: Artificial Sequence
<220> FEATURE:
<223> OTHER INFORMATION: suppression oligo

<400> SEQUENCE: 147
uucuuccagg ugugcgggca 20

<210> SEQ ID NO 148
<211> LENGTH: 20
<212> TYPE: RNA
<213> ORGANISM: Artificial Sequence
<220> FEATURE:
<223> OTHER INFORMATION: suppression oligo

<400> SEQUENCE: 148
agauccccgc gccauuccug 20

<210> SEQ ID NO 149
<211> LENGTH: 20
<212> TYPE: RNA
<213> ORGANISM: Artificial Sequence
<220> FEATURE:
<223> OTHER INFORMATION: suppression oligo

<400> SEQUENCE: 149
augcagggaa gcuguccggg 20

<210> SEQ ID NO 150
<211> LENGTH: 20
<212> TYPE: RNA
<213> ORGANISM: Artificial Sequence
<220> FEATURE:
<223> OTHER INFORMATION: suppression oligo

<400> SEQUENCE: 150
auuccugugg ccgcaggaag 20

<210> SEQ ID NO 151
<211> LENGTH: 20
<212> TYPE: RNA
<213> ORGANISM: Artificial Sequence
<220> FEATURE:
<223> OTHER INFORMATION: suppression oligo

<400> SEQUENCE: 151
cagcggggag gucaaugcug 20

<210> SEQ ID NO 152
<211> LENGTH: 20
<212> TYPE: RNA

<213> ORGANISM: Artificial Sequence
<220> FEATURE:
<223> OTHER INFORMATION: suppression oligo

<400> SEQUENCE: 152
caggaauggc gcggggaucu 20

<210> SEQ ID NO 153
<211> LENGTH: 20
<212> TYPE: RNA
<213> ORGANISM: Artificial Sequence
<220> FEATURE:
<223> OTHER INFORMATION: suppression oligo

<400> SEQUENCE: 153
gacuacuucg ucggcacccu 20

<210> SEQ ID NO 154
<211> LENGTH: 20
<212> TYPE: RNA
<213> ORGANISM: Artificial Sequence
<220> FEATURE:
<223> OTHER INFORMATION: suppression oligo

<400> SEQUENCE: 154
gccaggauuu cgagccaaug 20

<210> SEQ ID NO 155
<211> LENGTH: 20
<212> TYPE: RNA
<213> ORGANISM: Artificial Sequence
<220> FEATURE:
<223> OTHER INFORMATION: suppression oligo

<400> SEQUENCE: 155
ggaacauuug gagggaggcg 20

<210> SEQ ID NO 156
<211> LENGTH: 20
<212> TYPE: RNA
<213> ORGANISM: Artificial Sequence
<220> FEATURE:
<223> OTHER INFORMATION: suppression oligo

<400> SEQUENCE: 156
gggaggucaa ugcuggggcu 20

<210> SEQ ID NO 157
<211> LENGTH: 20
<212> TYPE: RNA
<213> ORGANISM: Artificial Sequence
<220> FEATURE:
<223> OTHER INFORMATION: suppression oligo

<400> SEQUENCE: 157
uuggcucgaa auccuggccg 20

<210> SEQ ID NO 158
<211> LENGTH: 20
<212> TYPE: RNA
<213> ORGANISM: Artificial Sequence
<220> FEATURE:
<223> OTHER INFORMATION: suppression oligo

<400> SEQUENCE: 158
acggguucuu ccaggugugc 20

<210> SEQ ID NO 159
<211> LENGTH: 20
<212> TYPE: RNA
<213> ORGANISM: Artificial Sequence
<220> FEATURE:
<223> OTHER INFORMATION: suppression oligo

<400> SEQUENCE: 159
cacggguucu uccaggugug 20

<210> SEQ ID NO 160
<211> LENGTH: 20
<212> TYPE: RNA
<213> ORGANISM: Artificial Sequence
<220> FEATURE:
<223> OTHER INFORMATION: suppression oligo

<400> SEQUENCE: 160
cauugaccuc cccgcuggca 20

<210> SEQ ID NO 161
<211> LENGTH: 20
<212> TYPE: RNA
<213> ORGANISM: Artificial Sequence
<220> FEATURE:
<223> OTHER INFORMATION: suppression oligo

<400> SEQUENCE: 161
ccagcgggga ggucaaugcu 20

<210> SEQ ID NO 162
<211> LENGTH: 20
<212> TYPE: RNA
<213> ORGANISM: Artificial Sequence
<220> FEATURE:
<223> OTHER INFORMATION: suppression oligo

<400> SEQUENCE: 162
cccagcauug accuccccgc 20

<210> SEQ ID NO 163
<211> LENGTH: 20
<212> TYPE: RNA
<213> ORGANISM: Artificial Sequence
<220> FEATURE:
<223> OTHER INFORMATION: suppression oligo

<400> SEQUENCE: 163
cgcgcucgug uacccggaca 20

<210> SEQ ID NO 164
<211> LENGTH: 20
<212> TYPE: RNA
<213> ORGANISM: Artificial Sequence
<220> FEATURE:
<223> OTHER INFORMATION: suppression oligo

<400> SEQUENCE: 164
cucccggcgc aggucgaaca 20

<210> SEQ ID NO 165
<211> LENGTH: 20
<212> TYPE: RNA
<213> ORGANISM: Artificial Sequence
<220> FEATURE:

<223> OTHER INFORMATION: suppression oligo

<400> SEQUENCE: 165
guguacccgg acacggugcc 20

<210> SEQ ID NO 166
<211> LENGTH: 20
<212> TYPE: RNA
<213> ORGANISM: Artificial Sequence
<220> FEATURE:
<223> OTHER INFORMATION: suppression oligo

<400> SEQUENCE: 166
ugcagggaag cuguccgggc 20

<210> SEQ ID NO 167
<211> LENGTH: 20
<212> TYPE: RNA
<213> ORGANISM: Artificial Sequence
<220> FEATURE:
<223> OTHER INFORMATION: suppression oligo

<400> SEQUENCE: 167
uucuuccagg ugugcgggca 20

<210> SEQ ID NO 168
<211> LENGTH: 447
<212> TYPE: PRT
<213> ORGANISM: Escherichia coli

<400> SEQUENCE: 168

Met Asp Gln Thr Tyr Ser Leu Glu Ser Phe Leu Asn His Val Gln Lys
1 5 10 15

Arg Asp Pro Asn Gln Thr Glu Phe Ala Gln Ala Val Arg Glu Val Met
20 25 30

Thr Thr Leu Trp Pro Phe Leu Glu Gln Asn Pro Lys Tyr Arg Gln Met
35 40 45

Ser Leu Leu Glu Arg Leu Val Glu Pro Glu Arg Val Ile Gln Phe Arg
50 55 60

Val Val Trp Val Asp Asp Arg Asn Gln Ile Gln Val Asn Arg Ala Trp
65 70 75 80

Arg Val Gln Phe Ser Ser Ala Ile Gly Pro Tyr Lys Gly Gly Met Arg
85 90 95

Phe His Pro Ser Val Asn Leu Ser Ile Leu Lys Phe Leu Gly Phe Glu
100 105 110

Gln Thr Phe Lys Asn Ala Leu Thr Thr Leu Pro Met Gly Gly Gly Lys
115 120 125

Gly Gly Ser Asp Phe Asp Pro Lys Gly Lys Ser Glu Gly Glu Val Met
130 135 140

Arg Phe Cys Gln Ala Leu Met Thr Glu Leu Tyr Arg His Leu Gly Ala
145 150 155 160

Asp Thr Asp Val Pro Ala Gly Asp Ile Gly Val Gly Gly Arg Glu Val
165 170 175

Gly Phe Met Ala Gly Met Met Lys Lys Leu Ser Asn Asn Thr Ala Cys
180 185 190

Val Phe Thr Gly Lys Gly Leu Ser Phe Gly Gly Ser Leu Ile Arg Pro
195 200 205

Glu Ala Thr Gly Tyr Gly Leu Val Tyr Phe Thr Glu Ala Met Leu Lys
210 215 220

```
Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Gly Val Ala Thr Ser Gly Leu Glu Met
    370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
        435                 440                 445
```

<210> SEQ ID NO 169
<211> LENGTH: 1344
<212> TYPE: DNA
<213> ORGANISM: Escherichia coli

<400> SEQUENCE: 169

```
atggatcaga catattctct ggagtcattc ctcaaccatg tccaaaagcg cgacccgaat      60

caaaccgagt tcgcgcaagc cgttcgtgaa gtaatgacca cactctggcc ttttcttgaa     120

caaaatccaa aatatcgcca gatgtcatta ctggagcgtc tggttgaacc ggagcgcgtg     180

atccagtttc gcgtggtatg ggttgatgat cgcaaccaga tacaggtcaa ccgtgcatgg     240

cgtgtgcagt tcagctctgc catcggcccg tacaaaggcg gtatgcgctt ccatccgtca     300

gttaaccttt ccattctcaa attcctcggc tttgaacaaa ccttcaaaaa tgccctgact     360

actctgccga tgggcggtgg taaaggcggc agcgatttcg atccgaaagg aaaaagcgaa     420

ggtgaagtga tgcgtttttg ccaggcgctg atgactgaac tgtatcgcca cctgggcgcg     480

gataccgacg ttccggcagg tgatatcggg gttggtggtc gtgaagtcgg ctttatggcg     540

gggatgatga aaaagctctc caacaatacc gcctgcgtct tcaccggtaa gggcctttca     600

tttggcggca gtcttattcg cccggaagct accggctacg gtctggttta tttcacagaa     660

gcaatgctaa aacgccacgg tatgggtttt gaagggatgc gcgtttccgt ttctggctcc     720

ggcaacgtcg cccagtacgc tatcgaaaaa gcgatggaat ttggtgctcg tgtgatcact     780

gcgtcagact ccagcggcac tgtagttgat gaaagcggat tcacgaaaga gaaactggca     840
```

cgtcttatcg aaatcaaagc cagccgcgat ggtcgagtgg cagattacgc caaagaattt 900
ggtctggtct atctcgaagg ccaacagccg tggtctctac cggttgatat cgccctgcct 960
tgcgccaccc agaatgaact ggatgttgac gccgcgcatc agcttatcgc taatggcgtt 1020
aaagccgtcg ccgaaggggc aaatatgccg accaccatcg aagcgactga actgttccag 1080
caggcaggcg tactatttgc accgggtaaa gcggctaatg ctggtggcgt cgctacatcg 1140
ggcctggaaa tggcacaaaa cgctgcgcgc ctgggctgga aagccgagaa agttgacgca 1200
cgtttgcatc acatcatgct ggatatccac catgcctgtg ttgagcatgg tggtgaaggt 1260
gagcaaacca actacgtgca gggcgcgaac attgccggtt ttgtgaaggt tgccgatgcg 1320
atgctggcgc agggtgtgat ttag 1344

<210> SEQ ID NO 170
<211> LENGTH: 80
<212> TYPE: DNA
<213> ORGANISM: Oryza sativa

<400> SEQUENCE: 170
ccctccctcc gcttccaaag aaacgccccc catcgccact atatacatac cccccccctct 60 cctcccatcc ccccaaccct 80

<210> SEQ ID NO 171
<211> LENGTH: 757
<212> TYPE: DNA
<213> ORGANISM: Oryza sativa

<400> SEQUENCE: 171
ctcgaggtca ttcatatgct tgagaagaga gtcgggatag tccaaaataa aacaaaggta 60
agattacctg gtcaaaagtg aaaacatcag ttaaaaggtg gtataaagta aaatatcggt 120
aataaaaggt ggcccaaagt gaaatttact cttttctact attataaaaa ttgaggatgt 180
ttttgtcggt actttgatac gtcatttttg tatgaattgg tttttaagtt tattcgcttt 240
tggaaatgca tatctgtatt tgagtcgggt tttaagttcg tttgcttttg taaatacaga 300
gggatttgta taagaaatat ctttagaaaa acccatatgc taatttgaca taatttttga 360
gaaaaatata tattcaggcg aattctcaca atgaacaata ataagattaa aatagctttc 420
ccccgttgca gcgcatgggt attttttcta gtaaaaataa aagataaact tagactcaaa 480
acatttacaa aaacaacccc taaagttcct aaagcccaaa gtgctatcca cgatccatag 540
caagcccagc ccaacccaac ccaacccaac ccaccccagt ccagccaact ggacaatagt 600
ctccacaccc ccccactatc accgtgagtt gtccgcacgc accgcacgtc tcgcagccaa 660
aaaaaaaaag aaagaaaaaa aagaaaaaga aaaaacagca ggtgggtccg ggtcgtgggg 720
gccggaaacg cgaggaggat cgcgagccag cgacgag 757

<210> SEQ ID NO 172
<211> LENGTH: 333
<212> TYPE: DNA
<213> ORGANISM: Cauliflower mosaic virus

<400> SEQUENCE: 172
catcgttgaa gatgcctctg ccgacagtgg tcccaaagat ggacccccac ccacgaggag 60
catcgtggaa aaagaagacg ttccaaccac gtcttcaaag caagtggatt gatgtgatat 120
ctccactgac gtaagggatg acgcacaatc ccactatcct tcgaggcctc atcgttgaag 180
atgcctctgc cgacagtggt cccaaagatg gacccccacc cacgaggagc atcgtggaaa 240
aagaagacgt tccaaccacg tcttcaaagc aagtggattg atgtgatatc tccactgacg 300
taagggatga cgcacaatcc cactatcctt cga 333

<210> SEQ ID NO 173
<211> LENGTH: 61
<212> TYPE: DNA
<213> ORGANISM: Triticum aestivum

<400> SEQUENCE: 173
aaccatcttc cacacactca agccacacta ttggagaaca cacagggaca acacaccata 60
a 61

<210> SEQ ID NO 174
<211> LENGTH: 480
<212> TYPE: DNA
<213> ORGANISM: Oryza sativa

<400> SEQUENCE: 174
ccgccgccgc cggtaaccac cccgcccctc tcctctttct ttctccgttt ttttttccgt 60
ctcggtctcg atctttggcc ttggtagttt gggtgggcga gaggcggctt cgtgcgcgcc 120
cagatcggtg cgcgggaggg gcgggatctc gcggctgggg ctctcgccgg cgtggatccg 180
gcccggatct cgcggggaat ggggctctcg gatgtagatc tgcgatccgc cgttgttggg 240
ggagatgatg gggggtttaa aatttccgcc gtgctaaaca agatcaggaa gaggggaaaa 300
gggcactatg gtttatattt ttatatattt ctgctgcttc gtcaggctta gatgtgctag 360
atctttcttt cttcttttg tgggtagaat ttgaatccct cagcattgtt catcggtagt 420
ttttcttttc atgatttgtg acaaatgcag cctcgtgcgg agcttttttg taggtagaag 480

<210> SEQ ID NO 175
<211> LENGTH: 943
<212> TYPE: DNA
<213> ORGANISM: Solanum tuberosum

<400> SEQUENCE: 175
accctgcaat gtgaccctag acttgtccat cttctggatt ggccaactta attaatgtat 60
gaaataaaag gatgcacaca tagtgacatg ctaatcacta taatgtgggc atcaaagttg 120
tgtgttatgt gtaattacta attatctgaa taagagaaag agatcatcca tatttcttat 180
cctaaatgaa tgtcacgtgt ctttataatt ctttgatgaa ccagatgcat tttattaacc 240
aattccatat acatataaat attaatcata tataattaat atcaattggg ttagcaaaac 300
aaatctagtc taggtgtgtt ttgctaatta ttgggggata gtgcaaaaag aaatctacgt 360
tctcaataat tcagatagaa aacttaataa agtgagataa tttacataga ttgcttttat 420
cctttgatat atgtgaaacc atgcatgata taaggaaaat agatagagaa ataatttttt 480
acatcgttga atatgtaaac aatttaattc aagaagctag gaatataaat attgaggagt 540
ttatgattat tattattatt ttgatgttca atgaagtttt ttttaatttc atatgaagta 600
tacaaaaatt cttcatagat ttttgtttct atgccgtagt tatctttaat atatttgtgg 660
ttgaagaaat ttattgctag aaacgaatgg attgtcaatt tttttttaaa gcaaatatat 720
atgaaattat actgtatatt attttagtca tgattaaaat gtggccttaa ttgaatcatc 780
tttctcattc attttttcaa aagcatatca ggatgattga tatttatcta ttttaaaaat 840
taatttaagg gttcaaatta aatttaactt aaaagtgtcc taaccgtagt taaaggttta 900

```
ctttaaaaaa atactatgaa aaatctaatc ttctatgaat cga                 943


<210> SEQ ID NO 176
<211> LENGTH: 454
<212> TYPE: PRT
<213> ORGANISM: Saccharomyces cerevisiae

<400> SEQUENCE: 176

Met Ser Glu Pro Glu Phe Gln Gln Ala Tyr Glu Glu Val Val Ser Ser
1               5                   10                  15

Leu Glu Asp Ser Thr Leu Phe Glu Gln His Pro Glu Tyr Arg Lys Val
            20                  25                  30

Leu Pro Ile Val Ser Val Pro Glu Arg Ile Ile Gln Phe Arg Val Thr
        35                  40                  45

Trp Glu Asn Asp Lys Gly Glu Gln Glu Val Ala Gln Gly Tyr Arg Val
    50                  55                  60

Gln Tyr Asn Ser Ala Lys Gly Pro Tyr Lys Gly Gly Leu Arg Phe His
65                  70                  75                  80

Pro Ser Val Asn Leu Ser Ile Leu Lys Phe Leu Gly Phe Glu Gln Ile
                85                  90                  95

Phe Lys Asn Ser Leu Thr Gly Leu Asp Met Gly Gly Gly Lys Gly Gly
            100                 105                 110

Leu Cys Val Asp Leu Lys Gly Arg Ser Asn Asn Glu Ile Arg Arg Ile
        115                 120                 125

Cys Tyr Ala Phe Met Arg Glu Leu Ser Arg His Ile Gly Gln Asp Thr
    130                 135                 140

Asp Val Pro Ala Gly Asp Ile Gly Val Gly Gly Arg Glu Ile Gly Tyr
145                 150                 155                 160

Leu Phe Gly Ala Tyr Arg Ser Tyr Lys Asn Ser Trp Glu Gly Val Leu
                165                 170                 175

Thr Gly Lys Gly Leu Asn Trp Gly Gly Ser Leu Ile Arg Pro Glu Ala
            180                 185                 190

Thr Gly Tyr Gly Leu Val Tyr Tyr Thr Gln Ala Met Ile Asp Tyr Ala
        195                 200                 205

Thr Asn Gly Lys Glu Ser Phe Glu Gly Lys Arg Val Thr Ile Ser Gly
    210                 215                 220

Ser Gly Asn Val Ala Gln Tyr Ala Ala Leu Lys Val Ile Glu Leu Gly
225                 230                 235                 240

Gly Thr Val Val Ser Leu Ser Asp Ser Lys Gly Cys Ile Ile Ser Glu
                245                 250                 255

Thr Gly Ile Thr Ser Glu Gln Val Ala Asp Ile Ser Ser Ala Lys Val
            260                 265                 270

Asn Phe Lys Ser Leu Glu Gln Ile Val Asn Glu Tyr Ser Thr Phe Ser
        275                 280                 285

Glu Asn Lys Val Gln Tyr Ile Ala Gly Ala Arg Pro Trp Thr His Val
    290                 295                 300

Gln Lys Val Asp Ile Ala Leu Pro Cys Ala Thr Gln Asn Glu Val Ser
305                 310                 315                 320

Gly Glu Glu Ala Lys Ala Leu Val Ala Gln Gly Val Lys Phe Ile Ala
                325                 330                 335

Glu Gly Ser Asn Met Gly Ser Thr Pro Glu Ala Ile Ala Val Phe Glu
            340                 345                 350

Thr Ala Arg Ser Thr Ala Thr Gly Pro Ser Glu Ala Val Trp Tyr Gly
        355                 360                 365
```

```
Pro Pro Lys Ala Ala Asn Leu Gly Gly Val Ala Val Ser Gly Leu Glu
    370                 375                 380

Met Ala Gln Asn Ser Gln Arg Ile Thr Trp Thr Ser Glu Arg Val Asp
385                 390                 395                 400

Gln Glu Leu Lys Arg Ile Met Ile Asn Cys Phe Asn Glu Cys Ile Asp
                405                 410                 415

Tyr Ala Lys Lys Tyr Thr Lys Asp Gly Lys Val Leu Pro Ser Leu Val
            420                 425                 430

Lys Gly Ala Asn Ile Ala Ser Phe Ile Lys Val Ser Asp Ala Met Phe
        435                 440                 445

Asp Gln Gly Asp Val Phe
    450


<210> SEQ ID NO 177
<211> LENGTH: 447
<212> TYPE: PRT
<213> ORGANISM: Corynebacterium efficiens

<400> SEQUENCE: 177

Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Asn Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Glu Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Ala Gly Asp Ile Gly Val Gly Gly Arg Glu Ile
                165                 170                 175

Gly Tyr Leu Phe Gly His Tyr Arg Arg Leu Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Phe Gly Thr Val Tyr Phe Val Gln Glu Met Ile
    210                 215                 220

Lys Ala Glu Gly Glu Thr Leu Glu Gly Lys Lys Val Ile Val Ser Gly
225                 230                 235                 240

Ser Gly Asn Val Ala Thr Tyr Ala Ile Gln Lys Val Gln Glu Leu Gly
                245                 250                 255

Ala Val Val Val Gly Phe Ser Asp Ser Ser Gly Trp Val Ser Thr Pro
            260                 265                 270

Asn Gly Val Asp Val Ala Lys Leu Arg Glu Ile Lys Glu Val Arg Arg
        275                 280                 285
```

```
Ala Arg Val Ser Ser Tyr Ala Asp Glu Val Glu Gly Ala Glu Tyr His
    290                 295                 300

Thr Asp Gly Ser Ile Trp Asp Leu Thr Ala Asp Ile Ala Leu Pro Cys
305                 310                 315                 320

Ala Thr Gln Asn Glu Leu Asp Gly Asp Asn Ala Arg Thr Leu Ala Asp
                325                 330                 335

Asn Gly Cys Arg Phe Val Ala Glu Gly Ala Asn Met Pro Ser Thr Pro
            340                 345                 350

Glu Ala Ile Asp Val Phe Arg Glu Arg Gly Val Leu Phe Gly Pro Gly
        355                 360                 365

Lys Ala Ala Asn Ala Gly Gly Val Ala Thr Ser Ala Leu Glu Met Gln
    370                 375                 380

Gln Asn Ala Ser Arg Asp Ser Trp Ser Phe Glu Tyr Thr Asp Glu Arg
385                 390                 395                 400

Leu His Arg Ile Met Lys Asn Ile Phe Lys Ser Cys Ala Asp Thr Ala
                405                 410                 415

Lys Glu Tyr Gly His Glu Lys Asn Tyr Val Val Gly Ala Asn Ile Ala
            420                 425                 430

Gly Phe Lys Lys Val Ala Asp Ala Met Leu Ala Gln Gly Val Ile
        435                 440                 445


<210> SEQ ID NO 178
<211> LENGTH: 447
<212> TYPE: PRT
<213> ORGANISM: Corynebacterium glutamicum

<400> SEQUENCE: 178

Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65                  70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Ala Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
```

```
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365

Lys Ala Ala Asn Ala Gly Gly Val Ala Thr Ser Ala Leu Glu Met Gln
    370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
            420                 425                 430

Gly Phe Lys Lys Val Ala Asp Ala Met Leu Ala Gln Gly Val Ile
        435                 440                 445


<210> SEQ ID NO 179
<211> LENGTH: 417
<212> TYPE: PRT
<213> ORGANISM: Halobacterium salinarum

<400> SEQUENCE: 179

Met Pro Glu Ala Asn Pro Phe Glu Ser Leu Gln Glu Gln Leu Asp Asp
1               5                   10                  15

Ala Gly Glu Phe Leu Asp Val Asn Ala Asp Val Leu Glu Arg Leu Lys
            20                  25                  30

His Pro Glu Arg Val Leu Glu Thr Thr Leu Ser Val Glu Met Asp Asp
        35                  40                  45

Gly Thr Ile Glu Thr Phe Lys Ala Phe Arg Ser Gln Phe Asn Gly Asp
    50                  55                  60

Arg Gly Pro Tyr Lys Gly Gly Ile Arg Tyr His Pro Gly Val Thr Arg
65                  70                  75                  80

Asp Glu Val Lys Ala Leu Ser Gly Trp Met Val Tyr Lys Thr Ala Val
                85                  90                  95

Ala Asp Ile Pro Tyr Gly Gly Gly Lys Gly Gly Ile Ile Leu Asp Pro
            100                 105                 110

Glu Glu Tyr Ser Asp Ser Glu Leu Glu Arg Ile Thr Arg Ala Phe Ala
        115                 120                 125

Thr Glu Leu Arg Pro Phe Ile Gly Glu Asp Lys Asp Val Pro Ala Pro
    130                 135                 140
```

```
Asp Val Asn Thr Gly Gln Arg Glu Met Asn Trp Ile Lys Asp Thr Tyr
145                 150                 155                 160

Glu Thr Leu Glu Asp Thr Thr Ala Pro Gly Val Ile Thr Gly Lys Ala
                165                 170                 175

Leu Glu Asn Gly Gly Ser Glu Gly Arg Val Asn Ala Thr Gly Arg Ser
            180                 185                 190

Thr Met Phe Ala Ala Arg Glu Val Phe Asp Tyr Leu Asp Arg Asp Leu
        195                 200                 205

Ser Asp Ala Thr Val Ala Val Gln Gly Tyr Gly Asn Ala Gly Ser Val
    210                 215                 220

Ala Ala Lys Leu Ile Ala Asp Gln Gly Ala Asp Val Val Ala Val Ser
225                 230                 235                 240

Asp Ser Ser Gly Ala Val His Asn Pro Asp Gly Leu Asp Thr Arg Ala
                245                 250                 255

Val Lys Ala Phe Lys Thr Glu Thr Gly Ser Val Ser Gly Tyr Glu Gly
            260                 265                 270

Ala Thr Glu Glu Leu Ser Asn Glu Ala Leu Leu Thr Met Asp Val Asp
        275                 280                 285

Leu Leu Val Pro Ala Ala Leu Glu Asn Ala Ile Asp Glu Asp Leu Ala
    290                 295                 300

His Asp Val Asp Ala Asp Val Val Val Glu Ala Ala Asn Gly Pro Leu
305                 310                 315                 320

Thr Pro Asp Ala Asp Asp Val Leu Thr Glu Arg Gly Val Thr Val Val
                325                 330                 335

Pro Asp Ile Leu Ala Asn Ala Gly Gly Val Thr Val Ser Tyr Phe Glu
            340                 345                 350

Trp Val Gln Asn Arg Gln Arg Phe Gln Trp Thr Glu Asp Arg Val Asn
        355                 360                 365

Glu Glu Leu Glu Ala Ile Ile Thr Asp Ala Phe Asp Ala Met Thr Asp
    370                 375                 380

Ala His Glu Asp Ala Gly Thr Pro Asn Leu Arg Thr Ala Ala Tyr Val
385                 390                 395                 400

Val Ala Val Gln Arg Val Val Asp Ala Tyr Glu Gly Ser Gly Ser Trp
                405                 410                 415

Pro
```

<210> SEQ ID NO 180
<211> LENGTH: 450
<212> TYPE: PRT
<213> ORGANISM: Laccaria bicolor

<400> SEQUENCE: 180

```
Met Val Leu Pro Val Glu Pro Glu Tyr Glu Gln Ala Leu Ser Glu Leu
1               5                   10                  15

Gln Asn Ser Leu Lys Pro Phe Leu Ala Ala Asn Pro Asp Tyr Glu Lys
            20                  25                  30

Ala Leu Glu Ile Val Gln Ile Pro Glu Arg Val Leu Gln Phe Arg Val
        35                  40                  45

Val Trp Glu Asp Asp Gln Gly Lys Ala Gln Val Asn Arg Gly Phe Arg
    50                  55                  60

Val Gln Tyr Asn Ser Ala Leu Gly Pro Tyr Lys Gly Gly Leu Arg Leu
65                  70                  75                  80

His Pro Ser Val Asn Leu Ser Ile Leu Lys Phe Leu Gly Phe Glu Gln
                85                  90                  95
```

```
Thr Phe Lys Asn Ala Leu Thr Gly Leu Ser Met Gly Gly Gly Lys Gly
            100                 105                 110

Gly Ser Asp Phe Asp Pro Lys Gly Lys Ser Asp Gly Glu Ile Arg Arg
        115                 120                 125

Phe Cys Thr Ser Phe Met Ser Glu Leu Phe Arg His Ile Gly Gln Asp
    130                 135                 140

Thr Asp Val Pro Ala Gly Asp Ile Gly Thr Gly Ala Arg Glu Ile Gly
145                 150                 155                 160

Tyr Leu Phe Gly Ala Tyr Lys Lys Leu Gln Asn Glu Phe Val Gly Met
                165                 170                 175

Leu Thr Gly Lys Gly Leu Ala Trp Gly Gly Ser Phe Ile Arg Pro Glu
            180                 185                 190

Ala Thr Gly Tyr Gly Leu Ile Tyr Tyr Val Glu His Met Ile Ala Lys
        195                 200                 205

Ala Ala Pro Glu Tyr Ser Leu Ser Lys Pro Glu Thr Leu Val Ala Ile
    210                 215                 220

Ser Gly Ser Gly Asn Val Ala Gln Phe Thr Ala Leu Lys Val Ile Glu
225                 230                 235                 240

Leu Gly Ala Thr Val Leu Ser Leu Ser Asp Ser Lys Gly Ser Leu Ile
                245                 250                 255

Ala Glu Lys Gly Tyr Thr Lys Glu Phe Ile Lys Glu Ile Gly Gln Leu
            260                 265                 270

Lys Leu Lys Gly Gly Ala Leu Glu Ser Leu Ala Gln Arg Glu Gly Tyr
        275                 280                 285

Thr Tyr His Ala Gly Lys Arg Pro Trp Ser Leu Leu Pro Val Val His
    290                 295                 300

Val Ala Leu Pro Gly Ala Thr Gln Asn Glu Val Ser Lys Thr Glu Ala
305                 310                 315                 320

Glu Asp Leu Ile Lys Ala Gly Val Arg Ile Val Ala Glu Gly Ser Asn
                325                 330                 335

Met Gly Cys Thr Glu Asp Ala Ile Ala Val Phe Glu Ala Ser Arg Lys
            340                 345                 350

Ala Gly Ala Gly Gly Val Trp Tyr Ala Pro Gly Lys Ala Ser Asn Cys
        355                 360                 365

Gly Gly Val Ala Val Ser Gly Leu Glu Met Ala Gln Asn Ser Gln Arg
    370                 375                 380

Leu Ala Trp Thr Thr Asp Gln Val Asp Gln Lys Leu Lys Lys Ile Met
385                 390                 395                 400

Ala Glu Cys Tyr Glu Ile Cys Leu Ser Ala Gly Thr Lys Trp Ser Gly
                405                 410                 415

Glu Glu Ile Lys Asp Gly Val Leu Pro Ser Leu Leu Ser Gly Ala Asn
            420                 425                 430

Val Ala Gly Phe Ile Lys Val Ala Asp Ala Met Arg Glu His Gly Asp
        435                 440                 445

Trp Trp
    450
```

<210> SEQ ID NO 181
<211> LENGTH: 390
<212> TYPE: PRT
<213> ORGANISM: Sulfolobus shibatae

<400> SEQUENCE: 181

```
Leu Asp Thr Leu Glu Ala Leu Ser Gln Pro Glu Arg Val Ile Gln Val
1               5                   10                  15
```

```
Lys Ile Gln Ile Arg Gly Ser Asp Gly Lys Leu Lys Thr Phe Met Gly
            20                  25                  30

Trp Arg Ser Gln His Asn Ser Ala Leu Gly Pro Tyr Lys Gly Gly Val
        35                  40                  45

Arg Tyr Ser Pro Asn Val Thr Gln Asp Glu Val Ile Ala Leu Ser Met
    50                  55                  60

Ile Met Thr Trp Lys Asn Ser Leu Leu Leu Leu Pro Tyr Gly Gly Gly
65                  70                  75                  80

Lys Gly Gly Ile Arg Val Asp Pro Lys Lys Leu Thr Leu Lys Glu Leu
                85                  90                  95

Glu Asp Leu Ser Arg Lys Tyr Val Gln Leu Ile His Asn Tyr Leu Gly
            100                 105                 110

Ser Asp Val Asp Ile Pro Ala Pro Asp Ile Asn Thr Asn Pro Gln Thr
        115                 120                 125

Met Ala Trp Phe Leu Asp Glu Tyr Ile Lys Ile Thr Gly Glu Val Asp
    130                 135                 140

Phe Ala Val Phe Thr Gly Lys Pro Ser Glu Leu Gly Gly Ile Gly Val
145                 150                 155                 160

Arg Leu Tyr Ser Thr Gly Leu Gly Val Ala Thr Ile Ala Arg Glu Ala
                165                 170                 175

Ala Asn Lys Phe Ile Gly Gly Ile Glu Gly Ser Arg Val Ile Ile Gln
            180                 185                 190

Gly Phe Gly Asn Val Gly Ser Phe Thr Ala Lys Phe Leu Asn Glu Met
        195                 200                 205

Gly Ala Lys Ile Ile Gly Val Ser Asp Ile Gly Gly Gly Val Ile Ser
    210                 215                 220

Asp Asp Gly Ile Asp Val Asn Lys Ala Leu Glu Val Val Gln Ser Thr
225                 230                 235                 240

Gly Ser Val Val Asn Tyr Pro Glu Gly Lys Lys Val Thr Asn Glu Glu
                245                 250                 255

Leu Leu Thr Ser Asp Cys Asp Ile Leu Ile Pro Ala Ala Val Glu Asn
            260                 265                 270

Val Ile Asn Lys Phe Asn Ala Pro Lys Val Lys Ala Lys Leu Ile Val
        275                 280                 285

Glu Gly Ala Asn Gly Pro Leu Ala Ala Asp Ala Asp Glu Ile Ile Lys
    290                 295                 300

Gln Arg Gly Ile Val Val Ile Pro Asp Ile Leu Ala Asn Ala Gly Gly
305                 310                 315                 320

Val Val Gly Ser Tyr Val Glu Trp Ala Asn Asn Lys Ser Gly Gly Ile
                325                 330                 335

Ile Ser Asp Glu Glu Ala Lys Lys Leu Ile Ile Asp Arg Met Thr Asn
            340                 345                 350

Ala Phe Asn Ala Leu Tyr Glu Phe His Lys Arg Lys Phe Ala Asp Gln
        355                 360                 365

Asp Leu Arg Thr Val Ala Met Ala Leu Arg Val Asp Arg Val Val Gly
    370                 375                 380

Met Lys Ala Arg Ala Ile
385                 390
```

<210> SEQ ID NO 182
<211> LENGTH: 457
<212> TYPE: PRT
<213> ORGANISM: Tuber borchii

<400> SEQUENCE: 182

```
Met Ser Asn Leu Ala Pro Glu Pro Glu Phe Gln Gln Ala Tyr Asn Glu
1               5                   10                  15

Leu Val His Ser Leu Arg Asp Gln Asn Ser Ser Arg Leu Pro Gln Ile
            20                  25                  30

Leu Arg Leu Leu Cys Leu Ser Ser Pro Pro Glu Arg Val Ile Gln Phe
        35                  40                  45

Arg Val Thr Trp Glu Asp Asp Lys Gly Asn Phe Gln Val Asn Arg Gly
    50                  55                  60

Tyr Arg Val Gln Phe Asn Ser Ala Leu Gly Pro Tyr Lys Gly Gly Leu
65                  70                  75                  80

Arg Phe His Pro Thr Val Asn Leu Ser Ile Leu Lys Phe Leu Gly Phe
                85                  90                  95

Glu Gln Thr Phe Lys Asn Ala Leu Thr Gly Leu Asn Met Gly Gly Gly
            100                 105                 110

Lys Gly Gly Ser Asp Phe Asp Pro Lys Gly Lys Ser Asp Asn Glu Ile
        115                 120                 125

Arg Arg Phe Cys Tyr Ser Phe Met Arg Glu Leu Ser Lys His Ile Gly
    130                 135                 140

Gln Phe Thr Asp Val Pro Ala Gly Asp Ile Gly Val Gly Gly Arg Glu
145                 150                 155                 160

Ile Gly Tyr Leu Phe Gly Ala Tyr Glu Ser Tyr Lys Asn Gln Phe Glu
                165                 170                 175

Gly Val Leu Thr Gly Lys Gly Ile Thr Trp Gly Gly Ser Leu Ile Arg
            180                 185                 190

Pro Glu Ala Thr Gly Tyr Gly Leu Val Tyr Tyr Val Ala His Met Ile
        195                 200                 205

Ser Tyr Ala Ser Gly Gly Lys Glu Thr Phe Ala Gly Lys Arg Val Ala
    210                 215                 220

Ile Ser Gly Ser Gly Asn Val Ala Gln Tyr Ala Ala Leu Lys Val Leu
225                 230                 235                 240

Glu Leu Gly Gly Lys Val Ile Thr Leu Ser Asp Ser Lys Gly Ala Leu
                245                 250                 255

Ile Ala Thr Gly Glu Glu Gly Phe Asn Glu Thr Asp Ile Glu Leu Ile
            260                 265                 270

Ala Lys Leu Lys Leu Asp Arg Gly Tyr Leu Thr Gln Leu His Ala Ala
        275                 280                 285

Glu Asp Ser Phe Lys Ser Arg Phe Lys Tyr Leu Pro Gly Glu Arg Pro
    290                 295                 300

Trp Cys His Val Asp Lys Val Asp Val Ala Leu Pro Ser Ala Thr Gln
305                 310                 315                 320

Asn Glu Val Ser Glu Gln Glu Ala Lys Glu Leu Ile Ala Ser Gly Cys
                325                 330                 335

Lys Phe Leu Ala Glu Gly Ser Asn Met Gly Ser Thr Gln Glu Ala Ile
            340                 345                 350

Asn Val Tyr Glu Glu Asp Arg Lys Ser Arg Lys Ala Asp Gly Leu Trp
        355                 360                 365

Tyr Gly Pro Ala Lys Ala Ala Asn Cys Gly Gly Val Ala Val Ser Gly
    370                 375                 380

Leu Glu Met Ala Gln Asn Ser Gln Arg Leu Thr Trp Thr Ser Glu Gln
385                 390                 395                 400

Val Asp Lys Glu Leu Ala Gly Ile Met Glu Arg Cys Phe Trp Asn Cys
                405                 410                 415
```

```
Leu Asn Pro Ala Lys Glu Tyr Phe Asp Ile Ala Glu Gly Glu Leu Pro
            420                 425                 430

Ser Leu Val Ala Gly Ala Asn Ile Ala Gly Tyr Val Lys Val Val Asn
        435                 440                 445

Ala Met Lys Ala Gln Gly Asp Trp Trp
    450                 455


<210> SEQ ID NO 183
<211> LENGTH: 457
<212> TYPE: PRT
<213> ORGANISM: Saccharomyces cerevisiae

<400> SEQUENCE: 183

Met Thr Ser Glu Pro Glu Phe Gln Gln Ala Tyr Asp Glu Ile Val Ser
1               5                   10                  15

Ser Val Glu Asp Ser Lys Ile Phe Glu Lys Phe Pro Gln Tyr Lys Lys
            20                  25                  30

Val Leu Pro Ile Val Ser Val Pro Glu Arg Ile Ile Gln Phe Arg Val
        35                  40                  45

Thr Trp Glu Asn Asp Asn Gly Glu Gln Glu Val Ala Gln Gly Tyr Arg
    50                  55                  60

Val Gln Phe Asn Ser Ala Lys Gly Pro Tyr Lys Gly Gly Leu Arg Phe
65                  70                  75                  80

His Pro Ser Val Asn Leu Ser Ile Leu Lys Phe Leu Gly Phe Glu Gln
                85                  90                  95

Ile Phe Lys Asn Ala Leu Thr Gly Leu Asp Met Gly Gly Gly Lys Gly
            100                 105                 110

Gly Leu Cys Val Asp Leu Lys Gly Lys Ser Asp Asn Glu Ile Arg Arg
        115                 120                 125

Ile Cys Tyr Ala Phe Met Arg Glu Leu Ser Arg His Ile Gly Lys Asp
    130                 135                 140

Thr Asp Val Pro Ala Gly Asp Ile Gly Val Gly Gly Arg Glu Ile Gly
145                 150                 155                 160

Tyr Leu Phe Gly Ala Tyr Arg Ser Tyr Lys Asn Ser Trp Glu Gly Val
                165                 170                 175

Leu Thr Gly Lys Gly Leu Asn Trp Gly Gly Ser Leu Ile Arg Pro Glu
            180                 185                 190

Ala Thr Gly Phe Gly Leu Val Tyr Tyr Thr Gln Ala Met Ile Asp Tyr
        195                 200                 205

Ala Thr Asn Gly Lys Glu Ser Phe Glu Gly Lys Arg Val Thr Ile Ser
    210                 215                 220

Gly Ser Gly Asn Val Ala Gln Tyr Ala Ala Leu Lys Val Ile Glu Leu
225                 230                 235                 240

Gly Gly Ile Val Val Ser Leu Ser Asp Ser Lys Gly Cys Ile Ile Ser
                245                 250                 255

Glu Thr Gly Ile Thr Ser Glu Gln Ile His Asp Ile Ala Ser Ala Lys
            260                 265                 270

Ile Arg Phe Lys Ser Leu Glu Glu Ile Val Asp Glu Tyr Ser Thr Phe
        275                 280                 285

Ser Glu Ser Lys Met Lys Tyr Val Ala Gly Ala Arg Pro Trp Thr His
    290                 295                 300

Val Ser Asn Val Asp Ile Ala Leu Pro Cys Ala Thr Gln Asn Glu Val
305                 310                 315                 320

Ser Gly Asp Glu Ala Lys Ala Leu Val Ala Ser Gly Val Lys Phe Val
```

```
                325                 330                 335

Ala Glu Gly Ala Asn Met Gly Ser Thr Pro Glu Ala Ile Ser Val Phe
            340                 345                 350

Glu Thr Ala Arg Ser Thr Ala Thr Asn Ala Lys Asp Ala Val Trp Phe
        355                 360                 365

Gly Pro Pro Lys Ala Ala Asn Leu Gly Gly Val Ala Val Ser Gly Leu
    370                 375                 380

Glu Met Ala Gln Asn Ser Gln Lys Val Thr Trp Thr Ala Glu Arg Val
385                 390                 395                 400

Asp Gln Glu Leu Lys Lys Ile Met Ile Asn Cys Phe Asn Asp Cys Ile
                405                 410                 415

Gln Ala Ala Gln Glu Tyr Ser Thr Glu Lys Asn Thr Asn Thr Leu Pro
            420                 425                 430

Ser Leu Val Lys Gly Ala Asn Ile Ala Ser Phe Val Met Val Ala Asp
        435                 440                 445

Ala Met Leu Asp Gln Gly Asp Val Phe
    450                 455


<210> SEQ ID NO 184
<211> LENGTH: 450
<212> TYPE: PRT
<213> ORGANISM: Hebeloma cylindrosporum

<400> SEQUENCE: 184

Met Val Lys Pro Phe Glu Pro Glu Phe Gln Gln Ala Leu Asp Glu Leu
1               5                   10                  15

Thr Thr Ser Leu Gln Pro Phe Leu Asp Ala Asn Pro Gln Tyr Lys Lys
            20                  25                  30

Ala Leu Glu Ile Val Gln Val Pro Glu Arg Val Leu Gln Phe Arg Val
        35                  40                  45

Val Trp Glu Asp Asp Gln Gly Val Ala Gln Val Asn His Gly Phe Arg
    50                  55                  60

Val Gln Tyr Asn Ser Ala Leu Gly Pro Tyr Lys Gly Gly Leu Arg Leu
65                  70                  75                  80

His Pro Ser Val Asn Leu Ser Ile Leu Lys Phe Leu Gly Phe Glu Gln
                85                  90                  95

Thr Phe Lys Asn Ala Leu Thr Gly Leu Ser Met Gly Gly Gly Lys Gly
            100                 105                 110

Gly Ser Asp Phe Asp Pro Lys Gly Lys Ser Asp Ser Glu Ile Arg Arg
        115                 120                 125

Phe Cys Phe Ser Phe Met Gly Glu Leu Phe Arg His Ile Gly Ser Asp
    130                 135                 140

Thr Asp Val Pro Ala Gly Asp Ile Gly Thr Gly Gly Arg Glu Ile Gly
145                 150                 155                 160

Phe Leu Phe Gly Ala Tyr Lys Lys Leu Arg Asn Glu Phe Thr Gly Met
                165                 170                 175

Leu Thr Gly Lys Gly Leu Thr Trp Gly Gly Ser Phe Ile Arg Pro Glu
            180                 185                 190

Ala Thr Gly Tyr Gly Leu Ile Tyr Phe Val Glu His Met Ile Ala Lys
        195                 200                 205

Ala Cys Pro Glu Tyr Ser Leu Asp Lys Pro Ser Thr Leu Val Ala Ile
    210                 215                 220

Ser Gly Ser Gly Asn Val Ala Gln Phe Thr Ala Leu Lys Val Ile Glu
225                 230                 235                 240
```

```
Leu Gly Ala Thr Val Leu Ser Leu Ser Asp Ser Lys Gly Ser Leu Ile
            245                 250                 255

Ser Asp Lys Gly Tyr Thr Lys Glu Phe Ile Arg Lys Val Ala Asp Leu
            260                 265                 270

Lys Leu Lys Gly Gly Ser Leu Ala Ser Leu Ala Asn Glu Glu Gly Tyr
        275                 280                 285

Thr Tyr His Ala Gly Ala Arg Pro Trp Thr Leu Ile Pro Thr Ile His
    290                 295                 300

Ile Ala Leu Pro Gly Ala Thr Gln Asn Glu Val Ser Ala Glu Glu Ala
305                 310                 315                 320

Glu Ala Leu Leu Lys Ala Gly Val Arg Ile Val Ala Glu Gly Ser Asn
            325                 330                 335

Met Gly Cys Thr Ala Asp Ala Ile Asp Ile Phe Glu Ser Ser Arg Lys
            340                 345                 350

Ala Gly Pro Gly Gly Val Trp Tyr Ala Pro Gly Lys Ala Ser Asn Cys
        355                 360                 365

Gly Gly Val Ala Val Ser Gly Leu Glu Met Ala Gln Asn Ser Gln Arg
    370                 375                 380

Leu Ala Trp Thr Thr Gln Glu Val Asp Ser Lys Leu Lys Asp Ile Met
385                 390                 395                 400

Ala Glu Cys Tyr Gly Ile Cys Leu Thr Ala Gly Thr Lys Trp Ser Gly
            405                 410                 415

Glu Glu Leu Thr Asp Glu Val Leu Pro Ser Leu Leu Ser Gly Ala Asn
            420                 425                 430

Val Ala Gly Phe Ile Lys Val Ala Asp Ala Met Lys Ala Gln Gly Asp
        435                 440                 445

Trp Trp
    450


<210> SEQ ID NO 185
<211> LENGTH: 454
<212> TYPE: PRT
<213> ORGANISM: Neurospora intermedia

<400> SEQUENCE: 185

Met Ser Asn Leu Pro Ser Glu Pro Glu Phe Glu Gln Ala Tyr Lys Glu
1               5                   10                  15

Leu Ala Tyr Thr Leu Glu Asn Ser Ser Leu Phe Gln Lys His Pro Glu
            20                  25                  30

Tyr Arg Thr Ala Leu Thr Val Ala Ser Ile Pro Glu Arg Val Ile Gln
        35                  40                  45

Phe Arg Val Val Trp Glu Asp Asp Asn Gly Asn Val Gln Val Asn Arg
    50                  55                  60

Gly Tyr Arg Val Gln Phe Asn Ser Ala Leu Gly Pro Tyr Lys Gly Gly
65                  70                  75                  80

Leu Arg Leu His Pro Ser Val Asn Leu Ser Ile Leu Lys Phe Leu Gly
                85                  90                  95

Phe Glu Gln Ile Phe Lys Asn Ala Leu Thr Gly Leu Ser Met Gly Gly
            100                 105                 110

Gly Lys Gly Gly Ala Asp Phe Asp Pro Lys Gly Lys Ser Asp Ala Glu
        115                 120                 125

Ile Arg Arg Phe Cys Cys Ala Phe Met Ala Glu Leu His Lys His Ile
    130                 135                 140

Gly Ala Asp Thr Asp Val Pro Ala Gly Asp Ile Gly Val Gly Gly Arg
145                 150                 155                 160
```

```
Glu Ile Gly Tyr Met Phe Gly Ala Tyr Arg Lys Ala Ala Asn Arg Phe
                165                 170                 175

Glu Gly Val Leu Thr Gly Lys Gly Leu Ser Trp Gly Gly Ser Leu Ile
            180                 185                 190

Arg Pro Glu Ala Thr Gly Tyr Gly Leu Val Tyr Tyr Val Gly His Met
        195                 200                 205

Leu Glu Tyr Ser Gly Ala Gly Ser Tyr Ala Gly Lys Arg Val Ala Leu
    210                 215                 220

Ser Gly Ser Gly Asn Val Ala Gln Tyr Ala Ala Leu Lys Leu Ile Glu
225                 230                 235                 240

Leu Gly Ala Thr Val Val Ser Leu Ser Asp Ser Lys Gly Ala Leu Val
                245                 250                 255

Ala Thr Gly Glu Ser Gly Ile Thr Val Glu Asp Ile Asn Ala Val Met
            260                 265                 270

Ala Ile Lys Glu Ala Arg Gln Ser Leu Thr Ser Phe Gln His Ala Gly
        275                 280                 285

His Leu Lys Trp Ile Glu Gly Ala Arg Pro Trp Leu His Val Gly Lys
    290                 295                 300

Val Asp Ile Ala Leu Pro Cys Ala Thr Gln Asn Glu Val Ser Lys Glu
305                 310                 315                 320

Glu Ala Glu Gly Leu Leu Ala Ala Gly Cys Lys Phe Val Ala Glu Gly
                325                 330                 335

Ser Asn Met Gly Cys Thr Leu Glu Ala Ile Glu Val Phe Glu Asn His
            340                 345                 350

Arg Lys Glu Lys Lys Gly Glu Ala Val Trp Tyr Ala Pro Gly Lys Ala
        355                 360                 365

Ala Asn Cys Gly Gly Val Ala Val Ser Gly Leu Glu Met Ala Gln Asn
    370                 375                 380

Ser Gln Arg Leu Asn Trp Thr Gln Ala Glu Val Asp Glu Lys Leu Lys
385                 390                 395                 400

Asp Ile Met Lys Asn Ala Phe Phe Asn Gly Leu Asn Thr Ala Lys Ile
                405                 410                 415

Tyr Val Glu Ala Ala Glu Gly Glu Leu Pro Ser Leu Val Ala Gly Ser
            420                 425                 430

Asn Ile Ala Gly Phe Val Lys Val Ala Gln Ala Met His Asp Gln Gly
        435                 440                 445

Asp Trp Trp Ser Lys Asn
    450


<210> SEQ ID NO 186
<211> LENGTH: 451
<212> TYPE: PRT
<213> ORGANISM: Schizosaccharomyces pombe

<400> SEQUENCE: 186

Met Ser Thr Pro Tyr Glu Pro Glu Phe Gln Gln Ala Tyr Lys Glu Ile
1               5                   10                  15

Val Gly Ser Ile Glu Ser Ser Lys Leu Phe Glu Val His Pro Glu Leu
            20                  25                  30

Lys Arg Val Leu Pro Ile Ile Ser Ile Pro Glu Arg Val Leu Glu Phe
        35                  40                  45

Arg Val Thr Trp Glu Asp Asp Lys Gly Asn Cys Arg Val Asn Thr Gly
    50                  55                  60

Tyr Arg Val Gln Phe Asn Ser Ala Leu Gly Pro Tyr Lys Gly Gly Leu
```

```
65                  70                  75                  80

Arg Phe His Pro Ser Val Asn Leu Ser Ile Leu Lys Phe Leu Gly Phe
                85                  90                  95

Glu Gln Ile Phe Lys Asn Ala Leu Thr Gly Leu Pro Met Gly Gly Gly
            100                 105                 110

Lys Gly Gly Ser Asp Phe Asp Pro Lys Gly Lys Ser Asp Asn Glu Ile
        115                 120                 125

Arg Arg Phe Ser Gln Ala Phe Met Arg Gln Leu Phe Arg Tyr Ile Gly
    130                 135                 140

Pro Gln Thr Asp Val Pro Ala Gly Asp Ile Gly Val Thr Gly Phe Val
145                 150                 155                 160

Val Met His Met Phe Gly Glu Tyr Lys Arg Leu Arg Asn Glu Tyr Ser
                165                 170                 175

Gly Val Val Thr Gly Lys His Met Leu Thr Gly Gly Ser Asn Ile Arg
            180                 185                 190

Pro Glu Ala Thr Gly Tyr Gly Val Val Tyr Tyr Val Lys His Met Ile
        195                 200                 205

Glu His Arg Thr Lys Gly Ala Glu Thr Leu Lys Gly Lys Arg Val Ala
    210                 215                 220

Ile Ser Gly Ser Gly Asn Val Ala Gln Tyr Ala Ala Leu Lys Cys Ile
225                 230                 235                 240

Gln Glu Gly Ala Ile Val Lys Ser Ile Ser Asp Ser Lys Gly Val Leu
                245                 250                 255

Ile Ala Lys Thr Ala Glu Gly Leu Val Pro Glu Glu Ile His Glu Ile
            260                 265                 270

Met Ala Leu Lys Glu Lys Arg Ala Ser Ile Ala Asp Ser Ala Ser Leu
        275                 280                 285

Cys Lys Lys His His Tyr Ile Ala Gly Ala Arg Pro Trp Thr Asn Val
    290                 295                 300

Gly Glu Ile Asp Ile Ala Leu Pro Cys Ala Thr Gln Asn Glu Val Ser
305                 310                 315                 320

Gly Glu Glu Ala Ala Ala Leu Ile Lys Gln Gly Cys Arg Tyr Val Ala
                325                 330                 335

Glu Gly Ser Asn Met Gly Ser Ser Ala Glu Ala Val Glu Val Phe Glu
            340                 345                 350

Lys Ser Arg Ala Ser Gly Glu Gly Cys Trp Leu Ala Pro Gly Lys Ala
        355                 360                 365

Ala Asn Ala Gly Gly Val Ala Val Ser Gly Leu Glu Met Ala Gln Asn
    370                 375                 380

Ala Gln Phe Ser Thr Trp Thr His Ala Glu Val Asp Ala Lys Leu Ala
385                 390                 395                 400

Gly Ile Met Gln Asn Ile Phe Glu Gln Ser Thr Asp Val Ala Ser Lys
                405                 410                 415

Tyr Cys Asp Ser Gly Ser Asn Asn Ile Pro Ser Leu Val Asp Gly Ala
            420                 425                 430

Asn Ile Ala Gly Phe Leu Lys Val Ala Thr Ala Met Gln Ala Val Gly
        435                 440                 445

Asp Trp Trp
    450
```

<210> SEQ ID NO 187
<211> LENGTH: 457
<212> TYPE: PRT
<213> ORGANISM: Agaricus bisporus

<400> SEQUENCE: 187

```
Met Val Leu Pro His Glu Pro Glu Phe Glu Gln Ala Leu His Glu Leu
1               5                   10                  15

Glu Thr Ser Leu Gln Pro Phe Leu Thr Thr Asn Pro Gln Tyr Lys Lys
            20                  25                  30

Ala Leu Glu Ile Ile Gln Val Pro Glu Arg Val Leu Gln Phe Arg Val
        35                  40                  45

Thr Trp Glu Asp Asp Gln Gly Lys Pro Gln Val Asn Arg Gly Phe Arg
    50                  55                  60

Val Gln Tyr Asn Ser Ala Leu Gly Pro Tyr Lys Gly Gly Leu Arg Leu
65                  70                  75                  80

His Pro Thr Val Asn Leu Ser Ile Leu Lys Phe Leu Gly Phe Glu Gln
                85                  90                  95

Thr Phe Lys Asn Ala Leu Thr Gly Leu Ser Met Gly Gly Gly Lys Gly
            100                 105                 110

Gly Ser Asp Phe Asp Pro Lys Gly Lys Ser Asp Asn Glu Ile Arg Arg
        115                 120                 125

Phe Cys Val Ala Phe Met Ser Glu Leu Phe Arg His Ile Gly Gln Asp
    130                 135                 140

Thr Asp Val Pro Ala Gly Asp Ile Gly Thr Gly Ala Arg Glu Ile Gly
145                 150                 155                 160

Phe Leu Phe Gly Ala Tyr Arg Arg Leu Lys Asn Glu Phe Thr Gly Met
                165                 170                 175

Leu Thr Gly Lys Gly Ile Asn Trp Gly Gly Ser Phe Ile Arg Pro Glu
            180                 185                 190

Ala Thr Gly Tyr Gly Leu Ile Tyr Tyr Val Glu His Met Ile Ala His
        195                 200                 205

Ala Cys Pro Glu Tyr Ser Leu Asp Arg Pro Ser Thr Leu Val Ala Ile
    210                 215                 220

Ser Gly Ser Gly Asn Val Ser Gln Phe Thr Ala Leu Lys Val Ile Glu
225                 230                 235                 240

Leu Gly Ala Thr Val Leu Ser Leu Ser Asp Ser Lys Gly Ser Leu Ile
                245                 250                 255

Ser Glu Lys Gly Tyr Thr Lys Glu Ala Ile Glu Lys Ile Ala Glu Leu
            260                 265                 270

Lys Leu Lys Gly Gly Ala Leu Glu Ala Ile Val Asp Asp Leu Gly Ala
        275                 280                 285

Gly Tyr Thr Tyr His Ala Gly Lys Arg Pro Trp Thr Leu Leu Pro Gln
    290                 295                 300

Val His Ile Ala Leu Pro Gly Ala Thr Gln Asn Glu Val Ser Gln Glu
305                 310                 315                 320

Glu Ala Glu Ala Leu Val Lys Ala Gly Thr Arg Ile Val Ala Glu Gly
                325                 330                 335

Ser Asn Met Gly Cys Thr Glu Glu Ala Ile Ala Ile Phe Glu Asn Ser
            340                 345                 350

Arg Arg Ala Ser Arg Ala Gly Val Trp Tyr Ala Pro Gly Lys Ala Ser
        355                 360                 365

Asn Cys Gly Gly Val Ala Val Ser Gly Leu Glu Met Ala Gln Asn Ser
    370                 375                 380

Gln Arg Leu Ala Trp Ser Thr Gln Glu Val Asp Ala Lys Leu Lys Ser
385                 390                 395                 400

Ile Met Ala Glu Cys Tyr Gln Ile Cys Tyr Thr Ala Gly Ser Arg Trp
```

```
                405                 410                 415

Ser Gly Glu Lys Val Ala Glu Gly Val Ala Glu Gly Glu Ala Leu Pro
            420                 425                 430

Ser Leu Leu Ser Gly Ala Asn Leu Ala Gly Phe Ile Lys Val Ala Asp
        435                 440                 445

Ala Met Lys Glu Gln Gly Asp Trp Trp
    450                 455


<210> SEQ ID NO 188
<211> LENGTH: 417
<212> TYPE: PRT
<213> ORGANISM: Halobacterium salinarum

<400> SEQUENCE: 188

Met Pro Glu Ala Asn Pro Phe Glu Ser Leu Gln Glu Gln Leu Asp Asp
1               5                   10                  15

Ala Gly Glu Phe Leu Asp Val Asn Ala Asp Val Leu Glu Arg Leu Lys
            20                  25                  30

His Pro Glu Arg Val Leu Glu Thr Thr Leu Ser Val Glu Met Asp Asp
        35                  40                  45

Gly Thr Ile Glu Thr Phe Lys Ala Phe Arg Ser Gln Phe Asn Gly Asp
    50                  55                  60

Arg Gly Pro Tyr Lys Gly Gly Ile Arg Tyr His Pro Gly Val Thr Arg
65                  70                  75                  80

Asp Glu Val Lys Ala Leu Ser Gly Trp Met Val Tyr Lys Thr Ala Val
                85                  90                  95

Ala Asp Ile Pro Tyr Gly Gly Gly Lys Gly Gly Ile Ile Leu Asp Pro
            100                 105                 110

Glu Glu Tyr Ser Asp Ser Glu Leu Glu Arg Ile Thr Arg Ala Phe Ala
        115                 120                 125

Thr Glu Leu Arg Pro Phe Ile Gly Glu Asp Lys Asp Val Pro Ala Pro
    130                 135                 140

Asp Val Asn Thr Gly Gln Arg Glu Met Asn Trp Ile Lys Asp Thr Tyr
145                 150                 155                 160

Glu Thr Leu Glu Asp Thr Thr Ala Pro Gly Val Ile Thr Gly Lys Ala
                165                 170                 175

Leu Glu Asn Gly Gly Ser Glu Gly Arg Val Asn Ala Thr Gly Arg Ser
            180                 185                 190

Thr Met Phe Ala Ala Arg Glu Val Phe Asp Tyr Leu Asp Arg Asp Leu
        195                 200                 205

Ser Asp Ala Thr Val Ala Val Gln Gly Tyr Gly Asn Ala Gly Ser Val
    210                 215                 220

Ala Ala Lys Leu Ile Ala Asp Gln Gly Ala Asp Val Val Ala Val Ser
225                 230                 235                 240

Asp Ser Ser Gly Ala Val His Asn Pro Asp Gly Leu Asp Thr Arg Ala
                245                 250                 255

Val Lys Ala Phe Lys Thr Glu Thr Gly Ser Val Ser Gly Tyr Glu Gly
            260                 265                 270

Ala Thr Glu Glu Leu Ser Asn Glu Ala Leu Leu Thr Met Asp Val Asp
        275                 280                 285

Leu Leu Val Pro Ala Ala Leu Glu Asn Ala Ile Asp Glu Asp Leu Ala
    290                 295                 300

His Asp Val Asp Ala Asp Val Val Val Glu Ala Ala Asn Gly Pro Leu
305                 310                 315                 320
```

```
Thr Pro Asp Ala Asp Asp Val Leu Thr Glu Arg Gly Val Thr Val Val
                325                 330                 335

Pro Asp Ile Leu Ala Asn Ala Gly Gly Val Thr Val Ser Tyr Phe Glu
            340                 345                 350

Trp Val Gln Asn Arg Gln Arg Phe Gln Trp Thr Glu Asp Arg Val Asn
        355                 360                 365

Glu Glu Leu Glu Ala Ile Ile Thr Asp Ala Phe Asp Ala Met Thr Asp
    370                 375                 380

Ala His Glu Asp Ala Gly Thr Pro Asn Leu Arg Thr Ala Ala Tyr Val
385                 390                 395                 400

Val Ala Val Gln Arg Val Val Asp Ala Tyr Glu Gly Ser Gly Ser Trp
                405                 410                 415

Pro


<210> SEQ ID NO 189
<211> LENGTH: 454
<212> TYPE: PRT
<213> ORGANISM: Neurospora crassa

<400> SEQUENCE: 189

Met Ser Asn Leu Pro Ser Glu Pro Glu Phe Glu Gln Ala Tyr Lys Glu
1               5                   10                  15

Leu Ala Tyr Thr Leu Glu Asn Ser Ser Leu Phe Gln Lys His Pro Glu
            20                  25                  30

Tyr Arg Thr Ala Leu Thr Val Ala Ser Ile Pro Glu Arg Val Ile Gln
        35                  40                  45

Phe Arg Val Val Trp Glu Asp Asp Asn Gly Asn Val Gln Val Asn Arg
    50                  55                  60

Gly Tyr Arg Val Gln Phe Asn Ser Ala Leu Gly Pro Tyr Lys Gly Gly
65                  70                  75                  80

Leu Arg Leu His Pro Ser Val Asn Leu Ser Ile Leu Lys Phe Leu Gly
                85                  90                  95

Phe Glu Gln Ile Phe Lys Asn Ala Leu Thr Gly Leu Ser Met Gly Gly
            100                 105                 110

Gly Lys Gly Gly Ala Asp Phe Asp Pro Lys Gly Lys Ser Asp Ala Glu
        115                 120                 125

Ile Arg Arg Phe Cys Cys Ala Phe Met Ala Glu Leu His Lys His Ile
    130                 135                 140

Gly Ala Asp Thr Asp Val Pro Ala Gly Asp Ile Gly Val Gly Gly Arg
145                 150                 155                 160

Glu Ile Gly Tyr Met Phe Gly Ala Tyr Arg Lys Ala Ala Asn Arg Phe
                165                 170                 175

Glu Gly Val Leu Thr Gly Lys Gly Leu Ser Trp Gly Gly Ser Leu Ile
            180                 185                 190

Arg Pro Glu Ala Thr Gly Tyr Gly Leu Val Tyr Tyr Val Gly His Met
        195                 200                 205

Leu Glu Tyr Ser Gly Ala Gly Ser Tyr Ala Gly Lys Arg Val Ala Leu
    210                 215                 220

Ser Gly Ser Gly Asn Val Ala Gln Tyr Ala Ala Leu Lys Leu Ile Glu
225                 230                 235                 240

Leu Gly Ala Thr Val Val Ser Leu Ser Asp Ser Lys Gly Ala Leu Val
                245                 250                 255

Ala Thr Gly Glu Ser Gly Ile Thr Val Glu Asp Ile Asn Ala Val Met
            260                 265                 270
```

```
Ala Ile Lys Glu Ala Arg Gln Ser Leu Thr Ser Phe Gln His Ala Gly
        275                 280                 285

His Leu Lys Trp Ile Glu Gly Ala Arg Pro Trp Leu His Val Gly Lys
    290                 295                 300

Val Asp Ile Ala Leu Pro Cys Ala Thr Gln Asn Glu Val Ser Lys Glu
305                 310                 315                 320

Glu Ala Glu Gly Leu Leu Ala Ala Gly Cys Lys Phe Val Ala Glu Gly
                325                 330                 335

Ser Asn Met Gly Cys Thr Leu Glu Ala Ile Glu Val Phe Glu Asn Asn
            340                 345                 350

Arg Lys Glu Lys Lys Gly Glu Ala Val Trp Tyr Ala Pro Gly Lys Ala
        355                 360                 365

Ala Asn Cys Gly Gly Val Ala Val Ser Gly Leu Glu Met Ala Gln Asn
    370                 375                 380

Ser Gln Arg Leu Asn Trp Thr Gln Ala Glu Val Asp Glu Lys Leu Lys
385                 390                 395                 400

Asp Ile Met Lys Asn Ala Phe Phe Asn Gly Leu Asn Thr Ala Lys Thr
                405                 410                 415

Tyr Val Glu Ala Ala Glu Gly Glu Leu Pro Ser Leu Val Ala Gly Ser
            420                 425                 430

Asn Ile Ala Gly Phe Val Lys Val Ala Gln Ala Met His Asp Gln Gly
        435                 440                 445

Asp Trp Trp Ser Lys Asn
    450


<210> SEQ ID NO 190
<211> LENGTH: 454
<212> TYPE: PRT
<213> ORGANISM: Saccharomyces uvarum

<400> SEQUENCE: 190

Met Ser Glu Pro Glu Phe Gln Gln Ala Tyr Asp Glu Val Val Ser Ser
1               5                   10                  15

Leu Glu Asp Ser Thr Leu Phe Glu Gln His Pro Lys Tyr Arg Lys Val
            20                  25                  30

Leu Pro Ile Val Ser Val Pro Glu Arg Ile Ile Gln Phe Arg Val Thr
        35                  40                  45

Trp Glu Asn Asp Lys Gly Glu Gln Glu Val Ala Gln Gly Tyr Arg Val
    50                  55                  60

Gln Tyr Asn Ser Ala Lys Gly Pro Tyr Lys Gly Gly Leu Arg Phe His
65                  70                  75                  80

Pro Ser Val Asn Leu Ser Ile Leu Lys Phe Leu Gly Phe Glu Gln Ile
                85                  90                  95

Phe Lys Asn Ser Leu Thr Gly Leu Asp Met Gly Gly Gly Lys Gly Gly
            100                 105                 110

Leu Cys Val Asp Leu Lys Gly Arg Ser Asn Asn Glu Ile Arg Arg Ile
        115                 120                 125

Cys Tyr Ala Phe Met Arg Glu Leu Ser Arg His Ile Gly Gln Asp Thr
    130                 135                 140

Asp Val Pro Ala Gly Asp Ile Gly Val Gly Gly Arg Glu Ile Gly Tyr
145                 150                 155                 160

Leu Phe Gly Ala Tyr Arg Thr Tyr Lys Asn Ser Trp Glu Gly Val Leu
                165                 170                 175

Thr Gly Lys Gly Leu Asn Trp Gly Gly Ser Leu Ile Arg Pro Glu Ala
            180                 185                 190
```

```
Thr Gly Tyr Gly Leu Val Tyr Tyr Thr Gln Ala Met Ile Asp Tyr Ala
        195                 200                 205

Thr Asn Gly Lys Glu Ser Phe Glu Gly Lys Arg Val Thr Ile Ser Gly
    210                 215                 220

Ser Gly Asn Val Ala Gln Phe Ala Ala Leu Lys Val Ile Glu Leu Gly
225                 230                 235                 240

Gly Thr Val Val Ser Leu Ser Asp Ser Lys Gly Cys Ile Ile Ser Glu
                245                 250                 255

Thr Gly Ile Thr Ser Glu Gln Val Ala Asp Ile Ser Ser Ala Lys Val
            260                 265                 270

Asn Phe Lys Ser Leu Glu Gln Ile Val Gly Glu Tyr Ser Thr Phe Thr
        275                 280                 285

Glu Asn Lys Val Gln Tyr Ile Ser Gly Ala Arg Pro Trp Thr His Val
    290                 295                 300

Gln Lys Val Asp Ile Ala Leu Pro Cys Ala Thr Gln Asn Glu Val Ser
305                 310                 315                 320

Gly Asp Glu Ala Lys Ala Leu Val Ala Gln Gly Val Lys Phe Val Ala
                325                 330                 335

Glu Gly Ser Asn Met Gly Ser Thr Pro Glu Ala Ile Ala Val Phe Glu
            340                 345                 350

Thr Ala Arg Ala Thr Ala Ser Thr Leu Lys Glu Ser Val Trp Tyr Gly
        355                 360                 365

Pro Pro Lys Ala Ala Asn Leu Gly Gly Val Ala Val Ser Gly Leu Glu
    370                 375                 380

Met Ala Gln Asn Ser Gln Arg Ile Thr Trp Ser Ser Glu Arg Val Asp
385                 390                 395                 400

Gln Glu Leu Lys Lys Ile Met Val Asn Cys Phe Asn Glu Cys Ile Asp
                405                 410                 415

Ser Ala Lys Lys Tyr Thr Lys Glu Gly Asn Ala Leu Pro Ser Leu Val
            420                 425                 430

Lys Gly Ala Asn Ile Ala Ser Phe Ile Lys Val Ser Asp Ala Met Phe
        435                 440                 445

Asp Gln Gly Asp Val Phe
    450
```

<210> SEQ ID NO 191
<211> LENGTH: 459
<212> TYPE: PRT
<213> ORGANISM: Schwanniomyces occidentalis

<400> SEQUENCE: 191

```
Met Ile Lys Asn Gly Leu Pro His Glu Pro Glu Phe Gln Gln Ala Tyr
1               5                   10                  15

Asn Glu Leu Val Ser Ala Leu Glu Glu Ser Thr Leu Phe Thr Glu Lys
            20                  25                  30

Pro Glu Tyr Lys Lys Val Ile Pro Val Val Ser Ile Pro Glu Arg Ile
        35                  40                  45

Ile Gln Phe Arg Val Ala Trp Glu Asn Asp Asn Gly Asp Val Glu Val
    50                  55                  60

Asn Asn Gly Phe Arg Val Gln Phe Asn Ser Ser Leu Gly Pro Tyr Lys
65                  70                  75                  80

Gly Gly Leu Arg Phe His Pro Ser Val Asn Leu Ser Ile Leu Lys Phe
                85                  90                  95

Leu Gly Phe Glu Gln Ile Phe Lys Asn Ala Leu Thr Gly Leu Ser Met
```

```
            100                 105                 110

Gly Gly Gly Lys Gly Gly Cys Asp Phe Asn Pro Lys Gly Arg Ser Asp
        115                 120                 125

Gly Glu Ile Arg Arg Phe Cys Val Ala Phe Met Arg Gln Leu Ala Arg
    130                 135                 140

Tyr Ile Gly Ala Asp Thr Asp Val Pro Ala Gly Asp Ile Gly Val Gly
145                 150                 155                 160

Gly Arg Glu Ile Gly Tyr Leu Phe Gly Ala Tyr Lys Gln Met Gln Asn
                165                 170                 175

Asn Trp Tyr Gly Val Leu Thr Gly Lys Gly Leu Thr Trp Gly Gly Ser
            180                 185                 190

Leu Ile Arg Pro Glu Ala Thr Gly Tyr Val Ser Phe Thr Thr Leu Lys
        195                 200                 205

Lys Met Ile Glu Lys Ala Thr Asn Gly Lys Glu Ser Phe Lys Gly Lys
    210                 215                 220

Arg Val Glu Leu Ser Gly Ser Gly Asn Val Ala Gln Tyr Ala Ala Leu
225                 230                 235                 240

Lys Val Ile Glu Leu Gly Gly Ile Val Val Ser Leu Ser Asp Ser Lys
                245                 250                 255

Gly Ser Ile Val Ser Lys Asn Gly Ile Val Pro Glu Gln Val Leu Glu
            260                 265                 270

Ile Ala Ala Ala Lys Leu Lys Phe Lys Ser Leu Glu Glu Ile Thr Lys
        275                 280                 285

Glu Ser Val Lys Leu Phe Ser Gly Glu Asn Ser Val Glu Tyr Leu Ala
    290                 295                 300

Gly Val Arg Pro Trp Ala Lys Val Gly His Phe Asp Val Ala Leu Pro
305                 310                 315                 320

Ser Ala Thr Gln Lys Glu Val Ser Gly Glu Glu Glu Ala Lys Ala Leu
                325                 330                 335

Val Glu Ala Gly Cys Lys Tyr Ile Ala Glu Gly Ser Asn Met Gly Ser
            340                 345                 350

Thr Lys Glu Ala Ile Asp Val Phe Glu Ala Asn Arg Ser Asn Asn Val
        355                 360                 365

Trp Tyr Ala Pro Gly Lys Ala Ala Asn Cys Gly Gly Val Ala Val Ser
    370                 375                 380

Gly Leu Glu Met Ala Gln Asn Ser Gln Arg Val Gln Trp Ser Ala Glu
385                 390                 395                 400

Glu Val Asp Ala Lys Leu Lys Asn Ile Met Tyr Thr Cys Phe Asp Asn
                405                 410                 415

Cys Tyr Asp Pro Ala Ile Lys Tyr Ser Ala Glu Lys Asn Ala Asp Gly
            420                 425                 430

Leu Pro Ser Leu Leu Lys Gly Ala Asn Ile Ala Ser Phe Ile Lys Val
        435                 440                 445

Ala Asp Ala Met Phe Asp Gln Gly Asp Val Tyr
    450                 455


<210> SEQ ID NO 192
<211> LENGTH: 428
<212> TYPE: PRT
<213> ORGANISM: Synechocystis sp.

<400> SEQUENCE: 192

Met Ala Gly Ser Leu Phe Ala Asp Ala Ser Lys Arg Leu Glu Lys Ala
1               5                   10                  15
```

```
Leu Lys Tyr Val Ala Ile Ser Asp Asp Ala Gly Glu Arg Leu Lys Tyr
            20                  25                  30

Pro Lys Thr Ser Leu Ser Val Ser Ile Pro Val Arg Met Asp Asp Gly
        35                  40                  45

Ser Leu Lys Ile Phe Pro Gly Tyr Arg Val Arg Tyr Asp Asp Thr Arg
    50                  55                  60

Gly Pro Gly Lys Gly Gly Val Arg Tyr His Pro Asn Val Thr Met Asp
65                  70                  75                  80

Glu Val Gln Ser Leu Ala Phe Trp Met Thr Phe Lys Cys Ala Leu Leu
                85                  90                  95

Asn Leu Pro Phe Gly Gly Ala Lys Gly Gly Ile Thr Leu Asn Pro Lys
            100                 105                 110

Glu Leu Ser Arg Ala Glu Leu Glu Arg Leu Ser Arg Gly Tyr Ile Glu
        115                 120                 125

Ala Ile Ala Asp Phe Ile Gly Pro Asp Ile Asp Ile Leu Ala Pro Asp
    130                 135                 140

Val Tyr Thr Asn Glu Met Met Met Gly Trp Met Met Asp Gln Tyr Ser
145                 150                 155                 160

Ile Ile Arg Arg Lys Ile Ser Pro Ala Val Val Thr Gly Lys Pro Val
                165                 170                 175

Thr Met Gly Gly Ser Gln Gly Arg Asn Thr Ala Thr Gly Thr Gly Ala
            180                 185                 190

Phe Tyr Ile Met Gln Gly Met Leu Pro Lys Phe Asp Gln Tyr Pro Glu
        195                 200                 205

Asn Thr Thr Val Ala Val Gln Gly Phe Gly Asn Ala Gly Met Val Val
    210                 215                 220

Ala Glu Cys Leu Tyr Gln Asp Gly Tyr Lys Val Val Ala Ile Ser Asp
225                 230                 235                 240

Ser Gln Gly Gly Ile Tyr Asn Glu Gln Gly Ile Asp Ile Pro Ala Val
                245                 250                 255

Ile Asp Tyr Lys Gln Arg His Arg Thr Leu Ala Gly Met Tyr Cys Asp
            260                 265                 270

Gln Ala Ile Cys Asp Leu Gly Glu Asn Gln Gln Ile Ser Asn Ala Glu
        275                 280                 285

Leu Leu Ala Leu Asp Val Asp Val Leu Ile Pro Ala Ala Leu Glu Asn
    290                 295                 300

Gln Ile Thr Arg Asp Asn Ala Asp Gln Val Arg Ala Arg Tyr Ile Phe
305                 310                 315                 320

Glu Val Ala Asn Gly Pro Thr Thr Thr Ala Ala Asp Asp Ile Leu Ala
                325                 330                 335

Ser Lys Gly Ile Tyr Val Phe Pro Asp Ile Leu Val Asn Ala Gly Gly
            340                 345                 350

Val Thr Val Ser Tyr Phe Glu Trp Val Gln Asn Arg Ser Gly Leu Tyr
        355                 360                 365

Trp Ser Ala Lys Glu Val Asn Asp Arg Leu Lys Glu Lys Met Val Glu
    370                 375                 380

Glu Ala Glu His Val Trp Asn Ile Thr Gln Glu Leu Asp Val Asn Val
385                 390                 395                 400

Arg Thr Ala Ala Tyr Ile His Ala Leu Asn Arg Leu Ser Glu Ala Met
                405                 410                 415

Asp Ala Lys Gly Thr Arg Asp Tyr Tyr Gln Asp Ser
            420                 425
```

<210> SEQ ID NO 193
<211> LENGTH: 1528
<212> TYPE: DNA
<213> ORGANISM: Oryza sativa

<400> SEQUENCE: 193
ggaagctaac tagtcacggc gaatacatga cgacatcggc ctacaacgca caacttcttg 60
gcataaaagc ttcaatttca atgcccctat ctggaagccc taggcgccgc gcaaatgtaa 120
aacattcgct tcgcttggct tgttatccaa aatagagtat ggacctccga cagattggca 180
acccgtgggt aatcgaaaat ggctccatct gccccttttgt cgaaggaatc aggaaacggc 240
cctcacctcc tggcggagtg tagatatgtg aaagaatcta ggcgacactt gcagactgga 300
caacatgtga acaaataaga ccaacgttat ggcaacaagc ctcgacgcta ctcaagtggt 360
gggaggccac cgcatgttcc aacgaagcgc caaagaaagc cttgcagact ctaatgctat 420
tagtcgccta ggatatttgg aatgaaagga accgcagagt ttttcagcac caagagcttc 480
cggtggctag tctgatagcc aaaattaagg aggatgccaa aacatgggtc ttggcgggcg 540
cgaaacacct tgataggtgg cttacctttt aacatgttcg ggccaaaggc cttgagacgg 600
taaagttttc tatttgcgct tgcgcatgta caattttatt cctctattca atgaaattgg 660
tggctcactg gttcattaaa aaaaaaagaa tctagcctgt tcgggaagaa gaggatttta 720
ttcgtgagag agagagagag agagagagag agagggagag agaaggagga ggaggatttt 780
caggcttcgc attgcccaac ctctgcttct gttggcccaa gaagaatccc aggcgcccat 840
gggctggcag tttaccacgg acctacctag cctaccttag ctatctaagc gggccgacct 900
agtagctacg tgcctagtgt agattaaagt tggcgggcca gcaggaagcc acgctgcaat 960
ggcatcttcc cctgtccttc gcgtacgtga aaacaaaccc aggtaagctt agaatcttct 1020
tgcccgttgg actgggacac ccaccaatcc caccatgccc cgatattcct ccggtctcgg 1080
ttcatgtgat gtcctctctt gtgtgatcac ggagcaagca ttcttaaacg gcaaaagaaa 1140
atcaccaact tgctcacgca gtcacgctgc accgcgcgaa gcgacgcccg ataggccaag 1200
atcgcgagat aaaataacaa ccaatgatca taaggaaaca agcccgcgat gtgtcgtgtg 1260
cagcaatctt ggtcatttgc gggatcgagt gcttcacggc taaccaaata ttcggccgat 1320
gatttaacac attatcagcg tagatgtacg tacgatttgt taattaatct acgagccttg 1380
ctagggcagg tgttctgcca gccaatccag atcgccctcg tatgcacgct cacatgatgg 1440
cagggcaggg ttcacatgag ctctaacggt cgattaatta atcccggggc tcgactataa 1500
atacctccct aatcccatga tcaaaacc 1528

<210> SEQ ID NO 194
<211> LENGTH: 1280
<212> TYPE: DNA
<213> ORGANISM: Setaria italica

<400> SEQUENCE: 194
tccaccgatc atcacacaca gccagtagtg gggtgggcc aagcaatcag gcacccggca 60
atgcgagctg atgcgtgatg atggtgctac caacaaactg actataaaat ttctgatttg 120
aaagggattg gcctcgatat tttattagct ccccggcttt tgtcacgaca cgttagcatg 180
cgtgccttct agaagctagt ccgggtatta ccgctagaaa gttcccgaaa tgaagcattt 240
accacccgta aagctcattt ttctttatga tgagtagaca cggtaccaac attgaggacc 300
gattggttgg ctcccaaaat ctgccctgcc aaactagggc aagttcataa attttgacat 360

```
tcgcttggtt ggcaatcaat taaatcctat tctaaaattc ttgcctaggt tttgatataa    420
catgccctat attttggtct actcaaattt tggtatggta aattttgaac accaacaaat    480
caggctatta tttatcttat ctctttctca atttcattac acagcaaggc agtaattaaa    540
aggaccgtat atacaatgga tgtaagaata aaatgtataa gtagaaatat attggcatgc    600
ctcgtgctgg tgcatgtcga tatgctctca attagaagtt ggagacaggt tatgcttagg    660
atagtcccaa cctatgatat ctgtgtgtct atactgccac ataagtaaga catcacttta    720
gaaattacat tctacaacct ataatttctt agtgtggatc cttaattaat tcatcatctc    780
tcctctcaat tcctcatcaa ttatgaagac accatcttct tccaatgcaa atttaacact    840
gtctaggatc taggttcagg tgttgatact gggtcttgca tgagatccag tttcttgttc    900
ttccaattct ctctcattta atatataatc acataagcaa aagatcctat gtagctgcac    960
aattaatgct atggaaacta tcctaatcgg agggttggga ctgctcctgc ctatggcggc   1020
ttattcccca tttgcctaac ctgaaaatcg aaagggagtg catgacaggg caaacactag   1080
tgttgcctgc atcaataatc gtccatgatt atatagaggt agcatgactt ttttaggcgt   1140
cgtgtcctaa tcaatcagaa aagaaagcca acctaatcgc tatgggccgc aaccaccgat   1200
gcgactatgc gagtatatgg aacccgttgc tactccccca ctatatatcg tggagtctga   1260
tggcaatcca acggcagacg                                               1280
```

<210> SEQ ID NO 195
<211> LENGTH: 1435
<212> TYPE: DNA
<213> ORGANISM: Arabidopsis thaliana

<400> SEQUENCE: 195

```
taggaaaaaa gtttatattc ctacccaaac tttcggcacc agagacaaat taggtttgtt     60
cagaaaatca gtcgctcatc gacagactta acaccacaaa atcatcagaa tttctttggg    120
acaaaatgga aaatgttctt cacggctcca cctaccaaaa tttcgatatc aagctcaaaa    180
gcatacacaa actataacta attccatagt tacgtaatct taacttcgaa ttcaacaaca    240
catgcatgca tcgactgaat cttcaacaaa tgcaatcaaa cacacaaaat tgctaccaaa    300
aaaatatgat ttttttttta tgatttcaat tttcatccgg cacttagtcc aaaacttttt    360
ttgtgtgtca acatttttta aaaaaatctt taaacggata tctgatctaa gagcatgttc    420
ataggtgata cttacaaaat atttttaaga aattttttag tattatttat aatgtttgtt    480
taataaatat atataagatt ttttgctttt atcaaatgtg accaatcaga agaaaccacg    540
tcagatgata ctgatatgac aaatatgata ctgatcaaac atattctaat tgctttacta    600
atataaaaat aatttttgga cttgtgatac tctaaaaata tcacccatat acatggtcta    660
atatatggat cgtaaaaaac tcatatataa tattaataag tagtagaaga gcgtagacca    720
tgtcctgggt cgtcgtccaa atgaccacaa gaagatttca aaacagagga aaatatttct    780
cattaaataa gttttcctga cgcataagat aacattatta caagattcag aaaaagaaag    840
gtgaaaggat aatgtttctc ctactatata agatgtgtac atctgaaaaa atatgaatat    900
atttgtaacg tttgactgtt attacatgat taatacgata taaatattaa catttttttt    960
caaaataaaa gtaatatagt aaggaaatga aaagaggcat gaagcatgcc tctttttttg   1020
gtcggctgcc gtttacaatt gccaattgcg atagttactc ttcttgcgtg tacgactttt   1080
gttttttttt acatattcgc caataatttg acgttttcta ttagtttgtt tgatactctg   1140
ttgtcttgct aaaactcaat aaaacattaa attactttct tgaatgaagc tggaacaaat   1200
```

ctaacataaa tagaaaatga tgggcaagtt gatgttattc gtaaatttat ttagattata 1260
ttatataaaa agcaatccaa ttatatatct catatataca atttcttatc ttactttgtc 1320
aatgtcatat acgtaactaa aacttgcgga aatagaaaat gccacgtgta tggtggacat 1380
aatccgaatc tctctctttc ttctataaat agtggccatt cccattggtt gaaat 1435

<210> SEQ ID NO 196
<211> LENGTH: 1940
<212> TYPE: DNA
<213> ORGANISM: Zea mays

<400> SEQUENCE: 196
caaatatcca ctcacagcca tacccgtggt tgcaacaaat atctatccac aaccatacct 60
gcgggtaaat tcatatccat gtacgtgctc attaggtttt ggacaggttt tgtatatatg 120
tcggatatga cagagacaat cattttcaac aactcaatag cataatcaat caaaattctt 180
cccaatttta cctgaacaca caattaaaaa cttaataaaa aaattatata aatacacatg 240
tcttttaaca atcaatattc tcaacacgac aacatggaag acgcgtcgga ctagaagggg 300
tggagcgctg gggaccactg gggaagcgac agtgaggctc accggcagtg tggactaaag 360
atccgagagc agttgggcgg gcgactggtg tcggattgag ggacacgaag gggcgacgat 420
agtgtggact gaataaccaa gagcagttgg cgcgagcggt tggcgtagtc ttgaggtgta 480
ggcaagaagg gacaaccacg agcgtatgag gtgcgggttg tggctagggg cactagagat 540
tagaaggggt agacgtctgc caggtgcgaa cggtacaggt gttgcggccc cgtaggactt 600
ggaaggggac acatgacgta gttcaagaaa ccagcaaggc tagaaggggt gaccataagt 660
gggaaattag gagttcacgg agttagggtt tgctctttgt tgtgtaatat gagcaaaaca 720
aaaataaata aactatatgc tgatttcgga tatgcaacag gtaatccgtg ggtggaaggt 780
aatattctaa tccgtgtccg ctcgactttg gatctggtac gaatctgacc catgcttcga 840
aacatgtatc catgctcgtt tccattggat cctatggata tttgaatcca tgatcaaatt 900
tccattccta gatagctaga ttagagtaat gttccgttta gatgtcgata ttggagggtg 960
tggaattgaa ttgggttcaa ttacaaatca gccatgctat tgaaatgagt tgtaattcca 1020
atactaatgt ttggatgtca ctgaattgga gtttggaatt gtgtggtcta attccattca 1080
atacagagga gtaatgctct gtattaggag agggggtctc tagttgtagt ccaattccag 1140
gggattgggt atttgattcc aaatctcaat tatgtgcata accaaacaat agaattctag 1200
aaaagctgat ttcaattcct aattcggtgc tccaatatct acatccaaac agggtataat 1260
gcaattcttc gcttcctatg gatggtcttt tagattttgt attggctaat gatattagac 1320
gtttcttatt tttgtctttc gttgaatgtt tttcgattga tgtcggggta tgaatccatg 1380
actttttcca tcactagaaa atatactgtc agaaaaaata gtgctgaatt agtgaatttg 1440
atccatcata atggagttgt cattctactt tgcacttgca ctaccggcag cccgcagcag 1500
gacggctgac aagctcgcac taagtcatcg atttgtggtc actaatgcgg agctcgcact 1560
tgcgtgactc atcgagttgt gggcttgtgg ccttgtgggt ggaacggtgg aatccacctc 1620
aggatgccac agaaaaaggt ttaaaaaaac tgttgcaccg agccaccgag agagcacaag 1680
acccccacga ccgcaggtca agccgtactg gactggaccg gaccggacac acgcccagaa 1740
agccctgcag cagaactgca gaagacacgg ccgcggcaga agagcccaaa tcacggccgc 1800
aaaagccacg cacgcggcgc ttgtcctgcg cggcgcacgg aaacccacct ccacggcggc 1860
accccgtgcg tcggctgctt gctgccccag tgccgccccg cgttcccttc gctcccgccg 1920
acaccgacgc cgccactgcc 1940

<210> SEQ ID NO 197
<211> LENGTH: 1099
<212> TYPE: DNA
<213> ORGANISM: Oryza sativa

<400> SEQUENCE: 197
cagcggggca gcgcaacaca aaaagggggg aggatgccgg cgaccacgct agtgaccatg 60
aagcaagatg atgtgaaagg gaggaccgga cgagggttgg acctctgctg ccgacatgaa 120
gagcgtgatg tgtagaagga gatgttagac cagatgccga cgcaactagc cctggcaagg 180
tcacccgact gatatcgctg cttgcccttg tcctcatgta cacaatcagc ttgcttatct 240
ctcccatact ggtcgtttgt ttcccgtggc cgaaatagaa gaagacagag gtaggttttg 300
ttagagaatt ttagtggtat tgtagcctat ttgtaatttt gttgtacttt attgtattaa 360
tcaataaagg tgtttcattc tattttgact caatgttgaa tccattgatc tcttggtgtt 420
gcactcagta tgttagaata ttacattccg ttgaaacaat cttggttaag ggttggaaca 480
tttttatccg ttcgtgaaac atccgtaata ttttcgttga aacaattttt atcgacagca 540
ccgtccaaca atttacacca atttggacgt gtgatacata gcagtcccca agtgaaactg 600
accaccagtt gaaaggtata caaagtgaac ttattcatct aaaagaccgc agagatgggc 660
cgtgggccgt ggcctgcgaa acgcagcgtt caggcccatg agcatttatt ttttaaaaaa 720
atatttcaca acaaaaaaga gaacggataa aatccatcga aaaaaaaaaa ctttcctacg 780
catcctctcc tatctccatc cacggcgagc actcatccaa accgtccatc cacgcgcaca 840
gtacacacac atagttatcg tctctccccc cgatgagtca ccacccgtgt cttcgagaaa 900
cgcctcgccc gacaccgtac gtggcgccac cgccgcgcct gccgcctgga cacgtccggc 960
tcctctccac gccgcgctgg ccaccgtcca ccggctcccg cacacgtctc cctgtctccc 1020
tccacccatg ccgtggcaat cgagctcatc tcctcgcctc ctccggctta taaatggcgg 1080
ccaccacctt cacctgctt 1099

<210> SEQ ID NO 198
<211> LENGTH: 1980
<212> TYPE: DNA
<213> ORGANISM: Zea mays

<400> SEQUENCE: 198
aaacactatg taggtgcctc ttgtgagtct ccaaatcttg tggaagacca caataaagtt 60
tgtattaccc gtttgtttga gcaaagatta gtgtgcgggc ttgacctttg tggtcggcga 120
agcgggaatt agggttgaaa gagatccagc tctttgtggg cgcctcaacg aggaagtagg 180
gcacctttgt tgtgtgaccg aacctcagga taaatcttgt gtctcttgtg ttcttgttca 240
ttgtgtttgt tcgtgttcct cgttctctca ccattccgtg gaagatttgt tcatatcttt 300
ttggtgtgtg gattttgaga agtgtccttc tcagatctac tactttgaac cctatggatc 360
atctagaaca ttttattttt taagttaact gggtgaattt cgagatcaat ttagttttat 420
atctcattct ttagttgagc tcgtgcaaac cggttgaacc ggttttacct agttcgtttc 480
tagtttttgt taaaaaagtt ttcgcttgtc tattcaccct ctataggcaa ctttcaatta 540
tgtaatcact tttttttct tttttctgtt taaaatctca gtttcaaact tccaattgat 600
tttgaatacg aggtttgggt ttaaattcat attggaggca aaaatcgaaa gttccacgtg 660

```
atgctaggtt ttatttcggt tttctatctc ctattgtttt tcacgtttca acttgattca    720
aattctagtt ttttttaact taagcacaat taaatacaac ataaaaacaa catggattca    780
agttctattt caatttttat taactattat gttgtctagt ctgttcaagc acataatact    840
tataaatata aaattaaacg aaatcacata tttccacaaa tcttgggtac tacactcgga    900
gacgacgatg gattccatct caatttggat gttgattata gctctatttc agttgtcact    960
gttgtcctaa cacgccctat tgtgcatgat agtgcacgtg ctcaacgtaa aagaaaagag   1020
atcagtaaca agtagcagca ctgtacaagg taagccgtga ttcaattaaa actgtttgag   1080
caattcagtt gctagatcgt tccaccatcg ataattcgat atgtacgatg atataaaaag   1140
agcccataag tttgtcttga aaaggttgat caaataattt aaattagatg ataaaaaaca   1200
tggaagatgt gggagtggac gacggctatg aagaatagta ctatatcagg tttatacgta   1260
aaatttattt ttgaaatgtt tttataatct gtttgaattg tattttttgc ttaattatgt   1320
gattggatgt tttttcatga aatgtcgagt tttattttaa ataaaattct gtaaagagaa   1380
gttgctgcgc tgagaaaact ataaatcgat agtaaaggct gtacgcaacg tttaagtcct   1440
tgtttgaatg cgtatgaatc tgagaaagtt cagaatgatt aaatcttttt tatttaattt   1500
taatttgaga gagattaagt tctctccaat tctctttaat ttagacgtaa tcgaacaagc   1560
tggttgccaa actagatgag tacattttgt ccactgccat agagccatcg actacaaaag   1620
tctagaacac agtggaaagc accagacaac gcgcgaccaa aagggcccag gccccagcgc   1680
cccagtccgg gggttgtgtt cgccgacctg tgcgtgcctg ctcgtcacgt cacgtcccta   1740
tttgcccgtc ttcctcccct ccagaccctt ctcgaacgcc ccttcgttct ggatccaacg   1800
gtcggtctct gccgggctcg aacgttctcg aaaccacgtc acccccgata aaaccccacg   1860
cacagcctcc tcccttcctc aaccatcatt gcaaaagcga agcaagcaat ccgaattctc   1920
tgcgatttct ctagatctcg accaccccta ctagttttgg ttcctccttt cgttcgagag   1980
```

<210> SEQ ID NO 199
<211> LENGTH: 2000
<212> TYPE: DNA
<213> ORGANISM: Zea mays

<400> SEQUENCE: 199

```
cggaaggccg gtgaatatgg agatcagcta agggtgtaga atgataacct tacagttttg     60
tatttagatt cgtggactct gatgaaagca agcacataat attacacgca caggaaattg    120
tagcatgcat gctgctacat gattcctcta tttttgattt gccggtcctt tttgtctttt    180
tttttaaata cataggtttt gatttgtatc tgagaaaaac actatatcta gtagtagtgt    240
agtaataata taatctatgt atctaaaaaa atcaaaatga cttagaattt agaatgagta    300
gaatagaaat taagtgatcc aacctataag atggttttag aaatcaagat aagcaagacc    360
ctctcgctac cagaatccct gtatggctgt ctctcccgct cacgtgggaa aaggaaataa    420
agggagagga gaaacaaaag tgttggcgtt gatttggacg ttaaacatgg gtagatgaac    480
tatctagcgg tgctctatac gaagatgtgg acagtccatg gttctgagcc ggacggtctg    540
ctatctgagc gtaggagtga ccccttctct gcgtacgtcc atacgatcca cgtctggtgt    600
ttggatagtt cgcgatggcg cagatagtcg tcttgttcgc agcagatcta tatctcgtct    660
tccgggagag accccatagg ggaggagaga acctagggtg tgtcttcagg tcgttagacc    720
accaagacgt ctctagtcga cgtagagccg aaaaaagtga agattcgagg tagaggaagg    780
```

-continued

```
ctaaactaga actactccta atacataaga taaaatcata actaaaattg ttttaatcga    840

ttgtgtgagt ttaatcggtc gtaacccttt atctatataa aaggaatgtc tagacccgtt    900

acaaatcagt tctcgagtaa tctgattgat ttagctaaca aattcgacaa taaatcctga    960

atacgtggac ggatcgtgcc gctaaagaga cagtccggac tgcttttagt tctcaacaaa   1020

aattacaaaa ccatcactca cttacttccc agctgcctag gagcctagga ggctaggacc   1080

taggagctgg tgaggctatc cgcaaccgtt cccccctaaat ttttccccct atatcacttt   1140

tttgggtcac atcatcaaca ttccaccccc tattttttca tctcccgcag cggttccctc   1200

taaatactcc ccctatatcc cactacacta taaaatatca ttttttatac atacttttca   1260

tctattataa attttttatc tactaacaat tggaagcggg cccacgtgaa cagtgtttag   1320

aggggggaga gagataacgc cagaacgagg gggagagaga acgttacctt ttcgtagagc   1380

gctggctagc gtccaccgct gcggcgttgg gaggcgccct gtagccgcca tgcgagctac   1440

agggcaaggg gaggggggcgt cgcgccgcgt ccgttgcggc cagtctgaca gcacttcctg   1500

tcttcctcca cttcactgca gctgcagtgc acaccactct gtctgtttgt gaagcagcga   1560

gctgcacctg cacagcataa attctccagc cggccagacc ccacgcggcc ccagcatcag   1620

ataaaaaaag cgtcccagca gctgaaacat attttaagta cctgggctcc caaagaatct   1680

actggcacca gctgtttcct ttgccgcggc cagccgccca accgccggcc cggcgccttg   1740

ttccgttgtt cgtcaccacg gcttctccgc gtgtgaactc caacgtcgca gggcatacct   1800

ataaatacac ctcccacaaa accacacgct ccacacagct accactcagc tcaagctcga   1860

gacaagaaac cagaaccagc tcactcctca ctccacttcc actcccaaca gcaagctcaa   1920

gcagtcagtc accggcaggg gtcagggtca cagtcacagc agcagccatg gacacggccg   1980

gcctcgtcca gcacgcgacc                                               2000


<210> SEQ ID NO 200
<211> LENGTH: 469
<212> TYPE: DNA
<213> ORGANISM: Zea mays

<400> SEQUENCE: 200

ggtactcctg agatactata ccctcctgtt ttaaaatagt tggcattatc gaattatcat     60

tttacttttt aatgttttct cttcttttaa tatattttat gaattttaat gtattttaaa    120

atgttatgca gttcgctctg gacttttctg ctgcgcctac acttgggtgt actgggccta    180

aattcagcct gaccgaccgc ctgcattgaa taatggatga gcaccggtaa aatccgcgta    240

cccaactttc gagaagaacc gagacgtggc gggccgggcc accgacgcac ggcaccagcg    300

actgcacacg tcccgccggc gtacgtgtac gtgctgttcc ctcactggcc gcccaatcca    360

ctcatgcatg cccacgtaca cccctgccgt ggcgcgccca gatcctaatc ctttcgccgt    420

tctgcacttc tgctgcctat aaatggcggc atcgaccgtc acctgcttc                469
```